(12) United States Patent
Hovda et al.

(10) Patent No.: US 7,331,956 B2
(45) Date of Patent: Feb. 19, 2008

(54) METHODS AND APPARATUS FOR TREATING BACK PAIN

(75) Inventors: David Hovda, Mountain View, CA (US); Jean Woloszko, Austin, TX (US); Norman Sanders, Hillsborough, CA (US); Brian Martini, Menlo Park, CA (US)

(73) Assignee: ArthroCare Corporation, Austin, TX (US)

( * ) Notice: Subject to any disclaimer, the term of this patent is extended or adjusted under 35 U.S.C. 154(b) by 0 days.

(21) Appl. No.: 11/498,846

(22) Filed: Aug. 2, 2006

(65) Prior Publication Data

US 2007/0010809 A1    Jan. 11, 2007

Related U.S. Application Data

(63) Continuation of application No. 10/374,411, filed on Feb. 26, 2003, now abandoned, which is a continuation-in-part of application No. 09/676,194, filed on Sep. 28, 2000, now Pat. No. 6,602,248.

(51) Int. Cl.
*A61B 18/14* (2006.01)

(52) U.S. Cl. .......................... 606/32; 606/41; 606/49; 607/99

(58) Field of Classification Search .................. 606/32, 606/41, 49, 50; 607/99
See application file for complete search history.

(56) References Cited

U.S. PATENT DOCUMENTS

| | | | |
|---|---|---|---|
| 2,056,377 A | 10/1936 | Wappler | ..................... 125/303 |
| 3,633,425 A | 1/1972 | Sanford | ....................... 73/356 |
| 3,815,604 A | 6/1974 | O'Malley et al. | ........... 128/305 |
| 3,828,780 A | 8/1974 | Morrison, Jr. et al. | ...... 128/275 |

(Continued)

FOREIGN PATENT DOCUMENTS

DE    3930451 A1    3/1991

(Continued)

OTHER PUBLICATIONS

PCT International Search Report for PCT/US04/03614, 1 page, mailed Sep. 14, 2004.

(Continued)

*Primary Examiner*—Lee S. Cohen
(74) *Attorney, Agent, or Firm*—Brian E. Szymczak

(57) ABSTRACT

Apparatus and methods for treating back pain of a patient by denervation of an intervertebral disc or a region of the posterior longitudinal ligament by the controlled application of heat to a target tissue. In one embodiment, the invention may include a procedure combining both decompression of a disc, and denervation of the annulus fibrosus. In one embodiment, a method of the invention includes positioning an active electrode of an electrosurgical instrument in at least close proximity to an intervertebral disc, and applying at least a first high frequency voltage between the active electrode and a return electrode, wherein nervous tissue within the annulus fibrosus is inactivated, and discogenic pain of the patient is alleviated. In one embodiment, the invention includes positioning a first electrode of a dual-shaft electrosurgical instrument at a first location in relation to a target disc, positioning a second electrode of the instrument at a second location, and applying a high frequency voltage between the first and second electrodes, wherein the first and second electrodes are disposed on separate shafts of the instrument.

41 Claims, 75 Drawing Sheets

U.S. PATENT DOCUMENTS

| | | | |
|---|---|---|---|
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,161,950 A | 7/1979 | Doss et al. | 606/48 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,269,174 A | 5/1981 | Adair | 128/842 |
| 4,326,529 A | 4/1982 | Doss et al. | 128/303 |
| 4,381,007 A | 4/1983 | Doss | 128/303 |
| 4,449,926 A | 5/1984 | Weiss | 433/32 |
| 4,474,179 A | 10/1984 | Koch | 606/40 |
| 4,476,862 A | 10/1984 | Pao | 128/303 |
| 4,483,338 A | 11/1984 | Bloom et al. | 606/50 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,573,448 A | 3/1986 | Kambin | 606/170 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 606/41 |
| 4,896,671 A | 1/1990 | Cunningham et al. | 600/374 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 600/439 |
| 4,936,301 A | 6/1990 | Rexroth et al. | 606/45 |
| 4,943,290 A | 7/1990 | Rexroth et al. | 606/45 |
| 4,958,539 A | 9/1990 | Stasz et al. | 76/104.1 |
| 4,966,597 A | 10/1990 | Cosman | 606/50 |
| 4,967,765 A | 11/1990 | Turner et al. | 128/785 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,078,717 A | 1/1992 | Parins et al. | 606/48 |
| 5,080,660 A | 1/1992 | Buelna | 606/45 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,201,729 A | 4/1993 | Hertzmann et al. | 606/2 |
| 5,207,675 A | 5/1993 | Canady | 606/40 |
| 5,207,684 A | 5/1993 | Nobles | 606/108 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | 601/3 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,290,273 A | 3/1994 | Ton | 606/9 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,564 A | 6/1994 | Eggers | 606/47 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,336,443 A | 8/1994 | Odashima | 252/511 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,433,739 A * | 7/1995 | Sluijter et al. | 607/99 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,439,446 A | 8/1995 | Barry | 604/103 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,542,945 A | 8/1996 | Fritzsch | 606/48 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |

| Patent No. | Date | Inventor | Class |
|---|---|---|---|
| 5,571,189 A | 11/1996 | Kuslich | 623/17.12 |
| 5,584,872 A | 12/1996 | LaFontaine et al. | 607/117 |
| 5,609,151 A | 3/1997 | Mulier et al. | 128/642 |
| 5,617,854 A | 4/1997 | Munsif | 600/374 |
| 5,626,136 A | 5/1997 | Webster, Jr. | 600/373 |
| 5,626,576 A | 5/1997 | Janssen | 606/41 |
| 5,633,578 A | 5/1997 | Eggers | 323/301 |
| 5,647,869 A | 7/1997 | Goble et al. | 606/37 |
| 5,660,836 A | 8/1997 | Knowlton | 424/400 |
| 5,662,680 A | 9/1997 | Desai | 606/210 |
| 5,676,693 A | 10/1997 | LaFontaine | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,720,744 A | 2/1998 | Eggleston et al. | 606/40 |
| 5,725,524 A | 3/1998 | Mulier et al. | 606/41 |
| 5,762,629 A | 6/1998 | Kambin | 604/164.11 |
| 5,766,153 A | 6/1998 | Eggers et al. | 604/114 |
| 5,766,252 A | 6/1998 | Henry et al. | 623/17.16 |
| 5,785,705 A | 7/1998 | Baker | 606/32 |
| 5,807,306 A | 9/1998 | Shapland et al. | 604/21 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,820,580 A | 10/1998 | Edwards et al. | 604/22 |
| 5,823,955 A | 10/1998 | Kuck et al. | 600/374 |
| 5,836,875 A | 11/1998 | Webster, Jr. | 600/374 |
| 5,843,019 A | 12/1998 | Eggers et al. | 604/22 |
| 5,846,196 A | 12/1998 | Siekmeyer et al. | 600/374 |
| 5,849,009 A | 12/1998 | Bernaz | 606/36 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,877,289 A | 3/1999 | Thorpe et al. | 530/387.7 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,916,214 A | 6/1999 | Cosio et al. | 606/41 |
| 5,925,042 A | 7/1999 | Gough et al. | 606/41 |
| 5,941,869 A | 8/1999 | Patterson et al. | 604/508 |
| 5,944,715 A | 8/1999 | Goble et al. | 606/41 |
| 5,954,716 A | 9/1999 | Sharkey et al. | 606/32 |
| 5,980,504 A | 11/1999 | Sharkey et al. | 604/510 |
| 6,004,319 A | 12/1999 | Goble et al. | 606/48 |
| 6,007,570 A | 12/1999 | Sharkey et al. | 607/96 |
| 6,013,076 A | 1/2000 | Goble et al. | 606/41 |
| 6,014,584 A | 1/2000 | Hofmann et al. | 604/21 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,036,681 A | 3/2000 | Hooven | 604/506 |
| 6,039,734 A | 3/2000 | Goble et al. | 606/41 |
| 6,045,532 A | 4/2000 | Eggers et al. | 604/114 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,073,051 A * | 6/2000 | Sharkey et al. | 607/99 |
| 6,074,386 A | 6/2000 | Goble et al. | 606/34 |
| 6,086,584 A | 7/2000 | Miller et al. | 606/41 |
| 6,090,106 A | 7/2000 | Goble et al. | 606/41 |
| 6,093,186 A | 7/2000 | Goble et al. | 606/34 |
| 6,093,187 A | 7/2000 | Lecuyer | 606/45 |
| 6,095,149 A | 8/2000 | Sharkey et al. | 128/898 |
| 6,096,036 A | 8/2000 | Bowe et al. | 606/41 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,122,549 A | 9/2000 | Sharkey et al. | 607/99 |
| 6,126,682 A | 10/2000 | Sharkey et al. | 607/96 |
| 6,142,992 A | 11/2000 | Cheng et al. | 606/34 |
| 6,146,380 A | 11/2000 | Racz et al. | 606/41 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,176,857 B1 | 1/2001 | Ashley | 606/32 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,214,001 B1 | 4/2001 | Casscells et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 128/898 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,245,107 B1 | 6/2001 | Ferree | 606/61 |
| 6,254,600 B1 | 7/2001 | Willink et al. | 606/41 |
| 6,258,086 B1 | 7/2001 | Ashley et al. | 606/41 |
| 6,261,286 B1 | 7/2001 | Goble et al. | 606/34 |
| 6,261,311 B1 | 7/2001 | Sharkey et al. | 607/96 |
| 6,264,650 B1 | 7/2001 | Hovda et al. | 606/32 |
| 6,264,651 B1 | 7/2001 | Underwood et al. | 606/32 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 606/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,319,250 B1 | 11/2001 | Falwell et al. | 606/41 |
| 6,322,549 B1 | 11/2001 | Eggers et al. | 604/500 |
| 6,330,478 B1 | 12/2001 | Lee et al. | 607/101 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,402,740 B1 | 6/2002 | Ellis et al. | 606/28 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,428,576 B1 | 8/2002 | Haldimann | 623/17.16 |
| 6,432,103 B1 | 8/2002 | Ellsberry et al. | 606/41 |
| 6,464,695 B2 | 10/2002 | Hovda et al. | 606/32 |
| 6,468,270 B1 | 10/2002 | Hovda et al. | 606/32 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,497,704 B2 | 12/2002 | Ein-Gal | 606/41 |
| 6,500,173 B2 | 12/2002 | Underwood et al. | 606/32 |
| 6,517,498 B1 | 2/2003 | Burbank et al. | 600/564 |
| 6,530,922 B2 | 3/2003 | Cosman | 606/34 |
| 6,540,741 B1 | 4/2003 | Underwood et al. | 606/32 |

| | | | |
|---|---|---|---|
| 6,558,390 B2 | 5/2003 | Cragg | 606/80 |
| 6,562,033 B2 * | 5/2003 | Shah et al. | 606/41 |
| 6,575,968 B1 | 6/2003 | Eggers et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,604,003 B2 * | 8/2003 | Fredricks et al. | 607/99 |
| 6,620,155 B2 | 9/2003 | Underwood et al. | 606/32 |
| 6,620,156 B1 | 9/2003 | Garito et al. | 606/50 |
| 6,622,731 B2 | 9/2003 | Daniel et al. | 128/898 |
| 6,632,193 B1 | 10/2003 | Davison et al. | 604/22 |
| 6,632,220 B1 | 10/2003 | Eggers et al. | 606/41 |
| 6,635,087 B2 | 10/2003 | Angelucci et al. | 623/17.11 |
| 6,645,247 B2 | 11/2003 | Ferree | 623/17.11 |
| 6,679,886 B2 | 1/2004 | Weikel et al. | 606/79 |
| 6,712,811 B2 | 3/2004 | Underwood et al. | 606/32 |
| 6,726,684 B1 | 4/2004 | Woloszko et al. | 606/32 |
| 6,740,093 B2 | 5/2004 | Hochschuler et al. | 606/94 |
| 6,746,451 B2 | 6/2004 | Middleton et al. | 606/79 |
| 6,749,604 B1 | 6/2004 | Eggers et al. | 604/41 |
| 6,749,608 B2 | 6/2004 | Garito et al. | 606/45 |
| 6,758,846 B2 | 7/2004 | Goble et al. | 606/41 |
| 6,761,718 B2 | 7/2004 | Madsen | 606/50 |
| 6,770,071 B2 | 8/2004 | Woloszko et al. | 606/41 |
| 6,772,012 B2 | 8/2004 | Ricart et al. | 607/99 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,827,716 B2 | 12/2004 | Ryan et al. | 606/41 |
| 6,837,884 B2 | 1/2005 | Woloszko | 606/32 |
| 6,837,887 B2 | 1/2005 | Woloszko et al. | 606/41 |
| 6,837,888 B2 | 1/2005 | Ciarrocca et al. | 606/41 |
| 6,878,155 B2 | 4/2005 | Sharkey et al. | 607/96 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,974,480 B2 | 12/2005 | Messerli et al. | 623/17.11 |
| 6,991,631 B2 | 1/2006 | Woloszko et al. | 606/41 |
| 6,997,885 B2 | 2/2006 | Lubock et al. | 600/567 |
| 6,997,925 B2 | 2/2006 | Maguire et al. | 606/41 |
| 7,001,431 B2 | 2/2006 | Bao et al. | 623/17.12 |
| 7,004,941 B2 | 2/2006 | Tvinnereim et al. | 606/41 |
| 7,014,633 B2 | 3/2006 | Cragg | 604/500 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,108,696 B2 | 9/2006 | Daniel et al. | 606/41 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 2002/0029036 A1 | 3/2002 | Goble et al. | 606/38 |
| 2002/0049438 A1 | 4/2002 | Sharkey et al. | 606/41 |
| 2002/0082698 A1 | 6/2002 | Parenteau et al. | 623/17.16 |
| 2002/0095151 A1 | 7/2002 | Dahla et al. | 606/41 |
| 2002/0120337 A1 | 8/2002 | Cauthen | 623/17.16 |
| 2003/0013986 A1 | 1/2003 | Saadat | 600/549 |
| 2003/0014047 A1 | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0130738 A1 | 7/2003 | Hovda et al. | 623/17.11 |
| 2003/0158545 A1 | 8/2003 | Hovda et al. | 606/32 |
| 2003/0171743 A1 | 9/2003 | Tasto et al. | 606/32 |
| 2003/0208194 A1 | 11/2003 | Hovda et al. | 606/41 |
| 2003/0208196 A1 | 11/2003 | Stone | 606/41 |
| 2003/0212395 A1 | 11/2003 | Woloszko et al. | 606/32 |
| 2003/0212396 A1 | 11/2003 | Eggers et al. | 606/41 |
| 2004/0024399 A1 | 2/2004 | Sharps et al. | 606/32 |
| 2004/0049180 A1 | 3/2004 | Sharps et al. | 606/32 |
| 2004/0054366 A1 | 3/2004 | Davison et al. | 606/45 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Ricart et al. | 606/32 |
| 2006/0095031 A1 | 5/2006 | Ormsby | 606/34 |
| 2006/0129145 A1 | 6/2006 | Ormsby et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Sanders et al. | 606/32 |

FOREIGN PATENT DOCUMENTS

| | | |
|---|---|---|
| EP | 515 867 | 12/1992 |
| EP | 0703461 A2 | 3/1996 |
| EP | 0740926 A2 | 11/1996 |
| EP | 0 754 437 | 1/1997 |
| EP | 719162 B1 | 11/1997 |
| EP | 774926 B1 | 6/1999 |
| EP | 0 694 290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08524 | 4/1994 |
| WO | 94/08654 | 4/1994 |
| WO | 94/14383 | 7/1994 |
| WO | 94/26228 | 11/1994 |
| WO | 95/05781 | 3/1995 |
| WO | 95/05867 | 3/1995 |
| WO | 95/34259 | 12/1995 |
| WO | 96/00042 | 1/1996 |
| WO | 96/07360 | 3/1996 |
| WO | 96/20652 | 7/1996 |
| WO | 96/23449 | 8/1996 |
| WO | 96/41574 | 12/1996 |
| WO | 97/00070 | 1/1997 |
| WO | 97/00646 | 1/1997 |
| WO | 97/00647 | 1/1997 |
| WO | 97/24073 | 7/1997 |
| WO | 97/24074 | 7/1997 |
| WO | 97/24992 | 7/1997 |
| WO | 97/24993 | 7/1997 |

| | | |
|---|---|---|
| WO | 97/24994 | 7/1997 |
| WO | 97/48345 | 12/1997 |
| WO | 97/48346 | 12/1997 |
| WO | 98/00070 | 1/1998 |
| WO | 98/01087 | 1/1998 |
| WO | 98/03220 | 1/1998 |
| WO | 98/07468 | 2/1998 |
| WO | 98/11944 | 3/1998 |
| WO | 98/14131 | 4/1998 |
| WO | 98/17190 | 4/1998 |
| WO | 98/27879 | 7/1998 |
| WO | 98/27880 | 7/1998 |
| WO | 99/03414 | 1/1999 |
| WO | 99/42037 | 8/1999 |
| WO | 99/47058 | 9/1999 |
| WO | 99/51155 | 10/1999 |
| WO | 99/51158 | 10/1999 |
| WO | 00/07507 | 2/2000 |
| WO | 00/10475 | 3/2000 |
| WO | 00/62698 | 10/2000 |
| WO | 00/071043 | 11/2000 |
| WO | 01/26570 | 4/2001 |
| WO | 01/87154 | 5/2001 |
| WO | 01/82813 | 11/2001 |
| WO | 02/11635 | 2/2002 |
| WO | 02/36028 | 5/2002 |
| WO | 03/024506 | 3/2003 |
| WO | 2004/022155 | 3/2004 |
| WO | 2005/039390 | 5/2005 |
| WO | 2005/122938 | 12/2005 |
| WO | 2005/125287 | 12/2005 |

OTHER PUBLICATIONS

Pearce, John A. "Electrosurgery", pp. 17, 69-75, 87, John Wiley & Sons, New York, 1986.
J.W. Ramsey et al., "A Comparison of Bipolar and Monopolar Diathermy Probes in Experimental Animals", *Urological Research* vol. 13, pp. 99-102, 1985.
V.E. Elsasser et al., "An Instrument for Transurethral Resection without Leakage of Current" *Acta Medicotechnica* vol. 24, No. 4, pp. 129-134, 1976.
P.C. Nardella *SPIE* 1068:42-49 Radio Frequency Energy and Impedance Feedback, 1989.
R. Tucker et al., Abstract P14-11, p. 248, "A Bipolar Electrosurgical Turp Loop", Nov. 1989.
Saal et al., "Thermal Characteristics and the Lumbar Disc: Evaluation of a Novel Approach to Targeted Intradiscal Thermal Therapy", NASS-APS First Joint Meeting, Charleston SC, Apr. 1998.
R. Tucker et al. "A Comparison of Urologic Application of Bipolar Versus Monopolar Five French Electrosurgical Probes" *J. of Urology* vol. 141, pp. 662-665, 1989.
R. Tucker et al. "In vivo effect of 5 French Bipolar and Monopolar Electrosurgical Probes on the Porcine Bladder" *Urological Research* vol. 18, pp. 291-294, 1990.
Kramolowsky et al. "Use of 5F Bipolar Electrosurgical Probe in Endoscopic Urological Procedures" *J. of Urology* vol. 143, pp. 275-277, 1990.
Kramolowsky et al. "The Urological App of Electrosurgery" *J. of Urology* vol. 146, pp. 669-674, 1991.
Slager et al. "Spark Erosion of Arteriosclerotic Plaques" *Z. Kardiol.* 76:Suppl. 6, 67-71, 1987.
Slager et al. "Vaporization of Atherosclerotice Plaques by Spark Erosion" *JACC* 5(6):1382-6, Jun. 1985.
Olsen MD, Bipolar Laparoscopic Cholecstectomy Lecture (marked confidential), 12 pgs, Oct. 7, 1991.
Codman & Shurtleff, Inc. "The Malis Bipolar Electrosurgical System CMC-III Instruction Manual", 15 pgs, Jul. 1991.
Valley Forge's New Products, CLINICA, 475, 5, Nov. 6, 1991.
Valley Forge Scientific Corp., "Summary of Safety and Effective Information from 510K", 2pgs, 1991.

Codman & Shurtleff, Inc. "The Malis Bipolar coagulating and Bipolar Cutting System CMC-II" brochure, early, 2pgs, 1991.
L. Malis, "The Value of Irrigation During Bipolar Coagulation" See ARTC 21602. 1 pg, Apr. 9, 1993.
L. Malis, "Excerpted from a seminar by Leonard I. Malis, M.D. at the 1995 American Association of Neurological Surgeons Meeting," 1pg, 1995.
L. Malis, "Electrosurgery, Technical Note," *J. Neursurg.*, vol. 85, 970-975, Nov. 1996.
Ian E. Shuman, "Bipolar Versus Monopolar Electrosurgery: Clinical Applications," *Dentistry Today*, vol. 20, No. 12, 7 pgs, Dec. 2001.
Protell et al., "Computer-Assisted Electrocoagulation: Bipolar v. Monopolar in the Treatment of Experiemtnal Canine Gastric Ulcer Bleeding," *Gastroenterology* vol. 80, No. 3, pp. 451-455, 1981.
Cook et al., "Therapeutic Medical Devices: Application and Design", Prentice hall, Inc., 3pgs, 1982.
Valleylab SSE2L Instruction Manual, 11 pgs, Jan. 6, 1983.
Robert D. Tucker et al., "Demodulated Low Frequency Currents from Electrosurgical Procedures," *Surgery, Gynecology and Obstetrics*, 159:39-43, 1984.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Selikowitz et al., "Electric Current and Voltage Recordings on the Myocardium During Electrosurgical Procedures in Canines," *Surgery, Gynecology & Obstetrics*, vol. 164, 219-224, Mar. 1987.
J. O'Malley, Schaum's Outline of Theory and Problems of Basic Circuit Analysis, McGraw-Hill, 2$^{nd}$ Ed., pp. 3-5, 1992.
Amaud Wattiez et al., "Electrosurgery in Operative Endoscopy," Electrosurgical Effects, Blackwell Science, pp. 85-93, 1995.
Leslie A. Geddes, "Medical Device Accidents: With Illustrative Cases" CRC Press, 3 pgs, 1998.
Wyeth, "Electrosurgical Unit" pp. 1181-1202.
C.P. Swain, et al., "Which Electrode, A Comparison of four endoscopic methods of electrocoagulation in experimental bleeding ulcers" *Gut* vol. 25, pp. 1424-1431, 1987.
Piercey et al., "Electrosurgical Treatment of Experimental Bleeding Canine Gastric Ulcers" *Gastroenterology* vol. 74(3) pp. 527-534, 1978.
A.K, Dobbie, "The Electrical Aspects of Surgical Diathermy, Bio Medical Engineering" *Bio-Medical Engineering* vol. 4, pp. 206-216, May 1969.
B. Lee et al. "Thermal Compression and Molding of Artherosclerotic Vascular Tissue with Use" JACC vol. 13(5), pp. 1167-1171, 1989.
K. Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
W. Honig, "The Mechanism of Cutting in Electrosurgery" *IEEE* pp. 58-65, 1975.
Pearce, John C., "Electrosurgery", Handbook of Biomedical Engineering, chapter 3, Academic Press Inc., N.Y., pp. 98-113, 1988.
M.B. Dennis et al. "Evolution of Electrofulguration in Control of Bleeding of Experimental Gastric Ulcers," Digestive Diseases and Sciences, vol. 24, No. 11, 845-848, Nov. 1979.
Letter from Department of Health to Jerry Malis dated Jul. 25, 1985, 1 pg, Jul. 25, 1985.
Letter from Jerry Malis to FDA dated Jul. 25, 1985, 2 pgs, Jul. 25, 1985.
Letter from Department of Health to Jerry Malis dated Jan. 24, 1991, 3 pgs, Jan. 24, 1991.
Leonard Malis, "Instrumentation for Microvascular Neurosurgery" *Cerebrovascular Surgery*, vol. 1, 245-260, 1985.
Valleylab, Inc. "Valleylab Part No. 945 100 102 A" Surgistat Service Manual, pp. 1-46, Jul. 1988.
Leonard I. Malis, "New Trends in Microsurgery and Applied Technology," *Advanced Technology in Neurosurgery*, 1-16, 1988.
Buchelt, et al. "Excimer Laser Ablation of Fibrocartilage: An In Vitro and In Vivo Study", Lasers in Surgery and Medicine, vol. 11, pp. 271-279, 1991.

Costello et al., "Nd: YAG Laser Ablation of the Prostate as a Treatment for Benign Prostatic Hypertrophy", Lasers in Surgery and Medicine, vol. 12, pp. 121-124, 1992.

Rand et al., "Effect of Elecctrocautery on Fresh Human Articular Cartilage", J. Arthro. Surg., vol. 1, pp. 242-246, 1985.

PCT International Search Report for PCT/US99/03339, 1 pg, mailed May 14, 1999.

PCT International Search Report for PCT/US99/17821, 1 pg, mailed Oct. 19, 1999.

PCT International Search Report for PCT/US00/13706, 1 pg, mailed Jul. 31, 2000.

PCT International Search Report for PCT/US00/28267, 1 pg, mailed Mar. 23, 2001.

PCT International Search Report for PCT/US01/15728, 1 pg, mailed Oct. 18, 2001.

PCT International Preliminary Examination Report for PCT/US01/15728, 4 pgs, mailed Jan. 23, 2003.

PCT International Search Report for PCT/US02/29469, 1 pg, mailed May 22, 2003.

PCT International Search Report for PCT/US03/27745, 1 pg, mailed Jul. 2, 2004.

PCT International Search Report for PCT/US05/20774 1 pg, mailed Oct. 26, 2005.

PCT Written Opinion of the International Searching Authority for PCT/US05/20774, 4pgs, mailed Oct. 26, 2005.

PCT International Search Report for PCT/US04/34949, 1 pg, mailed Mar. 28, 2006.

PCT Written Opinion of the International Searching Authority for PCT/US04/34949, 3pgs, mailed Mar. 28, 2006.

Supplementary EP Search Report for EP97932609, 2 pgs, mailed Dec. 19, 2000.

EPO Communication, Supplementary EP Search Report for EP99934236, 3 pgs, mailed Oct. 9, 2001.

EPO Communication, Supplementary EP Search Report for EP01935554, 5 pgs, mailed Feb. 27, 2006.

EPO Communication, Supplementary EP Search Report for EP03749423, 3 pgs, mailed Mar. 21, 2006.

AESCULAP, "Flexible endoscope", Micro, Neuro and Spine surgery, 3 pgs, no date available.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technolgy, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblast: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

\* cited by examiner

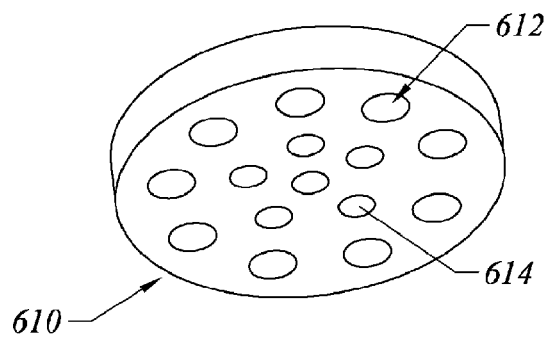
FIG. 14A
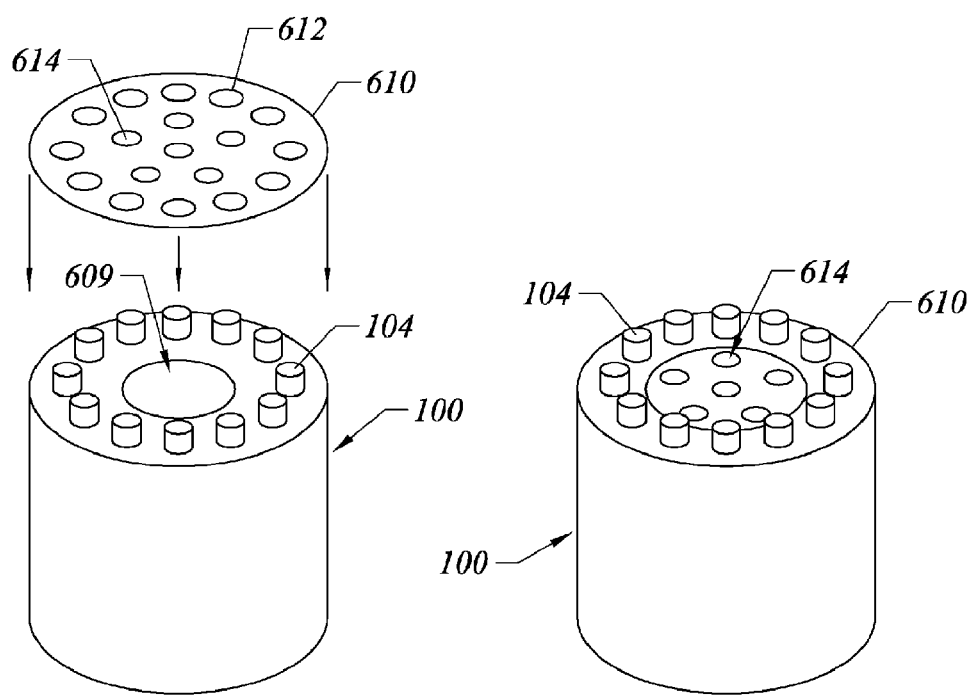
FIG. 14B
FIG. 14C

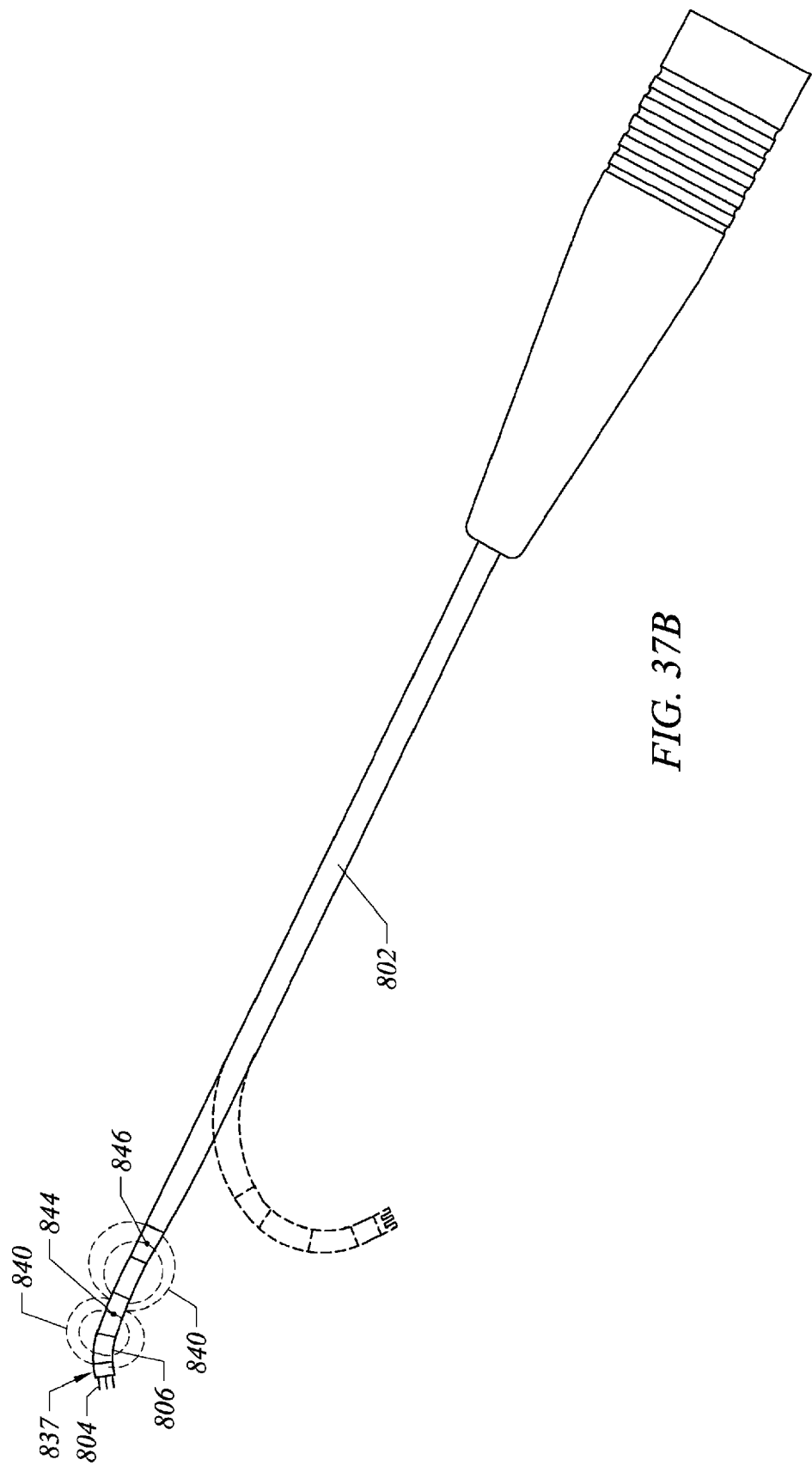

METHODS AND APPARATUS FOR TREATING BACK PAIN

RELATED APPLICATIONS

The present application is a Continuation of U.S. patent application Ser. No. 10/374,411, now abandoned. U.S. patent application Ser. No. 10/374,411 is a non-provisional of U.S. provisional application No. 60/359,319 the disclosure of which is incorporated herein by reference and U.S. patent application Ser. No. 10/374,411 is a Continuation-in-part of, and claims priority from U.S. patent application Ser. No. 09/676,194, filed Sep. 28, 2000, now U.S. Pat. No. 6,602,248.

The present invention is related to U.S. patent application Ser. No. 09/026,851, filed Feb. 20, 1999, which is a continuation-in-part of U.S. patent application Ser. No. 08/690,159, filed Jul. 18, 1996, the complete disclosure of which is incorporated herein by reference for all purposes. The present invention is also related to commonly assigned co-pending U.S. patent application Ser. No. 09/181,926, filed Oct. 28, 1998, U.S. patent application Ser. No. 09/130,804, filed Aug. 7, 1998, U.S. patent application Ser. No. 09/058,571, filed on Apr. 10, 1998, U.S. patent application Ser. No. 09/248,763, filed Feb. 12, 1999, U.S. patent application Ser. No. 09/026,698, filed Feb. 20, 1998, U.S. patent application Ser. No. 09/074,020, filed on May 6, 1998, U.S. patent application Ser. No. 09/010,382, filed Jan. 21, 1998, U.S. patent application Ser. No. 09/032,375, filed Feb. 27, 1998, U.S. patent application Ser. Nos. 08/977,845, filed on Nov. 25, 1997, 08/942,580, filed on Oct. 2, 1997, U.S. patent application Ser. No. 08/753,227, filed on Nov. 22, 1996, U.S. patent application Ser. No. 08/687,792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,697,882, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the spine. The present invention also relates to the treatment of intervertebral discs, ligaments, cartilage, tendons, and other tissue within the vertebral column. The invention further relates to apparatus and methods for the inactivation of nervous tissue in and around the spine to alleviate pain associated with defects of the spine or intervertebral discs.

The major causes of persistent, often disabling, back pain are disruption of the disc annulus, chronic inflammation of the disc (e.g., herniation), or relative instability of the vertebral bodies surrounding a given disc, such as the instability that often occurs due to a degenerative disease. It is thought that discogenic pain may account for up to 85% of cases of back pain. Disc degeneration appears to be almost universal, occurring as part of the aging process.

Intervertebral discs mainly function to cushion and tether the vertebrae, providing flexibility and stability to the patient's spine. Spinal discs comprise a central hydrophilic cushion, the nucleus pulposus, surrounded by a multi-layered fibrous ligament, the annulus fibrosus. As discs degenerate, they lose their water content and height, bringing the adjoining vertebrae closer together. This results in a weakening of the shock absorption properties of the disc and a narrowing of the nerve openings (foramina) of the spine which may pinch these nerves or nerve roots. This disc degeneration can eventually cause back and leg pain. Weakness in the annulus from degenerative discs or disc injury can allow fragments of nucleus pulposus from within the disc space to migrate into the spinal canal. There, displaced nucleus pulposus or protrusion of annulus fibrosus, e.g., herniation, may impinge on spinal nerve roots. The mere proximity of the nucleus pulposus or a damaged annulus to a nerve or nerve root can cause direct pressure against the nerve, resulting in pain, as well as sensory and motor deficit.

Often, inflammation from disc herniation can be treated successfully by non-surgical means, such as rest, therapeutic exercise, oral anti-inflammatory medications or epidural injection of corticosteroids. In some cases, the disc tissue is irreparably damaged, thereby necessitating removal of a portion of the disc or the entire disc to eliminate the source of inflammation and pressure. In more severe cases, the adjacent vertebral bodies must be stabilized following excision of the disc material to avoid recurrence of the disabling back pain. One approach to stabilizing the vertebrae, termed spinal fusion, is to insert an interbody graft or implant into the space vacated by the degenerative disc. In this procedure, a small amount of bone may be grafted and packed into the implants. This allows the bone to fuse together adjacent vertebral bodies, thereby preventing reoccurrence of the symptoms.

Until recently, spinal discectomy and fusion procedures resulted in major operations and traumatic dissection of muscle and bone removal or bone fusion. To overcome the disadvantages of traditional traumatic spine surgery, minimally invasive spine surgery was developed. In endoscopic spinal procedures, the spinal canal is not violated and therefore epidural bleeding with ensuing scarring is minimized or completely avoided. In addition, the risk of instability from ligament and bone removal is generally lower in endoscopic procedures than with open discectomy. Further, more rapid rehabilitation facilitates faster recovery and return to work.

Minimally invasive techniques for the treatment of spinal diseases or disorders include chemonucleolysis, laser techniques and mechanical techniques. These procedures generally require the surgeon to form a passage or operating corridor from the external surface of the patient to the spinal disc(s) for passage of surgical instruments, implants and the like. Typically, the formation of this operating corridor requires the removal of soft tissue, muscle or other types of tissue depending on the procedure (i.e., laparoscopic, thoracoscopic, arthroscopic, back, etc.). This tissue is usually removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments sever blood vessels within this tissue, usually causing profuse bleeding that obstructs the surgeon's view of the target site.

Once the operating corridor is established, the nerve root is retracted and a portion or all of the disc is removed with mechanical instruments, such as a pituitary rongeur. In addition to the above problems with mechanical instruments, there are serious concerns because these instruments are not precise, and it is often difficult, during the procedure, to differentiate between the target disc tissue, and other structures within the spine, such as bone, cartilage, ligaments, nerves and non-target tissue. Thus, the surgeon must be extremely careful to minimize damage to the cartilage and bone within the spine, and to avoid damaging nerves, such as the spinal nerves and the dura mater surrounding the spinal cord.

Lasers were initially considered ideal for spine surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, bones, ligaments, and spinal nerves often lie within close proximity of the spinal disc, it is essential to maintain a minimum depth of tissue damage, which cannot always be ensured with a laser.

Monopolar radiofrequency devices have been used in limited roles in spine surgery, such as to cauterize severed vessels to improve visualization of the surgical site. These monopolar devices, however, suffer from the disadvantage that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltages must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue or neighboring peripheral nerves.

Other disadvantages of conventional RF devices, particularly monopolar devices, is nerve stimulation and interference with nerve monitoring equipment in the operating room. In addition, these devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Many patients experience discogenic pain due to defects or disorders of intervertebral discs. Such disc defects include annular fissures, fragmentation of the nucleus pulposus, and contained herniation. A common cause of pain related to various disc disorders is compression of a nerve root by a distorted, bulging, or herniated disc. A posterior portion or region of the disc (corresponding to approximately the posterior one-third to one-half of the annulus fibrosus) is innervated by branches of the sinuvertebral nerve, such branches terminating in nociceptors. Stimulated nociceptors send pain messages following spinal injury or disc defects. In the case of discs having fissures, chemicals may reach nociceptors via a fissure and the chemicals may then lower the threshold for firing. In addition, pain is also caused by mechanical forces within the spine. Furthermore, it is thought that damaged or defective discs have increased innervation by branches of the sinuvertebral nerve, as compared with normal (undamaged) discs. The posterior longitudinal ligament, which is contiguous with the outer annulus, is also innervated by the sinuvertebral nerve. Thus, sensory (afferent) nerve fibers of the posterior longitudinal ligament may also be involved in back pain. There is a need for methods to treat the spine to alleviate the chronic, and often debilitating, back pain associated with innervation of the posterior of the disc and the posterior longitudinal ligament. The instant invention provides methods for decompressing nerve roots, wherein the volume of the disc is decreased. The instant invention also provides methods for electrosurgically inactivating nervous tissue within the disc and the posterior longitudinal ligament in order to alleviate back pain.

SUMMARY OF THE INVENTION

The present invention provides systems, apparatus, and methods for selectively applying electrical energy to structures within a patient's body, such as tissue within or around the spine. The systems and methods of the present invention are useful for ablation, resection, aspiration, collagen shrinkage, and/or hemostasis of tissue and other body structures in open and endoscopic spine surgery. In particular, the present invention includes methods for denervating intervertebral discs, and other spinal tissues, to alleviate back pain.

The present invention further relates to an electrosurgical probe including an elongated shaft having first and second curves in the distal end portion of the shaft, wherein the shaft can be rotated within an intervertebral disc to contact fresh tissue of the nucleus pulposus. The present invention also relates to an electrosurgical probe including an elongated shaft, wherein the shaft distal end can be guided to a specific target site within a disc, and the shaft distal end is adapted for localized ablation of targeted disc tissue.

The present invention further relates to a probe having an elongated shaft, wherein the shaft includes an active electrode, an insulating collar, and an outer shield, and wherein the active electrode includes a head having an apical spike and a cusp. The present invention still further relates to a method for ablating disc tissue with an electrosurgical probe, wherein the probe includes an elongated shaft, and the shaft distal end is guided to a specific target site within a disc.

Methods of the present invention include introducing one or more active electrode(s) into the patient's spine and positioning the active electrode(s) adjacent the target tissue, e.g., a disc. High frequency voltage is applied between the active electrode(s) and one or more return electrode(s) to volumetrically remove or ablate at least a portion of the target tissue, and the active electrode(s) are advanced through the space left by the ablated tissue to form a channel, hole, divot or other space in the disc tissue. The active electrode(s) are then removed from the channel, and other channels or holes may be formed at suitable locations in the disc. In some embodiments, high frequency voltage is applied to the active electrode(s) as they are removed from the hole or channel. The high frequency voltage is below the threshold for ablation of tissue to effect hemostasis of severed blood vessels within the tissue surface surrounding the hole. In addition, the high frequency voltage effects a controlled depth of thermal heating of the tissue surrounding the hole to thermally damage or create a lesion within the tissue surrounding the hole to debulk and/or stiffen the disc structure, thereby relieving neck or back pain.

In a specific configuration, electrically conductive media, such as isotonic saline or an electrically conductive gel, is delivered to the target site within the spine to substantially surround the active electrode(s) with the conductive media. The conductive media may be delivered through an instrument to the specific target site, or the entire target region may be filled with conductive media such that the electrode terminal(s) are submerged during the procedure. Alternatively, the distal end of the instrument may be dipped or otherwise applied to the conductive media prior to introduction into the patient's body. In all of these embodiments, the electrically conductive media is applied or delivered such that it provides a current flow path between the active and return electrode(s). In other embodiments, conductive fluid in the patient's tissue may be used as a substitute for, or as a supplement to, the electrically conductive media that is applied or delivered to the target site. For example, in some embodiments, the instrument is dipped into conductive media to provide a sufficient amount of fluid to initiate the requisite conditions for ablation. After initiation, the conductive fluid already present in the patient's tissue is used to sustain these conditions.

In an exemplary embodiment, the active electrode(s) are advanced into the target disc tissue in the ablation mode, where the high frequency voltage is sufficient to ablate or remove the target tissue through molecular dissociation or disintegration processes. In these embodiments, the high frequency voltage applied to the active electrode(s) is sufficient to vaporize an electrically conductive fluid (e.g., gel, saline, and/or intracellular fluid) between the active electrode(s) and the tissue. Within the vaporized fluid, a ionized plasma is formed and charged particles (e.g., electrons) cause the molecular breakdown or disintegration of several cell layers of the tissue. This molecular dissociation is accompanied by the volumetric removal of the tissue. This process can be precisely controlled to effect the volumetric removal of tissue as thin as 10 to 150 microns with minimal heating of, or damage to, surrounding or underlying tissue structures. A more complete description of this phenomenon is described in commonly assigned U.S. Pat. No. 5,697,882 the complete disclosure of which is incorporated herein by reference.

The active electrode(s) are usually removed from the holes or channels in the sub-ablation or thermal heating mode, where the high frequency voltage is below the threshold for ablation as described above, but sufficient to coagulate severed blood vessels and to effect thermal damage to at least the surface tissue surrounding the holes. In some embodiments, the active electrode(s) are immediately removed from the holes after being placed into the sub-ablation mode. In other embodiments, the physician may desire to control the rate of removal of the active electrode(s) and/or leave the active electrode(s) in the hole for a period of time, e.g., on the order of about 5 to 30 seconds, in the sub-ablation mode to increase the depth of thermal damage to the disc tissue.

In one method, high frequency voltage is applied, in the ablation mode, between one or more active electrode(s) and a return electrode spaced axially from the active electrode(s), and the active electrode(s) are advanced into the tissue to form a hole or channel as described above. High frequency voltage is then applied between the return electrode and one or more third electrode(s), in the thermal heating mode, as the electrosurgical instrument is removed from the hole. In one embodiment, the third electrode is a dispersive return pad on the external surface of the skin. In this embodiment, the thermal heating mode is a monopolar mode, in which current flows from the return electrode, through the patient's body, to the return pad. In other embodiments, the third electrode(s) are located on the electrosurgical instrument and the thermal heating mode is bipolar. In all of the embodiments, the third electrode(s) are designed to increase the depth of current penetration in the tissue over the ablation mode so as to increase the thermal damage applied to the disc.

In another method, the third or coagulation electrode is placed in the thermal heating mode at the same time that the active electrode(s) is placed in the ablation mode. In this embodiment, electric current is passed from the coagulation electrode, through the tissue surrounding the hole, to the return electrode at the same time that current is passing between the active and return electrodes. In a specific configuration, this is accomplished by reducing the voltage applied to the coagulation electrode with a passive or active voltage reduction element coupled between the power supply and the coagulation electrode. In this manner, when the coagulation electrode is advanced into the tissue, the electric circuit between the coagulation and return electrodes is closed by the tissue surrounding the hole, and thus immediately begins to heat and coagulate this tissue.

In another method, an electrosurgical instrument having an electrode assembly is dipped into electrically conductive fluid such that the conductive fluid is located around and between both active and return electrodes in the electrode assembly. The instrument is then introduced into the patient's spine either percutaneously or through an open procedure, and a plurality of holes are formed within the disc as described above. The instrument is removed from each hole in the thermal heating mode to create thermal damage and to coagulate blood vessels. Typically, the instrument will be dipped into the conductive fluid after being removed from each hole to ensure that sufficient conductive fluid exists for plasma formation and to conduct electric current between the active and return electrodes. This procedure reduces the volume of the intervertebral disc, which helps to alleviate neck and back pain.

In another aspect of the invention, a method for treating a degenerative intervertebral disc involves positioning one or more active electrode(s) adjacent to selected nerves embedded in the walls of the disc, and positioning one or more return electrode(s) in the vicinity of the active electrode(s) in or on the disc. A sufficient high frequency voltage difference is applied between the active and return electrodes to denervate the selected nerves or to break down enzyme systems and pain generating neurotransmitters in the disc, and thus relieve pain. In some embodiments, the current path between the active and return electrode(s) is generated at least in part by an electrically conductive fluid introduced to the target site. In others, the disc tissue completes this current path.

In another aspect of the invention, a method for treating degenerative intervertebral discs involves positioning one or more active electrode(s) adjacent to or within the nucleus pulposus, and positioning one or more return electrode(s) in the vicinity of the active electrode(s) in or on the disc. A sufficient high frequency voltage difference is applied between the active and return electrodes to reduce water content of the nucleus pulposus and/or shrink the collagen fibers within the nucleus pulposus to tighten the disc. In some embodiments, the current path between the active and return electrode(s) is generated at least in part by an electrically conductive fluid introduced to the target site. In others, the disc tissue completes this current path.

In yet another aspect of the invention, a method for treating degenerative intervertebral discs involves positioning one or more active electrode(s) adjacent to or within a annular fissure on the inner wall of the annulus fibrosus, and positioning one or more return electrode(s) in the vicinity of the active electrode(s) in or around the disc. A sufficient high frequency voltage difference is applied between the active and return electrodes to weld, seal, or shrink the collagen fibers in the annular fissure, thus repairing the fissure. Typically, the voltage is selected to provide sufficient energy to the fissure to raise the tissue temperature to at least about 50° C. to 70° C. for a sufficient time to cause the collagen fibers to shrink or weld together. In some embodiments, the current path between the active and return electrode(s) is generated at least in part by an electrically conductive fluid introduced to the target site. In others, the disc tissue completes this current path.

Systems according to the present invention generally include an electrosurgical instrument having a shaft with proximal and distal ends, an electrode assembly at the distal end and one or more connectors coupling the electrode assembly to a source of high frequency electrical energy. The instrument will comprise a probe or catheter shaft having a proximal end and a distal end which supports the electrode assembly. The probe or catheter may assume a wide variety of configurations, with the primary purpose being to introduce the electrode assembly to the patient's spine (in an open or endoscopic procedure) and to permit the treating physician to manipulate the electrode assembly from a proximal end of the shaft. The electrode assembly includes one or more active electrode(s) configured for tissue ablation, a return electrode spaced from the active electrode(s) on the instrument shaft and a third, coagulation electrode spaced from the return electrode on the instrument shaft.

The system further includes a power source coupled to the electrodes on the instrument shaft for applying a high frequency voltage between the active and return electrodes, and between the coagulation and return electrodes, at the same time. In one embodiment, the system comprises a voltage reduction element coupled between the power source and the coagulation electrode to reduce the voltage applied to the coagulation electrode. The voltage reduction element will typically comprise a passive element, such as a capacitor, resistor, inductor, or the like. In a representative embodiment, the power supply will apply a voltage of about 150 to 600 volts RMS between the active and return electrodes, and the voltage reduction element will reduce this voltage to about 20 to 300 volts RMS to the coagulation electrode. In this manner, the voltage delivered to the coagulation electrode is below the threshold for ablation of tissue, but high enough to coagulation and heat the tissue.

The active electrode(s) may comprise a single active electrode, or an electrode array, extending from an electrically insulating support member, typically made of an inorganic material such as ceramic, silicone rubber, or glass. The active electrode will usually have a smaller exposed surface area than the return and coagulation electrodes such that the current densities are much higher at the active electrode than at the other electrodes. Preferably, the return and coagulation electrodes have relatively large, smooth surfaces extending around the instrument shaft to reduce current densities, thereby minimizing damage to adjacent tissue.

The apparatus may further include a fluid delivery element for delivering electrically conducting fluid to the active electrode(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the electrode assembly or the target site. In this embodiment, the apparatus may not have a fluid delivery element. In both embodiments, the electrically conducting fluid will preferably generate a current flow path between the active electrode(s) and the return electrode(s).

The posterior portion of the annulus fibrosus is innervated by branches of the sinuvertebral nerve, such branches terminating in nociceptors within the annulus. Nociceptors are small, unmyelinated nerve fibers with free or small capsular-type nerve endings. Damaged or defective discs may have increased innervation from the sinuvertebral nerve, as compared with normal discs, thereby increasing the likelihood of pain messages from nociceptors within the disc. According to one aspect of the invention, there is provided a method for denervating a target intervertebral disc by the controlled heating of the posterior annulus fibrosus. In one embodiment, a method for denervating a target tissue involves advancing a working end of an electrosurgical instrument into the patient and positioning an active electrode in at least close proximity to the posterior of the annulus fibrosus. Positioning the active electrode in relation to a target tissue of the disc may be performed in an open procedure, endoscopically, or fluoroscopically. While the active electrode is suitably positioned with respect to the target disc, a high frequency voltage may be applied between the active electrode and a return electrode, such that nociceptors and/or other nervous tissue within the annulus of the disc are inactivated.

In one embodiment, denervation of an intervertebral disc involves coagulating nervous tissue within the annulus fibrosus by the controlled electrosurgical heating of the posterior of the annulus to a temperature sufficient to inactivate unmyelinated nerve fibers within the annulus, but insufficient to cause shrinkage of the annulus fibrosus. Typically, unmyelinated nerve fibers are inactivated by exposure to a temperature of about 45° C. This temperature is substantially below that required for the irreversible thermal contraction of collagen containing tissue, which is generally in the 60° C. to 70° C. range (Deak, G., et al., cited infra).

In another aspect of the invention, there is provided a method for electrosurgically denervating a region of the posterior longitudinal ligament (PLL) of a patient's spine. In one embodiment, such a method may employ an electrosurgical instrument having an elongate shaft and an electrode assembly disposed at the shaft distal end. The electrode assembly may be arranged laterally or terminally on the shaft, wherein the electrode assembly includes at least one active electrode and a return electrode. The shaft distal end is introduced into the patient, e.g., in an open procedure, and the electrode assembly is advanced towards a target region of the posterior longitudinal ligament. While the active electrode is positioned in at least close proximity to a targeted region of the posterior longitudinal ligament, a high frequency voltage is applied between the active electrode and the return electrode, whereby a target region of the posterior longitudinal ligament is denervated.

In another aspect of the invention, there is provided a method for decompressing the disc, and thereafter electrosurgically denervating the disc. The disc may be decompressed by contracting, coagulating, or stiffening nucleus pulposus tissue (in the sub-ablation mode), by ablation of nucleus pulposus tissue (in the ablation mode), or by a combination of these effects. Thereafter the disc may be denervated by the controlled heating of the posterior of the annulus fibrosus to a temperature sufficient to coagulate or inactivate unmyelinated nerve fibers (e.g., in the range of from about 45° C. to 50° C.).

According to another aspect of the invention, denervation of a target disc or other spinal tissue may also be performed in conjunction with other spinal procedures, such as procedures for spine stabilization (e.g., vertebral fusion procedures).

According to another aspect, the invention provides an electrosurgical system including a high frequency power supply and an electrode assembly affixed to a shaft, wherein the electrode assembly includes at least one electrode coupled to the high frequency power supply. The system may further include a temperature sensor unit for sensing a temperature in the vicinity of the shaft distal end during an electrosurgical procedure. The temperature sensor unit may be coupled to a temperature display unit for displaying the sensed temperature. The temperature sensor unit is further coupled to a temperature control unit. The temperature control unit is in turn coupled to the power supply for regulating the power output from the power supply in response to a temperature sensed by the temperature sensor unit. Accordingly, power supplied to the electrode assembly can be adjusted in response to a temperature sensed in the vicinity of the target tissue.

In another aspect of the invention, there is provided a method for treating a target tissue using a dual shaft electrosurgical instrument. The instrument has a first shaft and a second shaft, the first shaft having a first electrode disposed at the first shaft distal end, and the second shaft having a second electrode disposed at the second shaft distal end. The first and second shafts may be manipulated and introduced into the patient independently of each other, such that the spacing between a location of the first electrode and a location of the second electrode can be selected by the physician according to the particular target tissue or procedure. Thus, the first electrode may be positioned at a first location with respect to the target tissue, and thereafter the second electrode may be positioned at a second location with respect to the target tissue, such that the second electrode is suitably spaced from the first electrode. Once the first and second electrodes are appropriately positioned with respect to the target tissue and each other, a suitable voltage may be applied therebetween in order to ablate, coagulate, denervate, contract, or otherwise modify the target tissue.

According to another aspect of the invention, there is provided an apparatus including a dual-shaft electrosurgical instrument and a high frequency power supply. The instrument has a first shaft and a second shaft, the first shaft having a first electrode disposed at the first shaft distal end, and the second shaft having a second electrode disposed at the second shaft distal end. In one embodiment, the instrument includes a connection block, and both the first and second electrodes are electrically coupled to the connection block. In one embodiment, the instrument further includes a connection housing which houses the connection block. The proximal ends of both the first and second shafts may be mechanically attached to, and detached from, the connection housing. The first electrode may comprise an active electrode or an electrode array, while the second electrode may comprise one or more return electrodes.

For a further understanding of the nature and advantages of the invention, reference should be made to the following description taken in conjunction with the accompanying drawings.

BRIEF DESCRIPTION OF THE DRAWINGS

FIGS. 14A-14C illustrate an alternative embodiment incorporating a screen electrode;

FIGS. 37A-D illustrate four embodiments of electrosurgical probes specifically designed for treating spinal defects;

FIGS. 45A and 45B show a side view and an end view, respectively, of a curved shaft of an electrosurgical probe, in relation to an introducer needle;

DESCRIPTION OF SPECIFIC EMBODIMENTS

Figure 1:
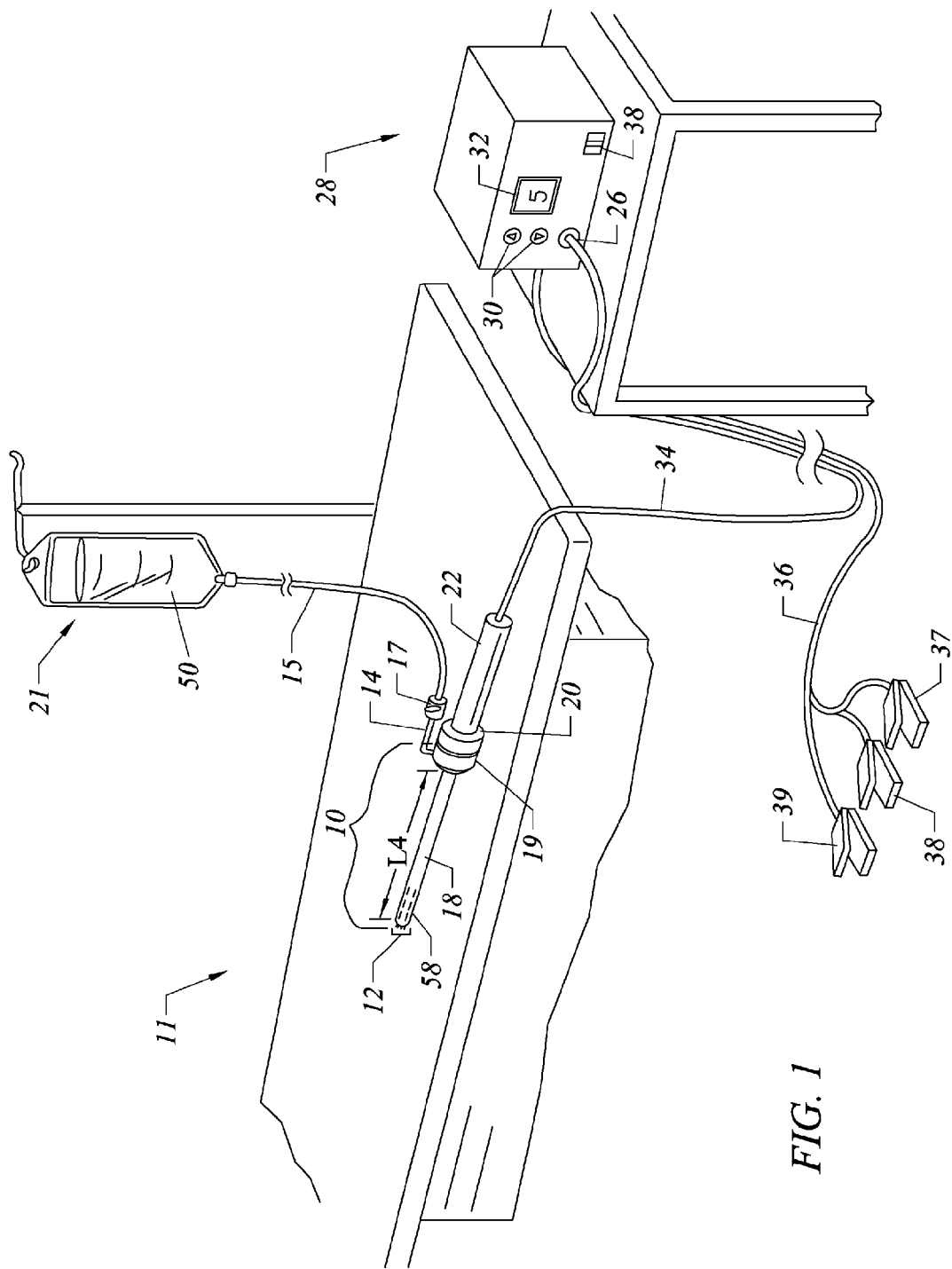
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying energy to a target location within or on a patient's body, particularly including tissue or other body structures in the spine. These procedures include treating degenerative discs, laminectomy/discectomy procedures for treating herniated discs, decompressive laminectomy for stenosis in the lumbosacral and cervical spine, localized tears or fissures in the annulus, nucleotomy, disc fusion procedures, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar discectomies. These procedures may be performed through open procedures, or using minimally invasive techniques, such as thoracoscopy, arthroscopy, laparoscopy, or the like.

In one embodiment, the present invention involves techniques for treating disc defects or disorders with RF energy. In some embodiments, RF energy is used to ablate, debulk, and/or stiffen the tissue structure of the disc to reduce the volume of the disc, thereby relieving neck and back pain. In one aspect of the invention, spinal disc tissue is volumetrically removed or ablated to form holes, channels, divots, or other spaces within the disc. In this procedure, a high frequency voltage difference is applied between one or more active electrode(s) and one or more return electrode(s) to develop high electric field intensities in the vicinity of the target tissue. The high electric field intensities adjacent the active electrode(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons, and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the active electrode(s) in the region between the distal tip of the active electrode(s) and the target tissue. The electrically conductive fluid may be a liquid or gas, such as isotonic saline, blood, or extracellular fluid, delivered to, or already present at, the target site, or a viscous fluid, such as a gel, applied to the target site. Since the vapor layer or vaporized region has a relatively high electrical impedance, it minimizes current flow into the electrically conductive fluid. This ionization, under the conditions described herein, induces the discharge of energetic electrons and photons from the vapor layer and to the surface of the target tissue. A more detailed description of this phenomenon, termed Coblation® can be found in commonly assigned U.S. Pat. No. 5,697,882, the complete disclosure of which is incorporated herein by reference.

Applicant believes that the principle mechanism of tissue removal in the Coblation® mechanism of the present invention is energetic electrons or ions that have been energized in a plasma adjacent to the active electrode(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a gas and ionizing the gas by driving an electric current through it, or by shining radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In some embodiments, the present invention applies high frequency (RF) electrical energy in an electrically conducting media environment to remove (i.e., resect, cut or ablate) a tissue structure and to seal transected vessels within the region of the target tissue. The present invention may also be useful for sealing larger arterial vessels, e.g., on the order of about 1 mm in diameter. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal(s). In other embodiments, the power supply is combined with the coagulation instrument such that the coagulation electrode is used when the power supply is in the coagulation mode (low voltage), and the electrode terminal(s) are used when the power supply is in the ablation mode (higher voltage).

In one method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

In some embodiments of the present invention, the tissue is purposely damaged in a thermal heating mode to create necrosed or scarred tissue at the tissue surface. The high frequency voltage in the thermal heating mode is below the threshold of ablation as described above, but sufficient to cause some thermal damage to the tissue immediately surrounding the electrodes without vaporizing or otherwise debulking this tissue in situ. Typically, it is desired to achieve a tissue temperature in the range of about 60° C. to 100° C. to a depth of about 0.2 to 5 mm, usually about 1 to 2 mm. The voltage required for this thermal damage will partly depend on the electrode configurations, the conductivity of the area immediately surrounding the electrodes, the time period in which the voltage is applied and the depth of tissue damage desired. With the electrode configurations described in this application (e.g., FIGS. 15A-15D), the voltage level for thermal heating will usually be in the range of about 20 to 300 volts RMS, preferably about 60 to 200 volts RMS. The peak-to-peak voltages for thermal heating with a square wave form having a crest factor of about 2 are typically in the range of about 40 to 600 volts peak-to-peak, preferably about 120 to 400 volts peak-to-peak. In some embodiments, capacitors or other electrical elements may be used to increase the crest factor up to 10. The higher the voltage is within this range, the less time required. If the voltage is too high, however, the surface tissue may be vaporized, debulked, or ablated, which is undesirable in certain procedures.

In other embodiments, the present invention may be used for treating degenerative discs with fissures or tears. In these embodiments, the active electrode and return electrode are positioned in or around the inner wall of the disc annulus such that the active electrode is adjacent to the fissure. High frequency voltage is applied between the active and return electrodes to heat the fissure and shrink the collagen fibers and create a seal or weld within the inner wall, thereby helping to close the fissure in the annulus. In these embodiments, the return electrode will typically be positioned proximally from the active electrode(s) on the instrument shaft, and an electrically conductive fluid will be applied to the target site to create the necessary current path between the active and return electrodes. In alternative embodiments, the disc tissue may complete this electrically conductive path.

The present invention is also useful for removing or ablating tissue around nerves, such as spinal, peripheral or cranial nerves. One of the significant drawbacks with the prior art shavers or microdebriders, conventional electrosurgical devices, and lasers is that these devices do not differentiate between the target tissue and the surrounding nerves or bone. Therefore, the surgeon must be extremely careful during these procedures to avoid damage to the bone or nerves within and around the target site. In the present invention, the Coblation® process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty material having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to tissue, will continue to conduct electric current to the return electrode. This selective ablation or removal of lower impedance tissue in combination with the Coblation® mechanism of the present invention allows the surgeon to precisely remove tissue around nerves or bone. Applicant has found that the present invention is capable of volumetrically removing tissue closely adjacent to nerves without impairment the function of the nerves, and without significantly damaging the tissue of the epineurium. One of the significant drawbacks with the prior art microdebriders, conventional electrosurgical devices and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation® process for removing tissue results in extremely small depths of collateral tissue damage as discussed above. This allows the surgeon to remove tissue close to a nerve without causing collateral damage to the nerve fibers.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break (typically on the order of about 8 eV). Accordingly, the present invention in its current configuration generally does not ablate or remove such fatty tissue. However, the present invention may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomenon can be found in co-pending U.S. patent application Ser. No. 09/032,375, filed Feb. 27, 1998, the complete disclosure of which is incorporated herein by reference.

The present invention also provides systems, apparatus, and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's brain or to the surgical staff. The high frequency voltage is preferably selected to effect controlled removal of these tissue cells while minimizing substantial tissue necrosis to surrounding or underlying tissue.

In other procedures, it may be desired to shrink or contract collagen connective tissue within the disc. In these procedures, the RF energy heats the disc tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp. 195-208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid.). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp. 127-133, 1980). Consequently, the controlled heating of tissue to a precise depth is critical to the achievement of therapeutic collagen shrinkage. A more detailed description of collagen shrinkage can be found in U.S. patent application Ser. No. 08/942,580 filed on Oct. 2, 1997.

The preferred depth of heating to effect the shrinkage of collagen in the heated region (i.e., the depth to which the tissue is elevated to temperatures between 60° C. to 70° C.) generally depends on (1) the thickness of the disc, (2) the location of nearby structures (e.g., nerves) that should not be exposed to damaging temperatures, and/or (3) the location of the collagen tissue layer within which therapeutic shrinkage is to be effected. The depth of heating is usually in the range from 1.0 to 5.0 mm.

The electrosurgical probe or catheter will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For endoscopic procedures within the spine, the shaft will have a suitable diameter and length to allow the surgeon to reach the target site (e.g., a disc). Thus, the shaft will usually have a length in the range of about 5.0 to 30.0 cm, and a diameter in the range of about 0.2 mm to about 20 mm. In an exemplary embodiment, the shaft may be delivered directly through the patient's back in a posterior approach. The shaft may be introduced into the patient through rigid or flexible endoscopes. Alternatively, the shaft may be a flexible catheter that is introduced through a percutaneous penetration in the patient. Specific shaft designs will be described in detail in connection with the figures hereinafter.

In an alternative embodiment, the probe may comprise a long, thin needle (e.g., on the order of about 1 mm in diameter or less) that can be percutaneously introduced through the patient's back directly into the spine. The needle will include one or more active electrode(s) for applying electrical energy to tissues within the spine. The needle may include one or more return electrode(s), or the return electrode may be positioned on the patient's back, as a dispersive pad. In either embodiment, sufficient electrical energy is applied through the needle to the active electrode(s) to either shrink the collagen fibers within the spinal disc, or to ablate tissue within the disc.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires, or other conductive elements, running axially therethrough, to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in and around the spinal cord, however, makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) will include the appropriate electrical connections for coupling the return electrode(s) and the electrode terminal(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L- or V shaped, or the like. Electrode edges may also be created by removing a portion of the elongate metal electrode to reshape the cross-section. For example, material can be ground along the length of a round or hollow wire electrode to form D- or C shaped wires, respectively, with edges facing in the cutting direction. Alternatively, material can be removed at closely spaced intervals along the electrode length to form transverse grooves, slots, threads, or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a pH less than 7.0 or by using a high velocity stream of abrasive particles (e.g., grit blasting) to create asperities on the surface of an elongated electrode. A more detailed description of such electrode configurations can be found in commonly assigned U.S. Pat. No. 5,843,019, the complete disclosure of which is incorporated herein by reference.

The return electrode is typically spaced proximally from the active electrode(s) a suitable distance to avoid electrical shorting between the active and return electrodes in the presence of electrically conductive fluid. In some embodiments described herein, the distal edge of the exposed surface of the return electrode is spaced about 0.5 to 25 mm from the proximal edge of the exposed surface of the active electrode(s), preferably about 1.0 to 5.0 mm. Of course, this distance may vary with different voltage ranges, conductive fluids, and depending on the proximity of tissue structures to active and return electrodes. The return electrode will typically have an exposed length in the range of about 1 to 20 mm.

The current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in commonly assigned U.S. Pat. No. 5,697,281, the contents of which are incorporated herein by reference. Alternatively, the body's natural conductive fluids, such as blood or extracellular fluid, may be sufficient to establish a conductive path between the return electrode(s) and the electrode terminal(s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal(s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, now U.S. Pat. No. 6,235,020, the complete disclosure of which is incorporated herein by reference.

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode(s) can be found in commonly assigned, co-pending U.S. patent application Ser. No. 09/010,382 now U.S. Pat. No. 6,190,381 entitled "Systems And Methods For Tissue Resection, Ablation And Aspiration", filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments, or ablation products do not flow through the patient's vasculature or into other portions of the body. In addition, it may be desirable to limit the amount of suction to limit the undesirable effect suction may have on hemostasis of severed blood vessels.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood, electrically conductive saline irrigant, or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors, and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the instrument may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. In some embodiments of the present invention, the tissue volume over which energy is dissipated (i.e., a high current density exists) may be more precisely controlled, for example, by the use of a multiplicity of small electrode terminals whose effective diameters or principal dimensions range from about 10 mm to 0.01 mm, preferably from about 2 mm to 0.05 mm, and more preferably from about 1 mm to 0.1 mm. In this embodiment, electrode areas for both circular and non-circular terminals will have a contact area (per electrode terminal) below 50 mm 2 for electrode arrays and as large as 75 mm$^2$ for single electrode embodiments. In multiple electrode array embodiments, the contact area of each electrode terminal is typically in the range from 0.0001 mm$^2$ to 1 mm$^2$, and more preferably from 0.001 mm$^2$ to 0.5 mm$^2$. The circumscribed area of the electrode array or electrode terminal is in the range from 0.25 mm$^2$ to 75 mm$^2$, preferably from 0.5 mm$^2$ to 40 mm$^2$. In multiple electrode embodiments, the array will usually include at least two isolated electrode terminals, often at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor layer and subsequent plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

In other embodiments, the active electrodes are spaced from the tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

The electrically conducting fluid should have a threshold conductivity to provide a suitable conductive path between the return electrode and the electrode terminal(s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck. The RMS (root mean square) voltage applied will usually be in the range from about 5 volts to 1000 volts, preferably being in the range from about 10 volts to 500 volts, often between about 150 to 400 volts depending on the electrode terminal size, the operating frequency and the operation mode of the particular procedure or desired effect on the tissue (i.e., contraction, coagulation, cutting or ablation). Typically, the peak-to-peak voltage for ablation or cutting with a square wave form will be in the range of 10 to 2000 volts and preferably in the range of 100 to 1800 volts and more preferably in the range of about 300 to 1500 volts, often in the range of about 300 to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 to 600 kHz may be used in certain procedures in which stray low frequency currents may be problematic. A description of one suitable power source can be found in co-pending U.S. patent application Ser. No. 09/058,571 and Ser. No. 09/058,336, filed Apr. 10, 1998, the complete disclosure of both applications are incorporated herein by reference for all purposes.

The power source may be current limited or otherwise controlled so that undesired heating of the target tissue or surrounding (non-target) tissue does not occur. In one embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in commonly assigned U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

Referring to FIG. 1, an exemplary electrosurgical system 11 for treatment of tissue in the spine will now be described in detail. Electrosurgical system 11 generally comprises an electrosurgical handpiece or probe 10 connected to a power supply 28 for providing high frequency voltage to a target site and a fluid source 21 for supplying electrically conducting fluid 50 to probe 10. In addition, electrosurgical system 11 may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 205 (see FIG. 2) in the probe 10 for aspirating the target site.

As shown, probe 10 generally includes a proximal handle 19 and an elongate shaft 18 having an array 12 of electrode terminals 58 at its distal end. A connecting cable 34 has a connector 26 for electrically coupling the electrode terminals 58 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 14 of probe 10 for supplying electrically conducting fluid 50 to the target site. Fluid supply tube 15 may be connected to a suitable pump (not shown), if desired.

Power supply 28 has an operator controllable voltage level adjustment 30 to change the applied voltage level, which is observable at a voltage level display 32. Power supply 28 also includes first, second, and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "sub-ablation" mode (e.g., coagulation or contraction of tissue). The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the sub-ablation mode, the power supply 28 applies a low enough voltage to the electrode terminals to avoid vaporization of the electrically conductive fluid and subsequent molecular dissociation of the tissue. The surgeon may automatically toggle the power supply between the ablation and sub-ablation modes by alternatively stepping on foot pedals 37, 38, respectively. In some embodiments, this allows the surgeon to quickly move between coagulation/thermal heating and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 2:
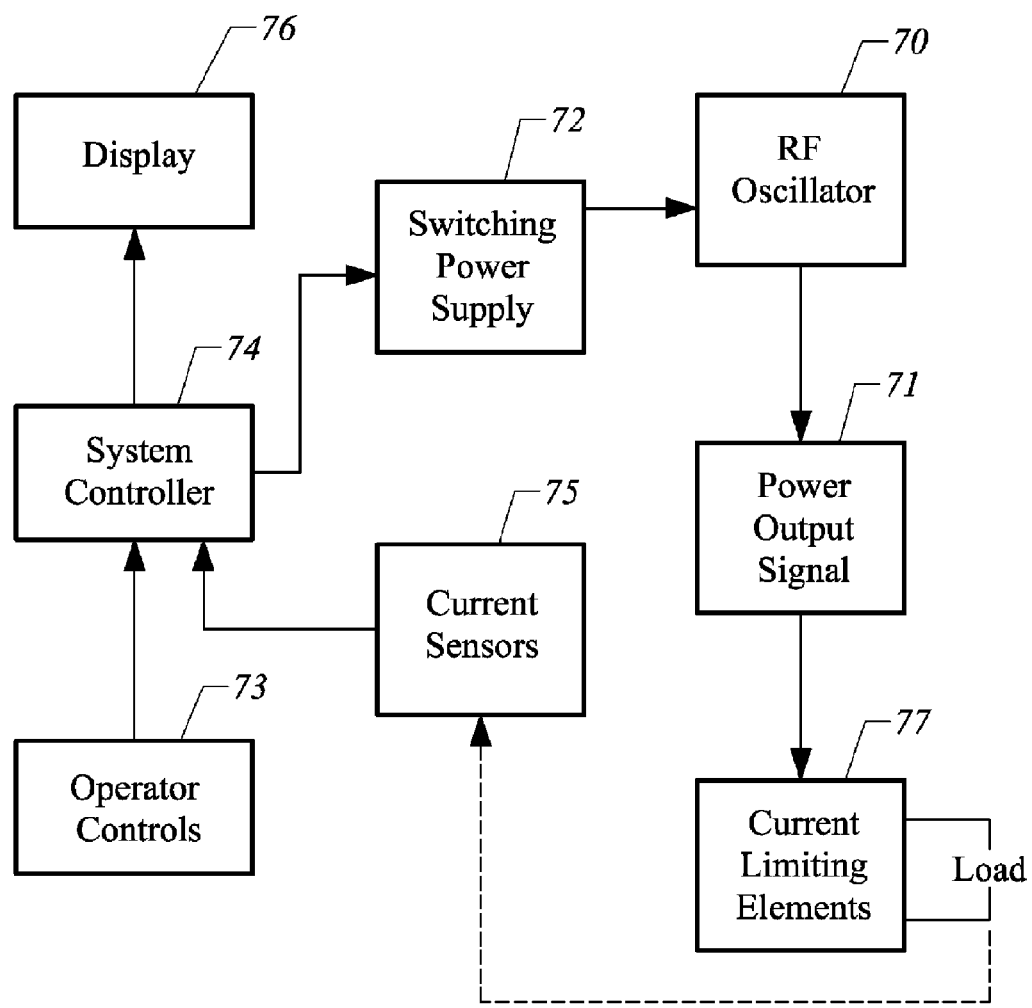
FIG. 2 schematically illustrates one embodiment of a power supply according to the present invention.
Figure 3:
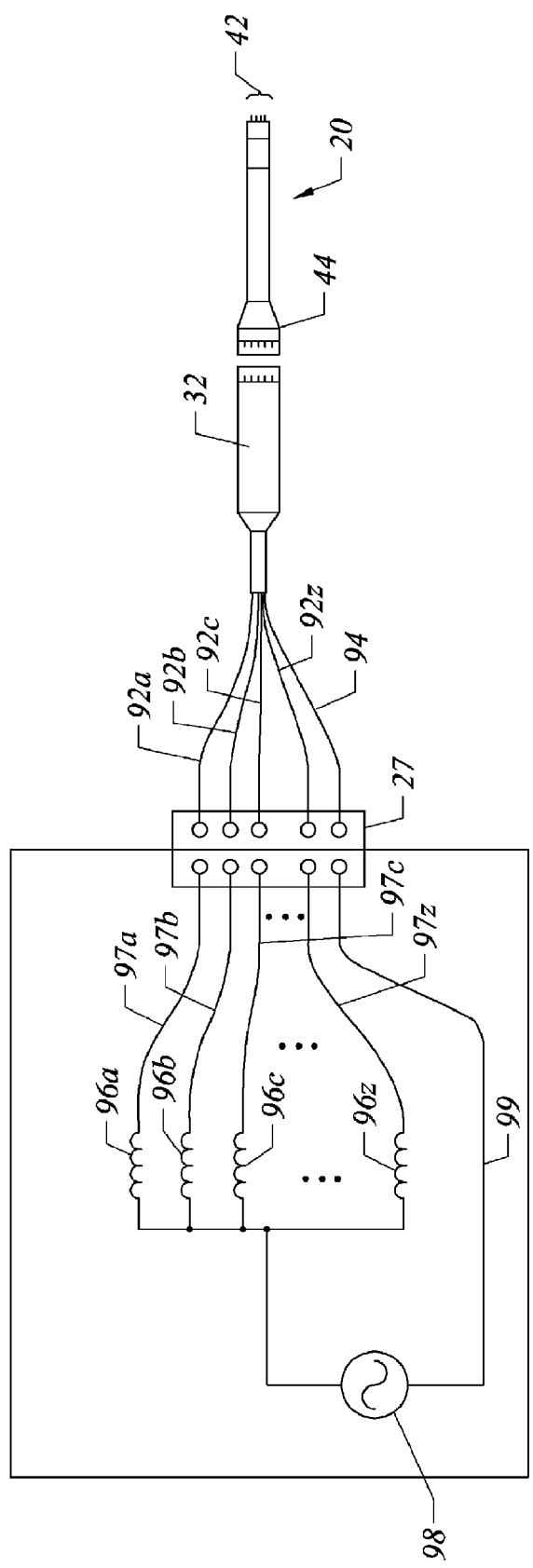
FIG. 3 illustrates an electrosurgical system incorporating a plurality of active electrodes and associated current limiting elements.

Referring now to FIGS. 2 and 3, a representative high frequency power supply for use according to the principles of the present invention will now be described. The high frequency power supply of the present invention is configured to apply a high frequency voltage of about 10 to 500 volts RMS between one or more electrode terminals (and/or coagulation electrode) and one or more return electrodes. In an exemplary embodiment, the power supply applies about 70-350 volts RMS in the ablation mode and about 20 to 90 volts in a sub-ablation mode, preferably 45 to 70 volts in the sub-ablation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular procedure, e.g., arthroscopic surgery, dermatological procedures, ophthalmic procedures, open surgery, or other endoscopic surgery procedures.

As shown in FIG. 2, the power supply generally comprises a radio frequency (RF) power oscillator 70 having output connections for coupling via a power output signal 71 to the load impedance, which is represented by the electrode assembly when the electrosurgical probe is in use. In the representative embodiment, RF oscillator 70 operates at about 100 kHz. The RF oscillator is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 71 is designed to incur minimal voltage decrease (i.e., sag) under load. This improves the applied voltage to the electrode terminals and the return electrode, which improves the rate of volumetric removal (ablation) of tissue.

Power is supplied to oscillator 70 by a switching power supply 72 coupled between the power line and the RF oscillator rather than a conventional transformer. The switching power supply 72 allows the generator to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 72 operates at about 100 kHz.

A controller 74 coupled to the operator controls 73 (i.e., foot pedals and voltage selector) and display 76, is connected to a control input of the switching power supply 72 for adjusting the generator output power by supply voltage variation. The controller 106 may be a microprocessor or an integrated circuit. The power supply may also include one or more current sensors 75 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries (μH), usually about 300 microhenries (μH), for each of the channels supplying current to the electrode terminals (see, e.g., FIG. 4).

Alternatively, in one embodiment, current limiting inductors are placed in series with each independent electrode terminal, where the inductance of the inductor is in the range of 10 μH to 50,000 μH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel). Power output signal may also be coupled to a plurality of current limiting elements 96, which are preferably located on the daughter board since the current limiting elements may vary depending on the application. A more complete description of a representative power supply can be found in commonly assigned U.S. patent application Ser. No. 09/058,571, previously incorporated herein by reference.

Figure 4:
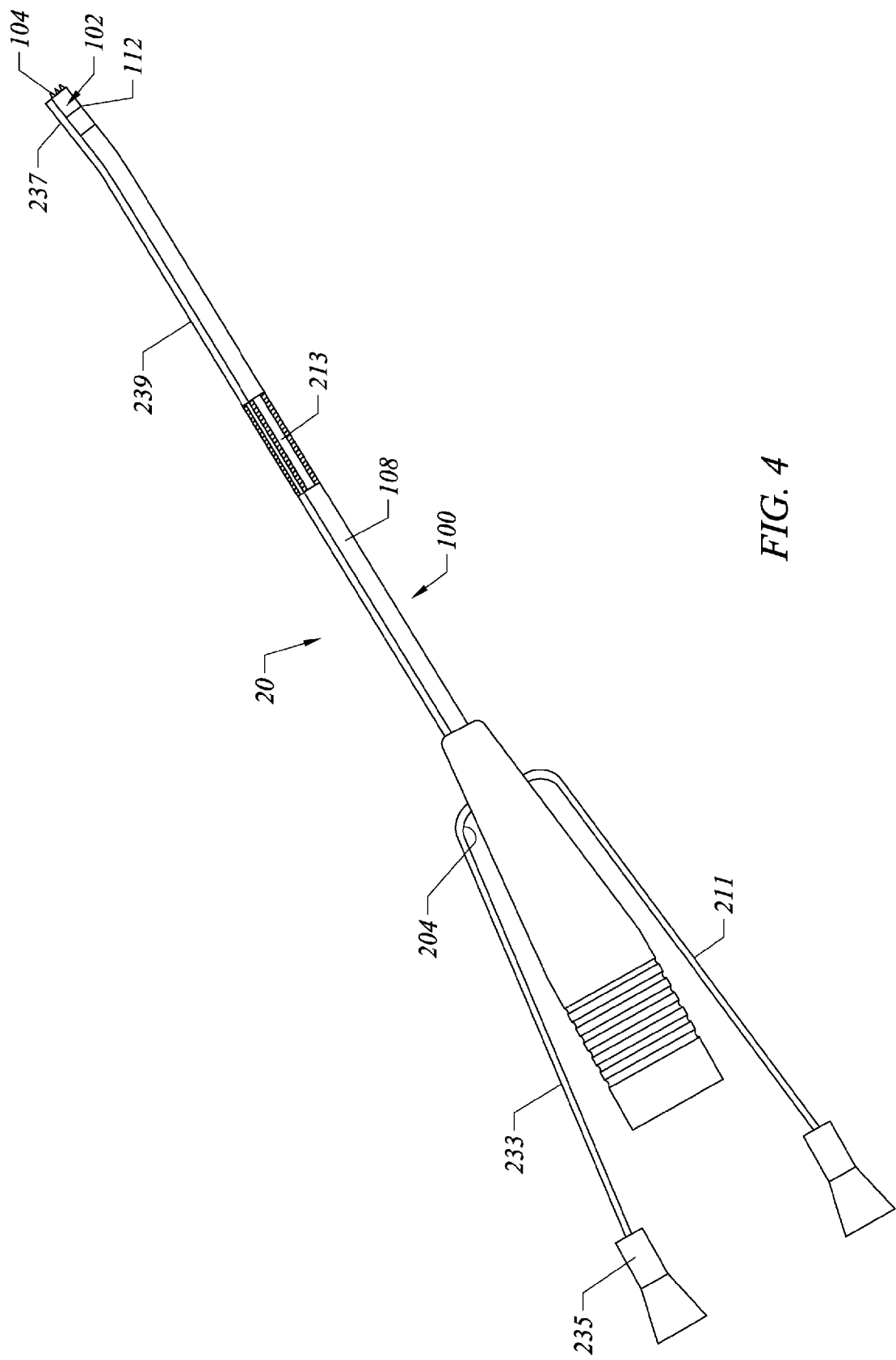
FIG. 4 is a side view of an electrosurgical probe according to the present invention.
Figure 5:
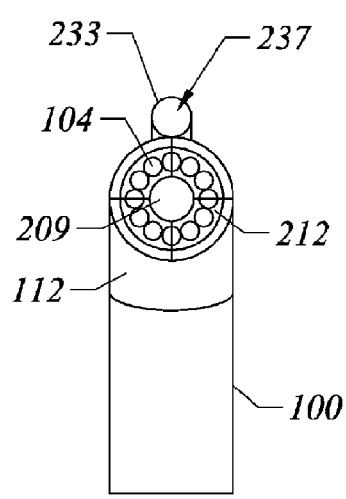
FIG. 5 is a view of the distal end portion of the probe of FIG. 4.
Figure 6:
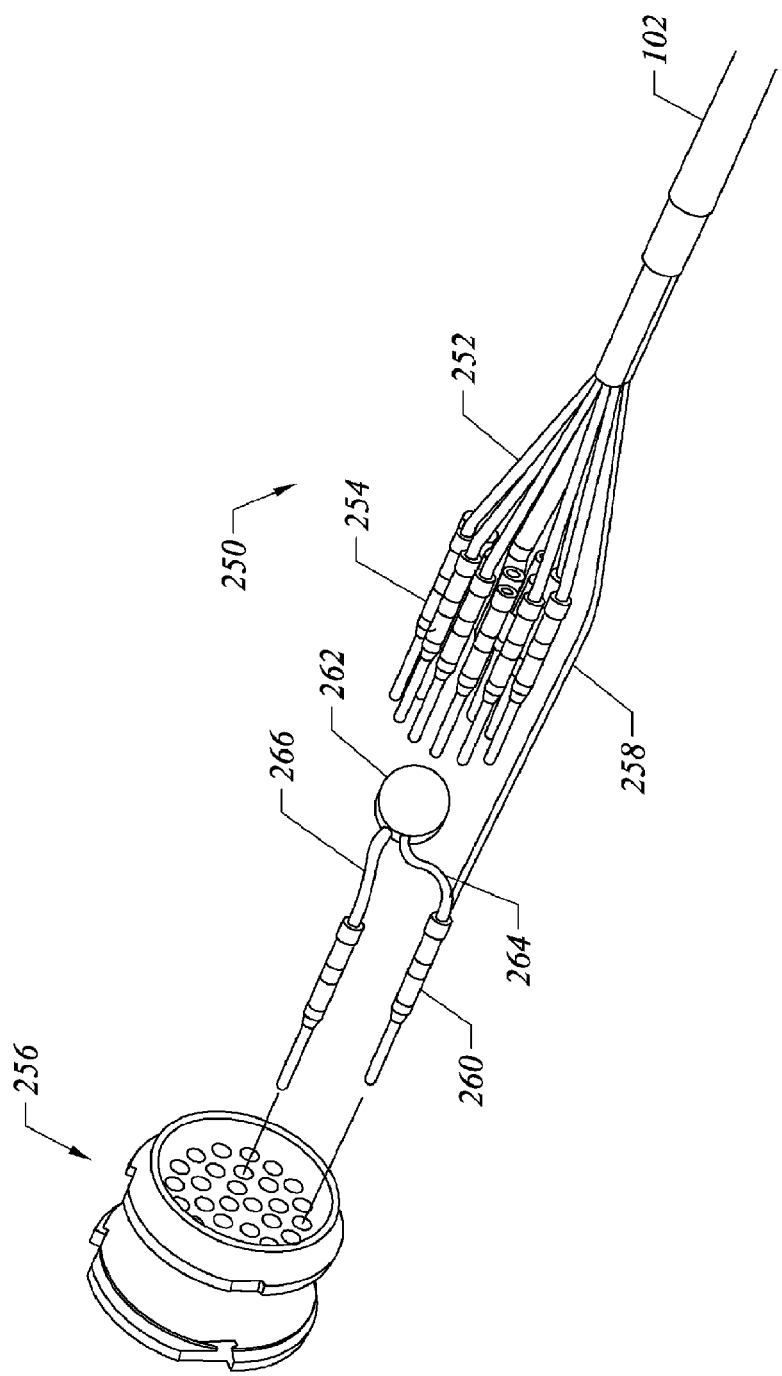
FIG. 6 is an exploded view of a proximal portion of the electrosurgical probe.

FIGS. 4-6 illustrate an exemplary electrosurgical probe 20 constructed according to the principles of the present invention. As shown in FIG. 4, probe 90 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis. Alternatively, the return electrode may comprise an annular band coupled to an insulating shaft and having a connector extending within the shaft to its proximal end.

Handle 204 typically comprises a plastic material that is easily molded into a suitable shape for handling by the surgeon. Handle 204 defines an inner cavity (not shown) that houses the electrical connections 250 (FIG. 6), and provides a suitable interface for connection to an electrical connecting cable 22 (see FIG. 1). Electrode support member 102 extends from the distal end of shaft 100 (usually about 1 to 20 mm), and provides support for a plurality of electrically isolated electrode terminals 104 (see FIG. 5). As shown in FIG. 4, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, fluid tube 239 is a plastic tubing that extends along the exterior of shaft 100 to a point just distal of return electrode 112 (see FIG. 5). In this embodiment, the fluid is directed through an opening 237 past return electrode 112 to the electrode terminals 104. Probe 20 may also include a valve 17 (FIG. 1) or equivalent structure for controlling the flow rate of the electrically conducting fluid to the target site.

As shown in FIG. 4, the distal portion of shaft 100 is preferably bent to improve access to the operative site of the tissue being treated. Electrode support member 102 has a substantially planar tissue treatment surface 212 (FIG. 5) that is usually at an angle of about 10 to 90 degrees relative to the longitudinal axis of shaft 100, preferably about 30 to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands and contracts by externally applied temperature changes. A more complete description of this embodiment can be found in U.S. Pat. No. 5,697,909, the complete disclosure of which has previously been incorporated herein by reference. Alternatively, the shaft 100 of the present invention may be bent by the physician to the appropriate angle using a conventional bending tool or the like.

In the embodiment shown in FIGS. 4-6, probe 20 includes a return electrode 112 for completing the current path between electrode terminals 104 and a high frequency power supply 28 (see FIG. 1). As shown, return electrode 112 preferably comprises an exposed portion of shaft 100 shaped as an annular conductive band near the distal end of shaft 100 slightly proximal to tissue treatment surface 212 of electrode support member 102, typically about 0.5 to 10 mm and more preferably about 1 to 10 mm. Return electrode 112 or shaft 100 is coupled to a connector 258 that extends to the proximal end of probe 10, where it is suitably connected to power supply 10 (FIG. 1).

As shown in FIG. 4, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered through fluid tube 233 to opening 237, as described above. Alternatively, the fluid may be delivered by a fluid delivery element (not shown) that is separate from probe 20. In arthroscopic surgery, for example, the body cavity will be flooded with isotonic saline and the probe 90 will be introduced into this flooded cavity. Electrically conducting fluid will be continually resupplied to maintain the conduction path between return electrode 112 and electrode terminals 104. In other embodiments, the distal portion of probe 20 may be dipped into a source of electrically conductive fluid, such as a gel or isotonic saline, prior to positioning at the target site. Applicant has found that the surface tension of the fluid and/or the viscous nature of a gel allows the conductive fluid to remain around the active and return electrodes for long enough to complete its function according to the present invention, as described below. Alternatively, the conductive fluid, such as a gel, may be applied directly to the target site.

Figure 8A:
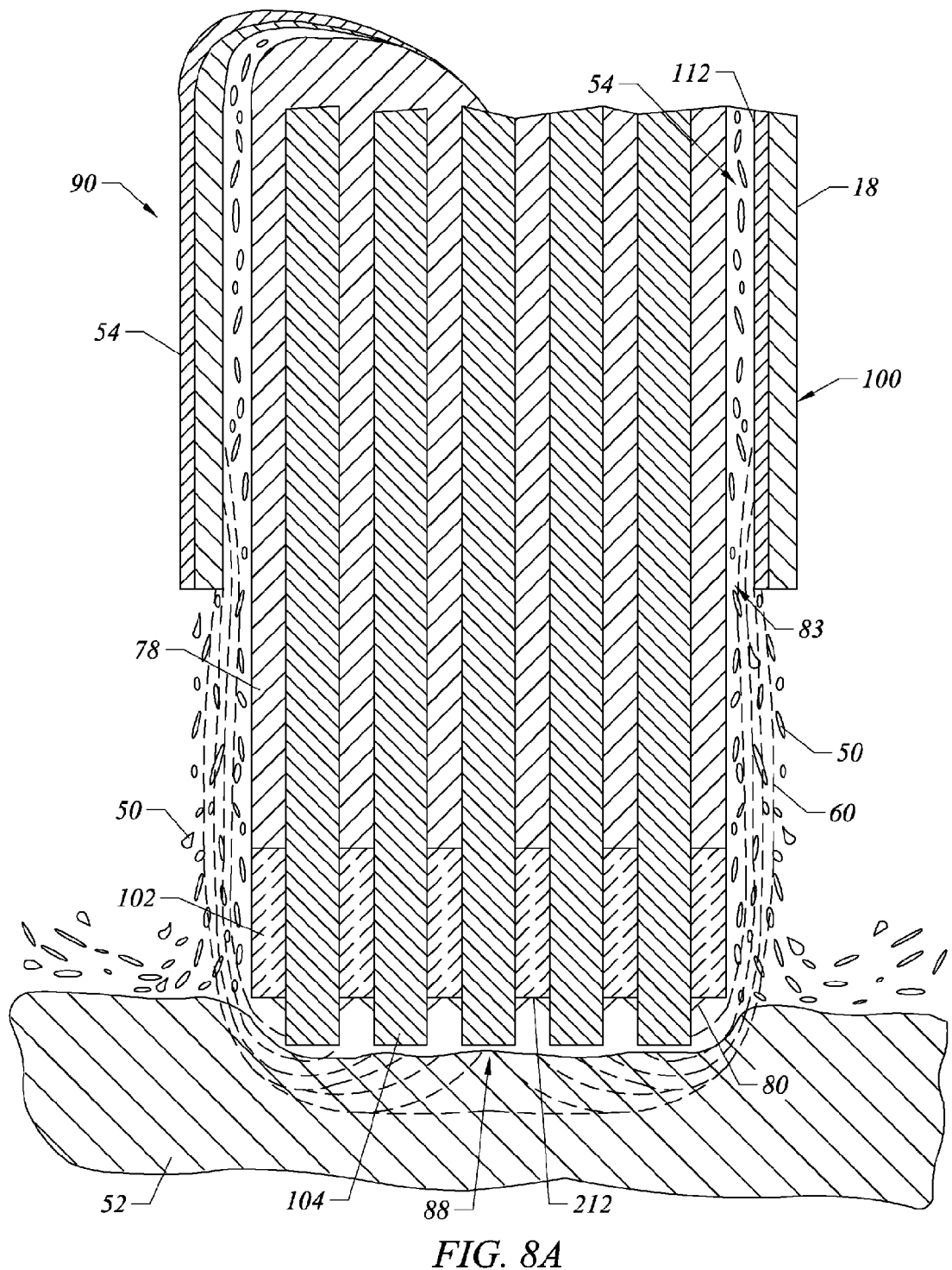
FIGS. 8A-8C are cross-sectional views of the distal portions of three different embodiments of an electrosurgical probe according to the present invention.
Figure 8B:
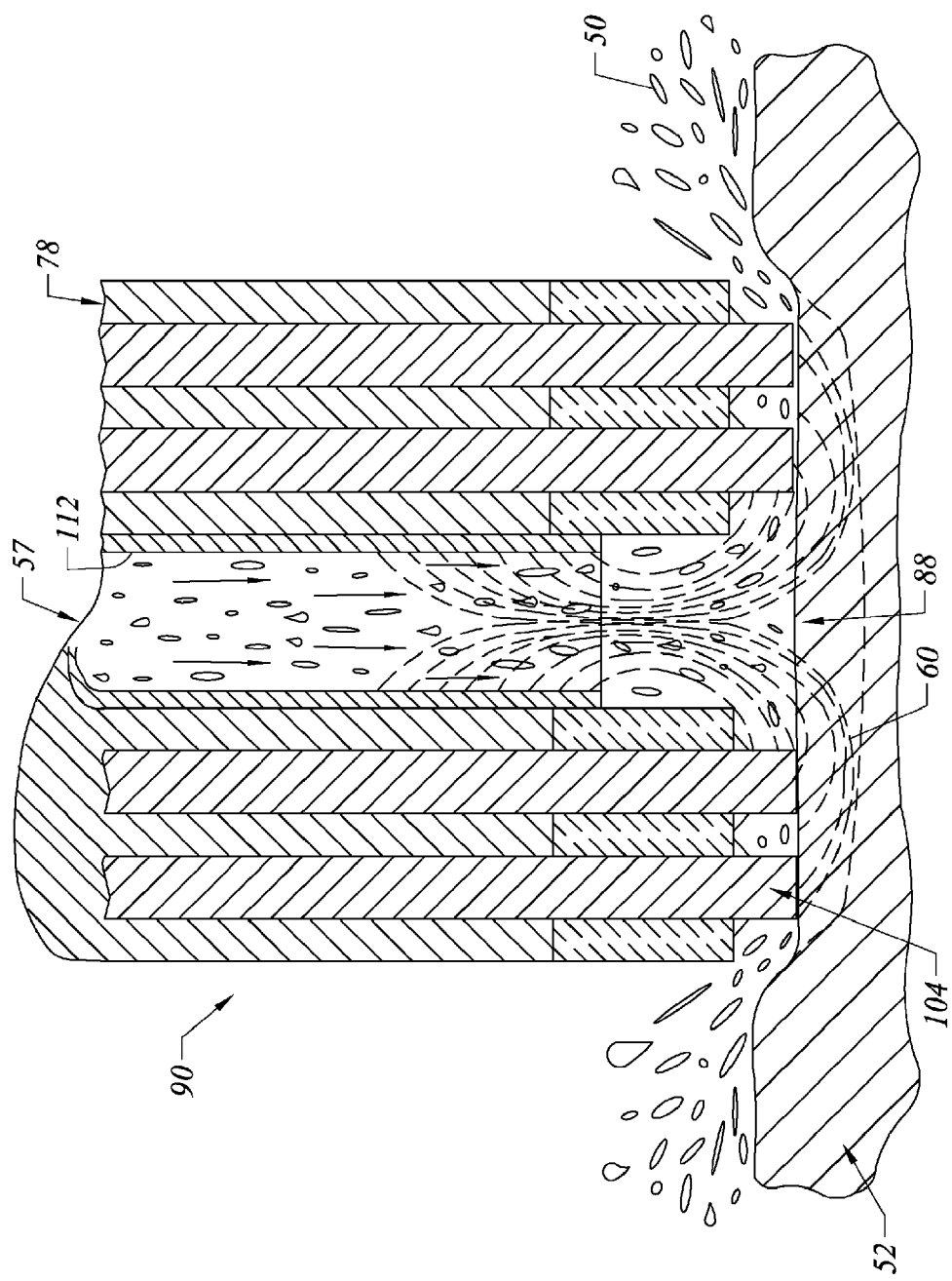

In alternative embodiments, the fluid path may be formed in probe 90 by, for example, an inner lumen or an annular gap between the return electrode and a tubular support member within shaft 100 (see FIGS. 8A and 8B). This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 90 via a fluid supply tube (not shown) that may or may not have a controllable valve. A more complete description of an electrosurgical probe incorporating one or more fluid lumen(s) can be found in commonly assigned U.S. Pat. No. 5,697,281, the complete disclosure of which is incorporated herein by reference.

Referring to FIG. 5, the electrically isolated electrode terminals 104 are spaced apart over tissue treatment surface 212 of electrode support member 102. The tissue treatment surface and individual electrode terminals 104 will usually have dimensions within the ranges set forth above. In the representative embodiment, the tissue treatment surface 212 has a circular cross-sectional shape with a diameter in the range of 1 mm to 20. The individual electrode terminals 104 preferably extend outward from tissue treatment surface 212 by a distance of about 0.1 to 4 mm, usually about 0.2 to 2 mm. Applicant has found that this configuration increases the high electric field intensities and associated current densities around electrode terminals 104 to facilitate the ablation of tissue as described in detail above.

In the embodiment of FIGS. 4-6, the probe includes a single, larger opening 209 in the center of tissue treatment surface 212, and a plurality of electrode terminals (e.g., about 3-15) around the perimeter of surface 212 (see FIG. 5). Alternatively, the probe may include a single, annular, or partially annular, electrode terminal at the perimeter of the tissue treatment surface. The central opening 209 is coupled to a suction lumen (not shown) within shaft 100 and a suction tube 211 (FIG. 4) for aspirating tissue, fluids and/or gases from the target site. In this embodiment, the electrically conductive fluid generally flows radially inward past electrode terminals 104 and then back through the opening 209. Aspirating the electrically conductive fluid during surgery allows the surgeon to see the target site, and it prevents the fluid from flowing into the patient's body.

Figure 7A:
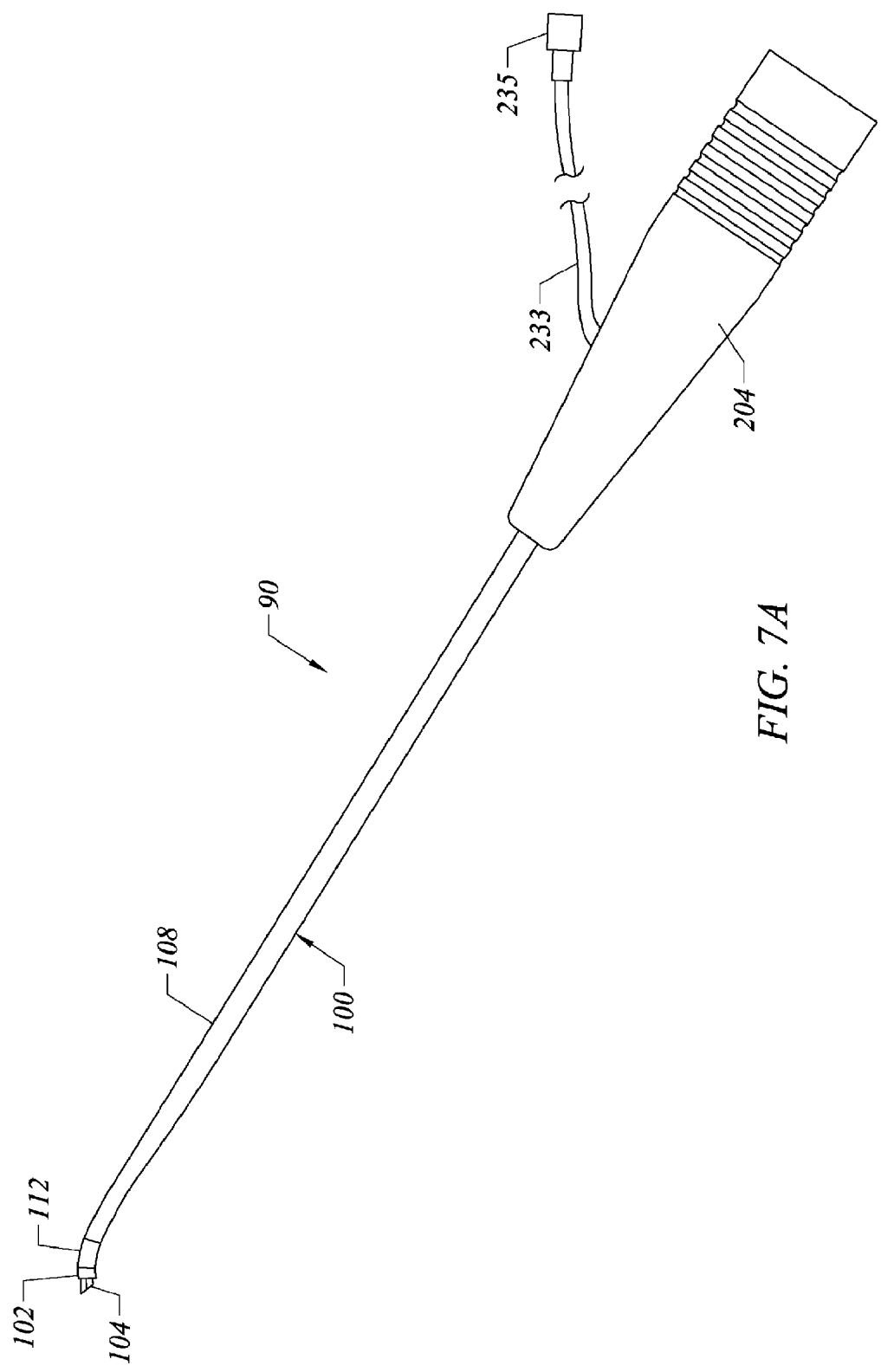
FIGS. 7A and 7B are perspective and end views, respectively, of an alternative electrosurgical probe incorporating an inner fluid lumen.
Figure 7B:
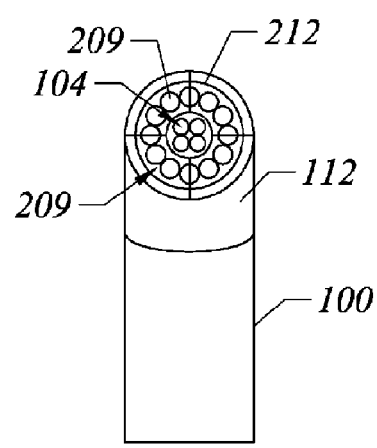

Of course, it will be recognized that the distal tip of probe may have a variety of different configurations. For example, the probe may include a plurality of openings 209 around the outer perimeter of tissue treatment surface 212 (see FIG. 7B). In this embodiment, the electrode terminals 104 extend distally from the center of tissue treatment surface 212 such that they are located radially inward from openings 209. The openings are suitably coupled to fluid tube 233 for delivering electrically conductive fluid to the target site, and suction tube 211 for aspirating the fluid after it has completed the conductive path between the return electrode 112 and the electrode terminals 104.

FIG. 6 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, the probe 20 further includes an identification element that is characteristic of the particular electrode assembly so that the same power supply 28 can be used for different electrosurgical operations. In one embodiment, for example, the probe 20 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. In some embodiments, the voltage reduction element allows the power supply 28 to apply two different voltages simultaneously to two different electrodes (see FIG. 15D). In other embodiments, the voltage reduction element primarily allows the electrosurgical probe 90 to be compatible with other ArthroCare generators that are adapted to apply higher voltages for ablation or vaporization of tissue. For thermal heating or coagulation of tissue, for example, the voltage reduction element will serve to reduce a voltage of about 100 to 170 volts RMS (which is a setting of 1 or 2 on the ArthroCare Model 970 and 980 (i.e., 2000) Generators) to about 45 to 60 volts RMS, which is a suitable voltage for coagulation of tissue without ablation (e.g., molecular dissociation) of the tissue.

Of course, for some procedures, the probe will typically not require a voltage reduction element. Alternatively, the probe may include a voltage increasing element or circuit, if desired. Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor. Further, it should be noted that the present invention can be used with a power supply that is adapted to apply a voltage within the selected range for treatment of tissue. In this embodiment, a voltage reduction element or circuitry may not be desired.

Figure 8C:
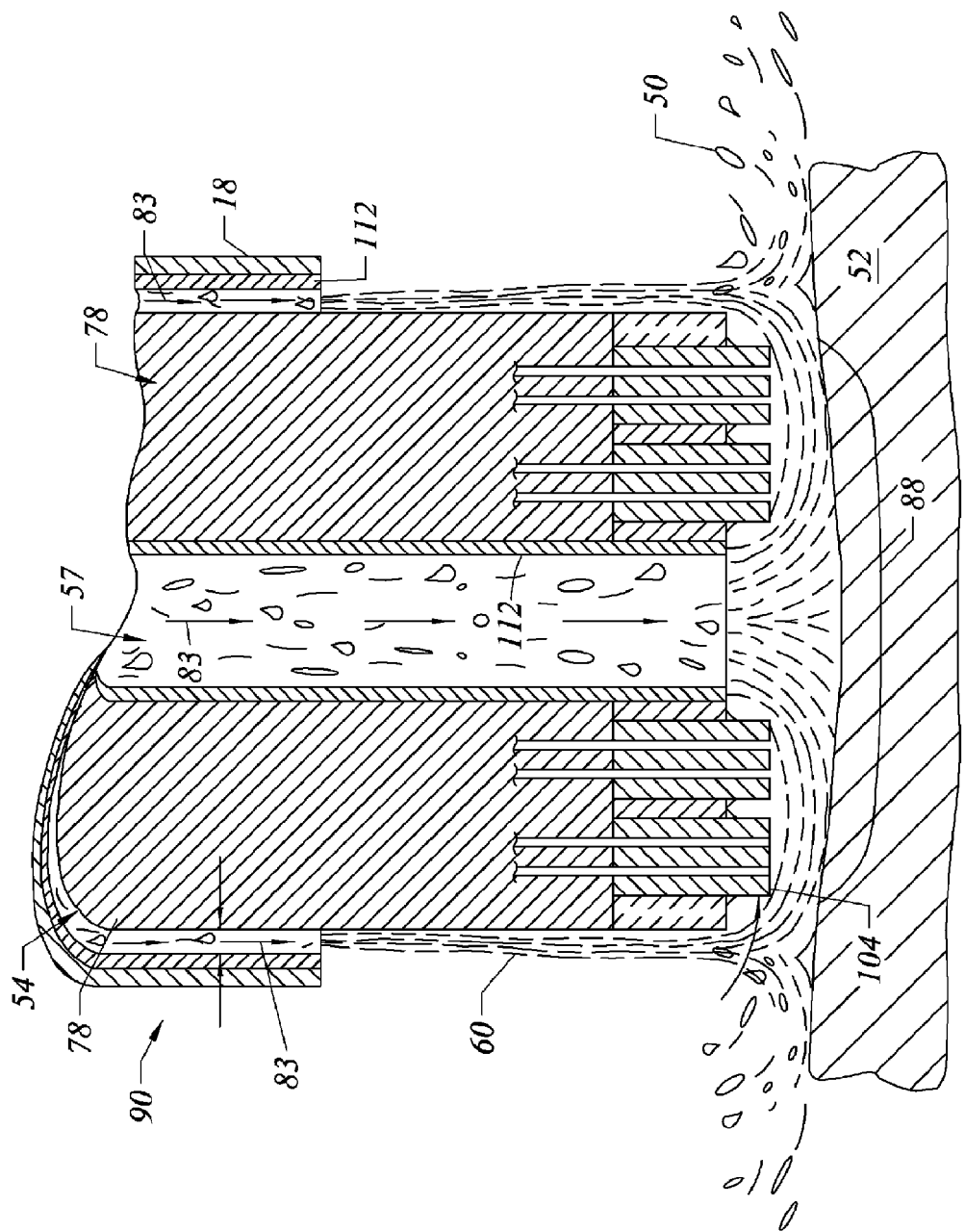

FIGS. 8A-8C schematically illustrate the distal portion of three different embodiments of probe 90 according to the present invention. As shown in 8A, electrode terminals 104 are anchored in a support matrix 102 of suitable insulating material (e.g., silicone rubber or a ceramic or glass material, such as alumina, zirconia, and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support matrix 102 is adhesively joined to a tubular support member 78 that extends most or all of the distance between matrix 102 and the proximal end of probe 90. Tubular member 78 preferably comprises an electrically insulating material, such as an epoxy or silicone-based material.

In a preferred construction technique, electrode terminals 104 extend through pre-formed openings in the support matrix 102 so that they protrude above tissue treatment surface 212 by the desired distance. The electrodes are then bonded to the tissue treatment surface 212 of support matrix 102, typically by an inorganic sealing material 80. Sealing material 80 is selected to provide effective electrical insulation, and good adhesion to both the alumina matrix 102 and the platinum or titanium electrode terminals. Sealing material 80 additionally should have a compatible thermal expansion coefficient and a melting point well below that of platinum or titanium and alumina or zirconia, typically being a glass or glass ceramic.

In the embodiment shown in FIG. 8A, return electrode 112 comprises an annular member positioned around the exterior of shaft 100 of probe 90. Return electrode 90 may fully or partially circumscribe tubular support member 78 to form an annular gap 54 therebetween for flow of electrically conducting liquid 50 therethrough, as discussed below. Gap 54 preferably has a width in the range of 0.25 mm to 4 mm. Alternatively, probe may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 56 and any adjacent body structure. Such direct electrical contact between a body structure (e.g., tendon) and an exposed electrode member 112 could result in unwanted heating and necrosis of the structure at the point of contact causing necrosis.

As shown in FIG. 8A, return electrode 112 is not directly connected to electrode terminals 104. To complete this current path so that terminals 104 are electrically connected to return electrode 112, electrically conducting liquid 50 (e.g., isotonic saline) is caused to flow along fluid path(s) 83. Fluid path 83 is formed by annular gap 54 between outer return electrode 112 and tubular support member. The electrically conducting liquid 50 flowing through fluid path 83 provides a pathway for electrical current flow between electrode terminals 104 and return electrode 112, as illustrated by the current flux lines 60 in FIG. 8A. When a voltage difference is applied between electrode terminals 104 and return electrode 112, high electric field intensities will be generated at the distal tips of terminals 104 with current flow from terminals 104 through the target tissue to the return electrode, the high electric field intensities causing ablation of tissue 52 in zone 88.

FIG. 8B illustrates another alternative embodiment of electrosurgical probe 90 which has a return electrode 112 positioned within tubular member 78. Return electrode 112 is preferably a tubular member defining an inner lumen 57 for allowing electrically conducting liquid 50 (e.g., isotonic saline) to flow therethrough in electrical contact with return electrode 112. In this embodiment, a voltage difference is applied between electrode terminals 104 and return electrode 112 resulting in electrical current flow through the electrically conducting liquid 50, as represented by current flux lines 60. As a result of the applied voltage difference and concomitant high electric field intensities at the tips of electrode terminals 104, tissue 52 becomes ablated or transected in zone 88.

FIG. 8C illustrates another embodiment of probe 90 that is a combination of the embodiments in FIGS. 8A and 8B. As shown, this probe includes both an inner lumen 57 and an outer gap or plurality of outer lumens 54 for flow of electrically conductive fluid. In this embodiment, the return electrode 112 may be positioned within tubular member 78 as in FIG. 8B, outside of tubular member 78 as in FIG. 8A, or in both locations.

Figure 9:
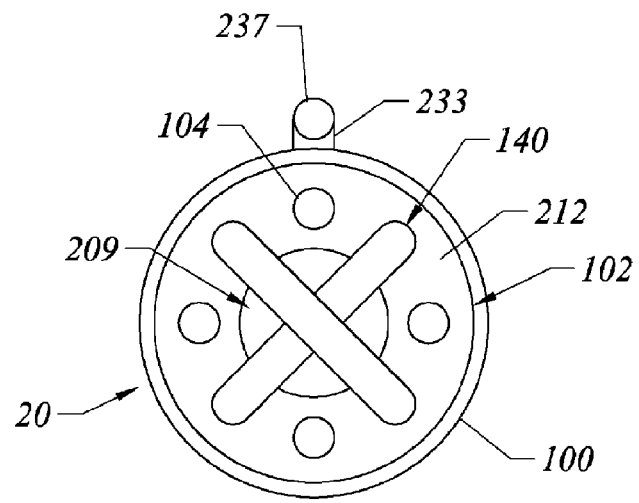
FIGS. 9-12 are end views of alternative embodiments of the probe of FIG. 4, incorporating aspiration electrode(s)
Figure 13:
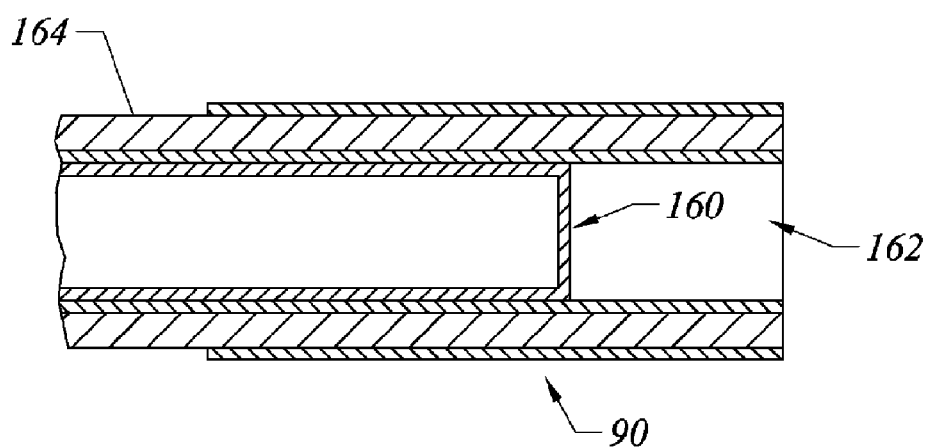
FIG. 13 is a side view of the distal portion of the shaft of an electrosurgical probe, according to one embodiment of the invention.

In some embodiments, the probe 20 will also include one or more aspiration electrode(s) coupled to the aspiration lumen for inhibiting clogging during aspiration of tissue fragments from the surgical site. As shown in FIG. 9, one or more of the active electrode terminals 104 may comprise loop electrodes 140 that extend across distal opening 209 of the suction lumen within shaft 100. In the representative embodiment, two of the electrode terminals 104 comprise loop electrodes 140 that cross over the distal opening 209. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 10 and 11. Alternatively, the electrodes may be formed within suction lumen proximal to the distal opening 209, as shown in FIG. 13. The main function of loop electrodes 140 is to ablate portions of tissue that are drawn into the suction lumen to prevent clogging of the lumen.

In some embodiments, loop electrodes 140 are electrically isolated from the other electrode terminals 104, which can be referred to hereinafter as the ablation electrodes 104. In other embodiments, the loop electrodes 140 and electrode terminals 104 may be electrically connected to each other such that both are activated together. Loop electrodes 140 may or may not be electrically isolated from each other. Loop electrodes 140 will usually extend only about 0.05 to 4 mm, preferably about 0.1 to 1 mm from the tissue treatment surface of electrode support member 104.

Figure 10:
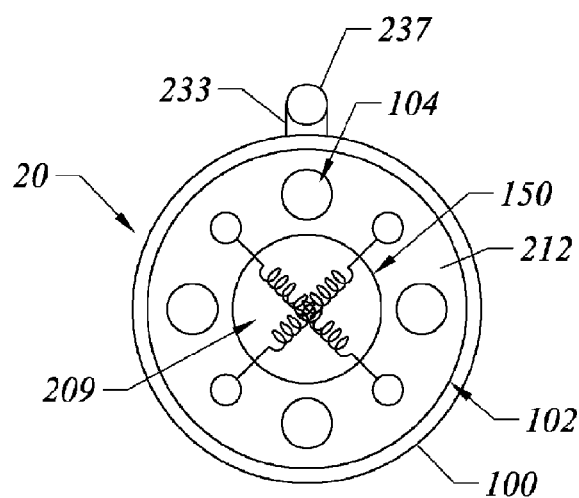
Figure 11:
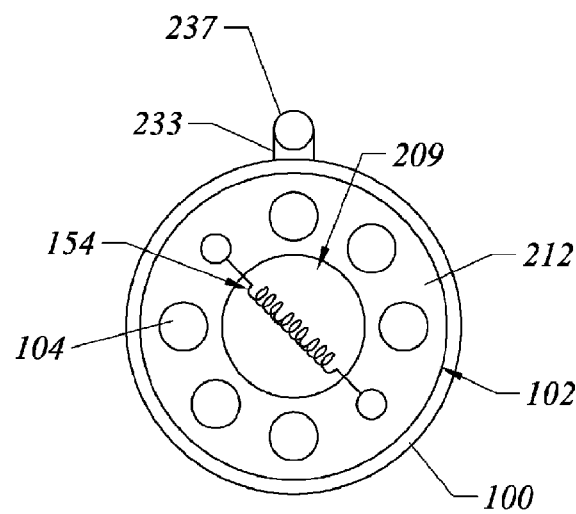

Referring now to FIGS. 10 and 11, alternative embodiments for aspiration electrodes will now be described. As shown in FIG. 10, the aspiration electrodes may comprise a pair of coiled electrodes 150 that extend across distal opening 209 of the suction lumen. The larger surface area of the coiled electrodes 150 usually increases the effectiveness of the electrodes 150 on tissue fragments passing through opening 209. In FIG. 11, the aspiration electrode comprises a single coiled electrode 152 passing across the distal opening 209 of suction lumen. This single electrode 152 may be sufficient to inhibit clogging of the suction lumen. Alternatively, the aspiration electrodes may be positioned within the suction lumen proximal to the distal opening 209. Preferably, these electrodes are close to opening 209 so that tissue does not clog the opening 209 before it reaches electrodes 154. In this embodiment, a separate return electrode 156 may be provided within the suction lumen to confine the electric currents therein.

Referring to FIG. 13, another embodiment of the present invention incorporates an aspiration electrode 160 within the aspiration lumen 162 of the probe. As shown, the electrode 160 is positioned just proximal of distal opening 209 so that the tissue fragments are ablated as they enter lumen 162. In the representation embodiment, the aspiration electrode 160 comprises a loop electrode that stretches across the aspiration lumen 162. However, it will be recognized that many other configurations are possible. In this embodiment, the return electrode 164 is located outside of the probe as in the previously embodiments. Alternatively, the return electrode(s) may be located within the aspiration lumen 162 with the aspiration electrode 160. For example, the inner insulating coating 163 may be exposed at portions within the lumen 162 to provide a conductive path between this exposed portion of return electrode 164 and the aspiration electrode 160. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 162 along with the tissue fragments.

Figure 12:
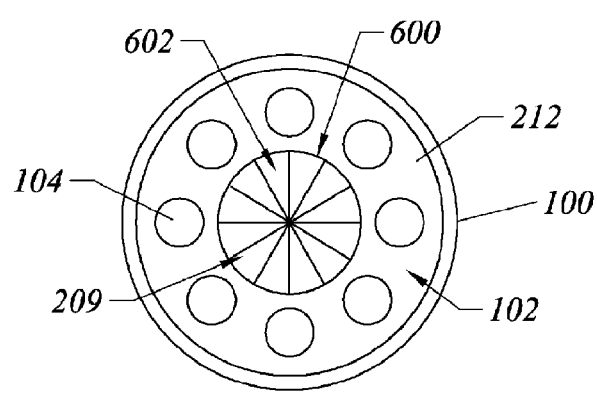

Referring to FIG. 12, another embodiment of the present invention incorporates a wire mesh electrode 600 extending across the distal portion of aspiration lumen 162. As shown, mesh electrode 600 includes a plurality of openings 602 to allow fluids and tissue fragments to flow through into aspiration lumen 162. The size of the openings 602 will vary depending on a variety of factors. The mesh electrode may be coupled to the distal or proximal surfaces of ceramic support member 102. Wire mesh electrode 600 comprises a conductive material, such as titanium, tantalum, steel, stainless steel, tungsten, copper, gold or the like. In the representative embodiment, wire mesh electrode 600 comprises a different material having a different electric potential than the active electrode terminal(s) 104. Preferably, mesh electrode 600 comprises steel and electrode terminal(s) comprises tungsten. Applicant has found that a slight variance in the electrochemical potential of mesh electrode 600 and electrode terminal(s) 104 improves the performance of the device. Of course, it will be recognized that the mesh electrode may be electrically insulated from active electrode terminal(s) as in previous embodiments Referring now to FIGS. 14A-14C, an alternative embodiment incorporating a metal screen 610 is illustrated. As shown, metal screen 610 has a plurality of peripheral openings 612 for receiving electrode terminals 104, and a plurality of inner openings 614 for allowing aspiration of fluid and tissue through opening 609 of the aspiration lumen. As shown, screen 610 is press fitted over electrode terminals 104 and then adhered to shaft 100 of probe 20. Similar to the mesh electrode embodiment, metal screen 610 may comprise a variety of conductive metals, such as titanium, tantalum, steel, stainless steel, tungsten, copper, gold or the like. In the representative embodiment, metal screen 610 is coupled directly to, or integral with, active electrode terminal(s) 104. In this embodiment, the active electrode terminal(s) 104 and the metal screen 610 are electrically coupled to each other.

Figure 15A:
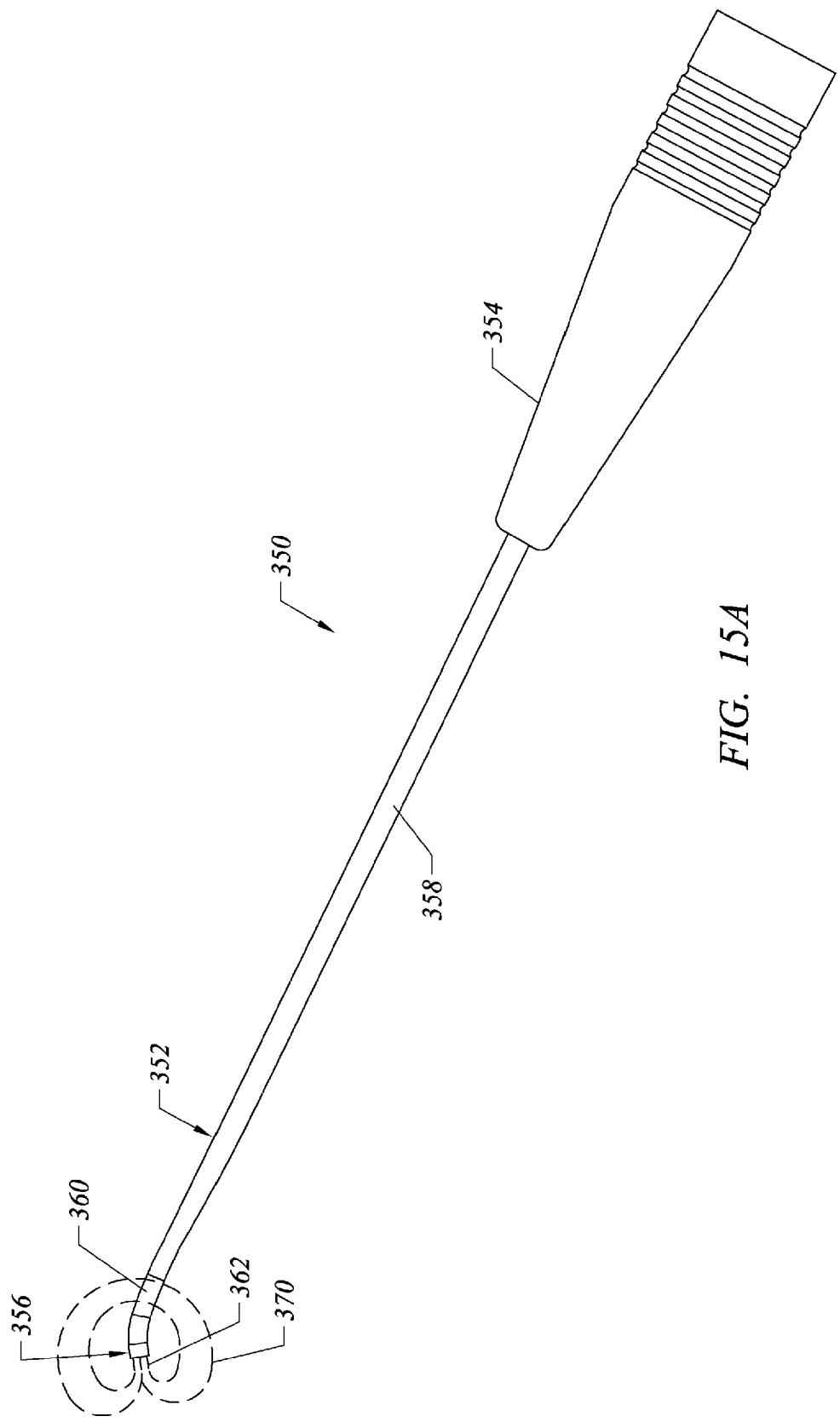
FIGS. 15A-15D illustrate four embodiments of electrosurgical probes specifically designed for treating spinal defects.

FIGS. 15A-15D illustrate embodiments of an electrosurgical probe 350 specifically designed for the treatment of herniated or diseased spinal discs. Referring to FIG. 15A, probe 350 comprises an electrically conductive shaft 352, a handle 354 coupled to the proximal end of shaft 352 and an electrically insulating support member 356 at the distal end of shaft 352. Probe 350 further includes a shrink wrapped insulating sleeve 358 over shaft 352, and exposed portion of shaft 352 that functions as the return electrode 360. In the representative embodiment, probe 350 comprises a plurality of active electrodes 362 extending from the distal end of support member 356. As shown, return electrode 360 is spaced a further distance from active electrodes 362 than in the embodiments described above. In this embodiment, the return electrode 360 is spaced a distance of about 2.0 to 50 mm, preferably about 5 to 25 mm. In addition, return electrode 360 has a larger exposed surface area than in previous embodiments, having a length in the range of about 2.0 to 40 mm, preferably about 5 to 20 mm. Accordingly, electric current passing from active electrodes 362 to return electrode 360 will follow a current flow path 370 that is further away from shaft 352 than in the previous embodiments. In some applications, this current flow path 370 results in a deeper current penetration into the surrounding tissue with the same voltage level, and thus increased thermal heating of the tissue. As discussed above, this increased thermal heating may have advantages in some applications of treating disc defects. Typically, it is desired to achieve a tissue temperature in the range of about 60° C. to 100° C. to a depth of about 0.2 to 5 mm, usually about 1 to 2 mm. The voltage required for this thermal damage will partly depend on the electrode configurations, the conductivity of the tissue and the area immediately surrounding the electrodes, the time period for which the voltage is applied and the depth of tissue damage desired. With the electrode configurations described in FIGS. 15A-15D, the voltage level for thermal heating will usually be in the range of about 20 to 300 volts RMS, preferably about 60 to 200 volts RMS. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked, or ablated, which is undesirable.

In alternative embodiments, the electrosurgical system used in conjunction with probe 350 may include a dispersive return electrode 450 (see FIG. 16) for switching between bipolar and monopolar modes. In this embodiment, the system will switch between an ablation mode, where the dispersive pad 450 is deactivated and voltage is applied between active and return electrodes 362, 360, and a sub-ablation or thermal heating mode, where the active electrode(s) 362 and deactivated and voltage is applied between the dispersive pad 450 and the return electrode 360. In the sub-ablation mode, a lower voltage is typically applied and the return electrode 360 functions as the active electrode to provide thermal heating and/or coagulation of tissue surrounding return electrode 360.

Figure 15B:
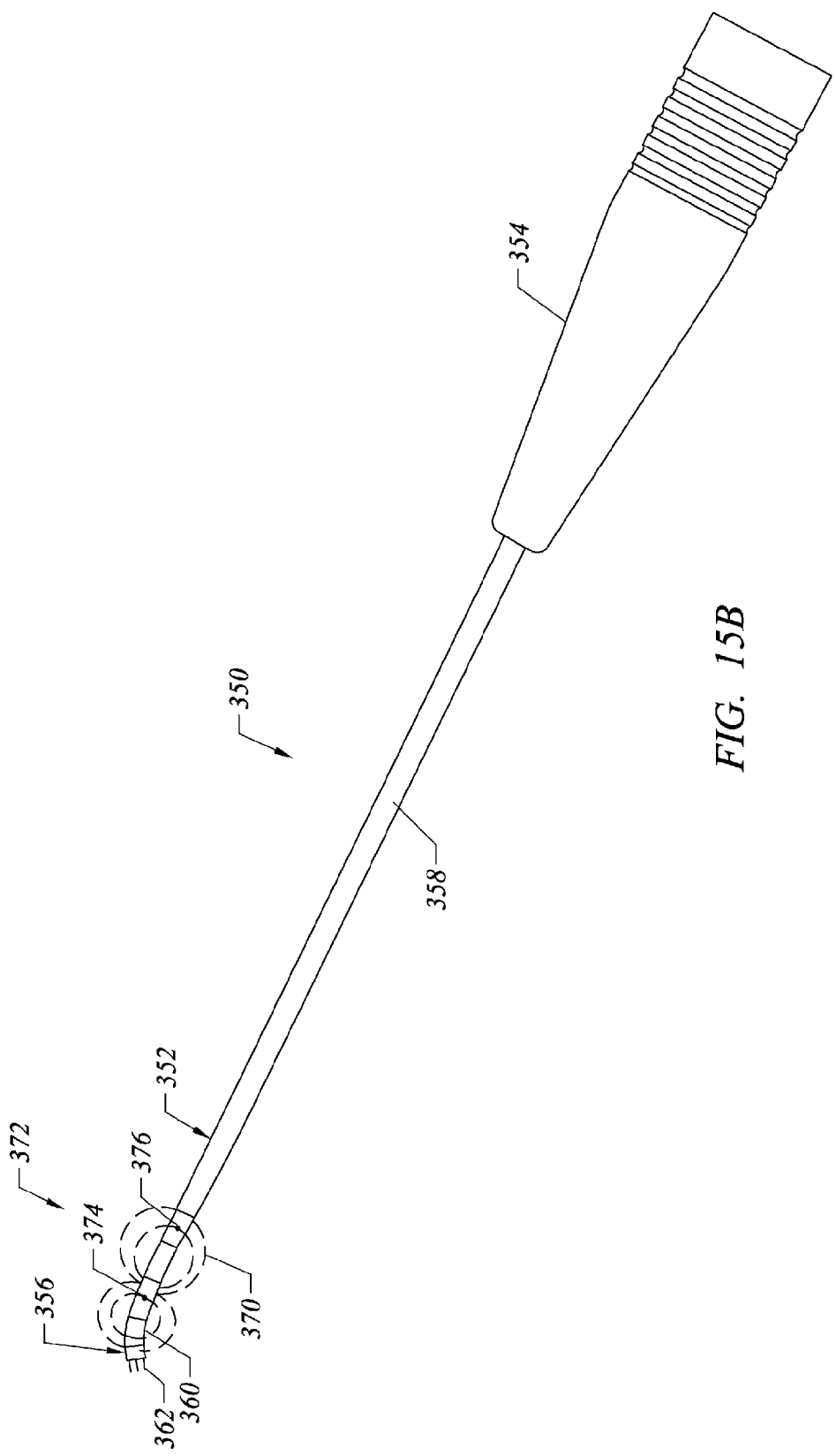

FIG. 15B illustrates yet another embodiment of the present invention. As shown, electrosurgical probe 350 comprises an electrode assembly 372 having one or more active electrode(s) 362 and a proximally spaced return electrode 360 as in previous embodiments. Return electrode 360 is typically spaced about 0.5 to 25 mm, preferably 1.0 to 5.0 mm from the active electrode(s) 362, and has an exposed length of about 1 to 20 mm. In addition, electrode assembly 372 includes two additional electrodes 374, 376 spaced axially on either side of return electrode 360. Electrodes 374, 376 are typically spaced about 0.5 to 25 mm, preferably about 1 to 5 mm from return electrode 360. In the representative embodiment, the additional electrodes 374, 376 are exposed portions of shaft 352, and the return electrode 360 is electrically insulated from shaft 352 such that a voltage difference may be applied between electrodes 374, 376 and electrode 360. In this embodiment, probe 350 may be used in at least two different modes, an ablation mode and a sub-ablation or thermal heating mode. In the ablation mode, voltage is applied between active electrode(s) 362 and return electrode 360 in the presence of electrically conductive fluid, as described above. In the ablation mode, electrodes 374, 376 are deactivated. In the thermal heating or coagulation mode, active electrode(s) 362 are deactivated and a voltage difference is applied between electrodes 374, 376 and electrode 360 such that a high frequency current 370 flows therebetween, as shown in FIG. 15B. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 372, 374.

Figure 15C:
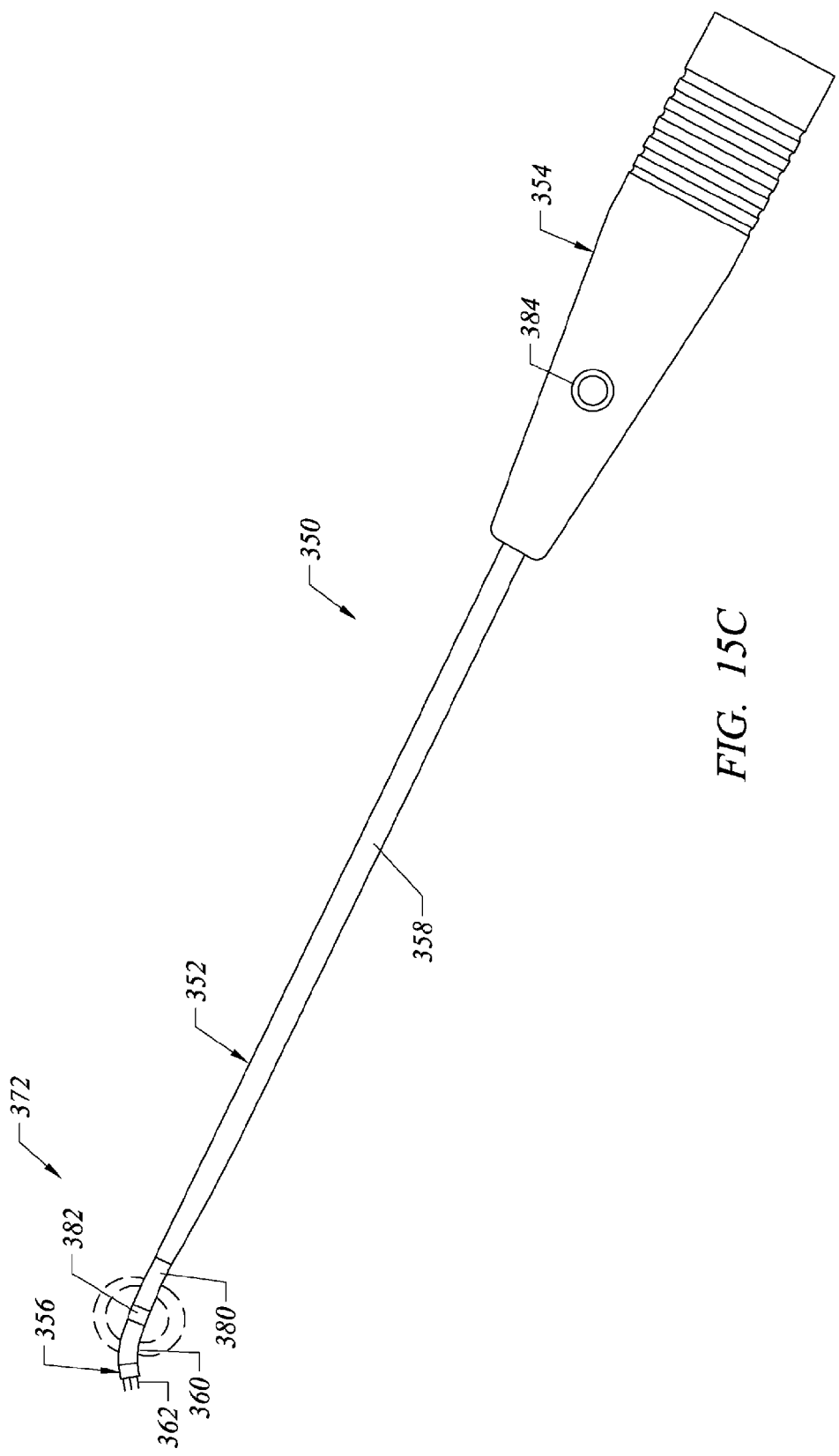

FIG. 15C illustrates another embodiment of probe 350 incorporating an electrode assembly 372 having one or more active electrode(s) 362 and a proximally spaced return electrode 360 as in previous embodiments. Return electrode 360 is typically spaced about 0.5 to 25 mm, preferably 1.0 to 5.0 mm from the active electrode(s) 362, and has an exposed length of about 1 to 20 mm. In addition, electrode assembly 372 includes a second active electrode 380 separated from return electrode 360 by an electrically insulating spacer 382. In this embodiment, handle 354 includes a switch 384 for toggling probe 350 between at least two different modes, an ablation mode and a sub-ablation or thermal heating mode. In the ablation mode, voltage is applied between active electrode(s) 362 and return electrode 360 in the presence of electrically conductive fluid, as described above. In the ablation mode, electrode 380 deactivated. In the thermal heating or coagulation mode, active electrode(s) 362 may be deactivated and a voltage difference is applied between electrode 380 and electrode 360 such that a high frequency current 370 flows therebetween. Alternatively, active electrode(s) 362 may not be deactivated as the higher resistance of the smaller electrodes may automatically send the electric current to electrode 380 without having to physically decouple electrode(s) 362 from the circuit. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 380.

Of course, it will be recognized that a variety of other embodiments may be used to accomplish similar functions as the embodiments described above. For example, electrosurgical probe 350 may include a plurality of helical bands formed around shaft 352, with one or more of the helical bands having an electrode coupled to the portion of the band such that one or more electrodes are formed on shaft 352 spaced axially from each other.

Figure 15D:
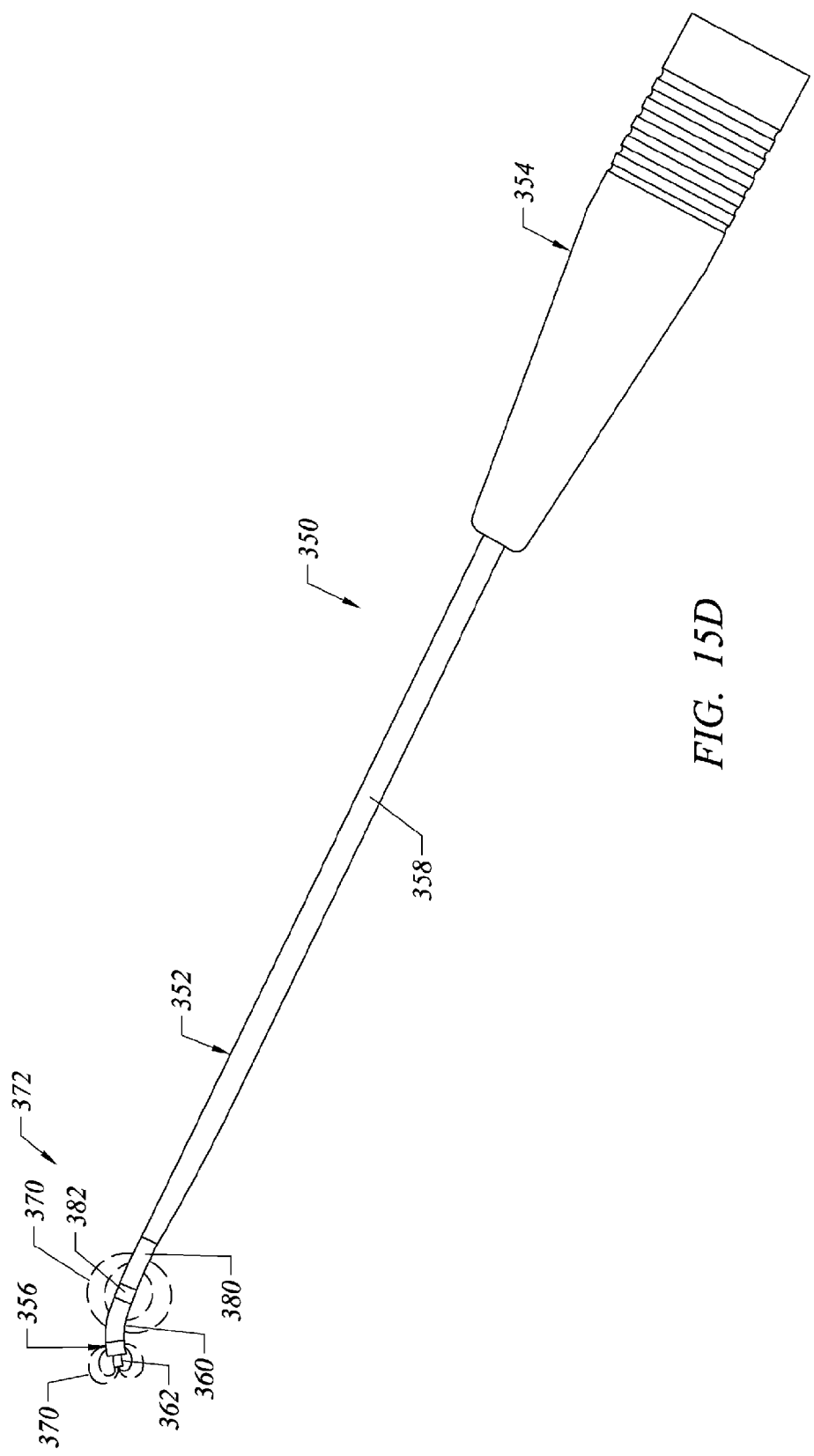

FIG. 15D illustrates another embodiment of the invention designed for channeling through tissue and creating lesions therein to treat spinal discs and/or snoring and sleep apnea. As shown, probe 350 is similar to the probe in FIG. 15C having a return electrode 360 and a third, coagulation electrode 380 spaced proximally from the return electrode 360. In this embodiment, active electrode 362 comprises a single electrode wire extending distally from insulating support member 356. Of course, the active electrode 362 may have a variety of configurations to increase the current densities on its surfaces, e.g., a conical shape tapering to a distal point, a hollow cylinder, loop electrode and the like. In the representative embodiment, support members 356 and 382 are constructed of inorganic material, such as ceramic, glass, silicone rubber, and the like. The proximal support member 382 may also comprise a more conventional organic material as this support member 382 will generally not be in the presence of a plasma that would otherwise etch or wear away an organic material.

The probe 350 in FIG. 15D does not include a switching element. In this embodiment, all three electrodes are activated when the power supply is activated. The return electrode 360 has an opposite polarity from the active and coagulation electrodes 362, 380 such that current 370 flows from the latter electrodes to the return electrode 360 as shown. In one embodiment, the electrosurgical system includes a voltage reduction element or a voltage reduction circuit for reducing the voltage applied between the coagulation electrode 380 and return electrode 360. The voltage reduction element allows the power supply 28 to, in effect, apply two different voltages simultaneously to two different electrodes. Thus, for channeling through tissue, the operator may apply a voltage sufficient to provide ablation of the tissue at the tip of the probe (i.e., tissue adjacent to the active electrode 362). At the same time, the voltage applied to the coagulation electrode 380 will be insufficient to ablate tissue. For thermal heating or coagulation of tissue, for example, the voltage reduction element will serve to reduce a voltage of about 100 to 300 volts RMS to about 45 to 90 volts RMS, which is a suitable voltage for coagulation of tissue without ablation (e.g., molecular dissociation) of the tissue.

In one representative embodiment, the voltage reduction element comprises a pair of capacitors forming a bridge divider (not shown) coupled to the power supply and coagulation electrode 380. The capacitors usually have a capacitance of about 200 to 500 pF (at 500 volts), and preferably about 300 to 350 pF (at 500 volts). Of course, the capacitors may be located in other places within the system, such as in, or distributed along the length of, the cable, the generator, the connector, etc. In addition, it will be recognized that other voltage reduction elements, such as diodes, transistors, inductors, resistors, capacitors, or combinations thereof, may be used in conjunction with the present invention. For example, the probe 350 may include a coded resistor (not shown) that is constructed to lower the voltage applied between the return and coagulation electrodes 360, 380. In addition, electrical circuits may be employed for this purpose.

Of course, for some procedures, the probe will typically not require a voltage reduction element. Alternatively, the probe may include a voltage increasing element or circuit, if desired. Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In one specific embodiment, the probe 350 is manufactured by first inserting an electrode wire (active electrode 362) through a ceramic tube (insulating member 360) such that a distal portion of the wire extends through the distal portion of the tube, and bonding the wire to the tube, typically with an appropriate epoxy. A stainless steel tube (return electrode 356) is then placed over the proximal portion of the ceramic tube, and a wire (e.g., nickel wire) is bonded, typically by spot welding, to the inside surface of the stainless steel tube. The stainless steel tube is coupled to the ceramic tube by epoxy, and the device is cured in an oven or other suitable heat source. A second ceramic tube (insulating member 382) is then placed inside of the proximal portion of the stainless steel tube, and bonded in a similar manner. The shaft 358 is then bonded to the proximal portion of the second ceramic tube, and an insulating sleeve (e.g. polyimide) is wrapped around shaft 358 such that only a distal portion of the shaft is exposed (i.e., coagulation electrode 380). The nickel wire connection will extend through the center of shaft 358 to connect return electrode 356 to the power supply. The active electrode 362 may form a distal portion of shaft 358, or it may also have a connector extending through shaft 358 to the power supply.

In use, the physician positions active electrode 362 adjacent to the tissue surface to be treated (i.e., a spinal disc). The power supply is activated to provide an ablation voltage between active and return electrodes 362, 360 and a coagulation or thermal heating voltage between coagulation and return electrodes 360, 380. An electrically conductive fluid is then provided around active electrode 362, and in the junction between the active and return electrodes 360, 362 to provide a current flow path therebetween. This may be accomplished in a variety of manners, as discussed above. The active electrode 362 is then advanced through the space left by the ablated tissue to form a channel in the disc. During ablation, the electric current between the coagulation and return electrode is typically insufficient to cause any damage to the surface of the tissue as these electrodes pass through the tissue surface into the channel created by active electrode 362. Once the physician has formed the channel to the appropriate depth, he or she will cease advancement of the active electrode, and will either hold the instrument in place for 5 to 30 seconds, or will immediately remove the distal tip of the instrument from the channel (see detailed discussion of this below). In either event, when the active electrode is no longer advancing, it will eventually stop ablating tissue.

Prior to entering the channel formed by the active electrode 362, an open circuit exists between return and coagulation electrodes 360, 380. Once coagulation electrode 380 enters this channel, electric current will flow from coagulation electrode 380, through the tissue surrounding the channel, to return electrode 360. This electric current will heat the tissue immediately surrounding the channel to coagulate any severed vessels at the surface of the channel. If the physician desires, the instrument may be held within the channel for a period of time to create a lesion around the channel, as discussed in more detail below.

Figure 16:
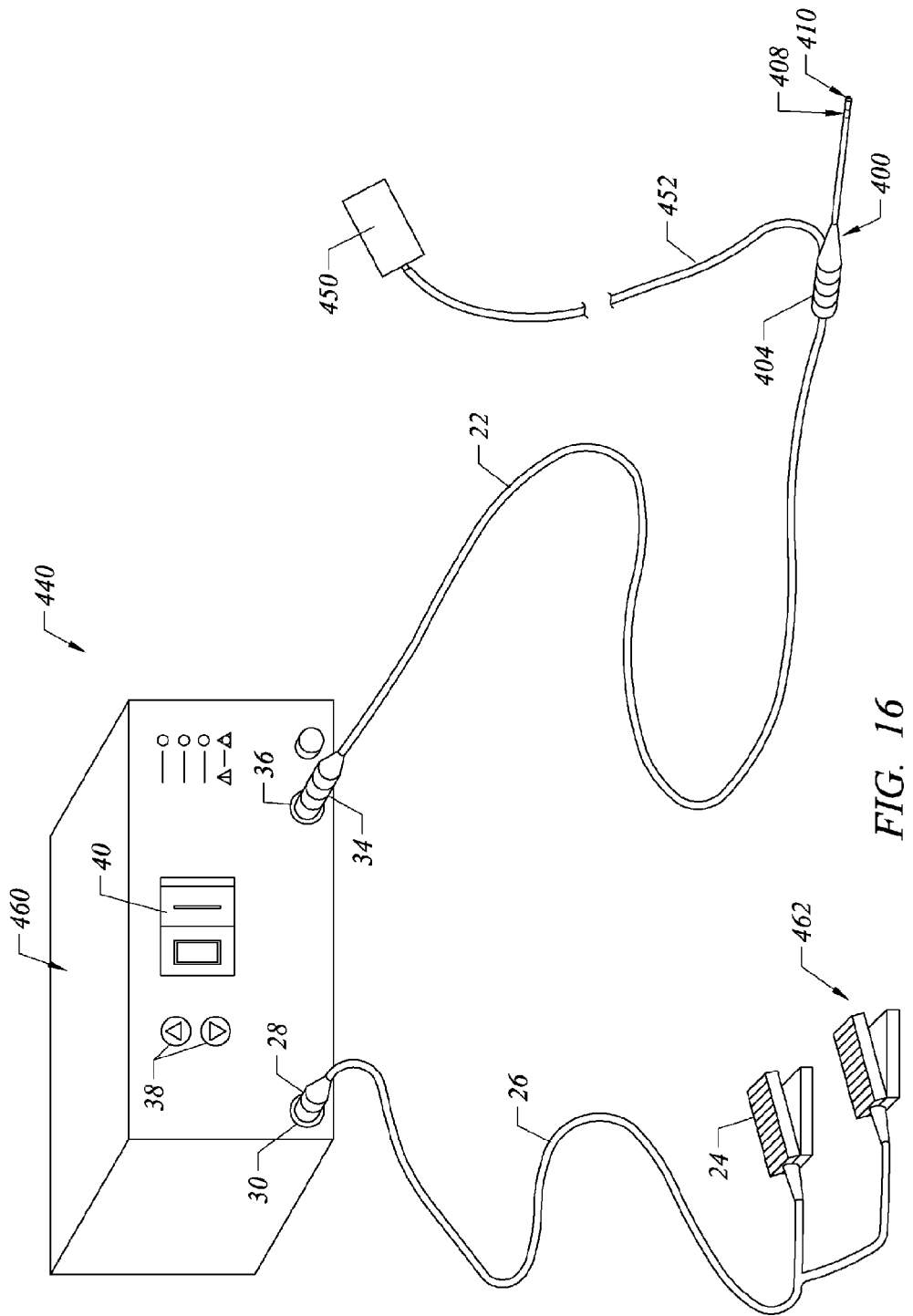
FIG. 16 illustrates an electrosurgical system incorporating a dispersive return pad for monopolar and/or bipolar operations.

FIG. 16 illustrates yet another embodiment of an electrosurgical system 440 incorporating a dispersive return pad 450 attached to the electrosurgical probe 400. In this embodiment, the invention functions in the bipolar mode as described above. In addition, the system 440 may function in a monopolar mode in which a high frequency voltage difference is applied between the active electrode(s) 410, and the dispersive return pad 450. In the exemplary embodiment, the pad 450 and the probe 400 are coupled together, and are both disposable, single-use items. The pad 450 includes an electrical connector 452 that extends into handle 404 of probe 400 for direct connection to the power supply. Of course, the invention would also be operable with a standard return pad that connects directly to the power supply. In this embodiment, the power supply 460 will include a switch, e.g., a foot pedal 462, for switching between the monopolar and bipolar modes. In the bipolar mode, the return path on the power supply is coupled to return electrode 408 on probe 400, as described above. In the monopolar mode, the return path on the power supply is coupled to connector 452 of pad 450, active electrode(s) 410 are decoupled from the electrical circuit, and return electrode 408 functions as the active electrode. This allows the surgeon to switch between bipolar and monopolar modes during, or prior to, the surgical. In some cases, it may be desirable to operate in the monopolar mode to provide deeper current penetration and, thus, a greater thermal heating of the tissue surrounding the return electrodes. In other cases, such as ablation of tissue, the bipolar modality may be preferable to limit the current penetration to the tissue.

In one configuration, the dispersive return pad 450 is adapted for coupling to an external surface of the patient in a region substantially close to the target region. For example, during the treatment of tissue in the head and neck, the dispersive return pad is designed and constructed for placement in or around the patient's shoulder, upper back, or upper chest region. This design limits the current path through the patient's body to the head and neck area, which minimizes the damage that may be generated by unwanted current paths in the patient's body, particularly by limiting current flow through the patient's heart. The return pad is also designed to minimize the current densities at the pad, to thereby minimize patient skin burns in the region where the pad is attached.

Figure 17:
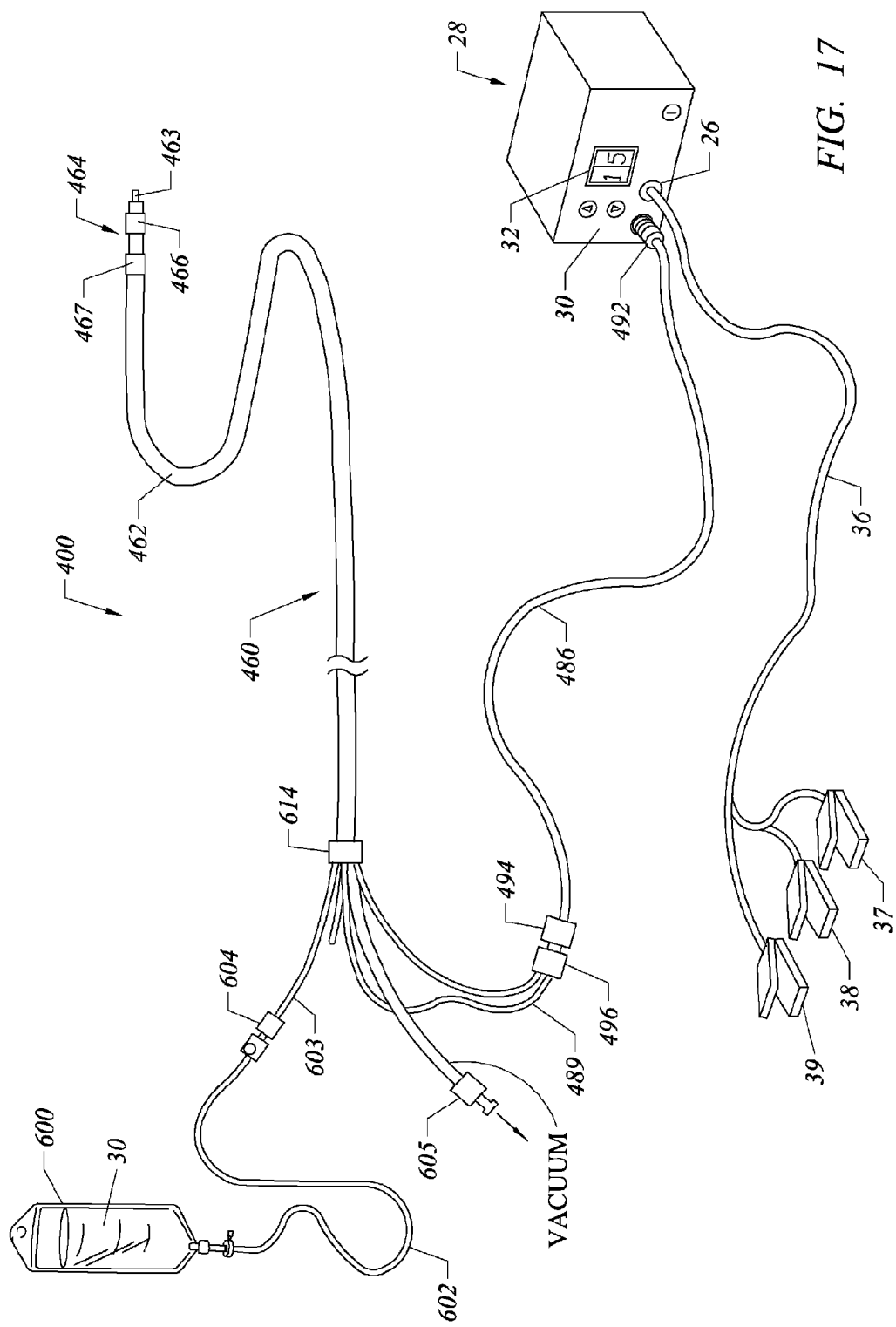
FIG. 17 illustrates a catheter system for electrosurgical treatment of intervertebral discs according to the present invention.
Figure 18:
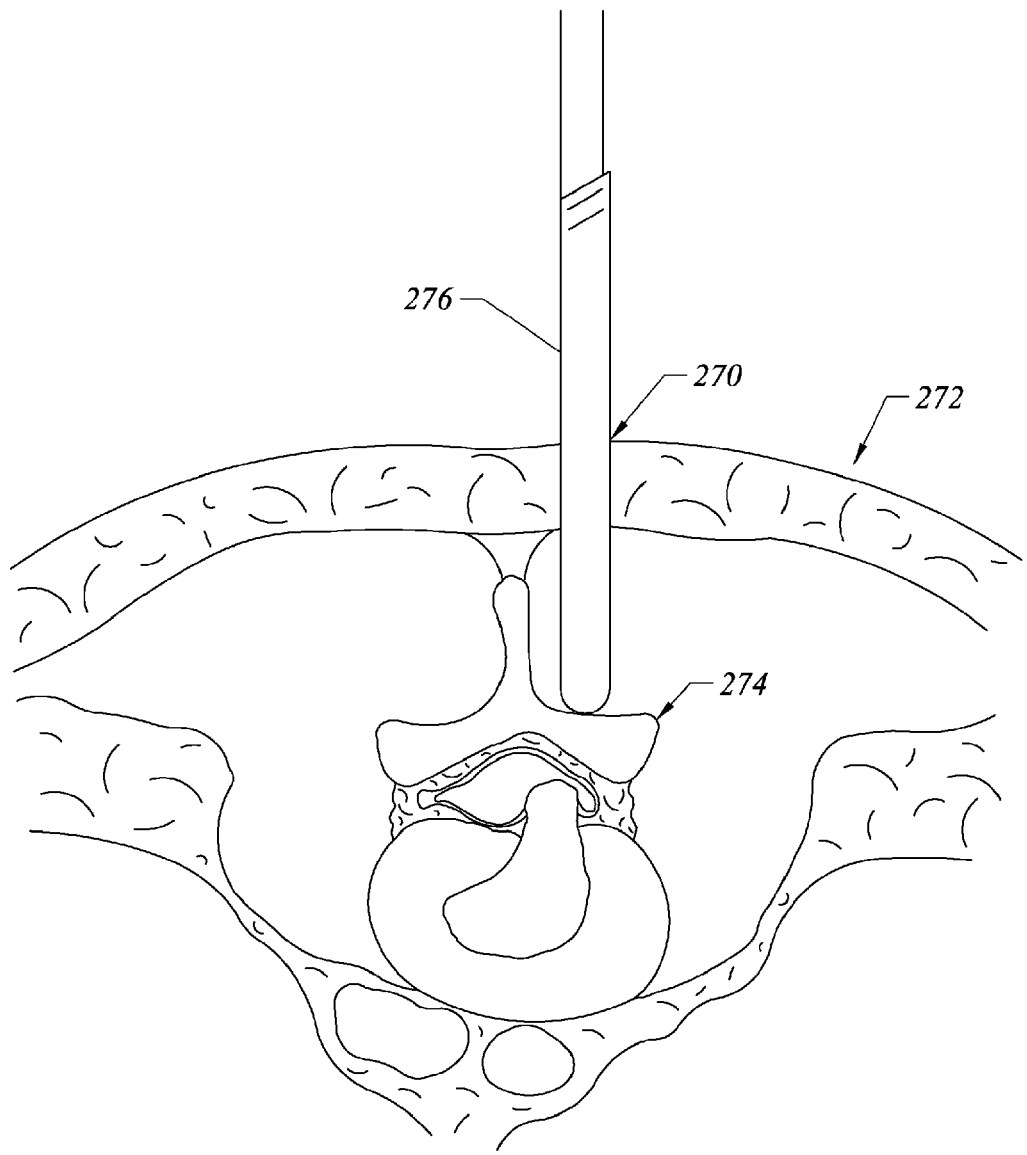
FIGS. 18-22 illustrate a method of performing a microendoscopic discectomy according to the principles of the present invention.

Referring to FIG. 17, the electrosurgical device according to the present invention may also be configured as a catheter system 400. As shown in FIG. 17, a catheter system 400 generally comprises an electrosurgical catheter 460 connected to a power supply 28 by an interconnecting cable 486 for providing high frequency voltage to a target tissue and an irrigant reservoir or source 600 for providing electrically conducting fluid to the target site. Catheter 460 generally comprises an elongate, flexible shaft body 462 including a tissue removing or ablating region 464 at the distal end of body 462. The proximal portion of catheter 460 includes a multi-lumen fitment 614 which provides for interconnections between lumens and electrical leads within catheter 460 and conduits and cables proximal to fitment 614. By way of example, a catheter electrical connector 496 is removably connected to a distal cable connector 494 which, in turn, is removably connectable to generator 28 through connector 492. One or more electrically conducting lead wires (not shown) within catheter 460 extend between one or more active electrodes 463 and a coagulation electrode 467 at tissue ablating region 464 and one or more corresponding electrical terminals (also not shown) in catheter connector 496 via active electrode cable branch 487. Similarly, a return electrode 466 at tissue ablating region 464 are coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque control for rotation of electrode terminals during tissue engagement. This rigid portion of the catheter body 462 preferably extends only about 7 to 10 mm while the remainder of the catheter body 462 is flexible to provide good trackability during advancement and positioning of the electrodes adjacent target tissue.

Conductive fluid 30 is provided to tissue ablation region 464 of catheter 460 via a lumen (not shown in FIG. 17) within catheter 460. Fluid is supplied to lumen from the source along a conductive fluid supply line 602 and a conduit 603, which is coupled to the inner catheter lumen at multi-lumen fitment 114. The source of conductive fluid (e.g., isotonic saline) may be an irrigant pump system (not shown) or a gravity-driven supply, such as an irrigant reservoir 600 positioned several feet above the level of the patient and tissue ablating region 8. A control valve 604 may be positioned at the interface of fluid supply line 602 and conduit 603 to allow manual control of the flow rate of electrically conductive fluid 30. Alternatively, a metering pump or flow regulator may be used to precisely control the flow rate of the conductive fluid.

System 400 further includes an aspiration or vacuum system (not shown) to aspirate liquids and gases from the target site. The aspiration system will usually comprise a source of vacuum coupled to fitment 614 by a aspiration connector 605.

The present invention is particularly useful in microendoscopic discectomy procedures, e.g., for decompressing a nerve root with a lumbar discectomy. As shown in FIGS. 18-23, a percutaneous penetration 270 is made in the patients' back 272 so that the superior lamina 274 can be accessed. Typically, a small needle (not shown) is used initially to localize the disc space level, and a guidewire (not shown) is inserted and advanced under lateral fluoroscopy to the inferior edge of the lamina 274. Sequential cannulated dilators 276 are inserted over the guide wire and each other to provide a hole from the incision 220 to the lamina 274. The first dilator may be used to "palpate" the lamina 274, assuring proper location of its tip between the spinous process and facet complex just above the inferior edge of the lamina 274. As shown in FIG. 21, a tubular retractor 278 is then passed over the largest dilator down to the lamina 274.

The dilators 276 are removed, establishing an operating corridor within the tubular retractor 278.

Figure 19:
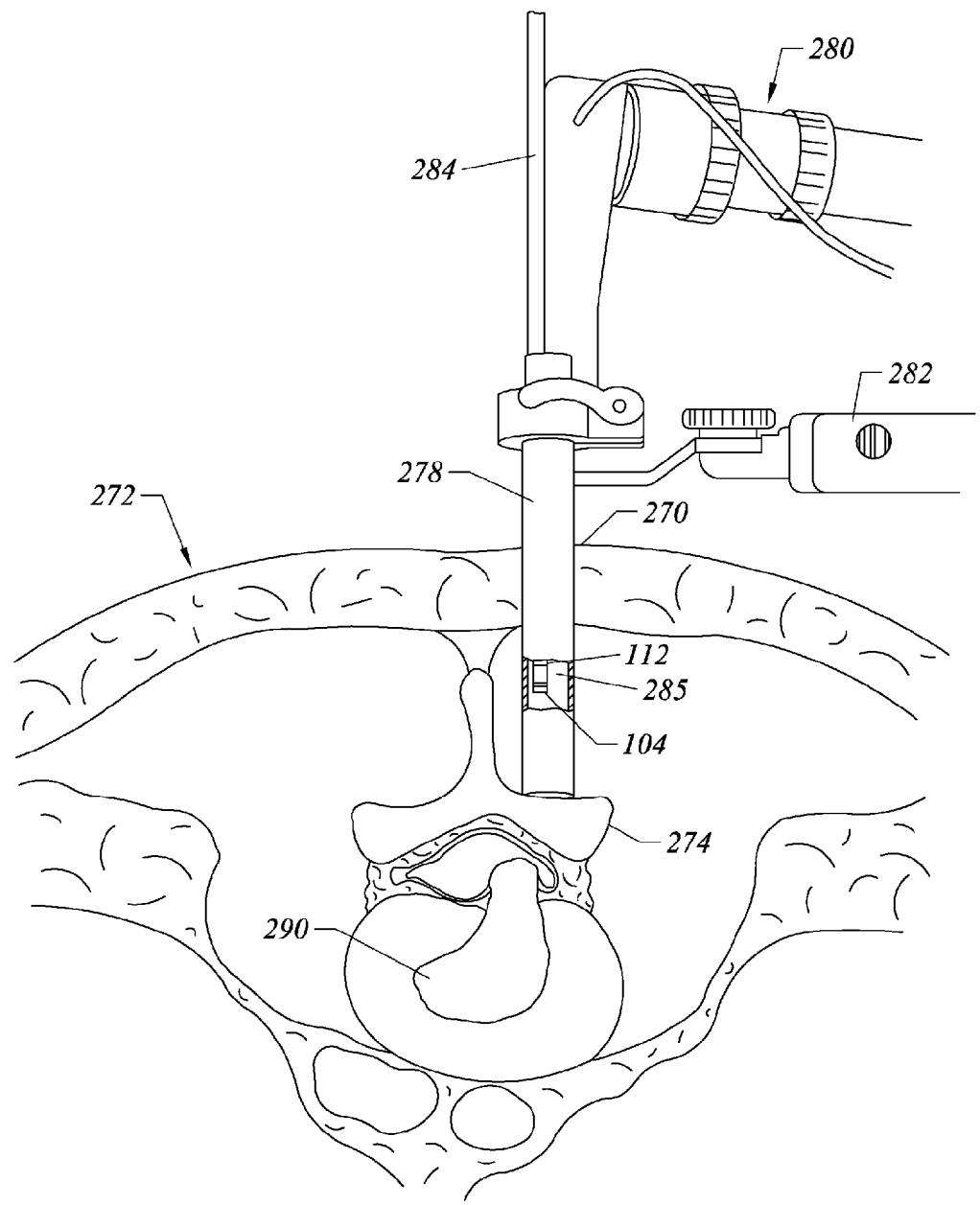

As shown in FIG. 19, an endoscope 280 is then inserted into the tubular retractor 278 and a ring clamp 282 is used to secure the endoscope 280. Typically, the formation of the operating corridor within retractor 278 requires the removal of soft tissue, muscle or other types of tissue that were forced into this corridor as the dilators 276 and retractor 278 were advanced down to the lamina 274. This tissue is usually removed with mechanical instruments, such as pituitary rongeurs, curettes, graspers, cutters, drills, microdebriders, and the like. Unfortunately, these mechanical instruments greatly lengthen and increase the complexity of the procedure. In addition, these instruments sever blood vessels within this tissue, usually causing profuse bleeding that obstructs the surgeon's view of the target site.

According to one aspect of the present invention, an electrosurgical probe or catheter 284 as described above is introduced into the operating corridor within the retractor 278 to remove the soft tissue, muscle and other obstructions from this corridor so that the surgeon can easily access and visualization the lamina 274. Once the surgeon has reached has introduced the probe 284, electrically conductive fluid 285 is delivered through tube 233 and opening 237 to the tissue (see FIG. 2). The fluid flows past the return electrode 112 to the electrode terminals 104 at the distal end of the shaft. The rate of fluid flow is controlled with valve 17 (FIG. 1) such that the zone between the tissue and electrode support 102 is constantly immersed in the fluid. The power supply 28 is then turned on and adjusted such that a high frequency voltage difference is applied between electrode terminals 104 and return electrode 112. The electrically conductive fluid provides the conduction path (see current flux lines) between electrode terminals 104 and the return electrode 112.

The high frequency voltage is sufficient to convert the electrically conductive fluid (not shown) between the target tissue and electrode terminal(s)104 into an ionized vapor layer or plasma (not shown). As a result of the applied voltage difference between electrode terminal(s) 104 and the target tissue (i.e., the voltage gradient across the plasma layer), charged particles in the plasma (e.g., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane.

During the process, the gases will be aspirated through opening 209 and suction tube 211 to a vacuum source. In addition, excess electrically conductive fluid, and other fluids (e.g., blood) will be aspirated from the operating corridor to facilitate the surgeon's view. During ablation of the tissue, the residual heat generated by the flow of electric current through the tissue (typically resulting in a temperature of less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure.

Another advantage of the present invention is the ability to precisely ablate soft tissue without causing necrosis or thermal damage to the underlying and surrounding tissues, nerves, or bone. In addition, the voltage can be controlled so that the energy directed to the target site is insufficient to ablate the lamina 274 so that the surgeon can literally clean the tissue off the lamina 274, without ablating or otherwise effecting significant damage to the lamina.

Figure 20:
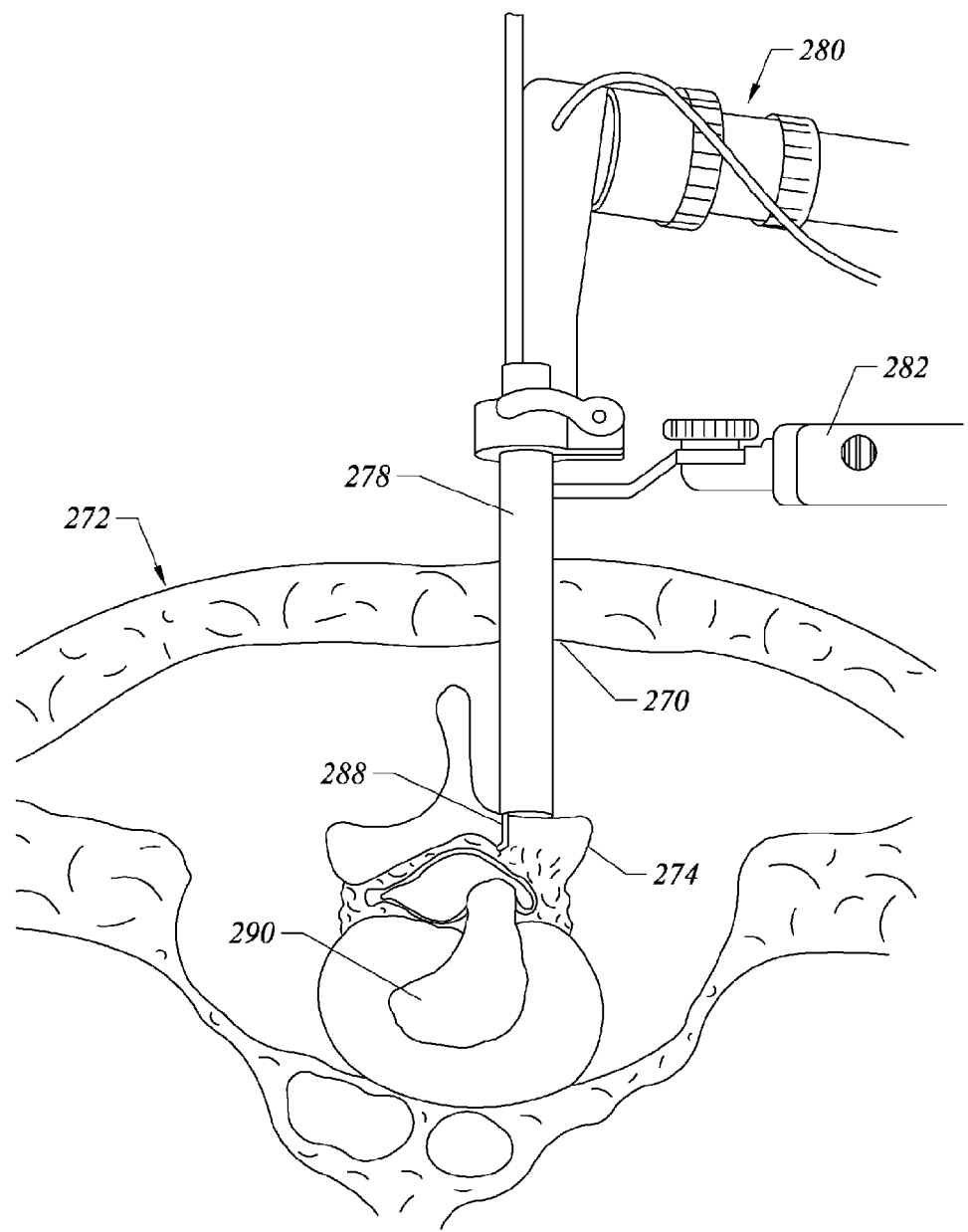
Figure 21:
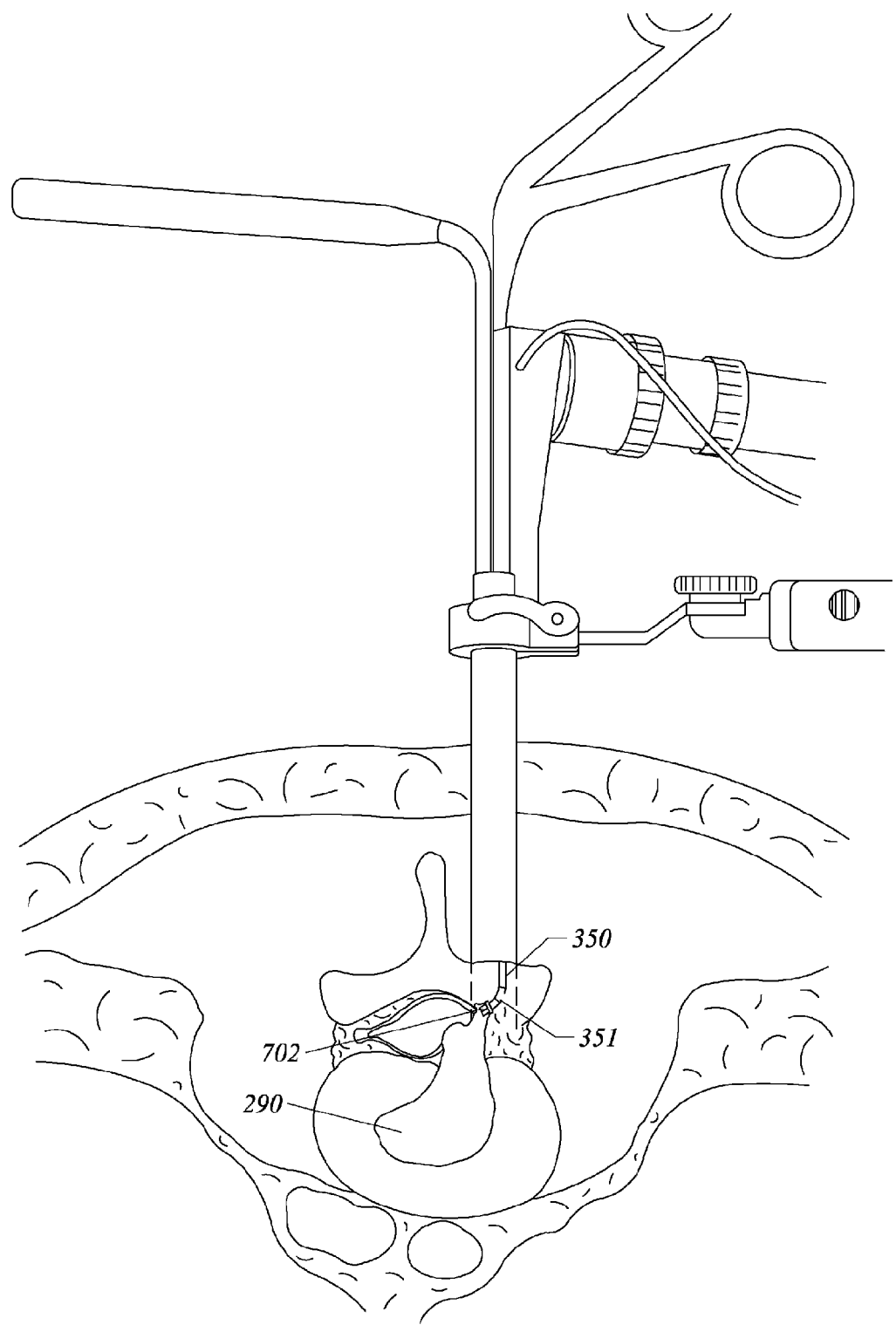

Referring now to FIGS. 20 and 21, once the operating corridor is sufficiently cleared, a laminotomy and medial facetectomy is accomplished either with conventional techniques (e.g., Kerrison punch or a high speed drill) or with the electrosurgical probe 284 as discussed above. After the nerve root is identified, medical retraction can be achieved with a retractor 288, or the present invention can be used to precisely ablate the disc. If necessary, epidural veins are cauterized either automatically or with the coagulation mode of the present invention. If an annulotomy is necessary, it can be accomplished with a microknife or the ablation mechanism of the present invention while protecting the nerve root with the retractor 288. The herniated disc 290 is then removed with a pituitary rongeur in a standard fashion, or once again through ablation as described above.

In another embodiment, the present invention involves a channeling technique in which small holes or channels are formed within the disc 290, and thermal energy is applied to the tissue surface immediately surrounding these holes or channels to cause thermal damage to the tissue surface, thereby stiffening and debulking the surrounding tissue structure of the disc. Applicant has discovered that such stiffening of the tissue structure in the disc helps to reduce the pressure applied against the spinal nerves by the disc, thereby relieving back and neck pain.

As shown in FIG. 21, the electrosurgical instrument 350 is introduced to the target site at the disc 290 as described above, or in another percutaneous manner (see FIGS. 23-25 below). The electrode assembly 351 is positioned adjacent to or against the disc surface, and electrically conductive fluid is delivered to the target site, as described above. Alternatively, the conductive fluid is applied to the target site, or the distal end of probe 350 is dipped into conductive fluid or gel prior to introducing the probe 350 into the patient. The power supply 28 is then activated and adjusted such that a high frequency voltage difference is applied to the electrode assembly as described above.

Depending on the procedure, the surgeon may translate the electrodes relative to the target disc tissue to form holes, channels, stripes, divots, craters, or the like within the disc. In addition, the surgeon may purposely create some thermal damage within these holes, or channels to form scar tissue that will stiffen and debulk the disc. In one embodiment, the physician axially translates the electrode assembly 351 into the disc tissue as the tissue is volumetrically removed to form one or more holes 702 therein (see also FIG. 22). The holes 702 will typically have a diameter of less than 2 mm, preferably less than 1 mm. In another embodiment (not shown), the physician translates the active electrode across the outer surface of the disc to form one or more channels or troughs. Applicant has found that the present invention can quickly and cleanly create such holes, divots, or channels in tissue with the cold ablation technology described herein. A more complete description of methods for forming holes or channels in tissue can be found in commonly assigned U.S. Pat. No. 5,683,366, the complete disclosure of which is incorporated herein by reference for all purposes.

Figure 22:
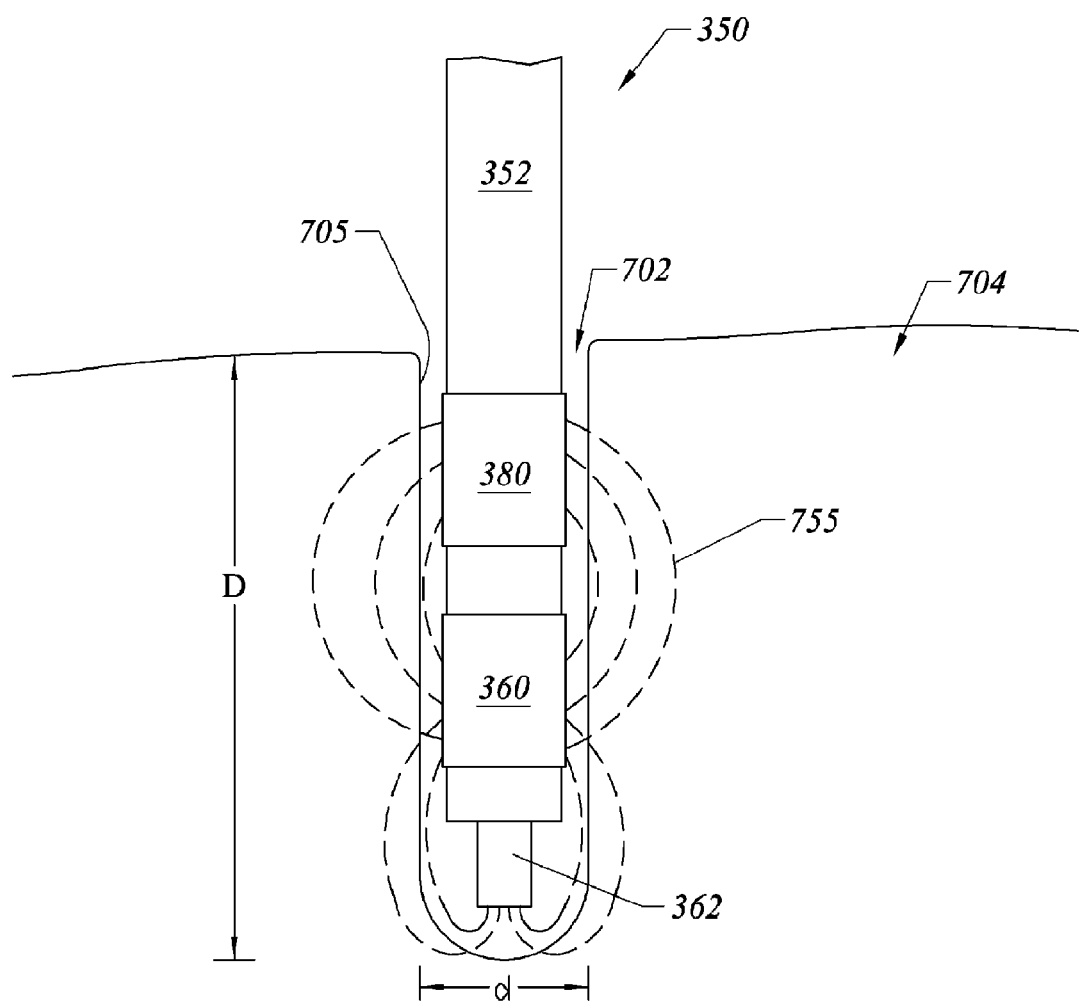

FIG. 22 is a more detailed viewed of the probe 350 of FIG. 15D forming a hole 702 in a disc 290. Hole 702 is preferably formed with the methods described in detail above. Namely, a high frequency voltage difference is applied between active and return electrodes 362, 360, respectively, in the presence of an electrically conductive fluid such that an electric current 361 passes from the active electrode 362, through the conductive fluid, to the return electrode 360. As shown in FIG. 22, this will result in shallow or no current penetration into the disc tissue 704. The fluid may be delivered to the target site, applied directly to the target site, or the distal end of the probe may be dipped into the fluid prior to the procedure. The voltage is sufficient to vaporize the fluid around active electrode 362 to form a plasma with sufficient energy to effect molecular dissociation of the tissue. The distal end of the probe 350 is then axially advanced through the tissue as the tissue is removed by the plasma in front of the probe 350. The holes 702 will typically have a depth D in the range of about 0.5 to 2.5 cm, preferably about 1.2 to 1.8 cm, and a diameter d of about 0.5 to 5 mm, preferably about 1.0 to 3.0 mm. The exact diameter will, of course, depend on the diameter of the electrosurgical probe used for the procedure.

During the formation of each hole 702, the conductive fluid between active and return electrodes 362, 360 will generally minimize current flow into the surrounding tissue, thereby minimizing thermal damage to the tissue. Therefore, severed blood vessels on the surface 705 of the hole 702 may not be coagulated as the electrodes 362 advance through the tissue. In addition, in some procedures, it may be desired to thermally damage the surface 705 of the hole 702 to stiffen the tissue. For these reasons, it may be desired in some procedures to increase the thermal damage caused to the tissue surrounding hole 702. In the embodiment shown in FIG. 15D, it may be necessary to either: (1) withdraw the probe 350 slowly from hole 702 after coagulation electrode 380 has at least partially advanced past the outer surface of the disc tissue 704 into the hole 702 (as shown in FIG. 22); or (2) hold the probe 350 within the hole 702 for a period of time, e.g., on the order of 1 to 30 seconds. Once the coagulation electrode is in contact with, or adjacent to, tissue, electric current 755 flows through the tissue surrounding hole 702 and creates thermal damage therein. The coagulation and return electrodes 380, 360 both have relatively large, smooth exposed surfaces to minimize high current densities at their surfaces, which minimizes damage to the surface 705 of hole. Meanwhile, the size and spacing of these electrodes 360, 380 allows for relatively deep current penetration into the tissue 704. In the representative embodiment, the thermal necrosis 706 will extend about 1.0 to 5.0 mm from surface 705 of hole 702. In this embodiment, the probe may include one or more temperature sensors (not shown) on probe coupled to one or more temperature displays on the power supply 28 such that the physician is aware of the temperature within the hole 702 during the procedure.

In other embodiments, the physician switches the electrosurgical system from the ablation mode to the sub-ablation or thermal heating mode after the hole 702 has been formed. This is typically accomplished by pressing a switch or foot pedal to reduce the voltage applied to a level below the threshold required for ablation for the particular electrode configuration and the conductive fluid being used in the procedure (as described above). In the sub-ablation mode, the physician will then remove the distal end of the probe 350 from the hole 702. As the probe is withdrawn, high frequency current flows from the active electrodes 362 through the surrounding tissue to the return electrode 360. This current flow heats the tissue and coagulates severed blood vessels at surface 704.

In another embodiment, the electrosurgical probe of the present invention can be used to ablate and/or contract soft tissue within the disc 290 to allow the annulus 292 to repair itself to prevent reoccurrence of this procedure. For tissue contraction, a sufficient voltage difference is applied between the electrode terminals 104 and the return electrode 112 to elevate the tissue temperature from normal body temperatures (e.g., 37° C.) to temperatures in the range of 45° C. to 90° C., preferably in the range from 60° C. to 70° C. This temperature elevation causes contraction of the collagen connective fibers within the disc tissue so that the disc 290 withdraws into the annulus 292.

In one method of tissue contraction according to the present invention, an electrically conductive fluid is delivered to the target site as described above, and heated to a sufficient temperature to induce contraction or shrinkage of the collagen fibers in the target tissue. The electrically conducting fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to the electrode terminal(s) in contact with the electrically conducting fluid. The current emanating from the electrode terminal(s) 104 heats the fluid and generates a jet or plume of heated fluid, which is directed towards the target tissue. The heated fluid elevates the temperature of the collagen sufficiently to cause hydrothermal shrinkage of the collagen fibers. The return electrode 112 draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the electrode terminal(s) 104 are held away from the tissue a sufficient distance such that the RF current does not pass into the tissue at all, but rather passes through the electrically conducting fluid back to the return electrode. In this embodiment, the primary mechanism for imparting energy to the tissue is the heated fluid, rather than the electric current.

In an alternative embodiment, the electrode terminal(s) 104 are brought into contact with, or close proximity to, the target tissue so that the electric current passes directly into the tissue to a selected depth. In this embodiment, the return electrode draws the electric current away from the tissue site to limit its depth of penetration into the tissue. Applicant has discovered that the depth of current penetration also can be varied with the electrosurgical system of the present invention by changing the frequency of the voltage applied to the electrode terminal and the return electrode. This is because the electrical impedance of tissue is known to decrease with increasing frequency due to the electrical properties of cell membranes which surround electrically conductive cellular fluid. At lower frequencies (e.g., less than 350 kHz), the higher tissue impedance, the presence of the return electrode and the electrode terminal configuration of the present invention (discussed in detail below) cause electric current to penetrate less deeply into the tissue, resulting in a smaller depth of tissue heating. In an exemplary embodiment, an operating frequency of about 100 to 200 kHz is applied to the electrode terminal(s) to obtain shallow depths of collagen shrinkage (e.g., usually less than 1.5 mm and preferably less than 0.5 mm).

In another aspect of the invention, the size (e.g., diameter or principal dimension) of the electrode terminals employed for treating the tissue are selected according to the intended depth of tissue treatment. As described previously in copending patent application PCT International Application, U.S. National Phase Serial No. PCT/US94/05168, the depth of current penetration into tissue increases with increasing dimensions of an individual active electrode (assuming other factors remain constant, such as the frequency of the electric current, the return electrode configuration, etc.). The depth of current penetration (which refers to the depth at which the current density is sufficient to effect a change in the tissue, such as collagen shrinkage, irreversible necrosis, etc.) is on the order of the active electrode diameter for the bipolar configuration of the present invention and operating at a frequency of about 100 kHz to about 200 kHz. Accordingly, for applications requiring a smaller depth of current penetration, one or more electrode terminals of smaller dimensions would be selected. Conversely, for applications requiring a greater depth of current penetration, one or more electrode terminals of larger dimensions would be selected.

Figure 23:
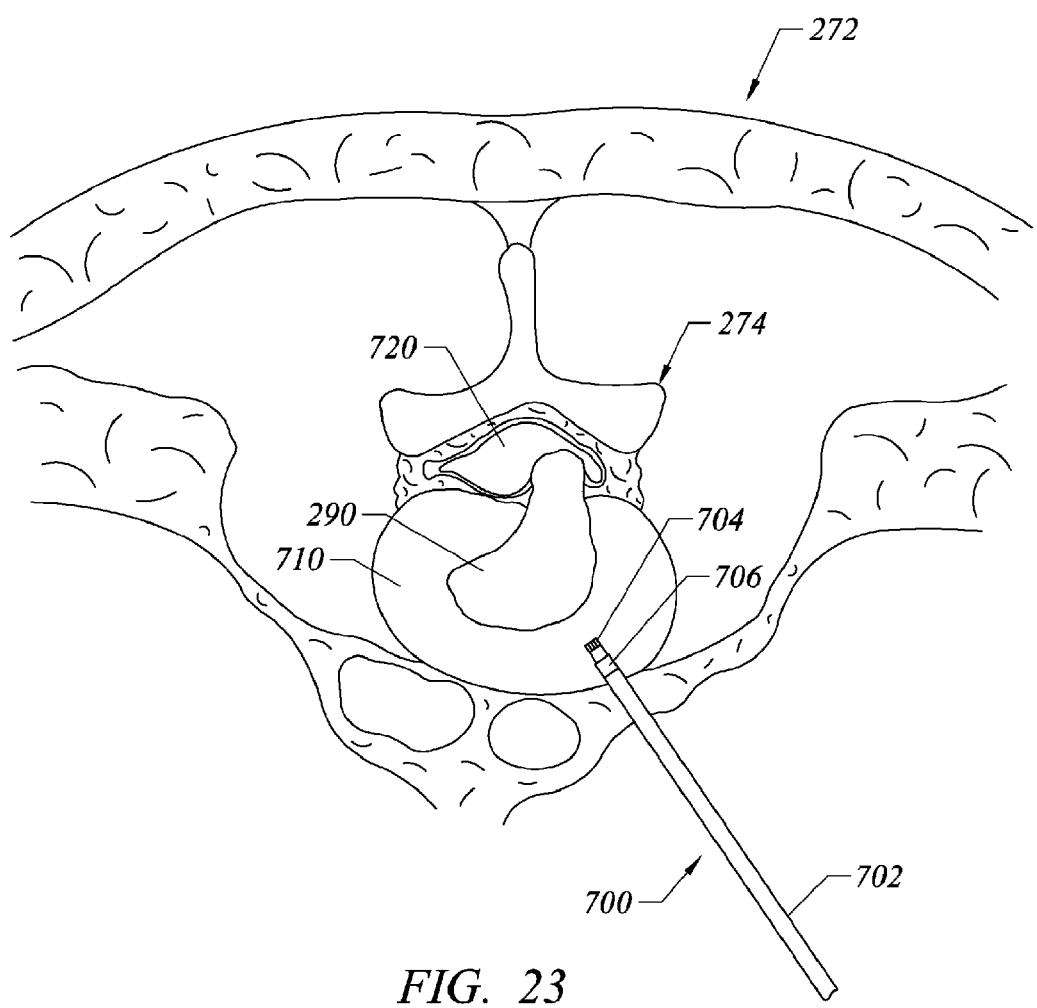
FIGS. 23-25 illustrates another method of treating a spinal disc with one of the catheters or probes of the present invention.
Figure 24:
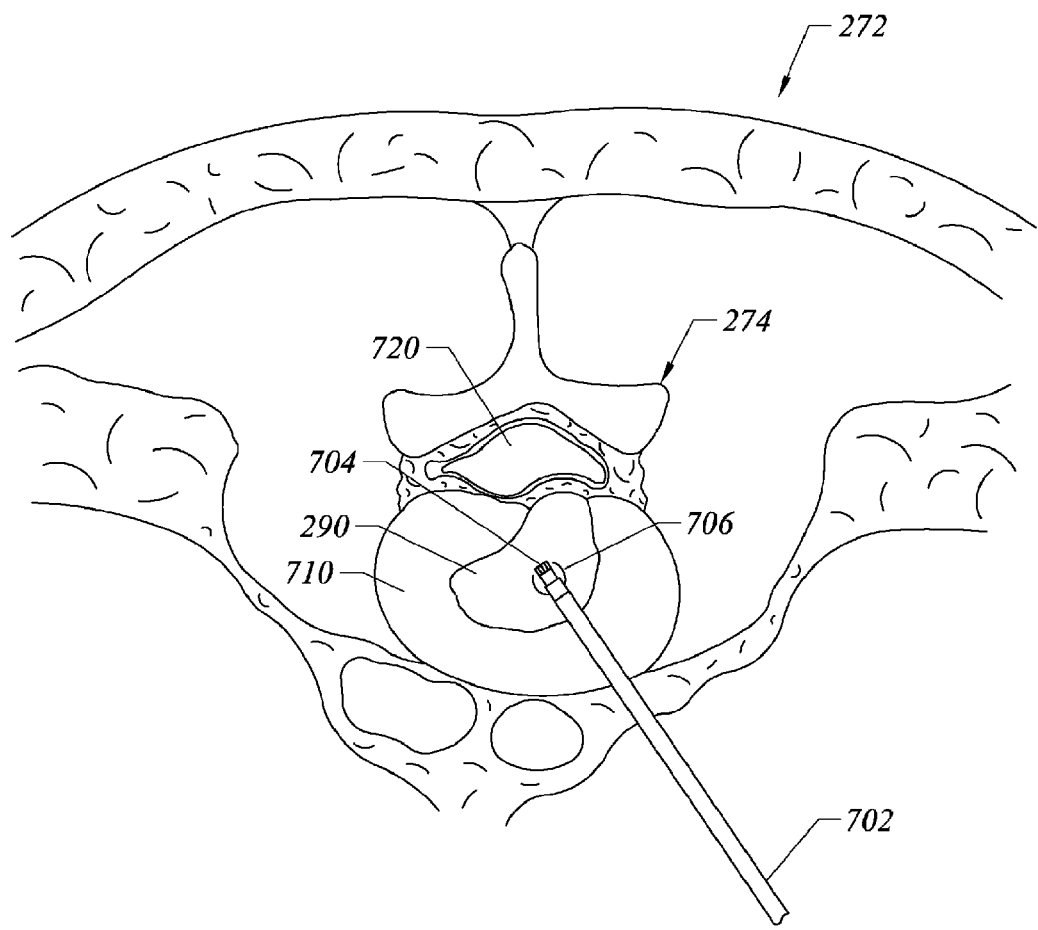
Figure 25:
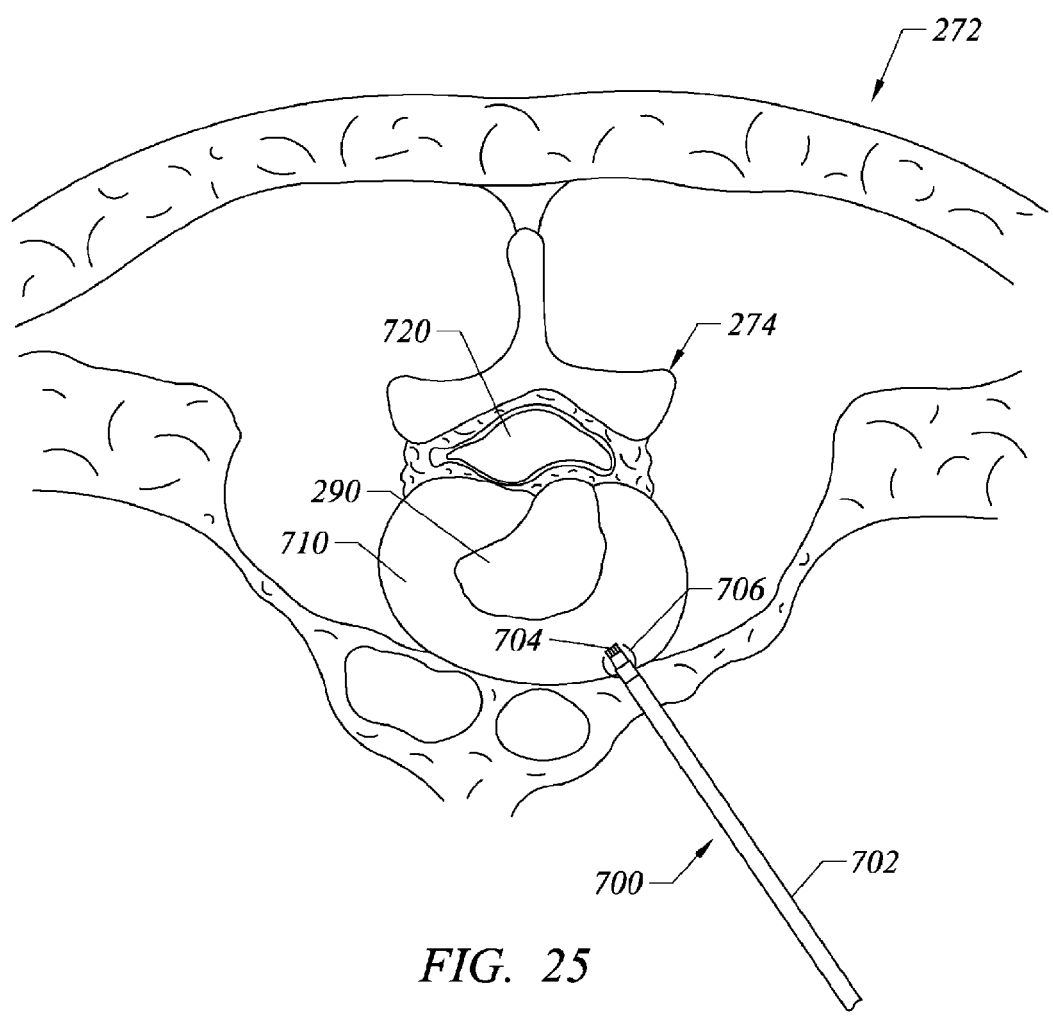

FIGS. 23-25 illustrate another system and method for treating swollen or herniated spinal discs according to the present invention. In this procedure, an electrosurgical probe 700 comprises a long, thin needle-like shaft 702 (e.g., on the order of about 1 mm in diameter or less) that can be percutaneously introduced into the spine. The shaft 702 may or may not be flexible, depending on the method of access chosen by the physician. The probe shaft 702 will include one or more active electrode(s) 704 for applying electrical energy to tissues within the spine. The probe 700 may include one or more return electrode(s) 706, or the return electrode may be positioned on the patient's back, as a dispersive pad (not shown). As discussed below, however, a bipolar design is preferable.

As shown in FIG. 23, the distal portion of shaft 702 is introduced, e.g., via a small percutaneous penetration, into the annulus 710 of the target spinal disc. To facilitate this process, the distal end of shaft 702 may taper down to a sharper point (e.g., a needle), which can then be retracted to expose active electrode(s) 704. Alternatively, the electrodes may be formed around the surface of the tapered distal portion of the shaft (not shown). In either embodiment, the distal end of the shaft is delivered through the annulus 710 to the target nucleus pulposus 290, which may be herniated, extruded, non-extruded, or simply swollen. While the distal end of probe 700 is positioned within the nucleus pulposus as shown in FIG. 24, a high frequency voltage is applied between active electrode(s) 704 and return electrode(s) 706 to heat the surrounding collagen containing tissue to suitable temperatures for contraction of collagen fibers (i.e., typically about 55° C. to about 70° C.). As discussed above, this procedure may be accomplished with a monopolar configuration, as well. However, applicant has found that the bipolar configuration shown in FIGS. 23-25 provides enhanced control of the high frequency current, which reduces the risk of spinal nerve damage.

As shown in FIGS. 24 and 25, once the nucleus pulposus 290 has been sufficiently contracted to retract from impingement on the nerve root 720, the probe 700 is removed from the target site. In a representative embodiment, application of the high frequency voltage between active and return electrode(s) 704, 706 is continued as the probe is withdrawn through the annulus 710. This voltage is sufficient to cause contraction of the collagen fibers within the annulus 710, which allows the annulus 710 to contract around the hole formed by probe 700, thereby improving the healing of this hole. Thus, the probe 700 seals its own passage as it is withdrawn from the disc.

Figure 26:
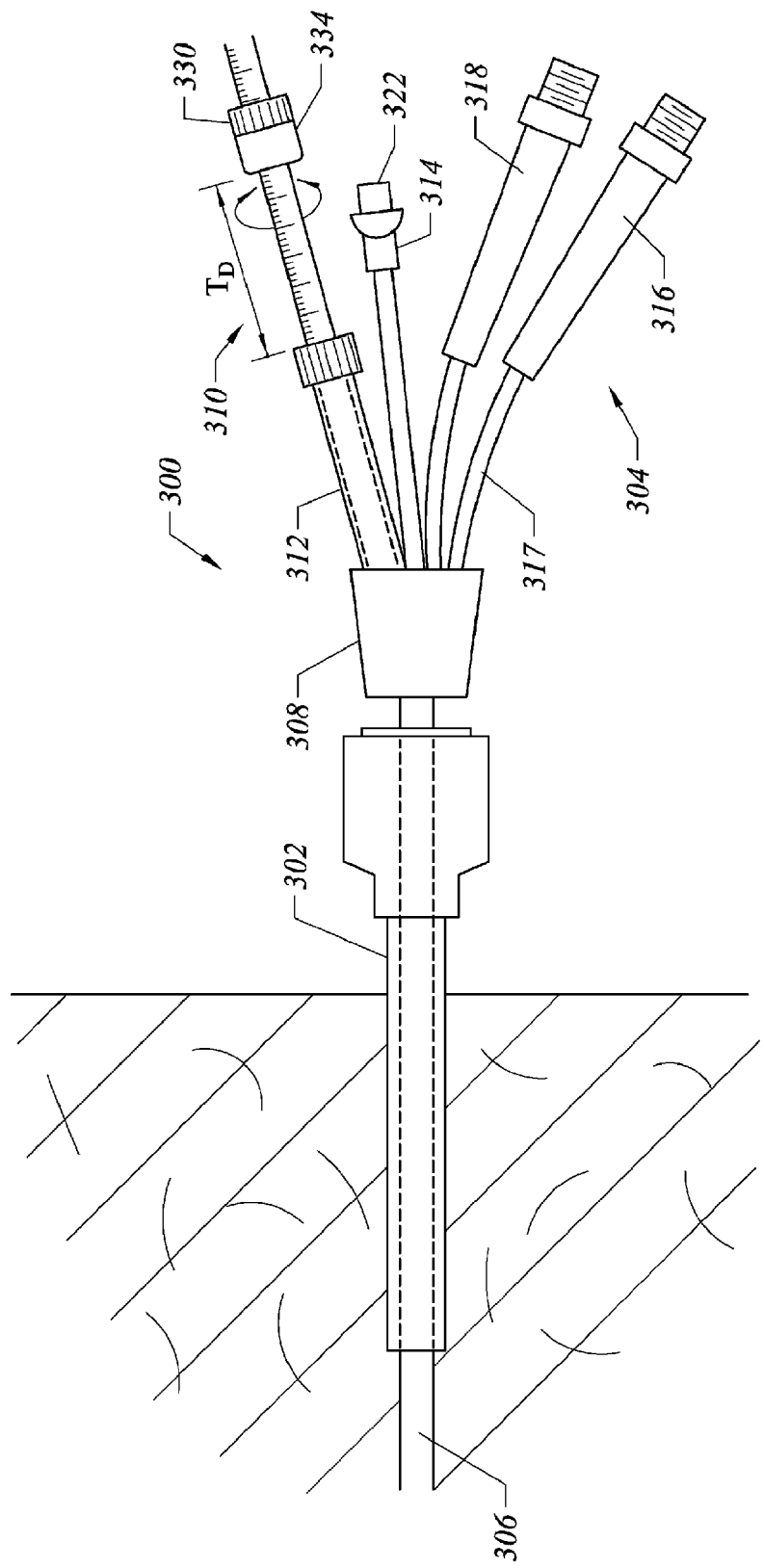
FIG. 26 is a schematic view of the proximal portion of another electrosurgical system for endoscopic spine surgery incorporating an electrosurgical instrument according to the present invention.
Figure 27:
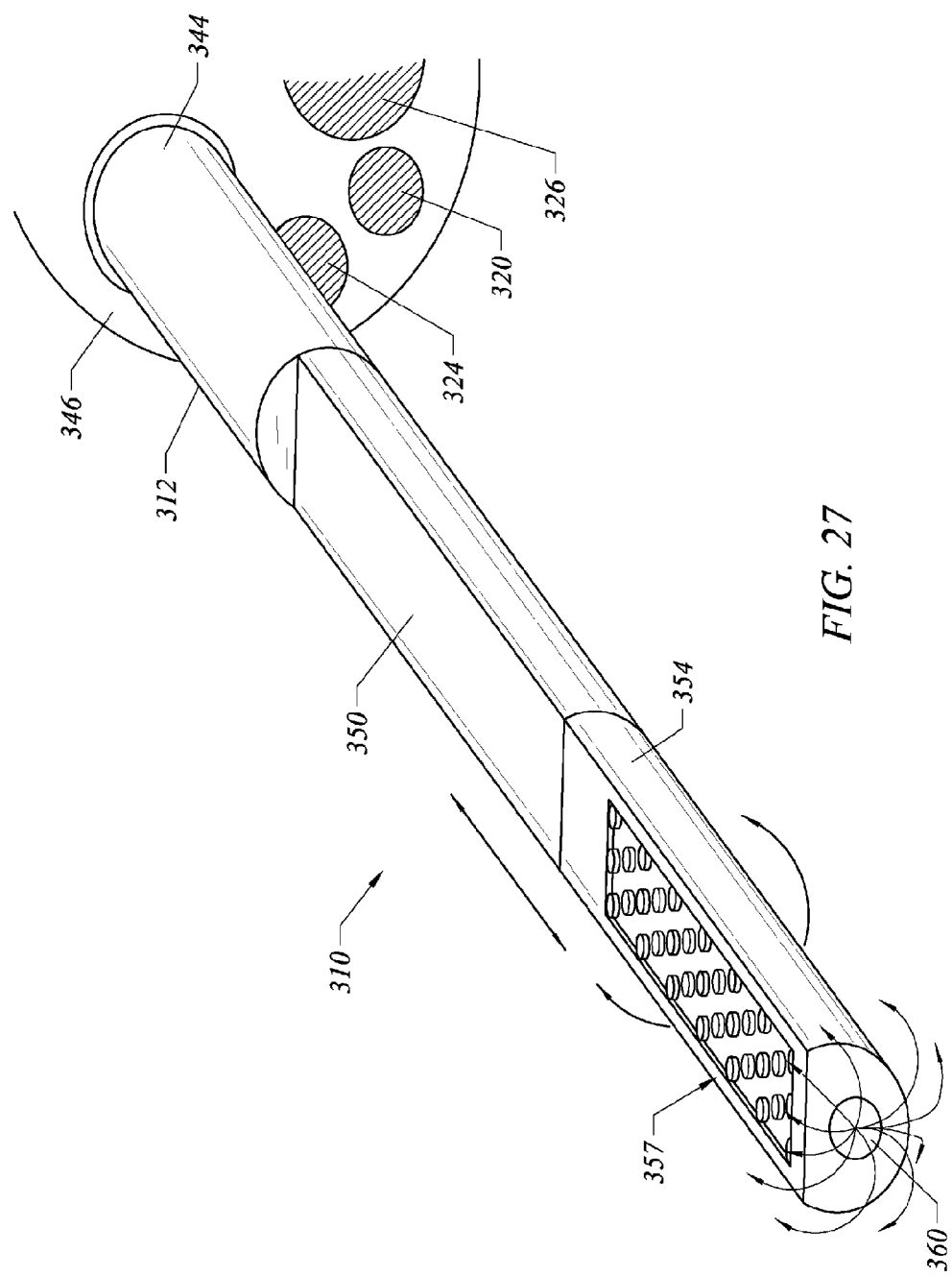
FIG. 27 is an enlarged view of a distal portion of the electrosurgical instrument of FIG. 26.
Figure 28:
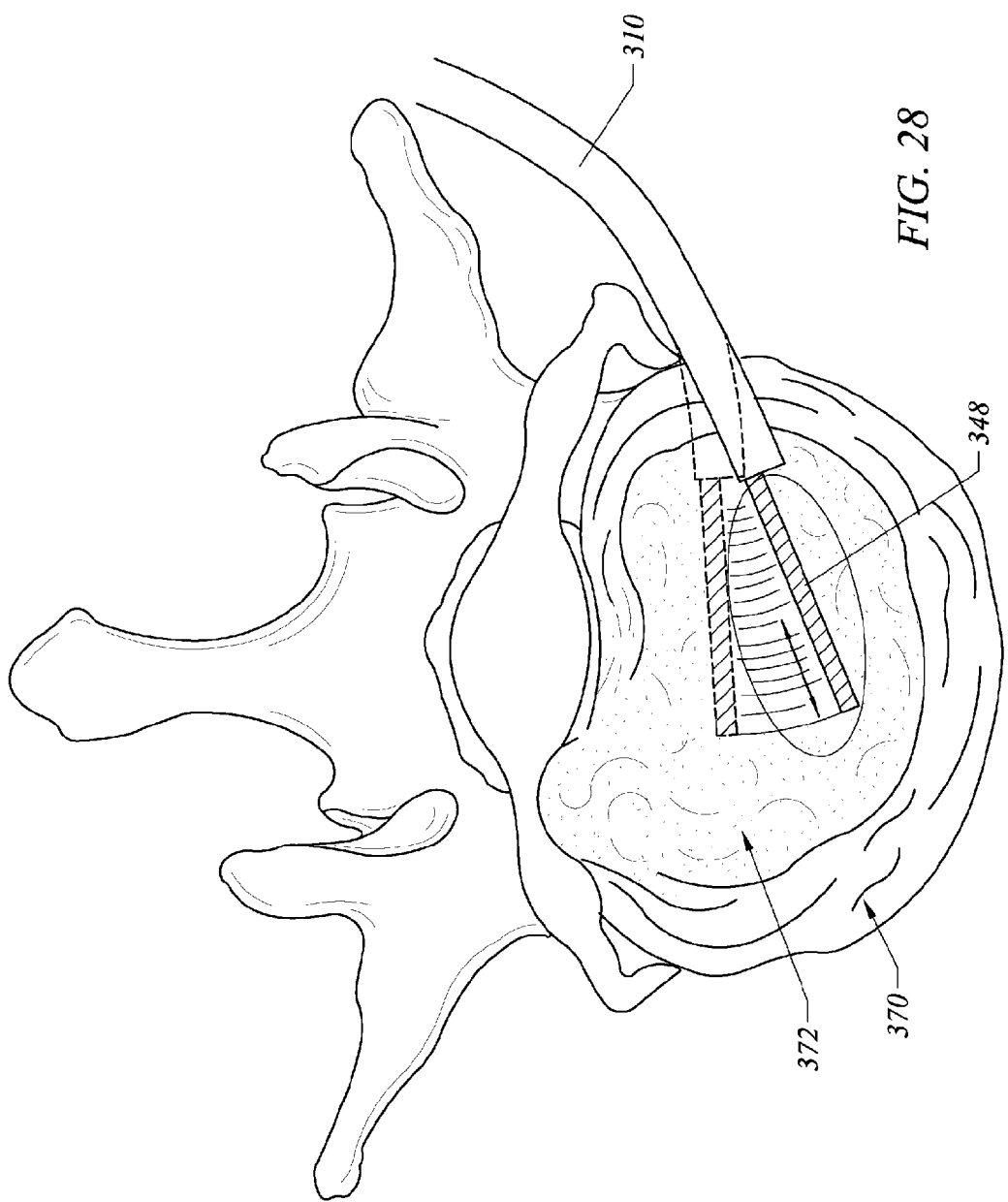
FIG. 28 illustrates a method of ablating a volume of tissue from the nucleus pulposus of a herniated disc with the electrosurgical system of FIG. 26.

FIGS. 26-28 illustrate an alternative electrosurgical system 300 specifically configured for endoscopic discectomy procedures, e.g., for treating extruded or non-extruded herniated discs. As shown in FIG. 26 system 300 includes a trocar cannula 302 for introducing a catheter assembly 304 through a percutaneous penetration in the patient to a target disc in the patient's spine. As discussed above, the catheter assembly 304 may be introduced through the thorax in a thoracoscopic procedure, through the abdomen in a laparoscopic procedure, or directly through the patient's back. Catheter assembly 304 includes a catheter body 306 with a plurality of inner lumens (not shown) and a proximal hub 308 for receiving the various instruments that will pass through catheter body 306 to the target site. In this embodiment, assembly 304 includes an electrosurgical instrument 310 with a flexible shaft 312, an aspiration catheter 314, an endoscope 316, and an illumination fiber shaft 318 for viewing the target site. As shown in FIGS. 26 and 27, aspiration catheter 314 includes a distal port 320 and a proximal fitment 322 for attaching catheter 314 to a source of vacuum (not shown). Endoscope 316 will usually comprise a thin metal tube 317 with a lens 324 at the distal end, and an eyepiece (not shown) at the proximal end.

In an exemplary embodiment, electrosurgical instrument 310 includes a twist locking stop 330 at a proximal end of the shaft 312 for controlling the axial travel distance $T_D$ of the probe. As discussed in detail below, this configuration allows the surgeon to "set" the distance of ablation within the disc. In addition, instrument 310 includes a rotational indicator 334 for displaying the rotational position of the distal portion of instrument 310 to the surgeon. This rotational indicator 334 allows the surgeon to view this rotational position without relying on the endoscope 316 if visualization is difficult, or if an endoscope is not being used in the procedure.

Referring now to FIG. 27, a distal portion 340 of electrosurgical instrument 310 and catheter body 306 will now be described. As shown, instrument 310 comprises a relatively stiff, but deflectable electrically insulating support cannula 312 and a working end portion 348 movably coupled to cannula 312 for rotational and translational movement of working end 348. Working end 348 of electrosurgical instrument 310 can be rotated and translated to ablate and remove a volume of nucleus pulposus within a disc. Support cannula 312 extends through an internal lumen 344 and beyond the distal end 346 of catheter body 306. Alternatively, support cannula 312 may be separate from instrument 310, or even an integral part of catheter body 306. The distal portion of working end 348 includes an exposed return electrode 350 separated from an active electrode array 352 by an insulating support member 354, such as ceramic. In the representative embodiment, electrode array 352 is disposed on only one side of support member 354 so that its other side is insulating and thus atraumatic to tissue. Instrument 310 will also include a fluid lumen (not shown) having a distal port 360 in working end 348 for delivering electrically conductive fluid to the target site.

In use, trocar cannula 302 is introduced into a percutaneous penetration suitable for endoscopic delivery to the target disc in the spine. A trephine (not shown) or other conventional instrument may be used to form a channel from the trocar cannula 302 through the annulus fibrosus 370 and into the nucleus pulposus. Alternatively, the probe 310 may be used for this purpose, as discussed above. The working end 348 of instrument 310 is then advanced through cannula 302 a short distance (e.g., about 7 to 10 mm) into the nucleus pulposus 372, as shown in FIG. 28. Once the electrode array 352 is in position, electrically conductive fluid is delivered through distal port 360 to immerse the active electrode array 352 in the fluid. The vacuum source may also be activated to ensure a flow of conductive fluid between electrode array 352 past return electrode 350 to suction port 320, if necessary. In some embodiments, the mechanical stop 330 may then be set at the proximal end of the instrument 310 to limit the axial travel distance of working end 348. Preferably, this distance will be set to minimize (or completely eliminate) ablation of the surrounding annulus.

The probe is then energized by applying a high frequency voltage between the electrode array 352 and return electrode 350 so that electric current flows through the conductive fluid from the array 352 to the return electrode 350. The electric current causes vaporization of the fluid and ensuing molecular dissociation of the nucleus pulposus tissue, as described in detail above. The instrument 310 may then be translated in an axial direction forwards and backwards to the preset limits. While still energized and translating, the working end 348 may also be rotated to ablate tissue surrounding the electrode array 352. In the representative embodiment, working end 348 will also include an inflatable gland 380 opposite electrode array 352 to allow deflection of working end relative to support cannula 312. As shown in FIG. 28, working end 348 may be deflected to produce a large diameter bore within the nucleus pulposus, which assures close contact with tissue surfaces to be ablated. Alternatively, the entire catheter body 306, or the distal end of catheter body 306 may be deflected to increase the volume of nucleus pulposus removed.

After the desired volume of nucleus pulposus has been removed (based on direct observation through port 324, or by kinesthetic feedback from movement of working end 348 of instrument 310), instrument 310 is withdrawn into catheter body 306 and the catheter body is removed from the patient. Typically, the preferred volume of removed tissue is about 0.2 cm$^3$ to 5.0 cm$^3$.

Figure 29:
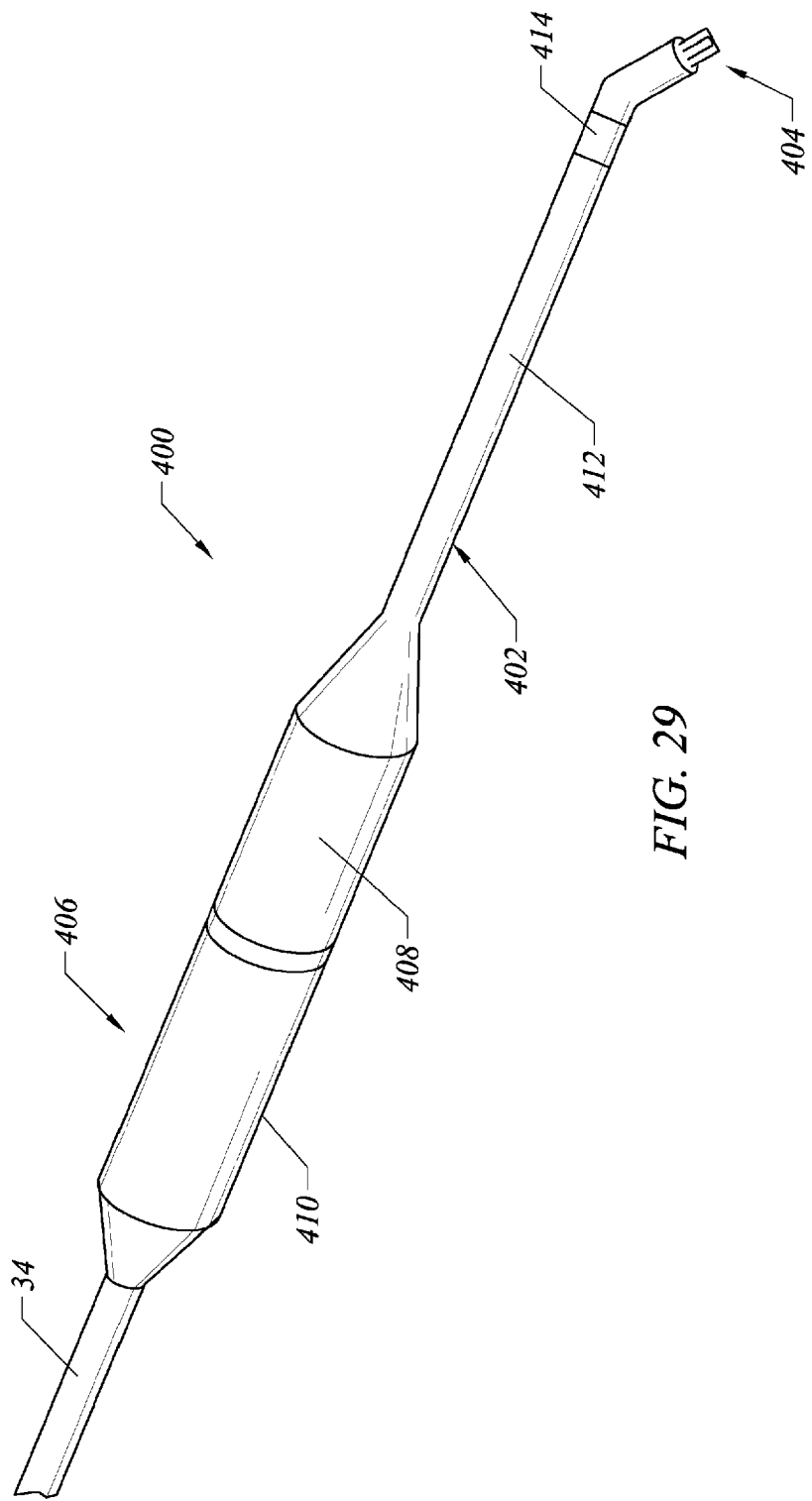
FIG. 29 illustrates a planar ablation probe for ablating tissue in confined spaces within a patient's body according to the present invention.
Figure 30:
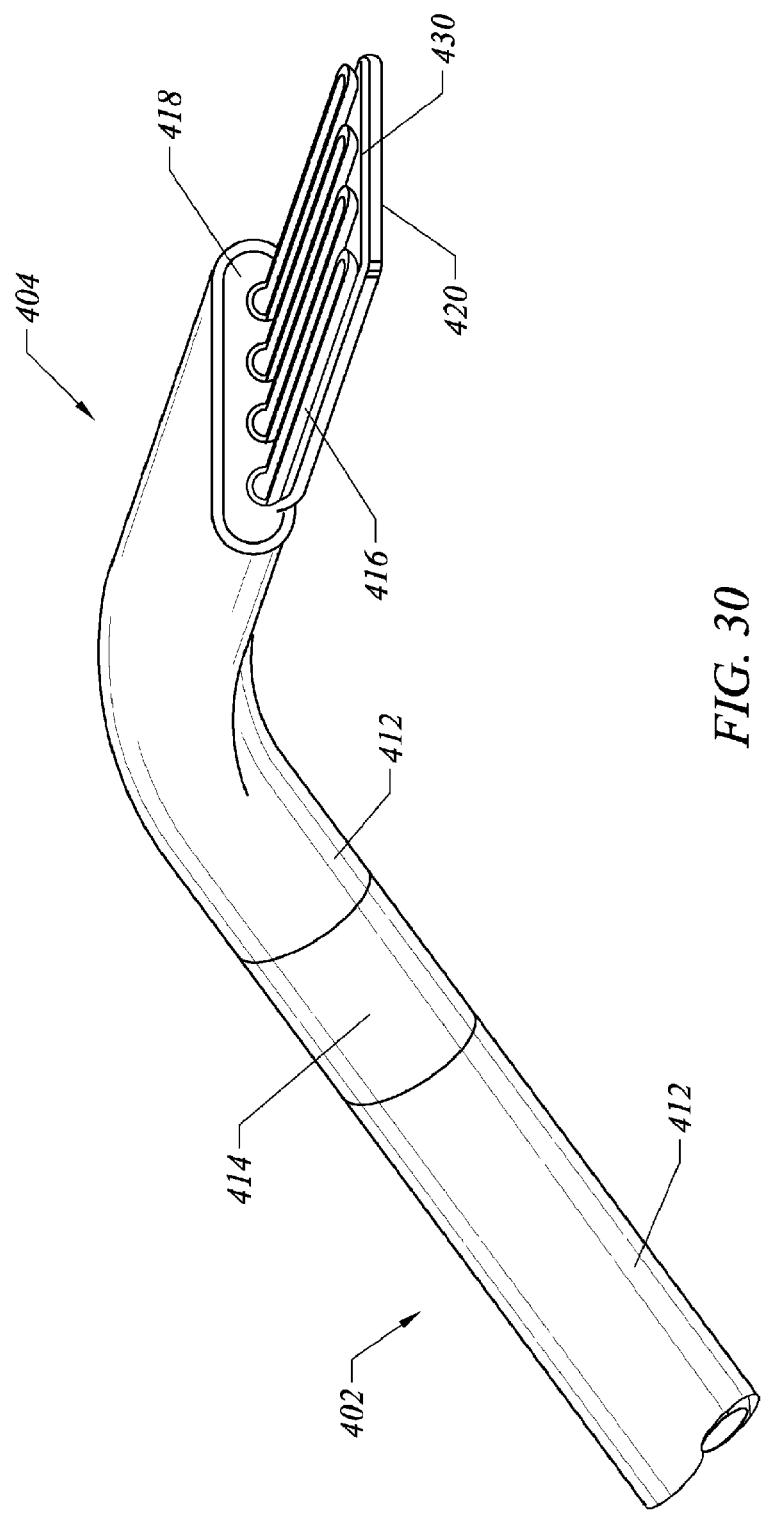
FIG. 30 illustrates a distal portion of the planar ablation probe of FIG. 29.
Figure 31:
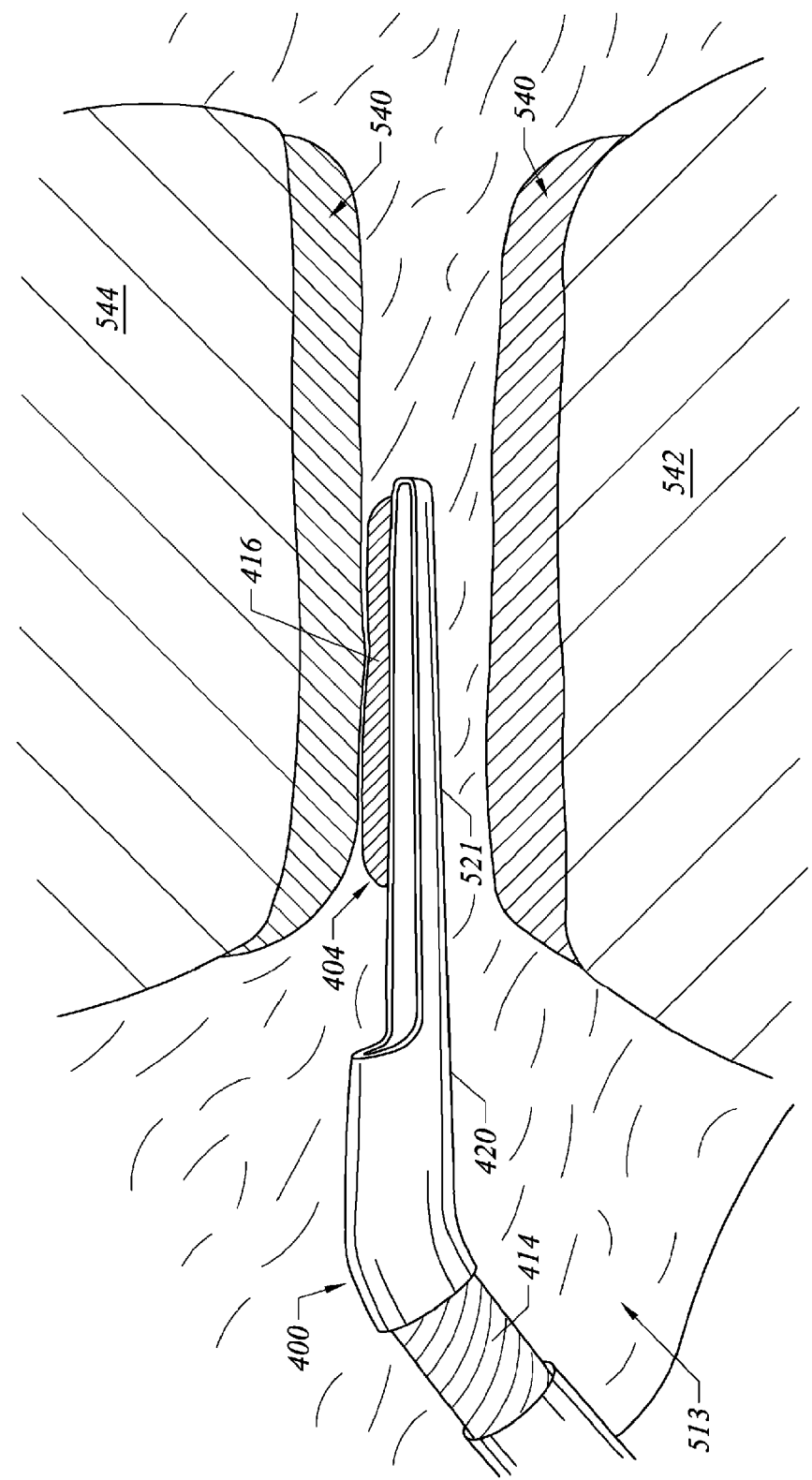
FIG. 31 is a schematic view illustrating the ablation of soft tissue from adjacent surfaces of the vertebrae with a planar ablation probe of the present invention.

Referring now to FIGS. 29-31, alternative systems and methods for ablating tissue in confined (e.g., narrow) body spaces will now be described. FIG. 29 illustrates an exemplary planar ablation probe 400 according to the present invention. Similar to the instruments described above, probe 400 can be incorporated into electrosurgical system 11 (or other suitable systems) for operation in either the bipolar or monopolar modalities. Probe 400 generally includes a support member 402, a distal working end 404 attached to the distal end of support member 402 and a proximal handle 408 attached to the proximal end of support member 402. As shown in FIG. 29, handle 406 includes a handpiece 408 and a power source connector 410 removably coupled to handpiece 408 for electrically connecting working end 404 with power supply 28 through cable 34 (see FIG. 1).

In the embodiment shown in FIG. 29, planar ablation probe 400 is configured to operate in the bipolar modality. Accordingly, an exposed portion of support member 402 functions as the return electrode and comprises an electrically conducting material, such as titanium, or alloys containing one or more of nickel, chromium, iron, cobalt, copper, aluminum, platinum, molybdenum, tungsten, tantalum or carbon. In one embodiment, support member 402 is an austenitic stainless steel alloy, such as stainless steel Type 304 from MicroGroup, Inc., Medway, Mass. As shown in FIG. 29, support member 402 is substantially covered by an insulating layer 412 to prevent electric current from damaging surrounding tissue. An exposed portion 414 of support member 402 functions as the return electrode for probe 400. Exposed portion 414 is preferably spaced proximally from active electrodes 416 by a distance of about 1 mm to 20 mm.

Referring to FIG. 30, planar ablation probe 400 further comprises a plurality of active electrodes 416 extending from an electrically insulating spacer 418 at the distal end of support member 402. Of course, it will be recognized that probe 400 may include a single electrode depending on the size of the target tissue to be treated and the accessibility of the treatment site (see FIG. 31, for example). Insulating spacer 418 is preferably bonded to support member 402 with a suitable epoxy adhesive 419 to form a mechanical bond and a fluid-tight seal. Electrodes 416 usually extend about 2.0 mm to 20 mm from spacer 418, and preferably less than 10 mm. A support tongue 420 extends from the distal end of support member 402 to support active electrodes 416. Support tongue 420 and active electrodes 416 have a substantially low profile to facilitate accessing narrow spaces within the patient's body, such as the spaces between adjacent vertebrae and between articular cartilage and the meniscus in the patient's knee. Accordingly, tongue 420 and electrodes 416 have a substantially planar profile, usually having a combined height He of less than 4.0 mm, preferably less than 2.0 mm and more preferably less than 1.0 mm. The width of electrodes 416 and support tongue 420 will usually be less than 10.0 mm and preferably between about 2.0 mm to 4.0 mm.

Support tongue 420 includes a "non-active" surface opposing active electrodes 416. The non-active surface may be covered with an electrically insulating layer (not shown) to minimize undesirable current flow into adjacent tissue or fluids. Furthermore, the non-active surface is preferably atraumatic, i.e., having a smooth planar surface with rounded corners, to minimize unwanted injury to tissue or nerves in contact therewith, such as disc tissue or the nearby spinal nerves, as the working end of probe 400 is introduced into a narrow, confined body space. Thus, the non-active surface of tongue 420 helps to minimize iatrogenic injuries to tissue and nerves so that working end 404 of probe 400 can safely access confined spaces within the patient's body, e.g., the vertebral column.

Referring to FIG. 31, a method for ablating tissue structures with planar ablation probe 400 according to the present invention will now be described. In particular, exemplary methods for removing soft tissue 540 from the surfaces of adjacent vertebrae 542, 544 in the spine will be described. In this procedure, at least the working end 404 of planar ablation probe 400 is introduced to a treatment site either by minimally invasive techniques or open surgery. Electrically conducting liquid is delivered to the treatment site, and voltage is applied from power supply 28 between active electrodes 416 and return electrode 414. The voltage is preferably sufficient to generate electric field intensities near active electrodes that form a vapor layer in the electrically conducting liquid, and induce the discharge of energy from the vapor layer to ablate tissue at the treatment site, as described in detail above.

Removal of this soft tissue 540 is often necessary, for example, in surgical procedures for fusing or joining adjacent vertebrae together. Following the removal of tissue 540, the adjacent vertebrae 542, 544 are stabilized to allow for subsequent fusion together to form a single monolithic vertebra. As shown, the low-profile of working end 404 of probe 400 (i.e., thickness values as low as 0.2 mm) allows access to and surface preparation of closely spaced vertebrae. In addition, the shaped electrodes 416 promote substantially high electric field intensities and associated current densities between active electrodes 416 and return electrode 414 to allow for the efficient removal of tissue attached to the surface of bone without significantly damaging the underlying bone. The "non-active" insulating side 521 of working end 404 also minimizes the generation of electric fields on this side 521 to reduce ablation of the adjacent vertebra 542.

The target tissue is generally not completely immersed in electrically conductive liquid during surgical procedures within the spine, such as the removal of soft tissue described above. Accordingly, electrically conducting liquid will preferably be delivered into the confined spaces 513 between adjacent vertebrae 542, 544 during this procedure. The fluid may be delivered through a liquid passage (not shown) within support member 402 of probe 400, or through another suitable liquid supply instrument.

Figure 32A:
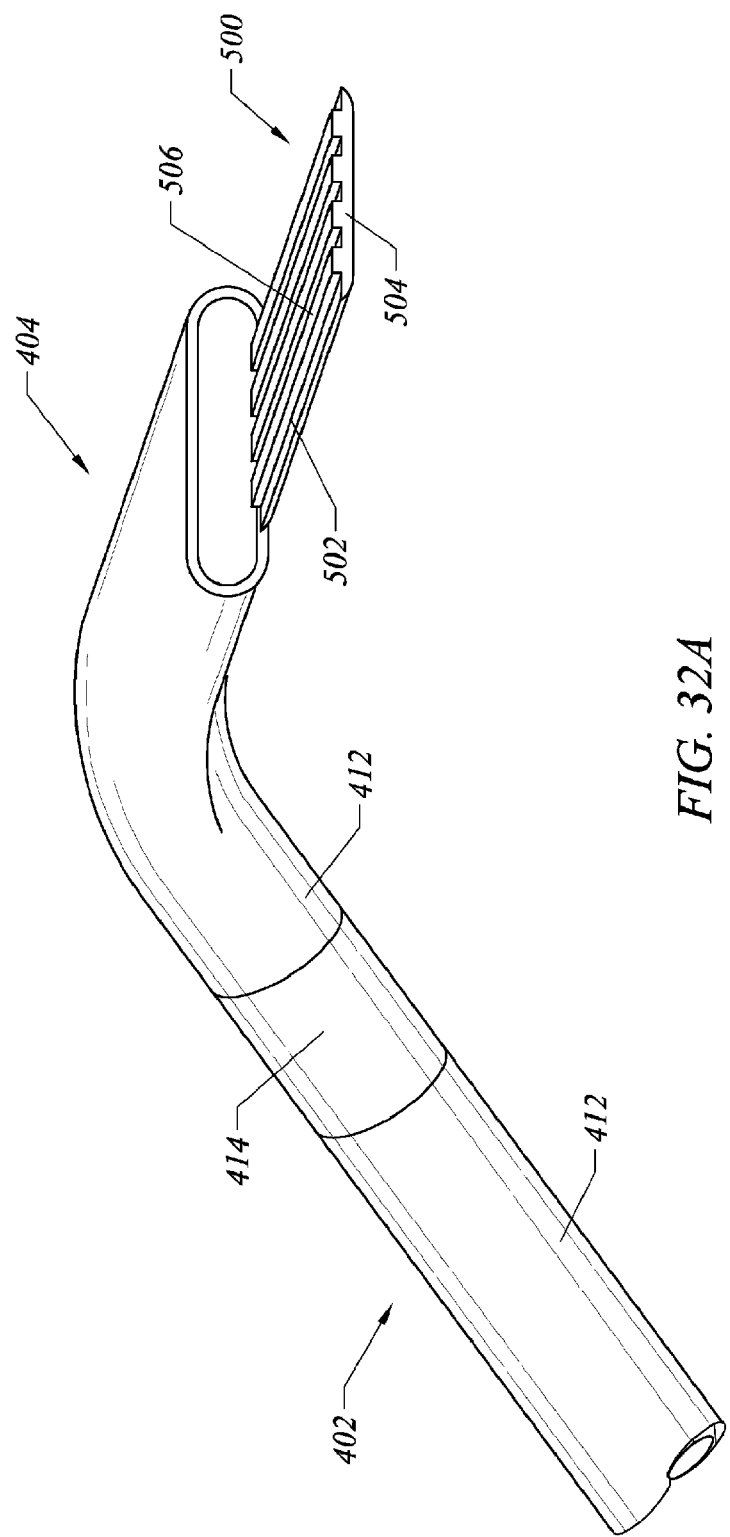
FIG. 32A is a perspective view of an alternative embodiment of the planar ablation probe incorporating a ceramic support structure with conductive strips printed thereon.
Figure 32B:
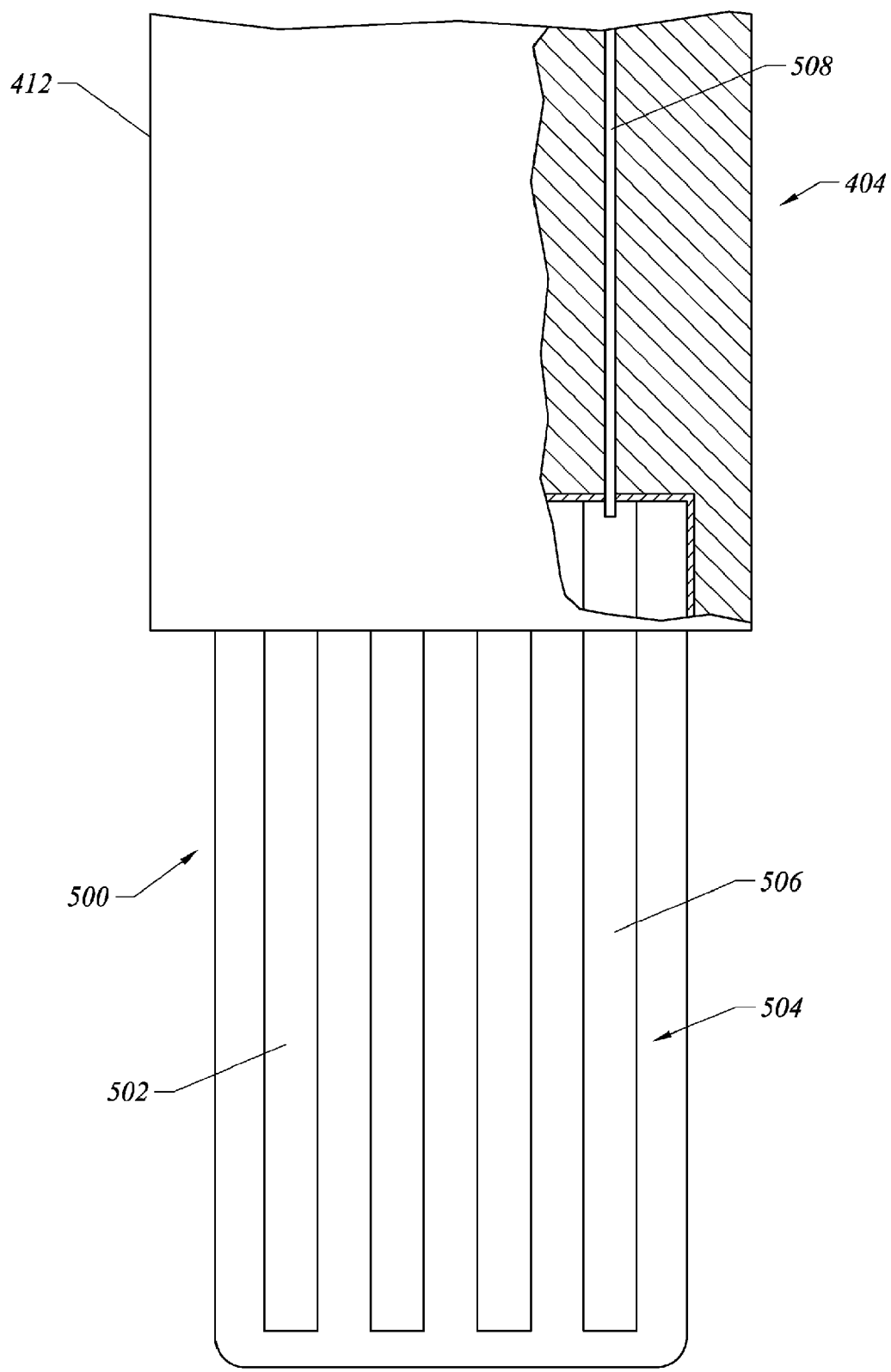
FIG. 32B is a top partial cross-sectional view of the planar ablation probe of FIG. 32A.
Figure 32C:
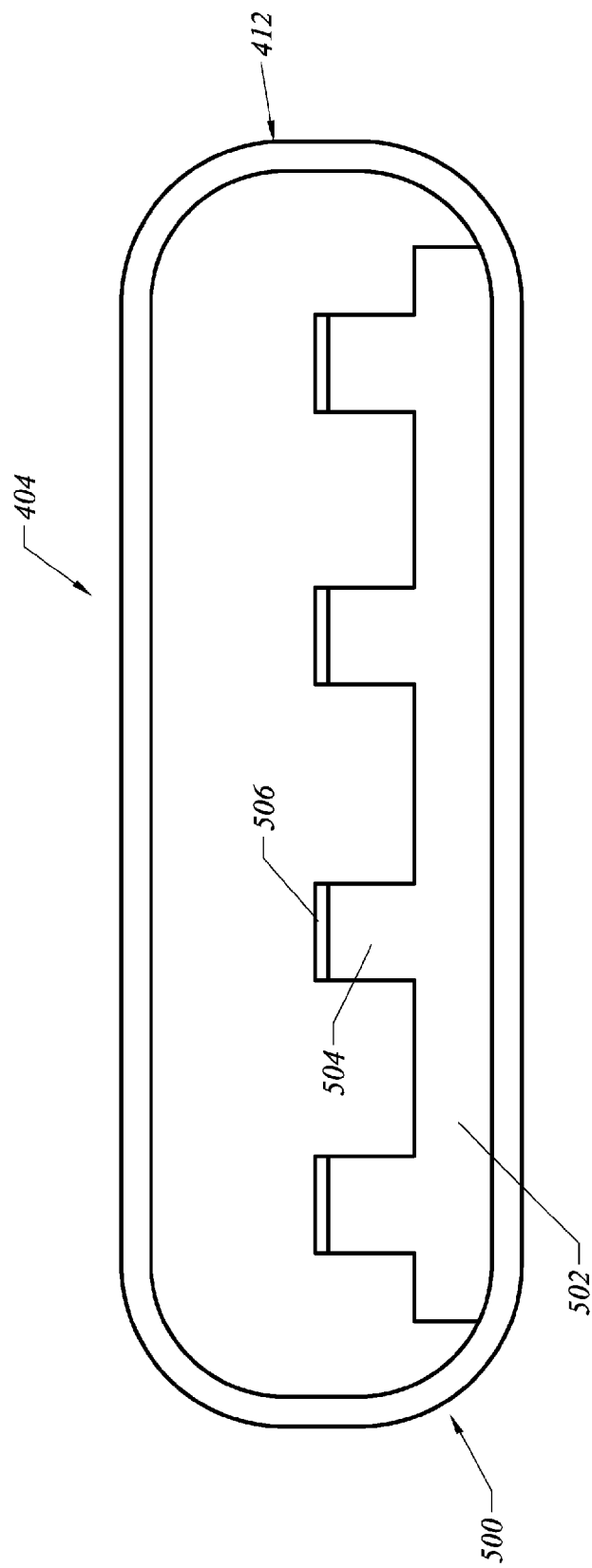
FIG. 32C is an end view of the probe of FIG. 32A.

Referring now to FIGS. 32A-C an alternative electrode support member 500 for a planar ablation probe 404 will be described in detail. As shown, electrode support member 500 preferably comprises a multilayer or single layer substrate 502 comprising a suitable high temperature, electrically insulating material, such as ceramic. The substrate 502 is a thin or thick film hybrid having conductive strips that are adhered to, e.g., plated onto, the ceramic wafer. The conductive strips typically comprise tungsten, gold, nickel, or equivalent materials. In the exemplary embodiment, the conductive strips comprise tungsten, and they are co-fired together with the wafer layers to form an integral package. The conductive strips are coupled to external wire connectors by holes or vias that are drilled through the ceramic layers, and plated or otherwise covered with conductive material.

In the representative embodiment, support member 500 comprises a single ceramic wafer having a plurality of longitudinal ridges 504 formed on one side of the wafer 502. Typically, the wafer 502 is green pressed and fired to form the required topography (e.g., ridges 504). A conductive material is then adhered to each ridge 504 to form conductive strips 506 extending axially over wafer 502 and spaced from each other. As shown in FIG. 32B, the conductive strips 506 are attached to lead wires 508 within shaft 412 of the probe 404 to electrically couple conductive strips 506 to the power supply 28 (FIG. 1). This embodiment provides a relatively low profile working end of probe 404 that has sufficient mechanical structure to withstand bending forces during the procedure.

Figure 33A:
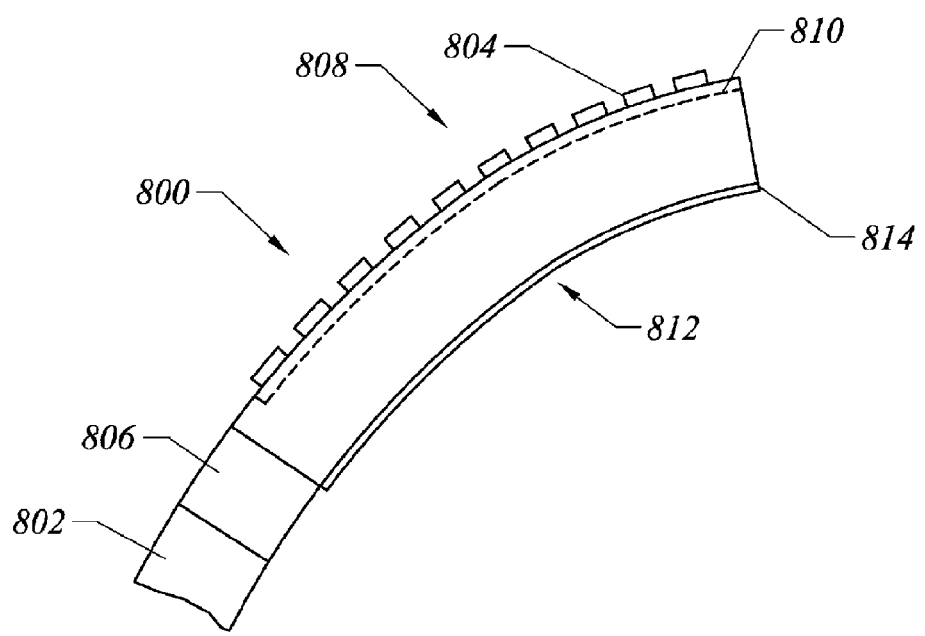
FIG. 33A illustrates an electrosurgical instrument having a curved distal tip and an insulator for protecting a dura mater.

FIGS. 33A to 39B illustrate systems and methods for treating and/or ablating tissue of spinal discs, according to one embodiment of the present invention. Electrosurgical probe 800 generally comprises a shaft 802 that can be introduced into the patient, e.g., percutaneously through the patient's back directly into the spine. The probe shaft 802 will include one or more active electrode(s) 804 for applying electrical energy to a target tissue of the disc or other spinal tissue. The system may include one or more return electrode(s) 806. The return electrode(s) 806 can be positioned proximal of the active electrode(s) 804 on the electrosurgical probe or on a separate instrument (not shown). The ablation probe 800 shown in FIG. 33A is configured to operate in the bipolar modality. In alternative embodiments, however, the return electrode 806 may be positioned on the patient's back, as a dispersive pad (not shown) so as to operate in a monopolar modality.

Figure 33B:
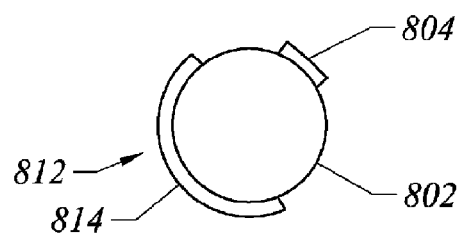
FIG. 33B is an end view of one embodiment of the instrument of FIG. 33A.
Figure 34:
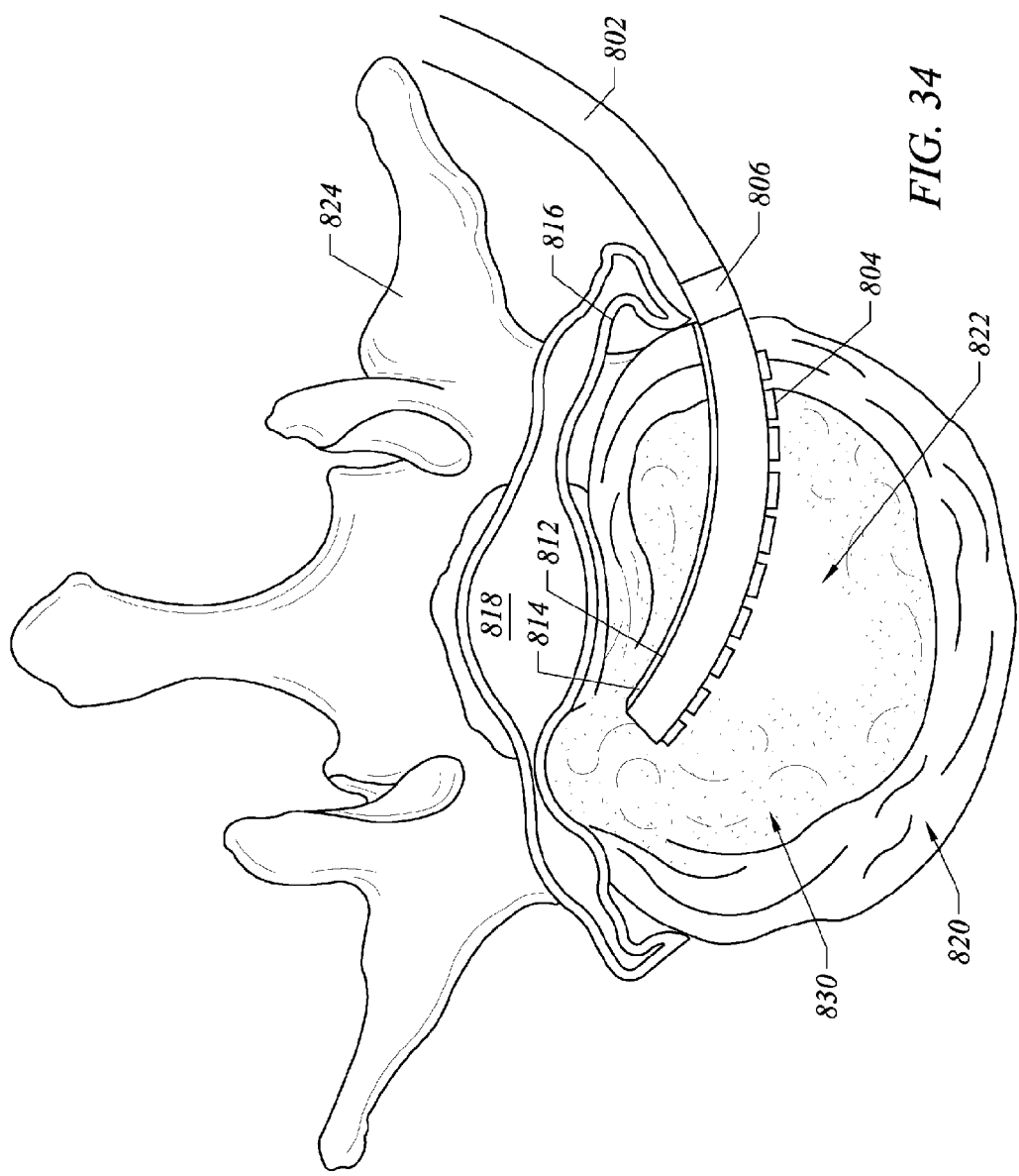
FIG. 34 illustrates the instrument of FIG. 33A being percutaneously introduced posteriorly into a target spinal disc.

In the exemplary embodiment shown in FIGS. 33A-B, the distal end of the shaft 802 is curved or bent to improve access to the disk being treated. The treatment surface 808 of the electrosurgical probe is usually curved or bent to an angle of about 10 degrees to 90 degrees relative to the longitudinal axis of shaft 100, preferably about 15 degrees to 60 degrees, and more preferably about 15 degrees. In alternative embodiments, the distal portion of shaft 802 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in commonly assigned U.S. Pat. No. 5,697,909, the complete disclosure of which is incorporated herein by reference. Alternatively, the shaft 802 of the present invention may be bent by the physician to the appropriate angle using a conventional bending tool or the like.

The active electrode(s) 804 typically extend from an active tissue treatment surface of an electrode support member 810 of the probe shaft 802. Opposite the active electrodes 802 is a non-active insulating side 812, which has an insulator 814 that is configured to protect the dura mater 816 and other non-target spinal cord tissue 818. The insulator 814 minimizes the generation of electric fields on the non-active side and reduces the electrical damage to the dura mater 816 and spinal column 818 during a procedure. While the insulator 814 is shown opposite the active electrode array 804, it will be appreciated that the insulator 814 can be positioned completely around the probe, be positioned around only portions of the probe, be along the sides of the active electrode array, and the like.

The tissue treatment surface 808 and individual active electrodes 804 will usually have dimensions within the ranges set forth above. In some embodiments, the active electrodes 804 can be disposed within or on an insulating support member 810, as described above. In the representative embodiment, the surface of the active electrodes 804 has a circular cross-sectional shape with a diameter in the range of about 1 mm to 30 mm, usually about 2 mm to 20 mm. The individual active electrodes 804 preferably extend outward from tissue treatment surface 808 by a distance of about 0.1 mm to 8 mm, usually about 0.2 mm to 4 mm. Applicant has found that this configuration increases the high electric field intensities and associated current densities around active electrodes 804 to facilitate the ablation of tissue, as described in detail above. Of course, it will be recognized that the active electrodes may have a variety of different configurations. For example, instead of an array of active electrodes, a single active electrode may be used.

An exemplary method for ablating and removing at least a portion of the target spinal disc 822 will now be described. Removal of the degenerative or damaged disc 822 is necessary, for example, in surgical procedures during placement of a cage or the fusing or joining adjacent vertebrae together. Following the removal of the disc 822, the adjacent vertebrae 824 are stabilized to allow for subsequent fusion together to form a single monolithic vertebra. During such procedures it would be preferable to protect the dura mater 816 and spinal cord 818 from damage from the electrosurgical probe 800.

In use, the distal end of probe 800 is introduced into a treatment site either by minimally invasive techniques or open surgery. The distal portion of electrosurgical probe 800 can be introduced into the patient through a percutaneous penetration 826, e.g., via a cannula. The insertion of probe 800 and advancement of the working end towards the disc may be guided by an endoscope (not shown) which includes a light source and a video camera, to allow the surgeon to selectively visualize a zone within the vertebral column. The distal portion of shaft 802 can be introduced posteriorly through a small percutaneous penetration in the patient's back.

To maintain a clear field of view and to facilitate the generation of a vapor layer, a transparent, electrically conductive irrigant (not shown), such as isotonic saline, can be injected into the treatment site either through a liquid passage in probe 800, or through a separate instrument. Suitable methods for delivering irrigant to a treatment site are described in commonly assigned U.S. Pat. No. 5,697,281 filed on Jun. 7, 1995, the contents of which are incorporated herein by reference.

After (or during) introduction of the electrosurgical probe 800 into the spinal disc 822, an electrically conductive liquid 830 can be delivered to the treatment site, and voltage can be applied from power supply 28 between active electrodes 804 and return electrode 806 through the conductive fluid. The voltage is preferably sufficient to generate electric field intensities near active electrodes 806 that form a vapor layer in the electrically conductive liquid so as to induce a discharge of energy from the vapor layer to ablate tissue at the treatment site, as described in detail above. As the probe shaft 802 is moved through the spinal disc 822, the insulator 814 can be positioned to engage the dura mater 816 and protect the dura mater 816 (and spinal cord 818) from damaging electrical current flow.

Figure 35A:
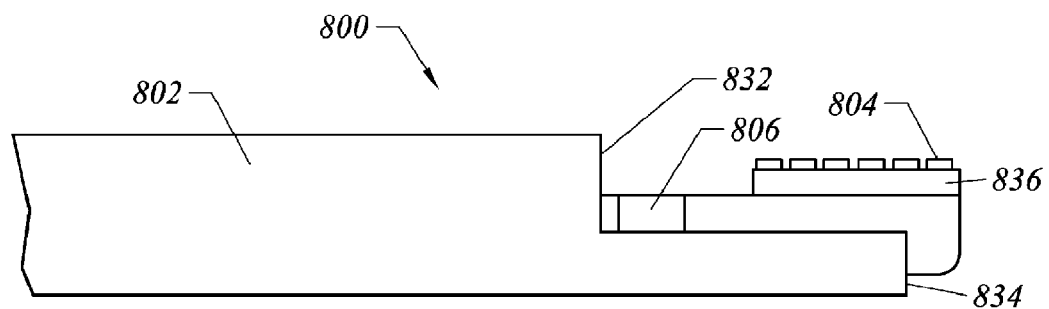
FIG. 35A is a side view of a working end of an electrosurgical probe having a fluid delivery lumen and an aspiration lumen.
Figure 35B:
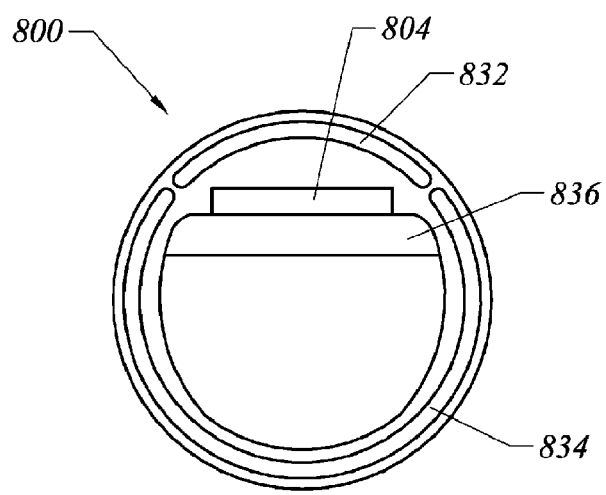
FIG. 35B is an end view of the electrosurgical probe of FIG. 35A.

FIGS. 35A and 35B show yet another embodiment of the present invention. The electrosurgical probe 800 includes an aspiration lumen 832 for aspirating the target area and a fluid delivery lumen 834 for directing an electrically conductive fluid 830 to the target area. In some implementations, the aspiration lumen 832 and the fluid delivery lumen 834 are coupled together in an annular pattern along the exterior of the electrosurgical probe. A distal end of the aspiration lumen 832 typically ends proximal of the return electrode 806 while the distal end of the fluid delivery lumen 834 extends to a point adjacent the distal end of the electrosurgical probe 800. As shown in FIG. 35B, the fluid delivery lumen 834 preferably occupies a larger portion of the annular region. In one specific embodiment, the fluid delivery lumen occupies approximately two-thirds of the annular region.

The electrosurgical probe may have a single active electrode 804 or an electrode array distributed over a contact surface of a probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment. In one specific configuration the electrosurgical probe comprises 23 active electrodes. Of course, it will be appreciated that the number, size, and configuration of the active electrodes may vary depending on the specific use of the electrosurgical probe (e.g. tissue contraction, tissue ablation, or the like).

The shaft 802 will usually house a plurality of wires or other conductive elements axially therethrough to permit connection of the electrode array 804 to a connector at the proximal end of the shaft (not shown). Each active electrode of the electrode array may be connected to a separate power source that is isolated from the other active electrodes. Alternatively, the active electrodes may be connected to each other at either the proximal or distal ends of the probe to form a single wire that couples to a power source.

The active electrode(s) 804 are typically supported by an electrically insulating electrode support member 836 that extends from the electrosurgical probe 800. Electrode support member 836 typically extends from the distal end of shaft 802 about 1 mm to 20 mm. Electrode support member 836 typically comprises an insulating material (e.g., ceramic or glass material, such as alumina, zirconia, and the like) which could be formed at the time of manufacture in a flat, hemispherical or other shape according to the requirements of a particular procedure.

Figure 36:
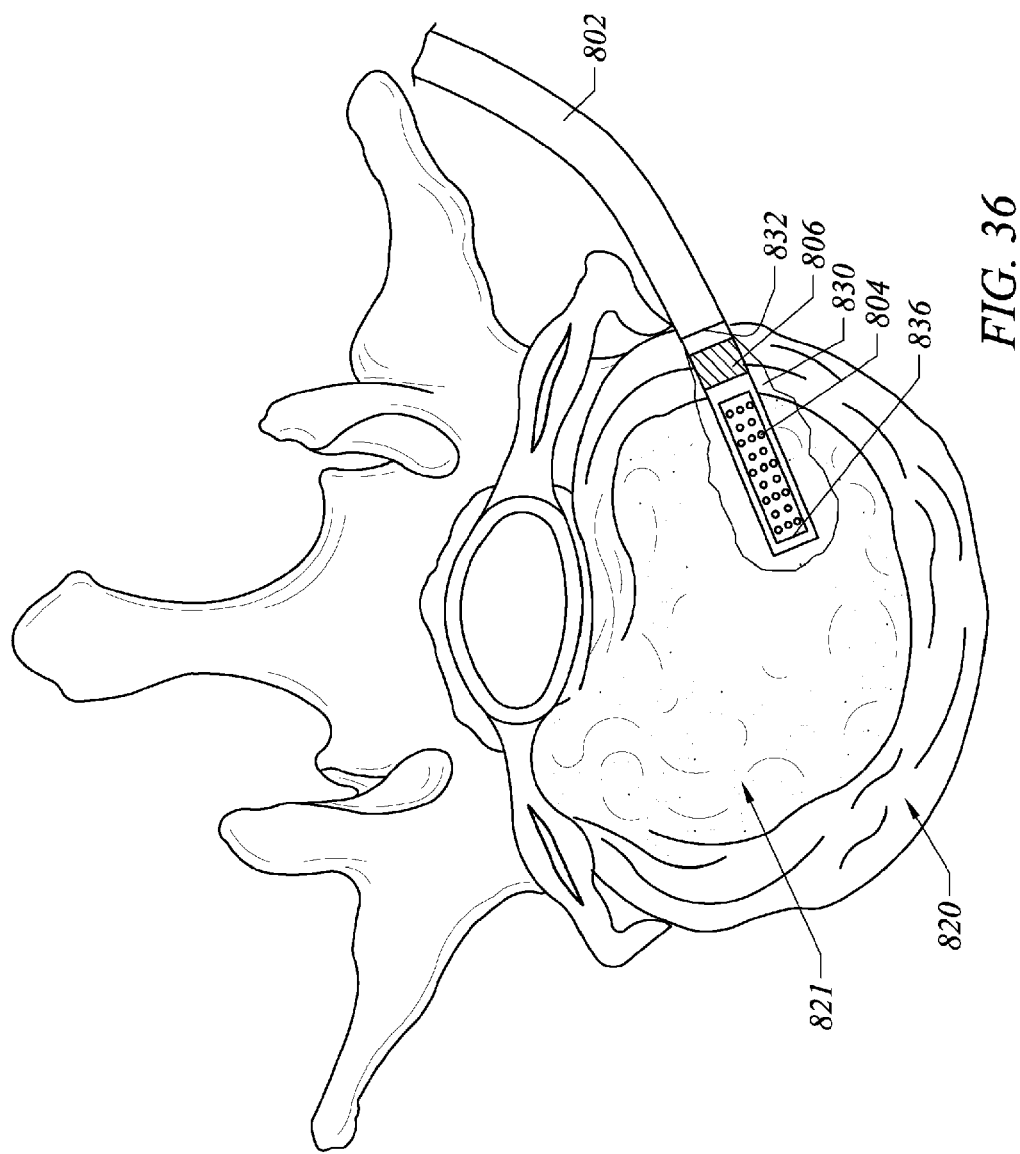
FIG. 36 illustrates an electrosurgical probe in relation to a target spinal disc.

In use, the electrosurgical probe 800 can be positioned adjacent the target tissue, as described above. When treating discs, the distal end of shaft 802 is typically delivered through the annulus to the nucleus pulposus 821, which may be herniated, extruded, non-extruded, or simply swollen. As shown in FIG. 36, high frequency voltage is applied between active electrode(s) 804 and return electrode(s) 806 to heat the surrounding collagen to suitable temperatures for contraction (i.e., typically about 55° C. to about 70° C.) or for ablation (i.e. typically less than 150° C.). As discussed above, this procedure may be accomplished with a monopolar configuration, as well. However, applicant has found that the bipolar configuration provides enhanced control of the high frequency current, which reduces the risk of spinal nerve damage.

In exemplary embodiments, an electrically conductive fluid 830 is delivered through fluid delivery lumen 834 to the target site. In these embodiments, the high frequency voltage applied to the active electrode(s) is sufficient to vaporize the electrically conductive fluid (e.g., gel or saline) between the active electrode(s) and the tissue. Within the vaporized fluid, a plasma is formed and charged particles (e.g., electrons) cause the molecular breakdown or disintegration of several cell layers of the tissue. This molecular dissociation is accompanied by the volumetric removal of the tissue. Because the aspiration lumen 832 is placed proximal of the return electrode (and typically outside of the spinal disc 822), the aspiration lumen 832 typically removes the air bubbles from the spinal disc and leaves the disc tissue relatively intact. Moreover, because the aspiration lumen 832 is spaced from the target area, the conductive fluid 830 is allowed to stay in the target area longer and the plasma can be created more aggressively.

Figure 37A:
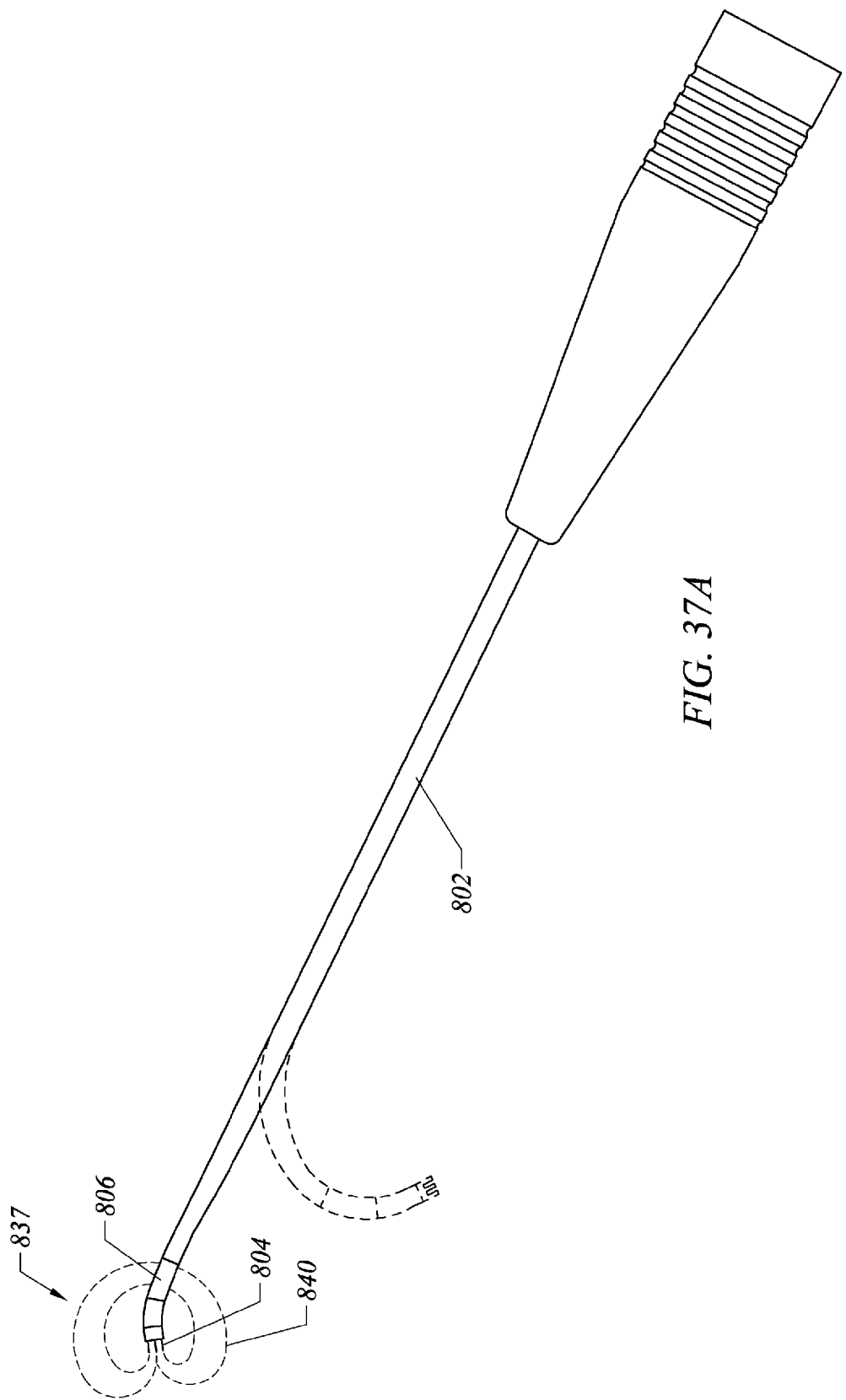

FIGS. 37A-D show embodiments of the electrosurgical probe of the present invention which have a curved or steerable distal tip for improving navigation of the electrosurgical probe 800 towards a target tissue or within the disc. Referring now to FIG. 37A, probe 800 comprises an electrically conductive shaft 802, a handle 803 coupled to the proximal end of shaft 802, and an electrically insulating support member 836 at the distal end of shaft 802. Probe 800 further includes an insulating sleeve 838 over shaft 802, and an exposed portion of shaft 802 that functions as the return electrode 806. In the representative embodiment, probe 800 comprises a plurality of active electrodes 804 extending from the distal end of support member 836. As shown, return electrode 806 is spaced a further distance from active electrodes 804 than in the embodiments described above. In this embodiment, the return electrode 806 is spaced a distance of about 2.0 mm to 50 mm, preferably about 5 mm to 25 mm. In addition, return electrode 806 has a larger exposed surface area than in previous embodiments, having a length in the range of about 2.0 mm to 40 mm, preferably about 5 mm to 20 mm. Accordingly, electric current passing from active electrodes 804 to return electrode 806 will follow a current flow path 840 that is further away from shaft 802 than in the previous embodiments. In some applications, this current flow path 840 results in a deeper current penetration into the surrounding tissue with the same voltage level, and thus increased thermal heating of the tissue. As discussed above, this increased thermal heating may have advantages in some applications of treating disc or other spinal disorders.

For certain procedures, it is desired to achieve a tissue temperature in the range of about 60° C. to 100° C. to a depth of about 0.2 mm to 5 mm, usually about 1 mm to 2 mm. The voltage required for this thermal effect will partly depend on the electrode configurations, the electrical conductivity of the tissue and of the area or milieu immediately surrounding the electrodes, the time period for which the voltage is applied, and the depth of tissue treatment desired. With the electrode configurations described in FIGS. 37A-D, the voltage level for thermal heating will usually be in the range of about 20 volts RMS to 300 volts RMS, preferably about 60 volts RMS to 200 volts RMS. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked or ablated, which may be undesirable in certain procedures.

As shown by the dotted lines in FIGS. 37A-D, the distal tip 837 of the electrosurgical probe 800 can have a preformed curvature or can be steered to a curved configuration. In some embodiments the distal tip 837 is made of a shape memory material that can be shaped to a desired configuration. In other embodiments, the distal tip 837 of the electrosurgical probe 800 is steerable or deflectable by the user. The flexible shaft and steerable distal tip may be combined with pull wires, shape memory actuators, heat actuated materials, or other conventional or proprietary mechanisms for effecting selective deflection of the distal tip of the shaft to facilitate positioning of the electrode or electrode array. A user can track the position of the steerable distal tip using fluoroscopy, optical fibers, transducers positioned on the probe, or the like.

In some embodiments, the electrosurgical probe 800 may include a dispersive return electrode 842 (FIG. 38) for switching between bipolar and monopolar modes. In this embodiment, the power supply 28 will typically include a switch, e.g., a foot pedal 843, for switching between the monopolar and bipolar modes. The system will switch between an ablation mode, where the dispersive pad 842 is deactivated and voltage is applied between active and return electrodes 804, 806, and a sub-ablation or thermal heating mode, where the active electrode(s) 804 and deactivated and voltage is applied between the dispersive pad 842 and the return electrode 806. In the sub-ablation mode, a lower voltage is typically applied and the return electrode 806 functions as the active electrode to provide thermal heating and/or coagulation of tissue surrounding return electrode 806. A more complete description of the use of the dispersive return electrode is described in co-pending U.S. patent application Ser. No. 09/316,472, filed May 21, 1999, the complete disclosure of which is incorporated by reference herein.

FIG. 37B illustrates yet another embodiment of the present invention. As shown, electrosurgical probe 800 comprises an electrode assembly having one or more active electrode(s) 804 and a proximally spaced return electrode 806 as in previous embodiments. Return electrode 806 is typically spaced about 0.5 mm to 25 mm, preferably 1.0 mm to 5.0 mm from the active electrode(s) 804, and has an exposed length of about 1 mm to 20 mm. In addition, the electrode assembly can include two additional electrodes 844, 846 spaced axially on either side of return electrode 806. Electrodes 844, 846 are typically spaced about 0.5 mm to 25 mm, preferably about 1 mm to 5 mm from return electrode 806. In the representative embodiment, the additional electrodes 844, 846 are exposed portions of shaft 802, and the return electrode 806 is electrically insulated from shaft 802 such that a voltage may be applied between electrodes 844, 846 and electrode 804. In this embodiment, probe 800 may be used in at least two different modes, an ablation mode and a sub-ablation or thermal heating mode. In the ablation mode, voltage is applied between active electrode(s) 804 and return electrode 806 in the presence of electrically conductive fluid, as described above. In the ablation mode, electrodes 844, 846 are deactivated. In the thermal heating or coagulation mode, active electrode(s) 804 are deactivated and a voltage is applied between electrodes 844, 846 and electrode 806 such that a high frequency current 840 flows therebetween, as shown in FIG. 37B. In the thermal heating mode a lower voltage is typically applied, below the threshold for plasma formation and ablation, but sufficient to cause some thermal damage to the tissue immediately surrounding the electrodes without vaporizing or otherwise debulking this tissue so that the current 840 provides thermal heating and/or coagulation of tissue surrounding electrodes 804, 844, 846.

Figure 37C:
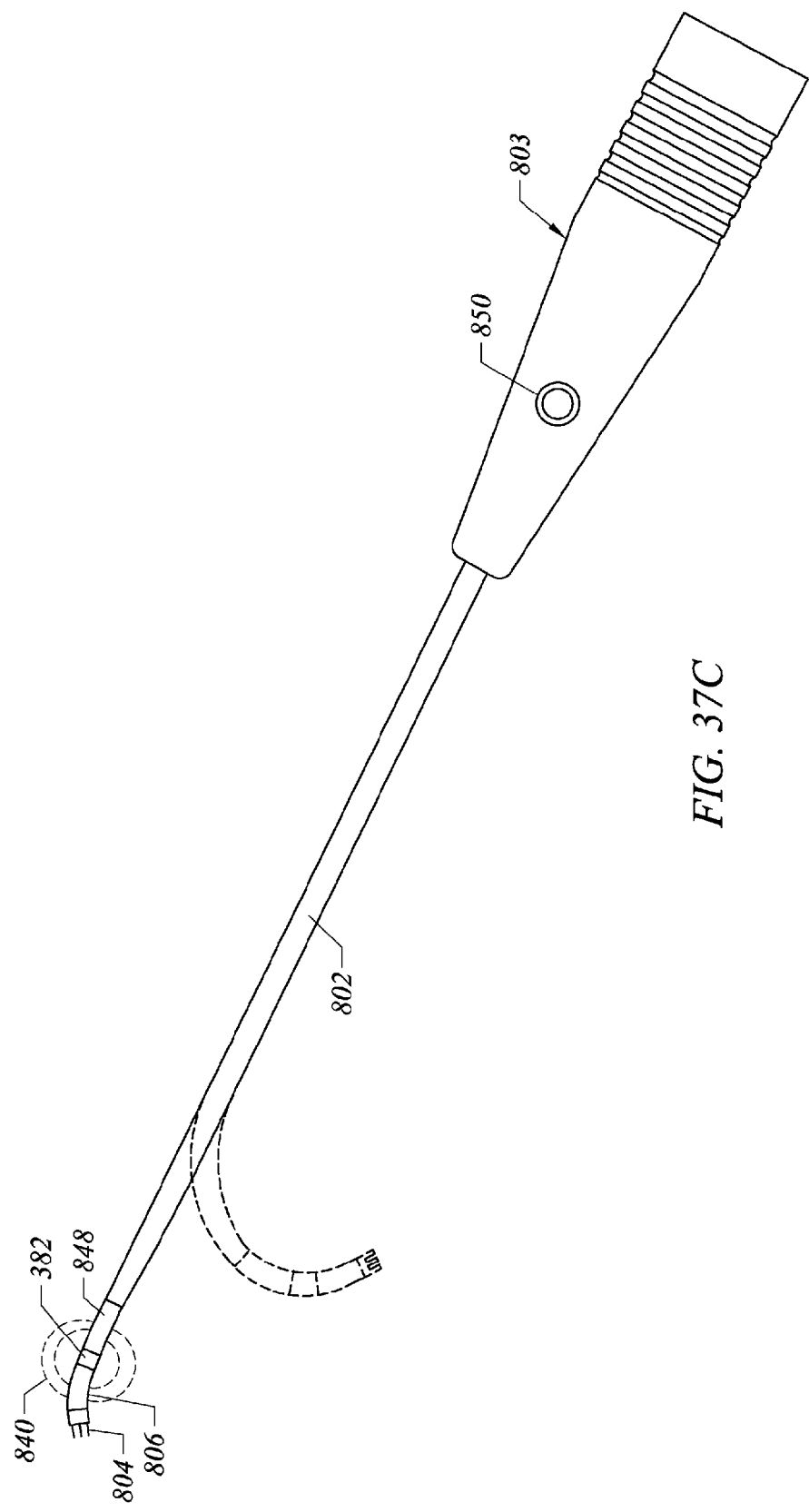

FIG. 37C illustrates another embodiment of probe 800 incorporating an electrode assembly having one or more active electrode(s) 804 and a proximally spaced return electrode 806 as in previous embodiments. Return electrode 806 is typically spaced about 0.5 mm to 25 mm, preferably 1.0 mm to 5.0 mm from the active electrode(s) 804, and has an exposed length of about 1 mm to 20 mm. In addition, the electrode assembly includes a second active electrode 848 separated from return electrode 360 by an electrically insulating spacer 382. In this embodiment, handle 803 includes a switch 850 for toggling probe 800 between at least two different modes, an ablation mode and a sub-ablation or thermal heating mode. In the ablation mode, voltage is applied between active electrode(s) 804 and return electrode 806 in the presence of electrically conductive fluid, as described above. In the ablation mode, electrode 848 is deactivated. In the thermal heating or coagulation mode, active electrode(s) 806 may be deactivated and a voltage difference is applied between electrode 848 and electrode 806 such that a high frequency current 840 flows therebetween. Alternatively, active electrode(s) 804 may not be deactivated as the higher resistance of the smaller electrodes may automatically send the electric current to electrode 848 without having to physically decouple electrode(s) 804 from the circuit. In the thermal heating mode, a lower voltage is typically applied, below the threshold for plasma formation and ablation, but sufficient to cause some thermal damage to the tissue immediately surrounding the electrodes without vaporizing or otherwise debulking this tissue so that the current 840 provides thermal heating and/or coagulation of tissue surrounding electrodes 804, 848.

Figure 37D:
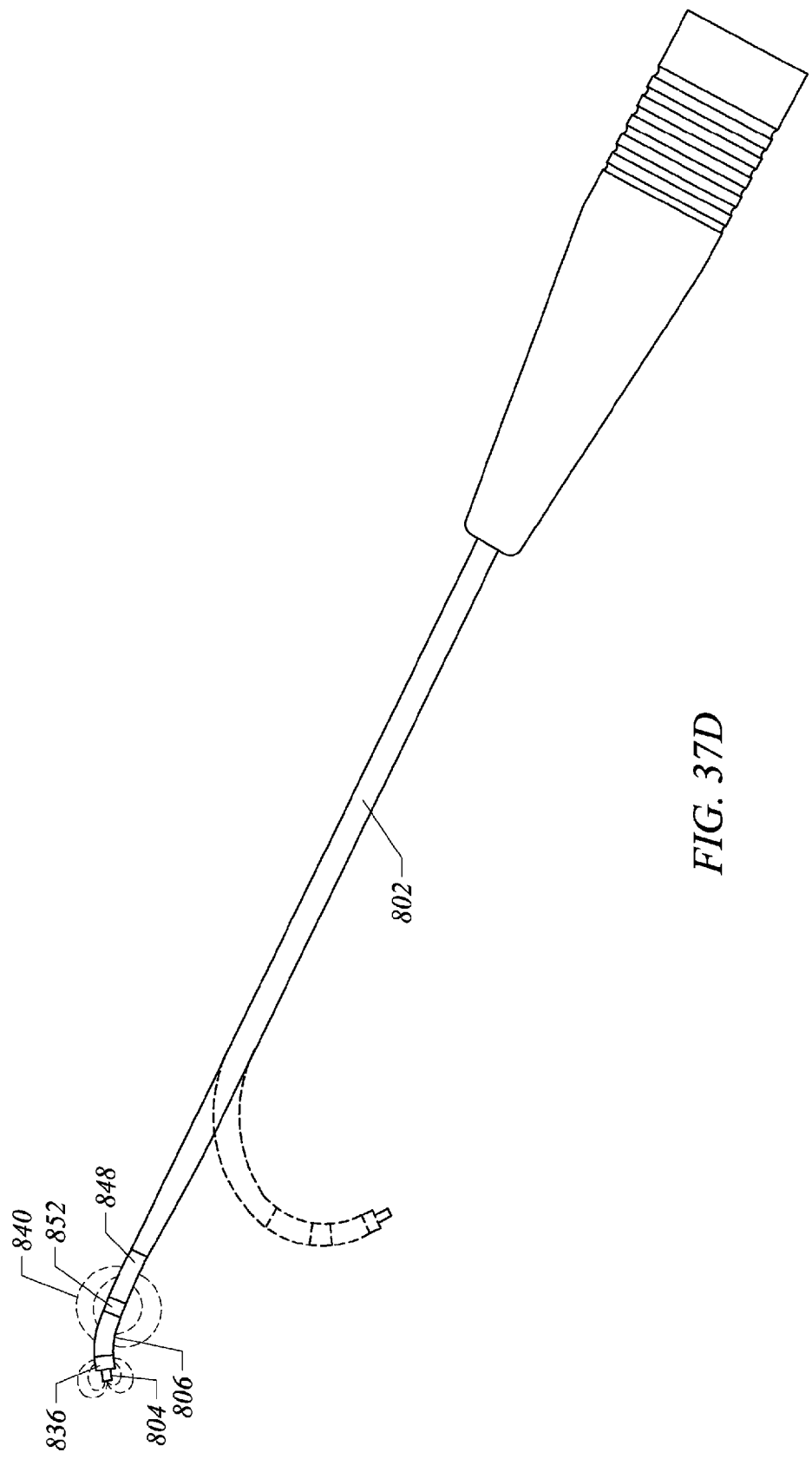
Figure 38:
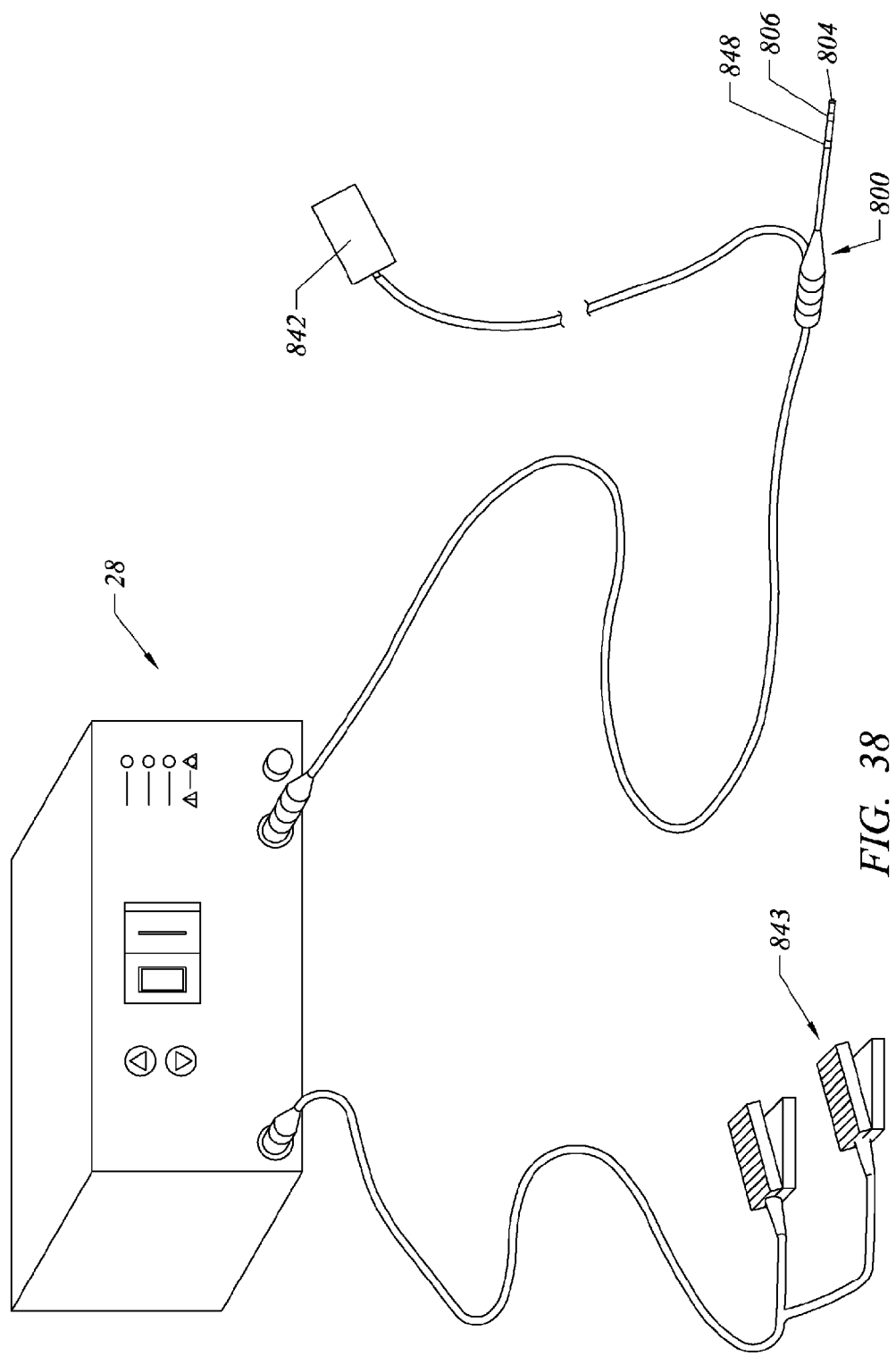
FIG. 38 illustrates an electrosurgical system having a dispersive return pad for monopolar and/or bipolar operations.

FIG. 37D illustrates yet another embodiment of the invention designed for channeling through tissue and creating lesions therein to treat the interior tissue of spinal discs. As shown, probe 800 is similar to the probe in FIG. 37C having a return electrode 806 and a third, coagulation electrode 848 spaced proximally from the return electrode 806. In this embodiment, active electrode 804 comprises a single electrode wire extending distally from insulating support member 836. Of course, the active electrode 804 may have a variety of configurations to increase the current densities on its surfaces, e.g., a conical shape tapering to a distal point, a hollow cylinder, loop electrode and the like. In the representative embodiment, support members 836 and 852 are constructed of inorganic material, such as ceramic, glass, silicone rubber, and the like. The proximal support member 852 may also comprise a more conventional organic material as this support member 852 will generally not be in the presence of a plasma that would otherwise etch or wear away an organic material.

The probe 800 in FIG. 37D does not include a switching element. In this embodiment, all three electrodes are activated when the power supply is activated. The return electrode 806 has an opposite polarity from the active and coagulation electrodes 804, 848 such that current 840 flows from the latter electrodes to the return electrode 806 as shown. In one embodiment, the electrosurgical system includes a voltage reduction element or a voltage reduction circuit for reducing the voltage applied between the coagulation electrode 848 and return electrode 806. The voltage reduction element allows the power supply 28 (FIG. 1) to, in effect, apply two different voltages simultaneously to two different electrodes. Thus, for channeling through tissue, the operator may apply a voltage sufficient to provide ablation of the tissue at the tip of the probe (i.e., tissue adjacent to the active electrode 804). At the same time, the voltage applied to the coagulation electrode 848 will be insufficient to ablate tissue. For thermal heating or coagulation of tissue, for example, the voltage reduction element will serve to reduce a voltage of about 100 volts RMS to 300 volts RMS to about 45 volts RMS to 90 volts RMS, which is a suitable voltage for coagulation of tissue without ablation (e.g., molecular dissociation) of the tissue.

In the representative embodiment, the voltage reduction element is a capacitor (not shown) coupled to the power supply and coagulation electrode 848. The capacitor usually has a capacitance of about 200 pF to 500 pF (at 500 volts) and preferably about 300 pF to 350 pF (at 500 volts). Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors, or combinations thereof, may be used in conjunction with the present invention. For example, the probe 800 may include a coded resistor (not shown) that is constructed to lower the voltage applied between the return and coagulation electrodes 806, 848. In addition, electrical circuits may be employed for this purpose.

Of course, for some procedures, the probe will typically not require a voltage reduction element. Alternatively, the probe may include a voltage increasing element or circuit, if desired. Alternatively or additionally, the cable 22 that couples the power supply 28 to the probe may be used as a voltage reduction element (FIG. 1). The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In use, the electrosurgical instruments of FIGS. 37A-D can be used to treat the tissue within the disc 822. In particular, the electrosurgical instrument 800 can be used to treat damaged discs (e.g., discs that are herniated, bulging, fissured, protruding, or the like), denervate selective nerves embedded in the annulus, cauterize granulation tissue that is ingrown into the annulus, seal fissures of the annulus, and the like. Preferably, the electrosurgical probe 800 can achieve these results in a minimally destructive manner so as to maintain the water content and tissue mass within the disc. Of course, the present invention can also be adapted to ablate tissue or reduce the water content within the disc. The instruments of FIGS. 37A-D may also be used to treat other spinal- and non-spinal tissue.

Figure 39:
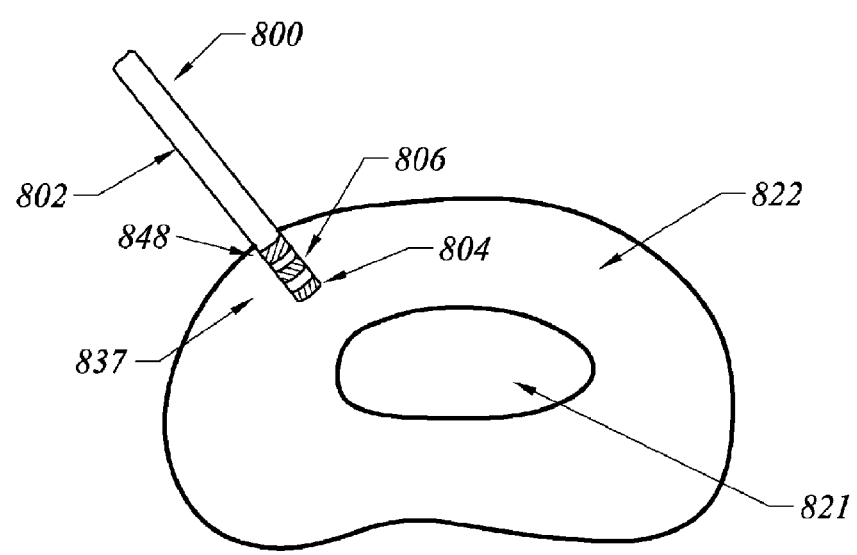

Referring now to FIG. 39, in some methods the physician positions active electrode 804 adjacent to the tissue surface to be treated (e.g., tissue of an intervertebral disc). The power supply is activated to provide an ablation voltage between active and return electrodes 804, 806 and a coagulation or thermal heating voltage between coagulation and return electrodes 806, 848. An electrically conductive fluid can then be provided around active electrode 804, and in the junction between the active and return electrodes 804, 806 to provide a current flow path therebetween. This may be accomplished in a variety of manners, as discussed above. The active electrode 804 is then advanced through the space left by the ablated tissue to form a channel in the disc. During ablation, the electric current between the coagulation and return electrode is typically insufficient to cause any damage to the surface of the tissue as these electrodes pass through the tissue surface into the channel created by active electrode 804. Once the physician has formed the channel to the appropriate depth, he or she will cease advancement of the active electrode, and will either hold the instrument in place for approximately 5 seconds to 30 seconds, or can immediately remove the distal tip of the instrument from the channel (see detailed discussion of this below). In either event, when the active electrode is no longer advancing, it will eventually stop ablating tissue.

Prior to entering the channel formed by the active electrode 804, an open circuit exists between return and coagulation electrodes 806, 848. Once coagulation electrode 848 enters this channel, electric current will flow from coagulation electrode 848, through the tissue surrounding the channel, to return electrode 806. This electric current will heat the tissue immediately surrounding the channel to coagulate any severed vessels at the surface of the channel. If the physician desires, the instrument may be held within the channel for a period of time to create a lesion around the channel.

In an exemplary embodiment, once the distal tip 837 of the electrosurgical probe 800 has channeled through the annulus fibrosus 822, the distal tip 837 can be steered or deflected to a particular target site within the disc. As the electrosurgical device is advanced into the disc, the physician can simultaneously steer the distal tip from the proximal end of the electrosurgical device. The physician can use fluoroscopy to monitor the position and movement of the distal end of the probe. Alternatively, the surgeon may insert an imaging device or transducer directly into the disc to monitor the position of the electrode array. The imaging device (not shown) can be positioned on the electrosurgical probe or it can be on a separate instrument.

Once the electrosurgical probe has been steered to the target position, a high frequency voltage can be delivered between the active electrode(s) and return electrode(s) in a bipolar mode or monopolar mode. In some embodiments, an electrically conductive fluid, such as isotonic saline, can be delivered to the active electrode. In monopolar embodiments, the conductive fluid need only be sufficient to surround the active electrode and to provide a layer of fluid between the electrode and the tissue. In bipolar embodiments, the conductive fluid preferably generates a current flow path between the active electrode(s) and the return electrode(s).

Depending on the procedure, the annulus can be ablated, contracted, sealed, or the like. For example, the high frequency voltage can be used to denervate the pain receptors in a fissure in the annulus fibrosus, deactivate the neurotransmitters, deactivate heat-sensitive enzymes, denervate nerves embedded in the wall of the annulus fibrosus, ablate granulation tissue in the annulus fibrosus, shrink collagen in the annulus fibrosus, or the like.

Figure 40A:
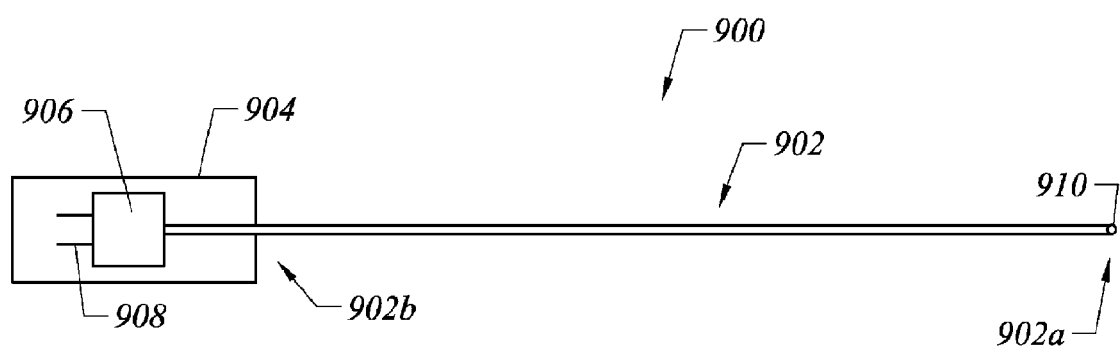
FIG. 40A is a side view of an electrosurgical probe according to the invention.

FIG. 40A is a side view of an electrosurgical probe 900, according to one embodiment of the invention. Probe 900 includes a shaft 902 having a distal end portion 902a and a proximal end portion 902b. An active electrode 910 is disposed on distal end portion 902a. Although only one active electrode is shown in FIG. 40A, embodiments including a plurality of active electrodes are also within the scope of the invention. Probe 900 further includes a handle 904 which houses a connection block 906 for coupling electrodes, e.g. active electrode 910, thereto. Connection block 906 includes a plurality of pins 908 adapted for coupling probe 900 to a power supply unit, e.g. power supply 28 (FIG. 1).

Figure 40B:
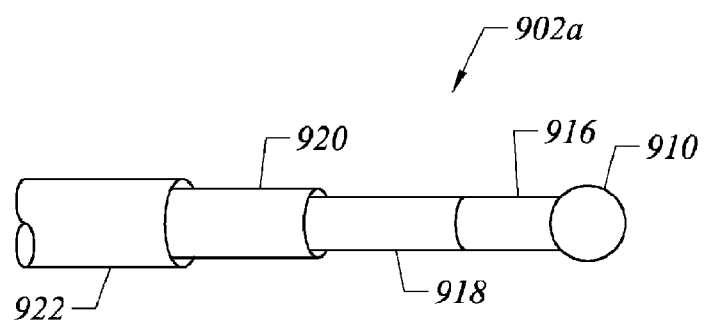
FIG. 40B is a side view of the distal end portion of the electrosurgical probe of FIG. 40A.
Figure 45B:
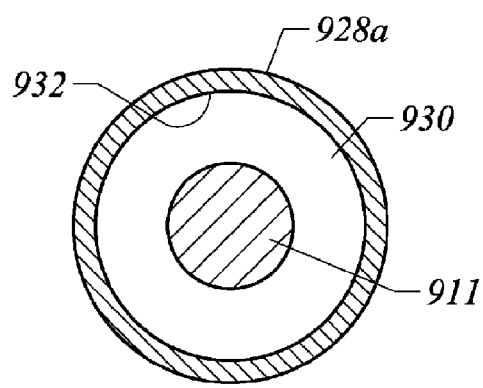

FIG. 40B is a side view of the distal end portion of the electrosurgical probe of FIG. 40A, showing details of shaft distal end portion 902a. Distal end portion 902a includes an insulating collar or spacer 916 proximal to active electrode 910, and a return electrode 918 proximal to collar 916. A first insulating sleeve (FIG. 42B) may be located beneath return electrode 918. A second insulating jacket or sleeve 920 may extend proximally from return electrode 918. Second insulating sleeve 920 serves as an electrical insulator to inhibit current flow into the adjacent tissue. In one embodiment, probe 900 further includes a shield 922 extending proximally from second insulating sleeve 920. Shield 922 may be formed from a conductive metal such as stainless steel, and the like. Shield 922 functions to decrease the amount of leakage current passing from probe 900 to a patient or a user (e.g., surgeon). In particular, shield 922 decreases the amount of capacitive coupling between return electrode 918 and an introducer needle 928 (FIG. 45A). Typically shield 922 is coupled to an outer floating conductive layer or cable shield (not shown) of a cable, e.g. cables 22, 34 (FIG. 1), connecting probe 900 to power supply 28. In this way, the capacitor balance of shaft 902 is disturbed. In one embodiment, shield 922 may be coated with a durable, hard compound such as titanium nitride. Such a coating has the advantage of providing reduced friction between shield 922 and introducer inner wall 932 as shaft 902 is axially translated within introducer needle 928 (e.g., FIGS. 45A, 45B).

Figure 41A:
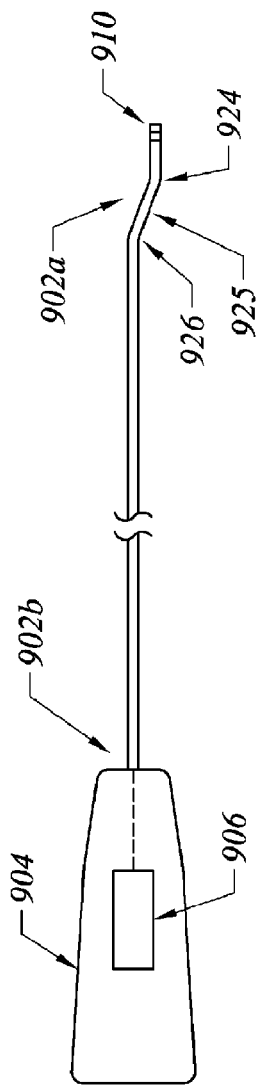
FIG. 41A is a side view of an electrosurgical probe having a curved shaft.

FIG. 41A is a side view of an electrosurgical probe 900 showing a first curve 924 and a second curve 926 located at distal end portion 902a, wherein second curve 926 is proximal to first curve 924. First curve 924 and second curve 926 may be separated by a linear (i.e. straight, or non-curved), or substantially linear, inter-curve portion 925 of shaft 902.

FIG. 41lB is a side view of shaft distal end portion 902a within a representative introducer needle 903 having an inner diameter D. Shaft distal end portion 902a includes first curve 924 and second curve 926 interspersed between inter-curve portion 925. In one embodiment, shaft distal end portion 902a includes a linear or substantially linear proximal portion 905 extending from proximal end portion 902b to second curve 926, a linear or substantially linear inter-curve portion 925 between first and second curves 924, 926, and a linear or substantially linear distal portion 909 between first curve 924 and tip 911. When shaft distal end portion 902a is located within introducer needle 903, first curve 924 subtends a first angle ∀ to the inner surface of needle 903 and second curve 926 subtends a second angle ∃ to the inner surface of needle 903. Shaft distal end portion 902a is designed such that tip 911 remains in the substantial center of introducer needle 903. Thus, as shaft distal end portion 902a is advanced through the distal opening (not shown) of needle 903, and then retracted back into the distal opening, tip 911 will always remain in the center of the needle 911 (even though the tip may curve outward from the axis of needle 911 upon its advancement past the distal opening of needle 911. This design allows a relatively soft tip 911 to be advanced and retracted through the opening of an introducer needle without catching on the edges of the needle.

Figure 41B:
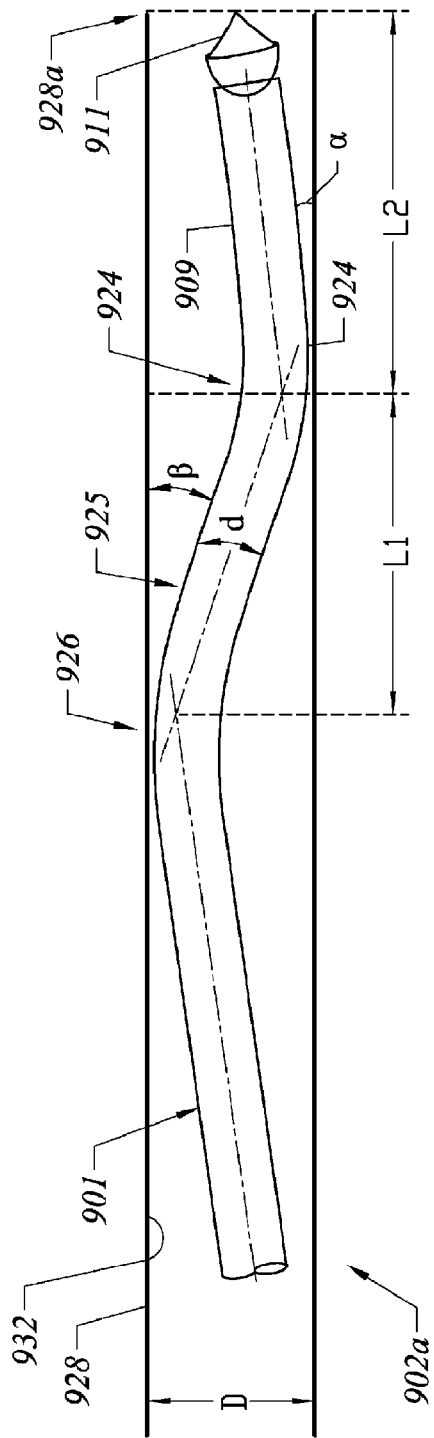
FIG. 41B is a side view of the distal end portion of the curved shaft of FIG. 41A, with the shaft distal end within an introducer device.

The S-curve design of shaft distal end portion 902a allows the tip 911 to be advanced and retracted through the distal opening of needle 903 while minimizing contact between tip 911 and the edges of the distal opening of needle 903. If end portion 902a included only one curve, for example, the tip 911 could come into contact with needle opening as it is retracted back into the opening. In preferred embodiments, the length L2 of distal portion 909 and the angle ∀ between distal portion 909 and the inner surface of needle 903 when shaft distal end portion 902a is compressed within needle 903 are selected such that tip 911 is substantially in the center of needle 903, as shown in FIG. 41B. Thus, as the length L2 increases, the angle ∀ will decrease and vice versa. The exact dimensions of length L2 and angle ∀ will depend on the inner diameter D of needle 903, the inner diameter d of shaft distal end portion 902a and the size of tip 911. The second angle ∃ will determine the deflection of tip 911 from the center of needle 903 when tip 911 and second curve 926 have passed through the distal opening of needle 903. Thus, when tip 911 is rotated circumferentially with respect to the needle axis, the second angle ∃ will effectively determine the size of the channel or lesion (depending on the application) in the tissue treated by tip 911.

In addition, shaft distal end portion 902a is designed such that curves 926, 924 are compressed slightly as portion 902a passes through the inner lumen of needle 911. The presence of first and second curves, 924, 926 provides a pre-defined bias in shaft 902 such that curves 924, 926 are greater when distal end portion 902a is advanced out through the distal opening of introducer needle 903. Thus, distal end portion 902a will contact a larger volume of tissue than a linear shaft having the same dimensions. In addition, this allows the physician to steer the tip 911 through a combination of axial movement of the distal opening (not shown) of needle 903 and the inherent curvature at the distal end portion 902a of the device.

Shaft 902 preferably has a length in the range of from about 4 cm to 30 cm. In one aspect of the invention, probe 900 is manufactured in a range of sizes having different lengths and/or diameters of shaft 902. A shaft of appropriate size can then be selected by the surgeon according to the body structure or tissue to be treated and the age or size of the patient. In this way, patients varying in size from small children to large adults can be accommodated. Similarly, for a patient of a given size, a shaft of appropriate size can be selected by the surgeon depending on the organ or tissue to be treated, for example, whether an intervertebral disc to be treated is in the lumbar spine or the cervical spine. For example, a shaft suitable for treatment of a disc of the cervical spine may be substantially smaller than a shaft for treatment of a lumbar disc. For treatment of a lumbar disc in an adult, shaft 902 is preferably in the range of from about 15 to 25 cm. For treatment of a cervical disc, shaft 902 is preferably in the range of from about 4 cm to about 15 cm.

The diameter of shaft 902 is preferably in the range of from about 0.5 to about 2.5 mm, and more preferably from about 1 to 1.5 mm. First curve 924 is characterized by a length, L1, while second curve 926 is characterized by a length L2 (FIG. 41B). Inter-curve portion 925 is characterized by a length, L3, while shaft 902 extends distally from first curve 924 a length L4. In one embodiment, L2 is greater than L1. Length L1 may be in the range of from about 0.5 mm to about 5 mm, while L2 may be in the range of from about 1 to about 10 mm. Preferably, L3 and L4 are each in the range of from about 1 mm to 6 mm.

Figure 42A:
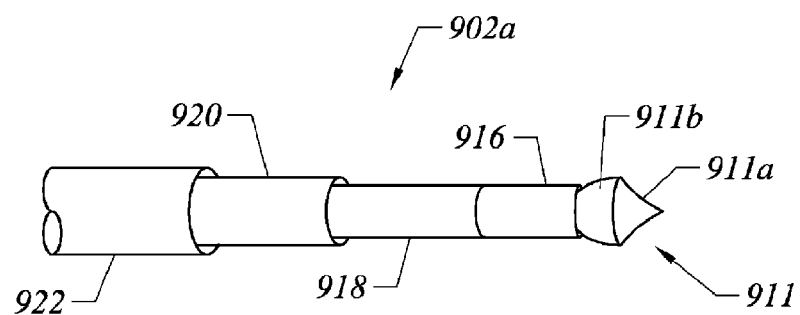
FIG. 42A is a side view of the distal end portion of an electrosurgical probe showing an active electrode having an apical spike and an equatorial cusp.

FIG. 42A is a side view of shaft distal end portion 902a of electrosurgical probe 900 showing a head 911 of active electrode 910 (the latter not shown in FIG. 42A), according to one embodiment of the invention. In this embodiment, electrode head 911 includes an apical spike 911a and an equatorial cusp 911b. Electrode head 911 exhibits a number of advantages as compared with, for example, an electrosurgical probe having a blunt, globular, or substantially spherical active electrode. In particular, electrode head 911 provides a high current density at apical spike 911a and cusp 911b. In turn, high current density in the vicinity of an active electrode is advantageous in the generation of a plasma; and, as is described fully hereinabove, generation of a plasma in the vicinity of an active electrode is fundamental to ablation of tissue with minimal collateral thermal damage according to certain embodiments of the instant invention. Electrode head 911 provides an additional advantage, in that the sharp edges of cusp 911b, and more particularly of apical spike 911a, facilitate movement and guiding of head 911 into tissue during surgical procedures, as described fully hereinbelow. In contrast, an electrosurgical probe having a blunt or rounded apical electrode is more likely to follow a path of least resistance, such as a channel which was previously ablated within nucleus pulposus tissue. Although certain embodiments of the invention depict head 911 as having a single apical spike, other shapes for the apical portion of active electrode 910 are also within the scope of the invention.

Figure 42B:
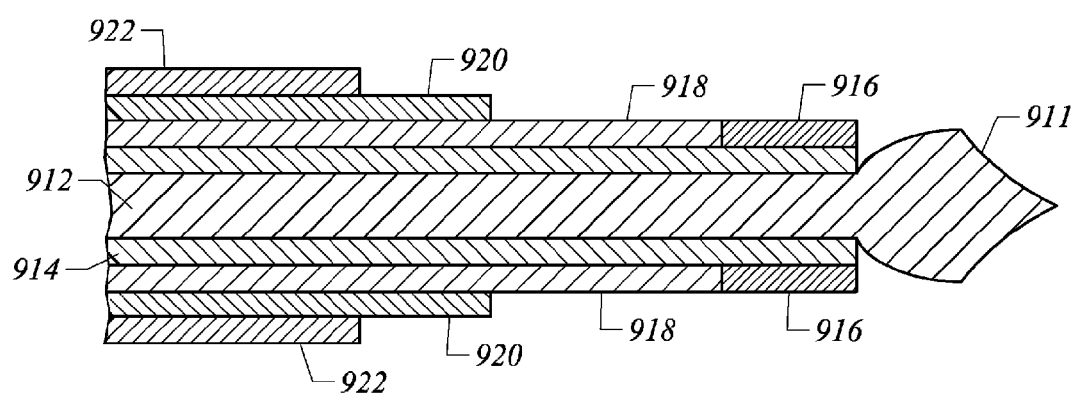
FIG. 42B is a cross-sectional view of the distal end portion of the electrosurgical probe of FIG. 42A.

FIG. 42B is a longitudinal cross-sectional view of distal end portion 902a of shaft 902. Apical electrode head 911 is in communication with a filament 912. Filament 912 typically comprises an electrically conductive wire encased within a first insulating sleeve 914. First insulating sleeve 914 comprises an insulator, such as various synthetic polymeric materials. An exemplary material from which first insulating sleeve 914 may be constructed is a polyimide. First insulating sleeve 914 may extend the entire length of shaft 902 proximal to head 911. An insulating collar or spacer 916 is disposed on the distal end of first insulating sleeve 914, adjacent to electrode head 911. Collar 916 preferably comprises a material such as a glass, a ceramic, or silicone rubber. The exposed portion of first insulating sleeve 914 (i.e., the portion proximal to collar 916) is encased within a cylindrical return electrode 918. Return electrode 918 may extend proximally the entire length of shaft 902. Return electrode 918 may comprise an electrically conductive material such as stainless steel, tungsten, platinum or its alloys, titanium or its alloys, molybdenum or its alloys, nickel or its alloys, and the like. A proximal portion of return electrode 918 is encased within a second insulating sleeve 920, so as to provide an exposed band of return electrode 918 located distal to second sleeve 920 and proximal to collar 916. Second sleeve 920 provides an insulated portion of shaft 920 which facilitates handling of probe 900 by the surgeon during a surgical procedure. A proximal portion of second sleeve 920 is encased within an electrically conductive shield 922. Second sleeve 920 and shield 922 may also extend proximally for the entire length of shaft 902.

Figure 43:
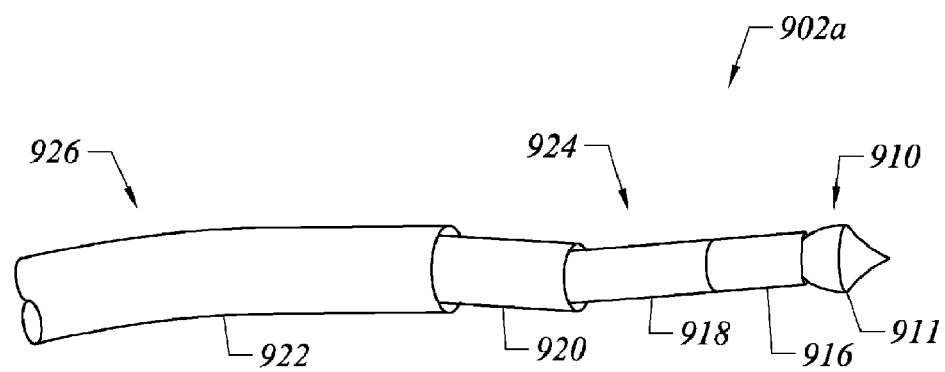
FIG. 43 is a side view of the distal end portion a shaft of an electrosurgical probe, indicating the location of a first curve and a second curve in relation to the head of the active electrode.

FIG. 43 is a side view of shaft distal end portion 902a of electrosurgical probe 900, indicating the position of first and second curves 924, 926, respectively. Probe 900 includes head 911, collar 916, return electrode 918, second insulating sleeve 920, and shield 922, generally as described with reference to FIGS. 42A, 42B. In the embodiment of FIG. 43, first curve 924 is located within return electrode 918, while second curve 926 is located within shield 922. However, according to various embodiments of the invention, shaft 902 may be provided in which one or more curves are present at alternative or additional locations or components of shaft 902, other than the location of first and second curves 924, 926, respectively, shown in FIG. 43.

Figure 44A:
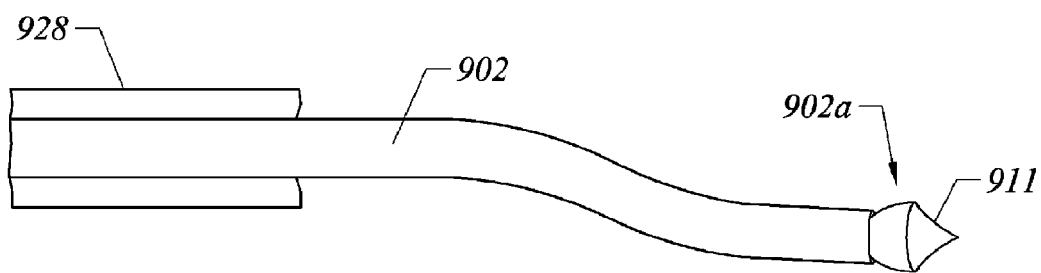
FIG. 44A shows the distal end portion of the shaft of an electrosurgical probe extended distally from an introducer needle.
Figure 44B:
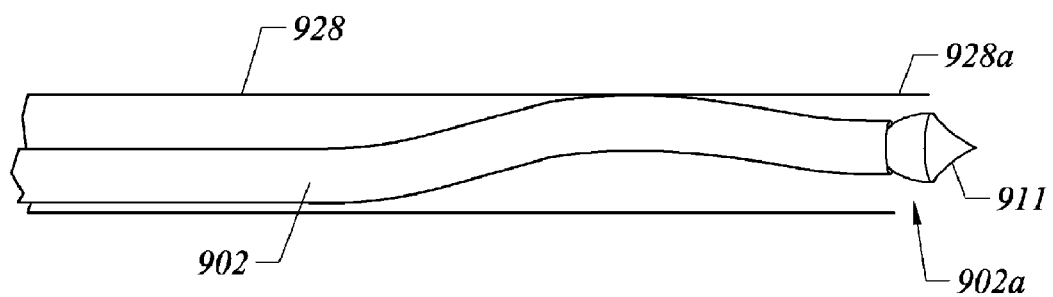
FIG. 44B illustrates the position of the active electrode in relation to the inner wall of the introducer needle upon retraction of the active electrode within the introducer needle.
Figure 451A:
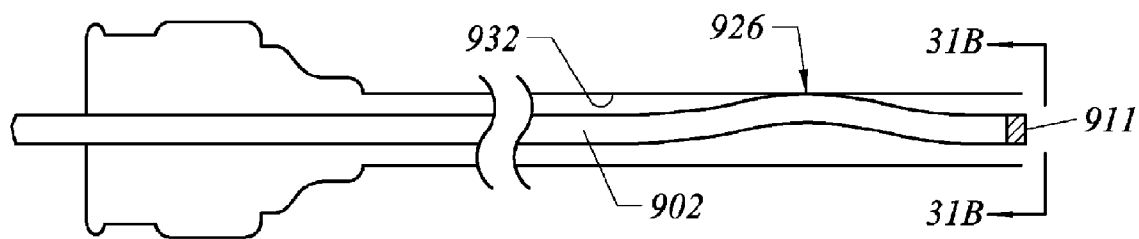

FIG. 44A shows distal end portion 902a of shaft 902 extended distally from an introducer needle 928, according to one embodiment of the invention. Introducer needle 928 may be used to conveniently introduce shaft 902 into tissue, such as the nucleus pulposus of an intervertebral disc. In this embodiment, due to the curvature of shaft distal end 902a, when shaft 902 is extended distally beyond introducer needle 928, head 911 is displaced laterally from the longitudinal axis of introducer needle 928. However, as shown in FIG. 44B, as shaft 902 is retracted into introducer needle 928, head 911 assumes a substantially central location within lumen 930 (see also FIG. 45B) of introducer 928. Such re-alignment of head 911 with the longitudinal axis of introducer 928 is achieved by specific design of the curvature of shaft distal end 902a, as accomplished by the instant inventors. In this manner, contact of various components of shaft distal end 902a (e.g., electrode head 911, collar 916, return electrode 918) is prevented, thereby not only facilitating extension and retraction of shaft 902 within introducer 928, but also avoiding a potential source of damage to sensitive components of shaft 902.

FIG. 45A shows a side view of shaft 902 in relation to an inner wall 932 of introducer needle 928 upon extension or retraction of electrode head 911 from, or within, introducer needle 928. Shaft 902 is located within introducer 928 with head 911 adjacent to introducer distal end 928a (FIG. 45B). Under these circumstances, curvature of shaft 902 may cause shaft distal end 902a to be forced into contact with introducer inner wall 932, e.g., at a location of second curve 926. Nevertheless, due to the overall curvature of shaft 902, and in particular the nature and position of first curve 924 (FIGS. 41A-B), head 911 does not contact introducer distal end 928a.

FIG. 45B shows an end view of electrode head 911 in relation to introducer needle 928 at a point during extension or retraction of shaft 902, wherein head 911 is adjacent to introducer distal end 928a (FIGS. 44B, 45B). In this situation, head 911 is substantially centrally positioned within lumen 930 of introducer 928. Therefore, contact between head 911 and introducer 928 is avoided, allowing shaft distal end 902a to be extended and retracted repeatedly without sustaining any damage to shaft 902.

Figure 46A:
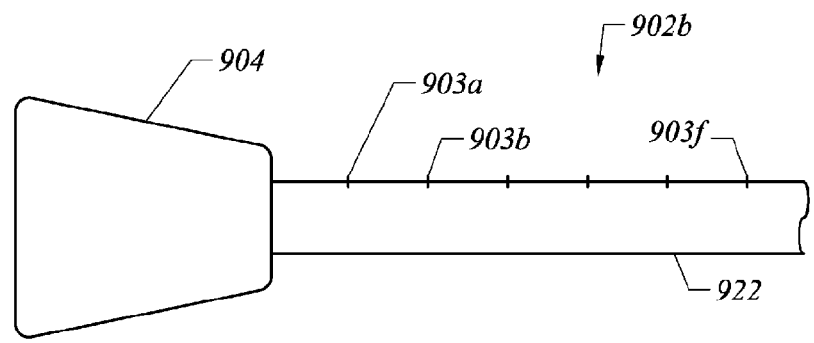
FIG. 46A shows the proximal end portion of the shaft of an electrosurgical probe, wherein the shaft includes a plurality of depth markings.

FIG. 46A shows shaft proximal end portion 902b of electrosurgical probe 900, wherein shaft 902 includes a plurality of depth markings 903 (shown as 903a-f in FIG. 46A). In other embodiments, other numbers and arrangements of depth markings 903 may be included on shaft 902. For example, in certain embodiments, depth markings may be present along the entire length of shield 922, or a single depth marking 903 may be present at shaft proximal end portion 902*b*. Depth markings serve to indicate to the surgeon the depth of penetration of shaft 902 into a patient's tissue, organ, or body, during a surgical procedure. Depth markings 903 may be formed directly in or on shield 922, and may comprise the same material as shield 922. Alternatively, depth markings 903 may be formed from a material other than that of shield 922. For example, depth markings may be formed from materials which have a different color and/or a different level of radiopacity, as compared with material of shield 922. For example, depth markings may comprise a metal, such as tungsten, gold, or platinum oxide (black), having a level of radiopacity different from that of shield 922. Such depth markings may be visualized by the surgeon during a procedure performed under fluoroscopy. In one embodiment, the length of the introducer needle and the shaft 902 are selected to limit the range of the shaft beyond the distal tip of the introducer needle.

Figure 46B:
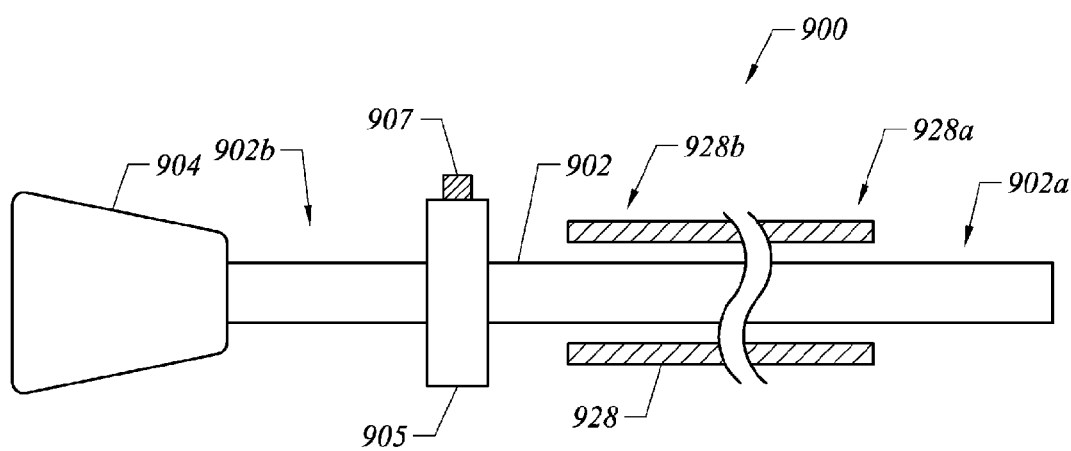
FIG. 46B shows the proximal end portion of the shaft of an electrosurgical probe, wherein the shaft includes a mechanical stop.

FIG. 46B shows a probe 900, wherein shaft 902 includes a mechanical stop 905. Preferably, mechanical stop 905 is located at shaft proximal end portion 902*b*. Mechanical stop 905 limits the distance to which shaft distal end 902*a* can be advanced through introducer 928 by making mechanical contact with a proximal end 928*b* of introducer 928. Mechanical stop 905 may be a rigid material or structure affixed to, or integral with, shaft 902. Mechanical stop 905 also serves to monitor the depth or distance of advancement of shaft distal end 902*a* through introducer 928, and the degree of penetration of distal end 902*a* into a patient's tissue, organ, or body. In one embodiment, mechanical stop 905 is movable on shaft 902, and stop 905 includes a stop adjustment unit 907 for adjusting the position of stop 905 and for locking stop 905 at a selected location on shaft 902.

Figure 47A:
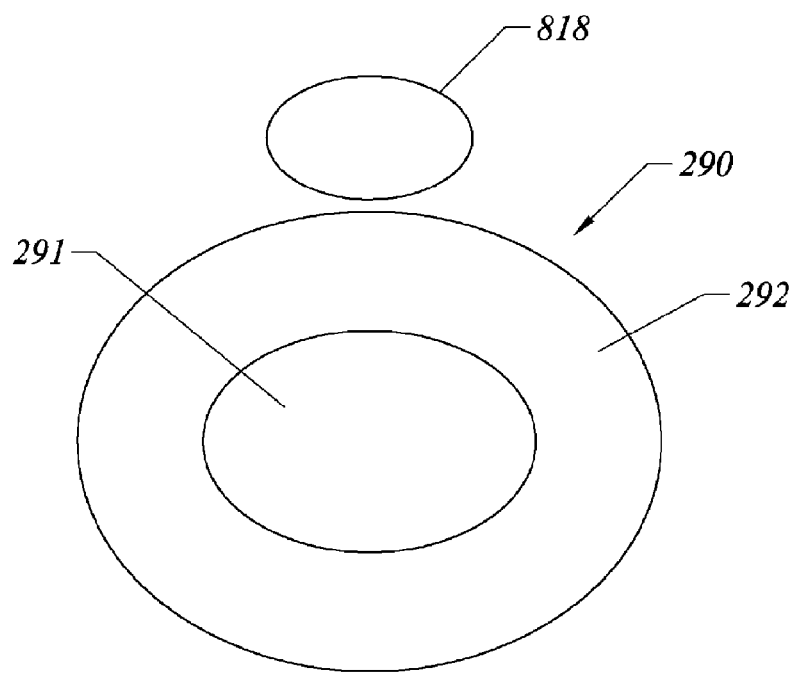
FIG. 47A schematically represents a normal intervertebral disc in relation to the spinal cord.
Figure 47B:
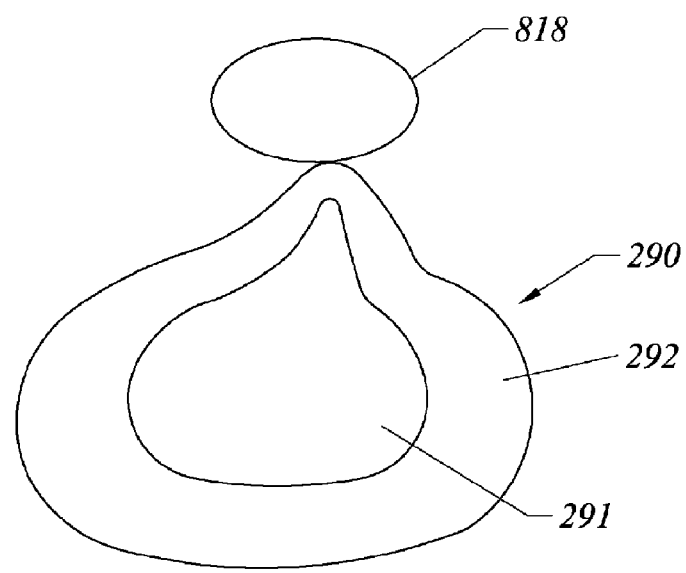
FIG. 47B schematically represents an intervertebral disc exhibiting a protrusion of the nucleus pulposus and a concomitant distortion of the annulus fibrosus.
Figure 47C:
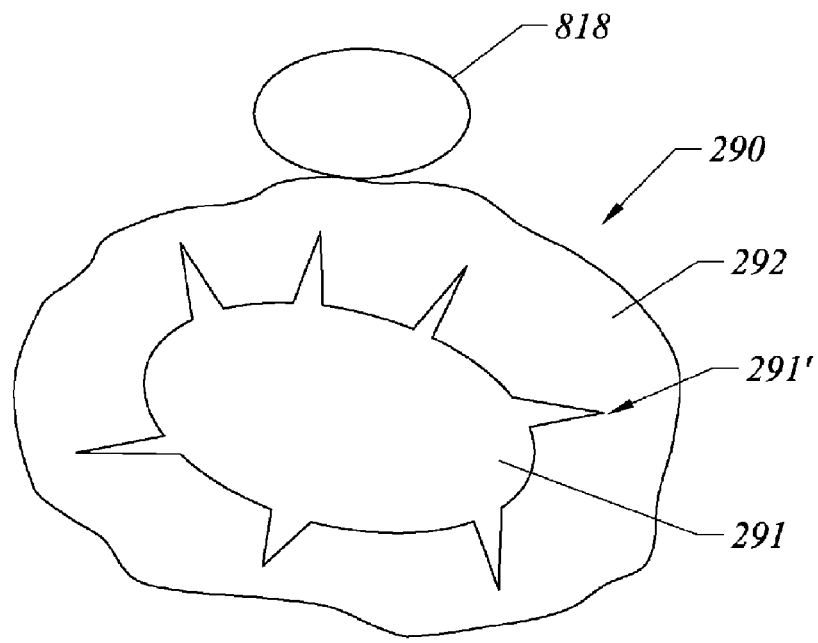
FIG. 47C schematically represents an intervertebral disc exhibiting a plurality of fissures within the annulus fibrosus and a concomitant distortion of the annulus fibrosus.
Figure 47D:
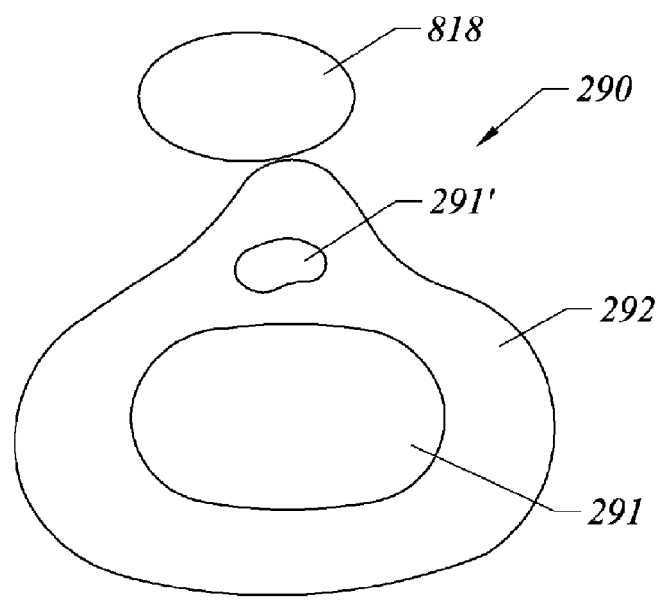
FIG. 47D schematically represents an intervertebral disc exhibiting fragmentation of the nucleus pulposus and a concomitant distortion of the annulus fibrosus.

FIG. 47A schematically represents a normal intervertebral disc 290 in relation to the spinal cord 720, the intervertebral disc having an outer annulus fibrosus 292 enclosing an inner nucleus pulposus 294. The nucleus pulposus is a relatively soft tissue comprising proteins and having a relatively high water content, as compared with the harder, more fibrous annulus fibrosus. FIGS. 47B-D each schematically represent an intervertebral disc having a disorder which can lead to discogenic pain, for example due to compression of a nerve root by a distorted annulus fibrosus. Thus, FIG. 47B schematically represents an intervertebral disc exhibiting a protrusion of the nucleus pulposus and a concomitant distortion of the annulus fibrosus. The condition depicted in FIG. 47B clearly represents a contained herniation, which can result in severe and often debilitating pain. FIG. 47C schematically represents an intervertebral disc exhibiting a plurality of fissures within the annulus fibrosus, again with concomitant distortion of the annulus fibrosus. Such annular fissures may be caused by excessive pressure exerted by the nucleus pulposus on the annulus fibrosus. Excessive pressure within the nucleus pulposus tends to intensify disc disorders associated with the presence of such fissures. FIG. 47D schematically represents an intervertebral disc exhibiting fragmentation of the nucleus pulposus and a concomitant distortion of the annulus fibrosus. In this situation, over time, errant fragment 294' of the nucleus pulposus tends to dehydrate and to diminish in size, often leading to a decrease in discogenic pain over an extended period of time (e.g., several months). For the sake of clarity, each FIG. 47B, 47C, 47D shows a single disorder. However, in practice more than one of the depicted disorders may occur in the same disc.

Many patients suffer from discogenic pain resulting, for example, from conditions of the type depicted in FIGS. 47B-D. However, only a small percentage of such patients undergo laminotomy or discectomy. Presently, there is a need for interventional treatment for the large group of patients who ultimately do not undergo major spinal surgery, but who sustain significant disability due to various disorders or defects of an intervertebral disc. A common disorder of intervertebral discs is a contained herniation in which the nucleus pulposus does not breach the annulus fibrosus, but a protrusion of the disc causes compression of the exiting nerve root, leading to radicular pain. Typical symptoms are leg pain compatible with sciatica. Such radicular pain may be considered as a particular form of discogenic pain. Most commonly, contained herniations leading to radicular pain are associated with the lumbar spine, and in particular with intervertebral discs at either L4-5 or L5-S1. Various disc defects are also encountered in the cervical spine. Methods and apparatus of the invention are applicable to all segments of the spine, including the cervical spine and the lumbar spine.

Figure 48:
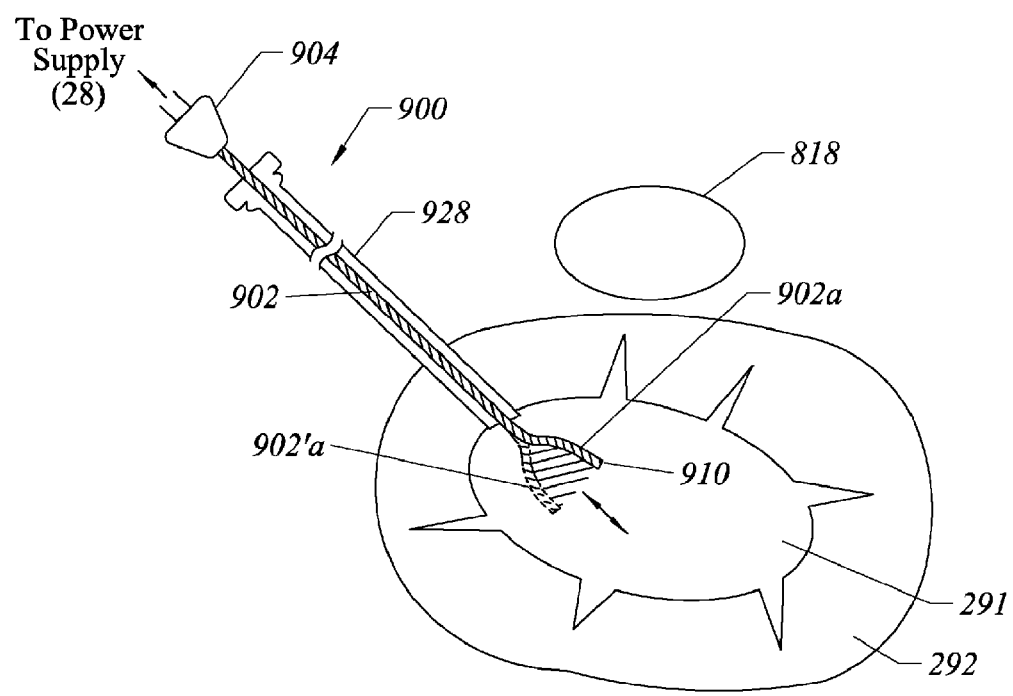
FIG. 48 schematically represents translation of a curved shaft of an electrosurgical probe within the nucleus pulposus for treatment of an intervertebral disc.

FIG. 48 schematically represents shaft 902 of probe 900 inserted within a nucleus pulposus of a disc having at least one fissure in the annulus. Shaft 902 may be conveniently inserted within the nucleus pulposus via introducer needle 928 in a minimally invasive percutaneous procedure. In one embodiment, a disc in the lumbar spine may be accessed via a posterolateral approach, although other approaches are possible and are within the scope of the invention. The preferred length and diameter of shaft 902 and introducer needle 928 to be used in a procedure will depend on a number of factors, including the region of the spine (e.g., lumbar, cervical) or other body region to be treated, and the size of the patient. Preferred ranges for shaft 902 are given elsewhere herein. In one embodiment for treatment of a lumbar disc, introducer needle 928 preferably has a diameter in the range of from about 50% to 150% the inside diameter of a 17 Gauge needle. In an embodiment for treatment of a cervical disc, introducer needle 928 preferably has a diameter in the range of from about 50% to 150% the inner diameter of a 20 Gauge needle.

Shaft 902 includes an active electrode 910, as described hereinabove. Shaft 902 features curvature at distal end 902*a*/902'*a*, for example, as described with reference to FIGS. 41A-B. By rotating shaft 902 through approximately 180°, shaft distal end 902*a* can be moved to a position indicated by the dashed lines and labeled as 902'*a*. Thereafter, rotation of shaft 902 through an additional 180° defines a substantially cylindrical three-dimensional space with a proximal conical area represented as a hatched area (shown between 902*a* and 902'*a*). The bi-directional arrow distal to active electrode 910 indicates translation of shaft 902 substantially along the longitudinal axis of shaft 902. By a combination of axial and rotational movement of shaft 902, a much larger volume of the nucleus pulposus can be contacted by electrode 910, as compared with a corresponding probe having a linear (non-curved) shaft. Furthermore, the curved nature of shaft 902 allows the surgeon to change the direction of advancement of shaft 902 by appropriate rotation thereof, and to guide shaft distal end 902*a* to a particular target site within the nucleus pulposus.

It is to be understood that according to certain embodiments of the invention, the curvature of shaft 902 is the same, or substantially the same, both prior to it being used in a surgical procedure and while it is performing ablation during a procedure, e.g., within an intervertebral disc. (One apparent exception to this statement, relates to the stage in a procedure wherein shaft 902 may be transiently "molded" into a somewhat more linear configuration by the constraints of introducer inner wall 932 during housing, or passing, of shaft 902 within introducer 928.) In contrast, certain prior art devices, and embodiments of the invention to be described hereinbelow (e.g., with reference to FIG. 54A, 54B), may be linear or lacking a naturally defined configuration prior to use, and then be steered into a selected configuration during a surgical procedure.

While shaft distal end 902a is at or adjacent to a target site within the nucleus pulposus, probe 900 may be used to ablate tissue by application of a first high frequency voltage between active electrode 910 and return electrode 918 (e.g., FIG. 40B), wherein the volume of the nucleus pulposus is decreased, the pressure exerted by the nucleus pulposus on the annulus fibrosus is decreased, and at least one nerve or nerve root is decompressed. Accordingly, discogenic pain experienced by the patient may be alleviated. Preferably, application of the first high frequency voltage results in formation of a plasma in the vicinity of active electrode 910, and the plasma causes ablation by breaking down high molecular weight disc tissue components (e.g., proteins) into low molecular weight gaseous materials. Such low molecular weight gaseous materials may be at least partially vented or exhausted from the disc, e.g., by piston action, upon removal of shaft 902 and introducer 928 from the disc and the clearance between the introducer 928 and the shaft 902. In addition, by-products of tissue ablation may be removed by an aspiration device (not shown in FIG. 48), as is well known in the art. In this manner, the volume and/or mass of the nucleus pulposus may be decreased.

Figure 52:
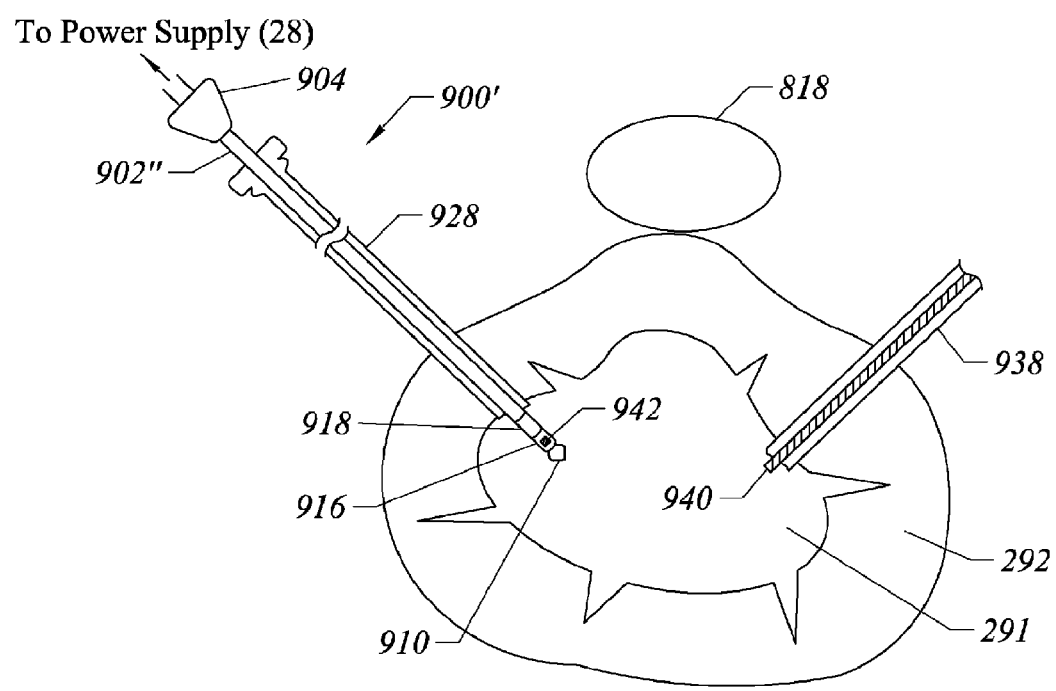
FIG. 52 shows treatment of an intervertebral disc using an electrosurgical probe and a separately introduced ancillary device, according to another embodiment of the invention.

In order to initiate and/or maintain a plasma in the vicinity of active electrode 910, a quantity of an electrically conductive fluid may be applied to shaft 902 and/or the tissue to ablated. The electrically conductive fluid may be applied to shaft 902 and/or to the tissue to be ablated, either before or during application of the first high frequency voltage. Examples of electrically conductive fluids are saline (e.g., isotonic saline), and an electrically conductive gel. An electrically conductive fluid may be applied to the tissue to be ablated before or during ablation. A fluid delivery unit or device may be a component of the electrosurgical probe itself, or may comprise a separate device, e.g., ancillary device 940 (FIG. 52). Alternatively, many body fluids and/or tissues (e.g., the nucleus pulposus, blood) at the site to be ablated are electrically conductive and can participate in initiation or maintenance of a plasma in the vicinity of the active electrode.

In one embodiment, after ablation of nucleus pulposus tissue by the application of the first high frequency voltage and formation of a cavity or channel within the nucleus pulposus, a second high frequency voltage may be applied between active electrode 910 and return electrode 918, wherein application of the second high frequency voltage causes coagulation of nucleus pulposus tissue adjacent to the cavity or channel. Such coagulation of nucleus pulposus tissue may lead to increased stiffness, strength, and/or rigidity within certain regions of the nucleus pulposus, concomitant with an alleviation of discogenic pain. Furthermore, coagulation of tissues may lead to necrotic tissue which is subsequently broken down as part of a natural bodily process and expelled from the body, thereby resulting in de-bulking of the disc. Although FIG. 48 depicts a disc having fissures within the annulus fibrosus, it is to be understood that apparatus and methods of the invention discussed with reference to FIG. 48 are also applicable to treating other types of disc disorders, including those described with reference to FIGS. 47B, 47D.

Figure 49:
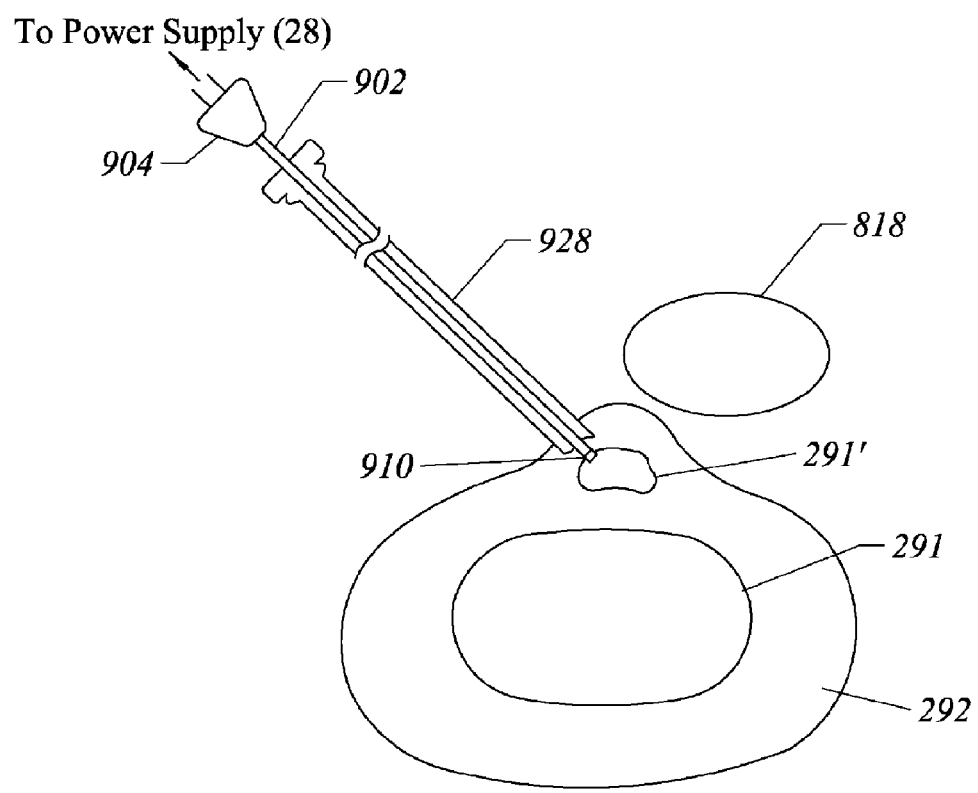
FIG. 49 shows a shaft of an electrosurgical probe within an intervertebral disc, wherein the shaft distal end is targeted to a specific site within the disc.

FIG. 49 shows shaft 902 of electrosurgical probe 900 within an intervertebral disc, wherein shaft distal end 902a is targeted to a specific site within the disc. In the situation depicted in FIG. 49, the target site is occupied by an errant fragment 294' of nucleus pulposus tissue. Shaft distal end 902 may be guided or directed, at least in part, by appropriate placement of introducer 928, such that active electrode 910 is in the vicinity of fragment 294'. Preferably, active electrode 910 is adjacent to, or in contact with, fragment 294'. Although FIG. 49 depicts a disc in which a fragment of nucleus pulposus is targeted by shaft 902, the invention described with reference to FIG. 49 may also be used for targeting other aberrant structures within an intervertebral disc, including annular fissures and contained herniations. In a currently preferred embodiment, shaft 902 includes at least one curve (not shown in FIG. 49), and other features described herein with reference to FIGS. 40A-46B, wherein shaft distal end 902a may be precisely guided by an appropriate combination of axial and rotational movement of shaft 902. The procedure illustrated in FIG. 49 may be performed generally according to the description presented with reference to FIG. 48. That is, shaft 902 is introduced into the disc via introducer 928 in a percutaneous procedure. After shaft distal end 902a has been guided to a target site, tissue at or adjacent to that site is ablated by application of a first high frequency voltage. Thereafter, depending on the particular condition of the disc being treated, a second high frequency voltage may optionally be applied in order to locally coagulate tissue within the disc.

Figure 50:
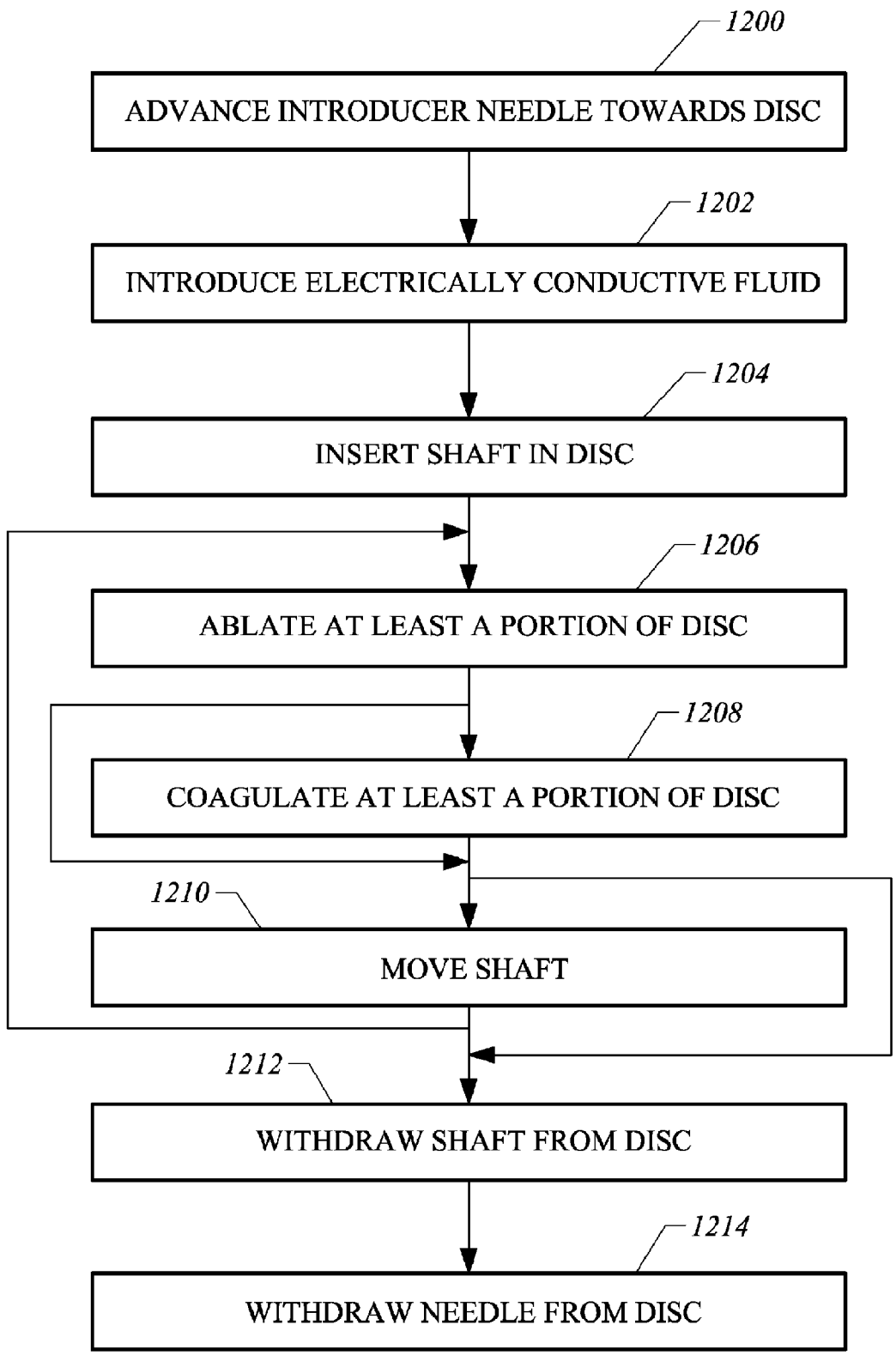
FIG. 50 schematically represents a series of steps involved in a method of ablating disc tissue according to the present invention.

FIG. 50 schematically represents a series of steps involved in a method of ablating disc tissue according to the present invention; wherein step 1200 involves advancing an introducer needle towards an intervertebral disc to be treated. The introducer needle has a lumen having a diameter greater than the diameter of the shaft distal end, thereby allowing free passage of the shaft distal end through the lumen of the introducer needle. In one embodiment, the introducer needle preferably has a length in the range of from about 3 cm to about 25 cm, and the lumen of the introducer needle preferably has a diameter in the range of from about 0.5 cm. to about 2.5 mm. Preferably, the diameter of the shaft distal end is from about 30% to about 95% of the diameter of the lumen. The introducer needle may be inserted in the intervertebral disc percutaneously, e.g. via a posterolateral approach. In one embodiment, the introducer needle may have dimensions similar to those of an epidural needle, the latter well known in the art.

Optional step 1202 involves introducing an electrically conductive fluid, such as saline, into the disc. In one embodiment, in lieu of step 1202, the ablation procedure may rely on the electrical conductivity of the nucleus pulposus itself. Step 1204 involves inserting the shaft of the electrosurgical probe into the disc, e.g., via the introducer needle, wherein the distal end portion of the shaft bears an active electrode and a return electrode. In one embodiment, the shaft includes an outer shield, first and second curves at the distal end portion of the shaft, and an electrode head having an apical spike, generally as described with reference to FIGS. 40A-46B.

Step 1206 involves ablating at least a portion of disc tissue by application of a first high frequency voltage between the active electrode and the return electrode. In particular, ablation of nucleus pulposus tissue according to methods of the invention serves to decrease the volume of the nucleus pulposus, thereby relieving pressure exerted on the annulus fibrosus, with concomitant decompression of a previously compressed nerve root, and alleviation of discogenic pain.

In one embodiment, the introducer needle is advanced towards the intervertebral disc until it penetrates the annulus fibrosus and enters the nucleus pulposus. The shaft distal end in introduced into the nucleus pulposus, and a portion of the nucleus pulposus is ablated. These and other stages of the procedure may be performed under fluoroscopy to allow visualization of the relative location of the introducer needle and shaft relative to the nucleus pulposus of the disc. Additionally or alternatively, the surgeon may introduce the introducer needle into the nucleus pulposus from a first side of the disc, then advance the shaft distal end through the nucleus pulposus until resistance to axial translation of the electrosurgical probe is encountered by the surgeon. Such resistance may be interpreted by the surgeon as the shaft distal end having contacted the annulus fibrosus at the opposite side of the disc. Then, by use of depth markings on the shaft (FIG. 46A), the surgeon can retract the shaft a defined distance in order to position the shaft distal end at a desired location relative to the nucleus pulposus. Once the shaft distal end is suitably positioned, high frequency voltage may be applied to the probe via the power supply unit.

After step 1206, optional step 1208 involves coagulating at least a portion of the disc tissue. In one embodiment, step 1206 results in the formation of a channel or cavity within the nucleus pulposus. Thereafter, tissue at the surface of the channel may be coagulated during step 1208. Coagulation of disc tissue may be performed by application of a second high frequency voltage, as described hereinabove. After step 1206 or step 1208, the shaft may be moved (step 1210) such that the shaft distal end contacts fresh tissue of the nucleus pulposus. The shaft may be axially translated (i.e. moved in the direction of its longitudinal axis), may be rotated about its longitudinal axis, or may be moved by a combination of axial and rotational movement. In the latter case, a substantially spiral path is defined by the shaft distal end. After step 1210, steps 1206 and 1208 may be repeated with respect to the fresh tissue of the nucleus pulposus contacted by the shaft distal end. Alternatively, after step 1206 or step 1208, the shaft may be withdrawn from the disc (step 1212). Step 1214 involves withdrawing the introducer needle from the disc. In one embodiment, the shaft and the needle may be withdrawn from the disc concurrently. Withdrawal of the shaft from the disc may facilitate exhaustion of ablation by-products from the disc. Such ablation by-products include low molecular weight gaseous compounds derived from molecular dissociation of disc tissue components, as described hereinabove. The above method may be used to treat any disc disorder in which Coblation® and or coagulation of disc tissue is indicated, including contained herniations. In one embodiment, an introducer needle may be introduced generally as described for step 1200, and a fluoroscopic fluid may be introduced through the lumen of the introducer needle for the purpose of visualizing and diagnosing a disc abnormality or disorder. Thereafter, depending on the diagnosis, a treatment procedure may be performed, e.g., according to steps 1202 through 1214, using the same introducer needle as access. In one embodiment, a distal portion, or the entire length, of the introducer needle may have an insulating coating on its external surface. Such an insulating coating on the introducer needle may prevent interference between the electrically conductive introducer needle and electrode(s) on the probe.

The size of the cavity or channel formed in a tissue by a single straight pass of the shaft through the tissue to be ablated is a function of the diameter of the shaft (e.g., the diameter of the shaft distal end and active electrode) and the amount of axial translation of the shaft. (By a "single straight pass" of the shaft is meant one axial translation of the shaft in a distal direction through the tissue, in the absence of rotation of the shaft about the longitudinal axis of the shaft, with the power from the power supply turned on.) In the case of a curved shaft, according to various embodiments of the instant invention, a larger channel can be formed by rotating the shaft as it is advanced through the tissue. The size of a channel formed in a tissue by a single rotational pass of the shaft through the tissue to be ablated is a function of the deflection of the shaft, and the amount of rotation of the shaft about its longitudinal axis, as well as the diameter of the shaft (e.g., the diameter of the shaft distal end and active electrode) and the amount of axial translation of the shaft. (By a "single rotational pass" of the shaft is meant one axial translation of the shaft in a distal direction through the tissue, in the presence of rotation of the shaft about the longitudinal axis of the shaft, with the power from the power supply turned on.) To a large extent, the diameter of a channel formed during a rotational pass of the shaft through tissue can be controlled by the amount of rotation of the shaft, wherein the "amount of rotation" encompasses both the rate of rotation (e.g., the angular velocity of the shaft), and the number of degrees through which the shaft is rotated (e.g. the number of turns) per unit length of axial movement. Typically, according to the invention, the amount of axial translation per pass (for either a straight pass or a rotational pass) is not limited by the length of the shaft. Instead, the amount of axial translation per single pass is preferably determined by the size of the tissue to be ablated. Depending on the size of the disc or other tissue to be treated, and the nature of the treatment, etc., a channel formed by a probe of the instant invention may preferably have a length in the range of from about 2 mm to about 50 mm, and a diameter in the range of from about 0.5 mm to about 7.5 mm. In comparison, a channel formed by a shaft of the instant invention during a single rotational pass may preferably have a diameter in the range of from about 1.5 mm to about 25 mm.

Figure 51:
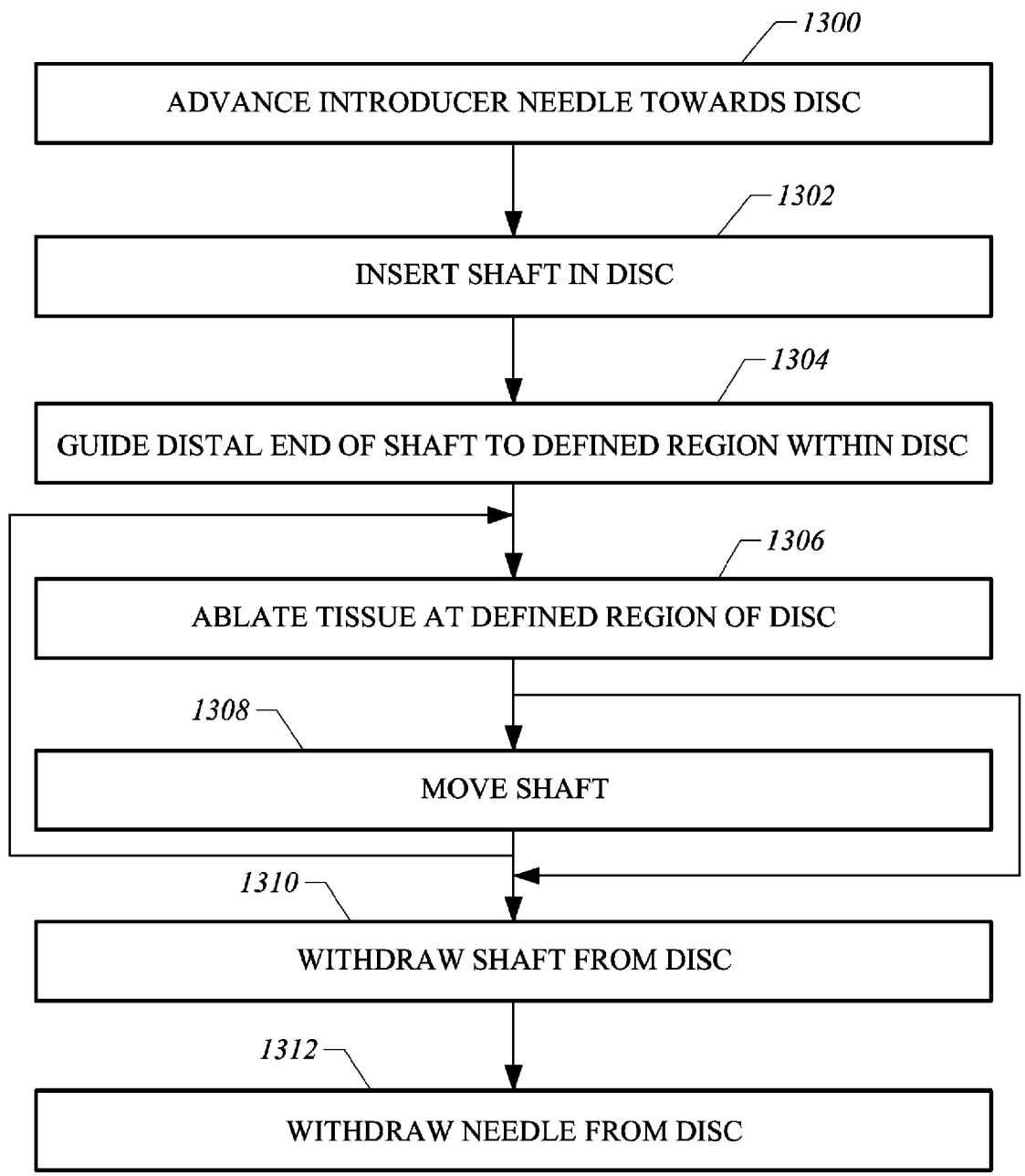
FIG. 51 schematically represents a series of steps involved in a method of guiding an electrosurgical probe to a target site within an intervertebral disc for ablation of targeted disc tissue, according to another embodiment of the invention.

A channel formed by a shaft of the instant invention during a single straight pass may preferably have a volume in the range of from about 1 $mm^3$, or less, to about 2,500 $mm^3$. More preferably, a channel formed by a straight pass of a shaft of the instant invention has a volume in the range of from about 10 $mm^3$ to about 2,500 $mm^3$, and more preferably in the range of from about 50 $mm^3$ to about 2,500 $mm^3$. In comparison, a channel formed by a shaft of the instant invention during a single rotational pass typically has a volume from about twice to about 15 times the volume of a channel of the same length formed during a single rotational pass, i.e., in the range of from about 2 $mm^3$ to about 4,000 $mm^3$, more preferably in the range of from about 50 $mm^3$ to about 2,000 $mm^3$. While not being bound by theory, the reduction in volume of a disc having one or more channels therein is a function of the total volume of the one or more channels. FIG. 51 schematically represents a series of steps involved in a method of guiding the distal end of a shaft of an electrosurgical probe to a target site within an intervertebral disc for ablation of specifically targeted disc tissue, wherein steps 1300 and 1302 are analogous to steps 1200 and 1204 of FIG. 50. Thereafter step 1304 involves guiding the shaft distal end to a defined region within the disc. The specific target site may be pre-defined as a result of a previous procedure to visualize the disc and its abnormality, e.g., via X-ray examination, endoscopically, or fluoroscopically. As an example, a defined target site within a disc may comprise a fragment of the nucleus pulposus that has migrated within the annulus fibrosus (see, e.g., FIG. 47D ) resulting in discogenic pain. However, guiding the shaft to defined sites associated with other types of disc disorders are also possible and is within the scope of the invention.

Guiding the shaft distal end to the defined target site may be performed by axial and/or rotational movement of a curved shaft, as described hereinabove. Or the shaft may be steerable, for example, by means of a guide wire, as is well known in the art. Guiding the shaft distal end may be performed during visualization of the location of the shaft relative to the disc, wherein the visualization may be performed endoscopically or via fluoroscopy. Endoscopic examination may employ a fiber optic cable (not shown). The fiber optic cable may be integral with the electrosurgical probe, or be part of a separate instrument (endoscope). Step 1306 involves ablating disc tissue, and is analogous to step 1206 (FIG. 50). Before or during step 1306, an electrically conductive fluid may be applied to the disc tissue and/or the shaft in order to provide a path for current flow between active and return electrodes on the shaft, and to facilitate and/or maintain a plasma in the vicinity of the distal end portion of the shaft. After the shaft distal end has been guided to a target site and tissue at that site has been ablated, the shaft may be moved locally, e.g., within the same region of the nucleus pulposus, or to a second defined target site within the same disc. The shaft distal end may be moved as described herein (e.g., with reference to step 1210, FIG. 50). Or, according to an alternative embodiment, the shaft may be steerable, e.g., by techniques well known in the art. Steps 1310 and 1312 are analogous to steps 1212 and 1214, respectively (described with reference to FIG. 50).

It is known in the art that epidural steroid injections can transiently diminish perineural inflammation of an affected nerve root, leading to alleviation of discogenic pain. In one embodiment of the invention, methods for ablation of disc tissue described hereinabove may be conveniently performed in conjunction with an epidural steroid injection. For example, ablation of disc tissue and epidural injection could be carried out as part of a single procedure, by the same surgeon, using equipment common to both procedures (e.g. visualization equipment). Combining Coblation® and epidural injection in a single procedure may provide substantial cost-savings to the healthcare industry, as well as a significant improvement in patient care.

As alluded to hereinabove, methods and apparatus of the present invention can be used to accelerate the healing process of intervertebral discs having fissures and/or contained herniations. In one method, the present invention is useful in microendoscopic discectomy procedures, e.g., for decompressing a nerve root with a lumbar discectomy. For example, as described above in relation to FIGS. 18-20, a percutaneous penetration can be made in the patient's back so that the superior lamina can be accessed. Typically, a small needle is used initially to localize the disc space level, and a guide wire is inserted and advanced under lateral fluoroscopy to the inferior edge of the lamina. Sequential cannulated dilators can be inserted over the guide wire and each other to provide a hole from the incision to the lamina. The first dilator may be used to "palpate" the lamina, assuring proper location of its tip between the spinous process and facet complex just above the inferior edge of the lamina. A tubular retractor can then be passed over the largest dilator down to the lamina. The dilators can then be removed, so as to establish an operating corridor within the tubular retractor. It should be appreciated however, that other conventional or proprietary methods can be used to access the target intervertebral disc. Once the target intervertebral disc has been accessed, an introducer device may be inserted into the intervertebral disc.

With reference to FIG. 52, in one embodiment, both introducer needle 928 and a second or ancillary introducer 938 may be inserted into the same disc, to allow introduction of an ancillary device 940 into the target disc via ancillary introducer 938. Ancillary device 940 may comprise, for example, a fluid delivery device, a return electrode, an aspiration lumen, a second electrosurgical probe, or an endoscope having an optical fiber component. Each of introducer needle 928 and ancillary introducer 938 may be advanced through the annulus fibrosus until at least the distal end portion of each introducer 928 and 938, is positioned within the nucleus pulposus. Thereafter, shaft 902" of electrosurgical probe 900' may be inserted through at least one of introducers 928, 938, to treat the intervertebral disc. Typically, shaft 902" of probe 900' has an outer diameter no larger than about 7 French (1 Fr: 0.33 mm), and preferably between about 6 French and 7 French.

Prior to inserting electrosurgical probe 900 into the intervertebral disc, an electrically conductive fluid can be delivered into the disk via a fluid delivery assembly (e.g., ancillary device 940) in order to facilitate or promote the Coblation® mechanism within the disc following the application of a high frequency voltage via probe 900'. By providing a separate device (940) for fluid delivery, the dimensions of electrosurgical probe 900' can be kept to a minimum. Furthermore, when the fluid delivery assembly is positioned within ancillary introducer 938, electrically conductive fluid can be conveniently replenished to the interior of the disc at any given time during the procedure. Nevertheless, in other embodiments, the fluid delivery assembly can be physically coupled to electrosurgical probe 900'.

In some methods, a radiopaque contrast solution (not shown) may be delivered through a fluid delivery assembly so as to allow the surgeon to visualize the intervertebral disc under fluoroscopy. In some configurations, a tracking device 942 can be positioned on shaft distal end portion 902"a. Additionally or alternatively, shaft 902" can be marked incrementally, e.g., with depth markings 903, to indicate to the surgeon how far the active electrode is advanced into the intervertebral disc. In one embodiment, tracking device 942 includes a radiopaque material that can be visualized under fluoroscopy. Such a tracking device 942 and depth markings 903 provide the surgeon with means to track the position of the active electrode 910 relative to a specific target site within the disc to which active electrode 910 is to be guided. Such specific target sites may include, for example, an annular fissure, a contained herniation, or a fragment of nucleus pulposus. The surgeon can determine the position of the active electrode 910 by observing the depth markings 903, or by comparing tracking device output, and a fluoroscopic image of the intervertebral disc to a pre-operative fluoroscopic image of the target intervertebral disc.

In other embodiments, an optical fiber (not shown) can be introduced into the disc. The optical fiber may be either integral with probe 900' or may be introduced as part of an ancillary device 940 via ancillary introducer 938. In this manner, the surgeon can visually monitor the interior of the intervertebral disc and the position of active electrode 910.

In addition to monitoring the position of the distal portion of electrosurgical probe 900', the surgeon can also monitor whether the probe is in Coblation® mode. In some embodiments, power supply 28 (e.g., FIG. 1) includes a controller having an indicator, such as a light, an audible sound, or a liquid crystal display (LCD), to indicate whether probe 900' is generating a plasma within the disc. If it is determined that the Coblation® mechanism is not occurring, (e.g., due to an insufficiency of electrically conductive fluid within the disc), the surgeon can then replenish the supply of the electrically conductive fluid to the disc.

Figure 53:
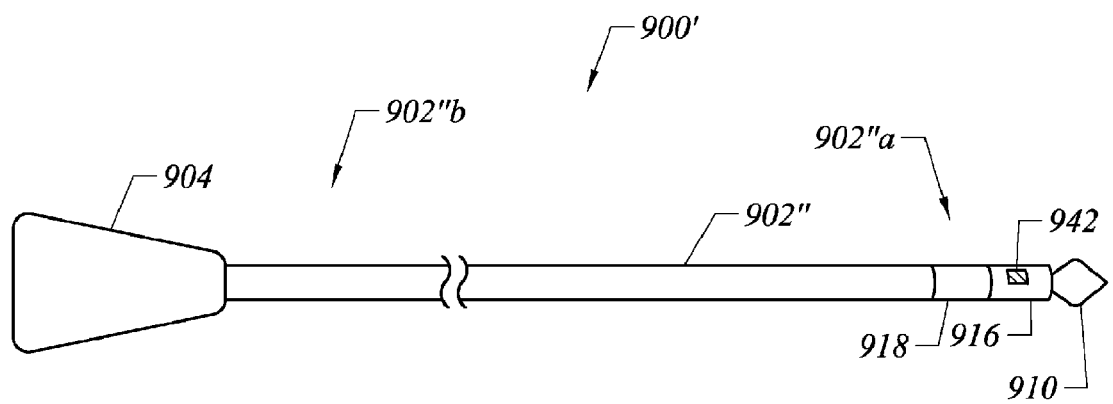
FIG. 53 is a side view of an electrosurgical probe having a tracking device.

FIG. 53 is a side view of an electrosurgical probe 900' including shaft 902" having tracking device 942 located at distal end portion 902"*a*. Tracking device 942 may serve as a radiopaque marker adapted for guiding distal end portion 902"*a* within a disc. Shaft 902" also includes at least one active electrode 910 disposed on the distal end portion 902"*a*. Preferably, electrically insulating support member or collar 916 is positioned proximal of active electrode 910 to insulate active electrode 910 from at least one return electrode 918. In some embodiments, the return electrode 918 is positioned on the distal end portion of the shaft 902" and proximal of the active electrode 910. In other embodiments, however, return electrode 918 can be omitted from shaft 902", in which case at least one return electrode may be provided on ancillary device 940, or the return electrode may be positioned on the patient's body, as a dispersive pad (not shown).

Although active electrode 910 is shown in FIG. 53 as comprising a single apical electrode, other numbers, arrangements, and shapes for active electrode 910 are within the scope of the invention. For example, active electrode 910 can include a plurality of isolated electrodes in a variety of shapes. Active electrode 910 will usually have a smaller exposed surface area than return electrode 918, such that the current density is much higher at active electrode 910 than at return electrode 918. Preferably, return electrode 918 has a relatively large, smooth surfaces extending around shaft 902" in order to reduce current densities in the vicinity of return electrode 918, thereby minimizing damage to non-target tissue.

While bipolar delivery of a high frequency energy is the preferred method of debulking the nucleus pulposus, it should be appreciated that other energy sources (i.e., resistive, or the like) can be used, and the energy can be delivered with other methods (i.e., monopolar, conductive, or the like) to debulk the nucleus.

Figure 54A:
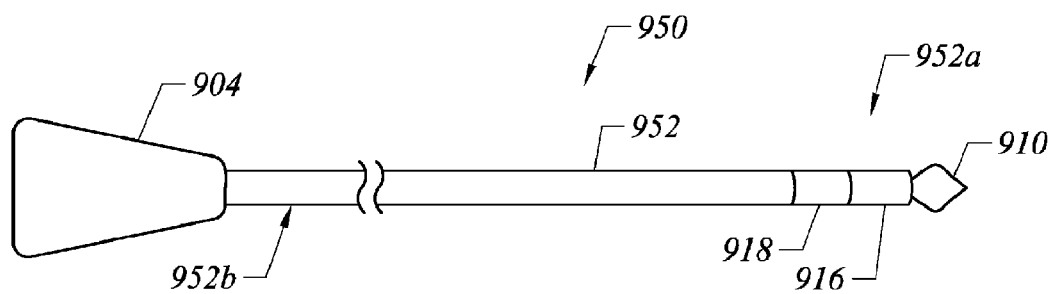
FIG. 54A shows a steerable electrosurgical probe wherein the shaft of the probe assumes a substantially linear configuration.
Figure 54B:
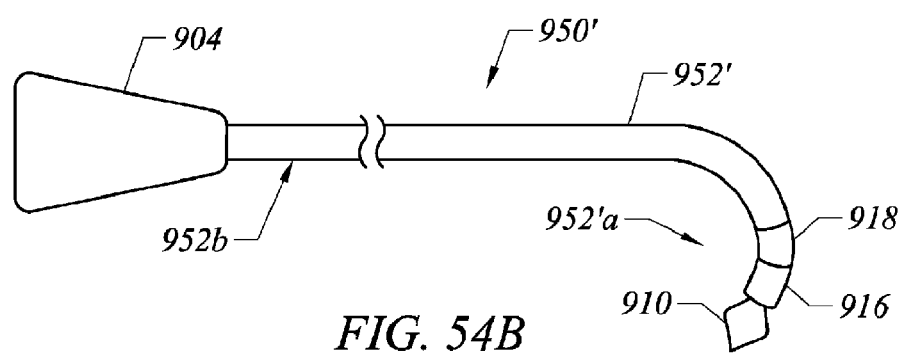
FIG. 54B shows the steerable electrosurgical probe of FIG. 54A, wherein the shaft distal end of the probe adopts a curved configuration.

FIG. 54A shows a steerable electrosurgical probe 950 including a shaft 952, according to another embodiment of the invention. Preferably, shaft 952 is flexible and may assume a substantially linear configuration as shown. Probe 950 includes handle 904, shaft distal end 952*a*, active electrode 910, insulating collar 916, and return electrode 918. As can be seen in FIG. 54B, under certain circumstances, e.g., upon application of a force to shaft 952 during guiding or steering probe 950 during a procedure, shaft distal end 952*a* can adopt a non-linear configuration, designated 952'*a*. The deformable nature of shaft distal end 952'*a* allows active electrode 910 to be guided to a specific target site within a disc.

Figure 55:
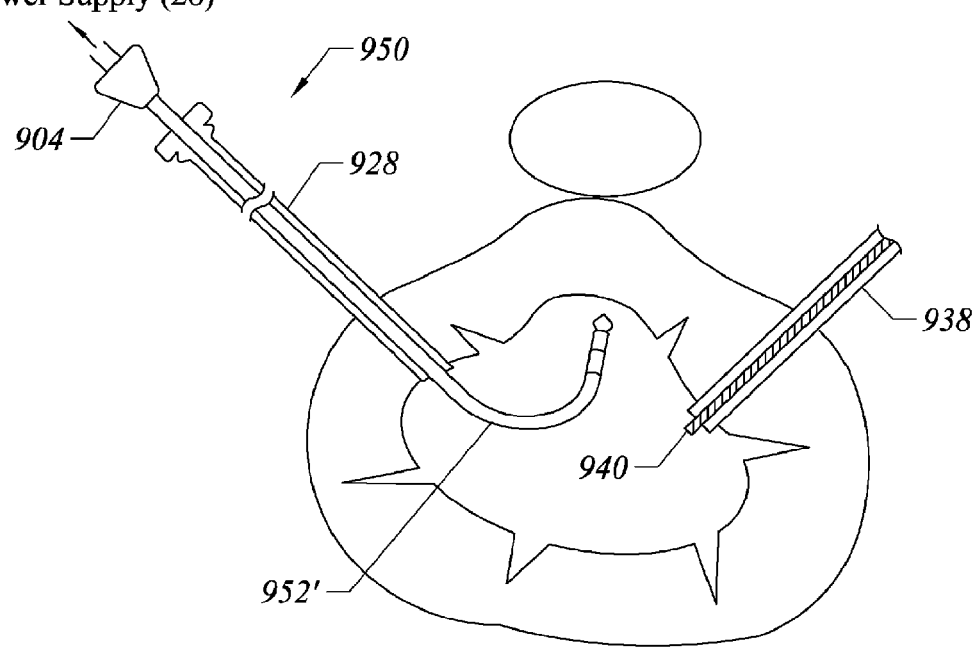
FIG. 55 shows a steerable electrosurgical probe and an ancillary device inserted within the nucleus pulposus of an intervertebral disc.

FIG. 55 shows steerable electrosurgical probe 950 inserted within the nucleus pulposus of an intervertebral disc. An ancillary device 940 and ancillary introducer 928 may also be inserted within the nucleus pulposus of the same disc. To facilitate the debulking of the nucleus pulposus adjacent to a contained herniation, shaft 952 (FIG. 54A) can be manipulated to a non-linear configuration, represented as 952'. Preferably, shaft 955/952' is flexible over at least shaft distal end 952*a* so as to allow steering of active electrode 910 to a position adjacent to the targeted disc abnormality. The flexible shaft may be combined with a sliding outer shield, a sliding outer introducer needle, pull wires, shape memory actuators, and other known mechanisms (not shown) for effecting selective deflection of distal end 952*a* to facilitate positioning of active electrode 910 within a disc.

Thus, it can be seen that the embodiment of FIG. 55 may be used for the targeted treatment of annular fissures, or any other disc abnormality in which Coblation® is indicated.

In one embodiment shaft 952 may have a suitable diameter and length to allow the surgeon to reach the target disc or vertebra by introducing the shaft through the thoracic cavity, the abdomen, or the like. Thus, shaft 952 may have a length in the range of from about 5.0 cm to 30.0 cm, and a diameter in the range of about 0.2 mm to about 20 mm. Alternatively, shaft 952 may be delivered percutaneously in a posterolateral approach. Regardless of the approach, shaft 952 may be introduced via a rigid or flexible endoscope. In addition, it should be noted that the methods described with reference to FIGS. 52 and 55 may also be performed in the absence of ancillary introducer 938 and ancillary device 940.

Figure 56A:
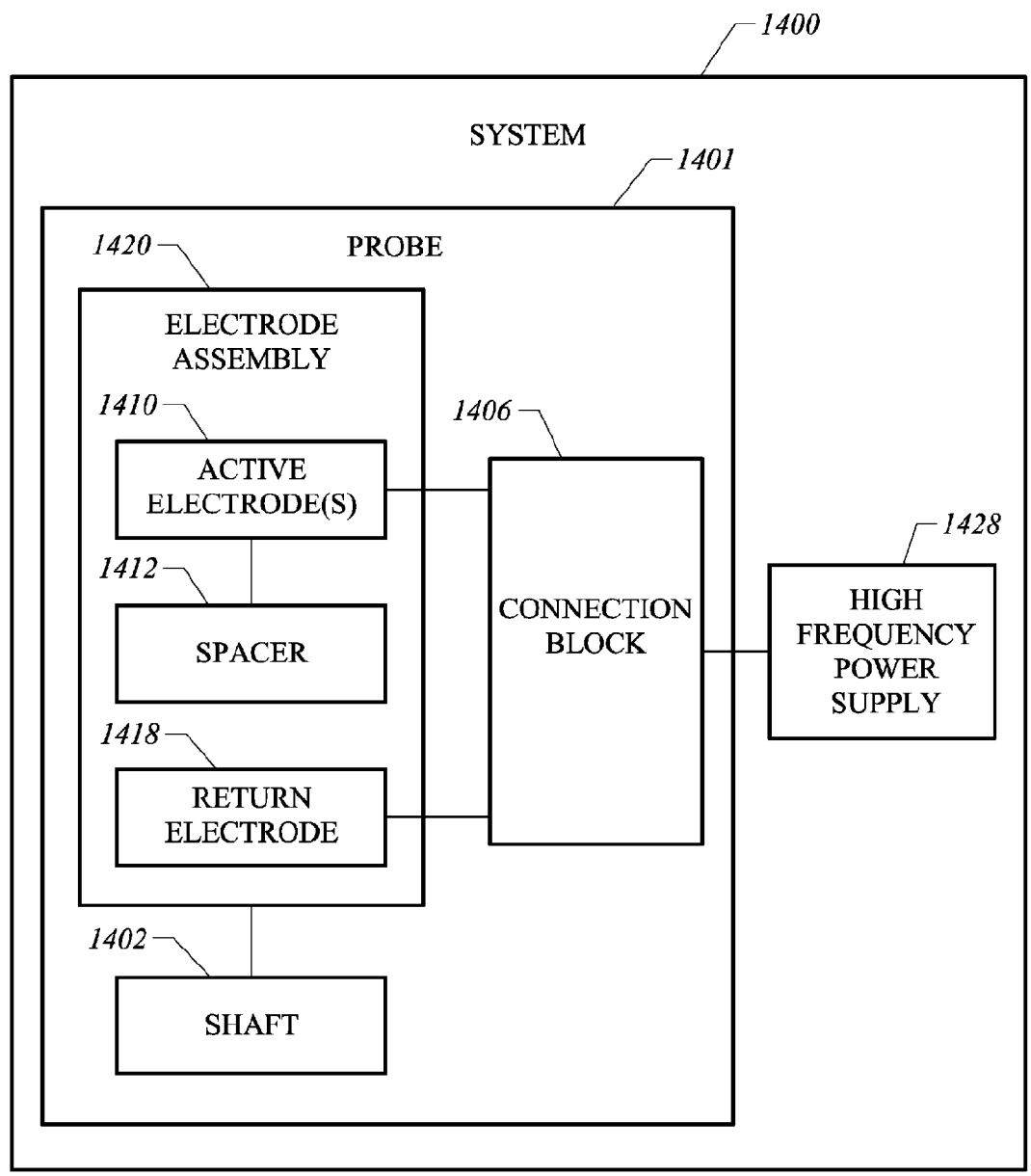
FIG. 56A is a block diagram schematically representing an electrosurgical system, according to one embodiment of the invention.

FIG. 56A is a block diagram schematically representing an electrosurgical system 1400, according to one embodiment of the invention. System 1400 includes an electrosurgical probe or instrument 1401 coupled to a high frequency power supply 1428. Instrument 1401 includes an electrode assembly 1420 and a shaft 1402. Electrode assembly 1420 is typically disposed at a distal or working end of shaft 1402. According to one aspect of the invention, shaft 1402 is biased, deflectable, or steerable such that electrode assembly 1420 can be guided or steered to a target tissue within a patient. Electrosurgical instruments having a biased, deflectable, or steerable shaft are described hereinabove. Electrode assembly 1420 includes an electrically insulating electrode support or spacer 1412, and at least one active electrode 1410 disposed on spacer 1412. Electrode assembly 1420 further includes a return electrode 1418 spaced from active electrode 1410 by spacer 1412. Active electrode 1410 and return electrode 1418 are independently coupled to a connection block 1406. Connection block 1406 provides a convenient mechanism for coupling active electrode 1410 and return electrode 1418 to opposite poles of power supply 1428. Connection block 1406 may be housed within a proximal housing (not shown) of the instrument.

Figure 56B:
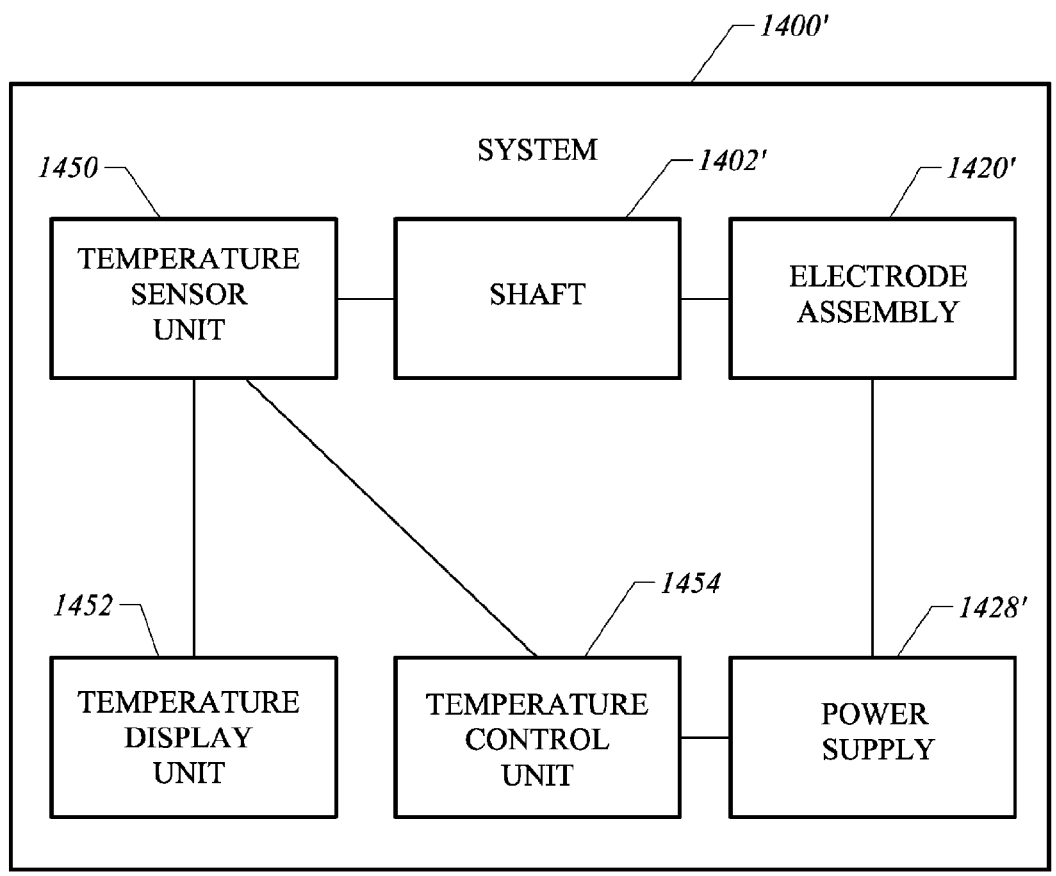
FIG. 56B is a block diagram schematically representing an electrosurgical system, according to another embodiment of the invention.

FIG. 56B is a block diagram schematically representing an electrosurgical system 1400', according to another embodiment of the invention. System 1400' includes an electrode assembly 1420' affixed to a shaft 1402'. Electrode assembly 1420' is typically disposed at a distal or working end of shaft 1402'. Electrode assembly 1420' includes at least one active electrode and a return electrode (e.g., FIG. 56A). The active and return electrodes are independently coupled to a high frequency power supply 1428'. System 1400' further includes a temperature sensor unit 1450 for sensing a temperature in the vicinity of the shaft distal end, e.g. the temperature of a target tissue adjacent to electrode assembly 1420', during use of system 1400'. Temperature sensor unit 1450 may be coupled to a temperature display unit 1452 for displaying the sensed temperature to an operator (e.g., a physician) of system 1400'. Temperature sensing and display devices are well known in the art.

Again with reference to FIG. 56B, temperature sensor unit 1450 is further coupled to a temperature control unit 1454. Temperature control unit 1454 is in turn coupled to power supply 1428' and regulates the power output from power supply 1428' in response to a temperature sensed by temperature sensor unit 1450. In this way, power supplied to electrode assembly 1420' can be reduced, or completely shut off, if a temperature sensed in the vicinity of the target tissue is at or above a pre-set value. Components and/or circuitry for regulating power output in response to sensed temperature data are also well known in the art. Typically, temperature sensor unit 1450 is located at the shaft working end, e.g., adjacent to electrode assembly 1420'. Temperature control unit 1454 and temperature display unit 1452 may be integral with power supply 1428', or may be separate devices of system 1400'. System 1400' may also include additional elements or features, such as those described for system 1400 with reference to FIG. 56A. In one embodiment, power output from power supply 1428' may be adjusted, or shut down, manually, e.g., via a foot pedal, in response to a sensed temperature displayed by temperature display unit 1452, or in response to an audible signal emitted to signal a sensed temperature of a pre-set value.

Figure 57:
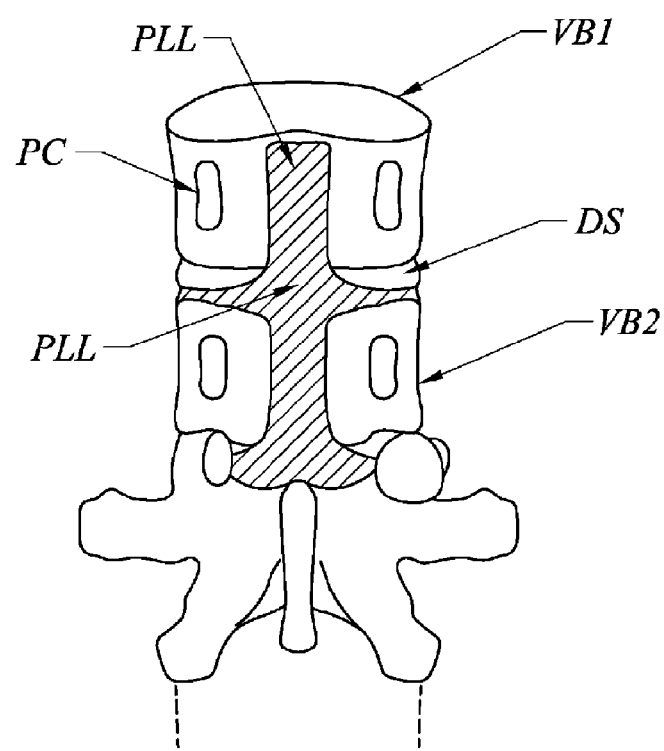
FIG. 57 is a posterior view of a portion of the spine showing the location of intervertebral discs and the posterior longitudinal ligament in relation to the vertebral bodies.

FIG. 57 is a posterior view of a section of the spine. (For illustrative purposes, the pedicles, PC of vertebral bodies, VB1 and VB2 are shown as being cut to expose the intervertebral discs, DS and the posterior longitudinal ligament, PLL, and to show the location of the discs and the PLL in relation to the vertebral bodies.) According to one aspect of the invention, target tissue for the electrosurgical treatment of back pain comprises nervous tissue of one or more discs and/or nervous tissue of the posterior longitudinal ligament (PLL). For example, nervous tissue targeted for inactivation (e.g., via electrosurgical coagulation or ablation) may comprise branches of the sinuvertebral nerve, which innervates the posterior region of the annulus fibrosus and the posterior longitudinal ligament.

Figure 58:
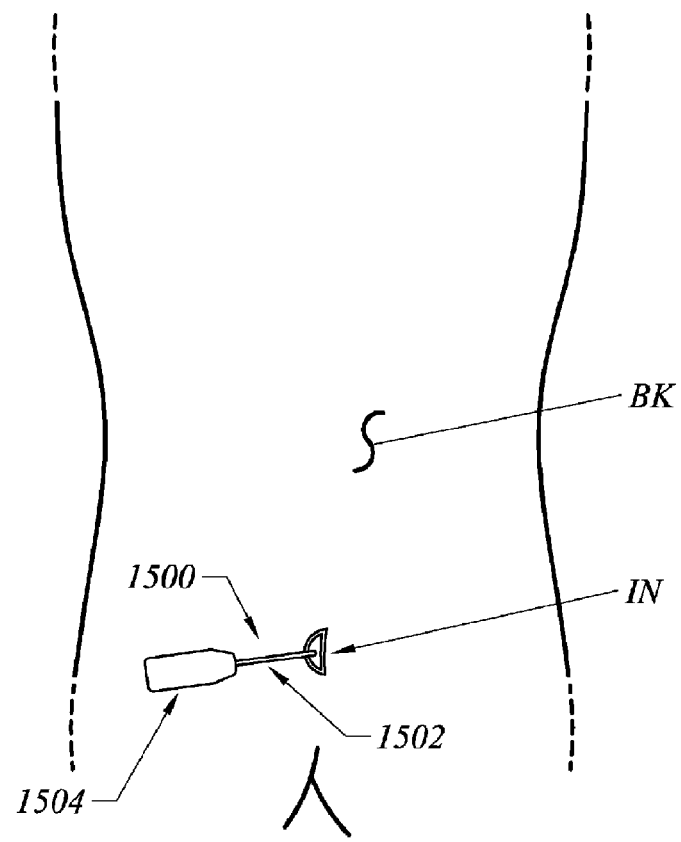
FIG. 58 schematically represents accessing a target tissue in the spine with an electrosurgical probe, according to one embodiment of the invention.

FIG. 58 schematically represents accessing a target tissue in the spine of a patient with an electrosurgical probe 1500 via an incision, IN, in the patient's back, BK. Probe 1500 includes a shaft 1502 and a handle 1504 affixed to a proximal end of shaft 1502. The distal end of shaft 1502 (obscured from view in FIG. 58) represents the working end of probe 1500. Probe 1500 typically includes an electrode assembly (not shown), having at least one active electrode, disposed at the distal end of shaft 1502. In addition, probe 1500 may have certain elements, features, and characteristics of the various embodiments of the invention as described hereinabove.

After the incision has been formed, the tissue may be dissected to the lamina of a vertebra, either electrosurgically or using mechanical cutting devices, and a portion of the lamina removed to access a target disc or portion of the posterior longitudinal ligament. In an alternative embodiment, the target tissue (e.g., disc tissue) may be accessed in a posterolateral approach using a deflectable or steerable probe or catheter. In one embodiment, the shaft is introduced into the patient via an introducer device, as described hereinabove (e.g., with reference to FIGS. 49, 52). In other embodiments, the electrode assembly may be introduced to a target site endoscopically. Furthermore, although FIG. 58 shows an incision such as might be made during a micro-open procedure, in alternative embodiments the shaft may be introduced percutaneously, with or without an introducer device.

Figure 59A:
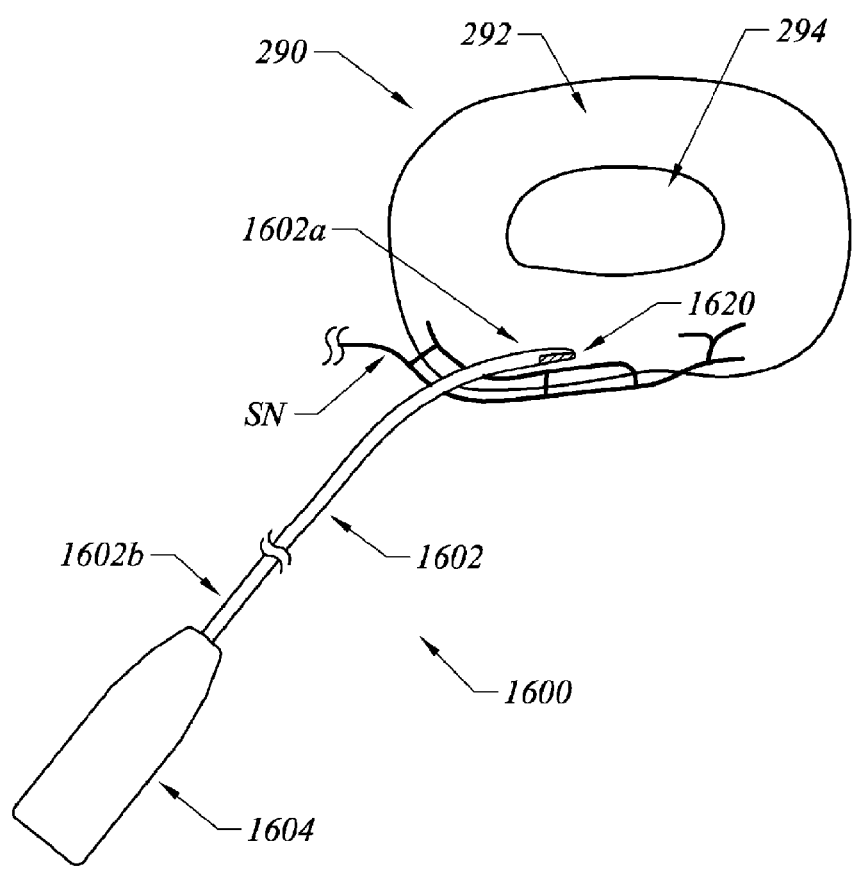
FIG. 59A schematically represents denervation of an intervertebral disc, according to one embodiment of the invention.

FIG. 59A schematically represents denervation of a portion of an intervertebral disc 290 using an electrosurgical instrument 1600, according to one embodiment of the invention. Instrument 1600 includes an elongate shaft 1602 having a shaft distal end 1602a and a shaft proximal end 1602b. Shaft distal end 1602a represents a working end of instrument 1600. Shaft distal end 1602a may be introduced into the patient and advanced towards the disc in an open procedure, endoscopically, or percutaneously, with or without an introducer device, as described hereinabove (e.g., with reference to FIG. 58). An electrode assembly 1620 is disposed at shaft distal end 1602a. As shown, electrode assembly 1620 is arranged laterally on shaft 1602. However, other arrangements for the electrode assembly are also within the scope of the invention.

Electrode assembly 1620 includes at least one active electrode terminal spaced from a return electrode by an electrically insulating spacer or electrode support, as described hereinabove (see, e.g., FIGS. 33A-B, 37A-D). In one embodiment, the return electrode is spaced proximally from the active electrode terminal(s), and the depth to which the tissue is treated can be determined, in part, by the length of the active electrode—return electrode spacing. In another embodiment, the electrode assembly comprises at least one elongate active electrode terminal and at least one return electrode arranged within a tissue treatment surface of an electrically insulating electrode support, wherein both the active electrode terminal(s) and the return electrode(s) are substantially flush with the tissue treatment surface. In one embodiment, the electrode assembly comprises a plurality of substantially rectangular active electrode terminals and a corresponding plurality of return electrodes alternating with the active electrode terminals. However, other configurations for the electrode assembly are also within the scope of the invention (see, e.g., FIGS. 33A-B, 37A-D). According to one aspect of the invention, a distal portion of the shaft surrounding or adjacent to the electrode assembly may have an electrically insulating coating adapted to protect non-target tissue during a procedure (see, e.g., FIGS. 33A-B). As shown, shaft distal end 1602a is in a curved configuration. Such a curved configuration may be attained by steering a flexible and steerable shaft distal end during advancement of the instrument working end towards the target tissue. In alternative embodiments, the shaft may be pre-bent to a specific configuration, either during manufacture, or by the surgeon prior to a particular procedure.

Again with reference to FIG. 59A, electrode assembly 1620 is shown as being positioned in a posterior region of the annulus fibrosus 292. The posterior of the annulus fibrosus 292 is innervated by branches of the sinuvertebral nerve. The sinuvertebral nerve is represented schematically in FIG. 59A by the structure labeled as SN. Branches of the sinuvertebral nerve terminate in unmyelinated nociceptors within the annulus fibrosus. In the embodiment of FIG. 59A, the electrode assembly, including active and return electrodes, is positioned within the annulus fibrosus. (In an alternative embodiment, a first electrode is positioned within the annulus fibrosus, and a second electrode is positioned outside the disc, adjacent to the posterior of the annulus (e.g., FIG. 61)). During a disc denervation procedure, branches of the sinuvertebral nerve, including the nociceptors within the disc, may be inactivated by the controlled application of heat. Typically, the posterior region of the annulus and/or branches of the sinuvertebral nerve are heated by the application of a high frequency voltage between the active electrode and the return electrode. The high frequency voltage is typically within the ranges cited hereinabove for the sub-ablation mode, e.g., from about 20 volts RMS to 90 volts RMS.

Unmyelinated nerve fibers are usually inactivated or killed by exposure to a temperature of about 45° C. Typically, the target tissue is heated to a temperature in the range of from about 43° C. to 53° C., and usually to a temperature in the range of from about 45° C. to 50° C. Irreversible shrinkage of mammalian collagen fibers generally occurs within a small temperature range from about 60° C. to 70° C. (Deak, G., et al., ibid.). Thus, the temperature used for inactivation of nervous tissue within the disc according to the instant invention is substantially below the minimum temperature required for thermal shrinkage of collage fibers, whereby the integrity of the annulus fibrosus is not compromised by the disc denervation procedure. Of course, in certain cases where a disc defect calls for shrinkage of a particular region of the annulus fibrosus, a higher temperature (e.g., in the 60° C. to 70° C. range) may be used to shrink collagen fibers of the annulus.

Figure 59B:
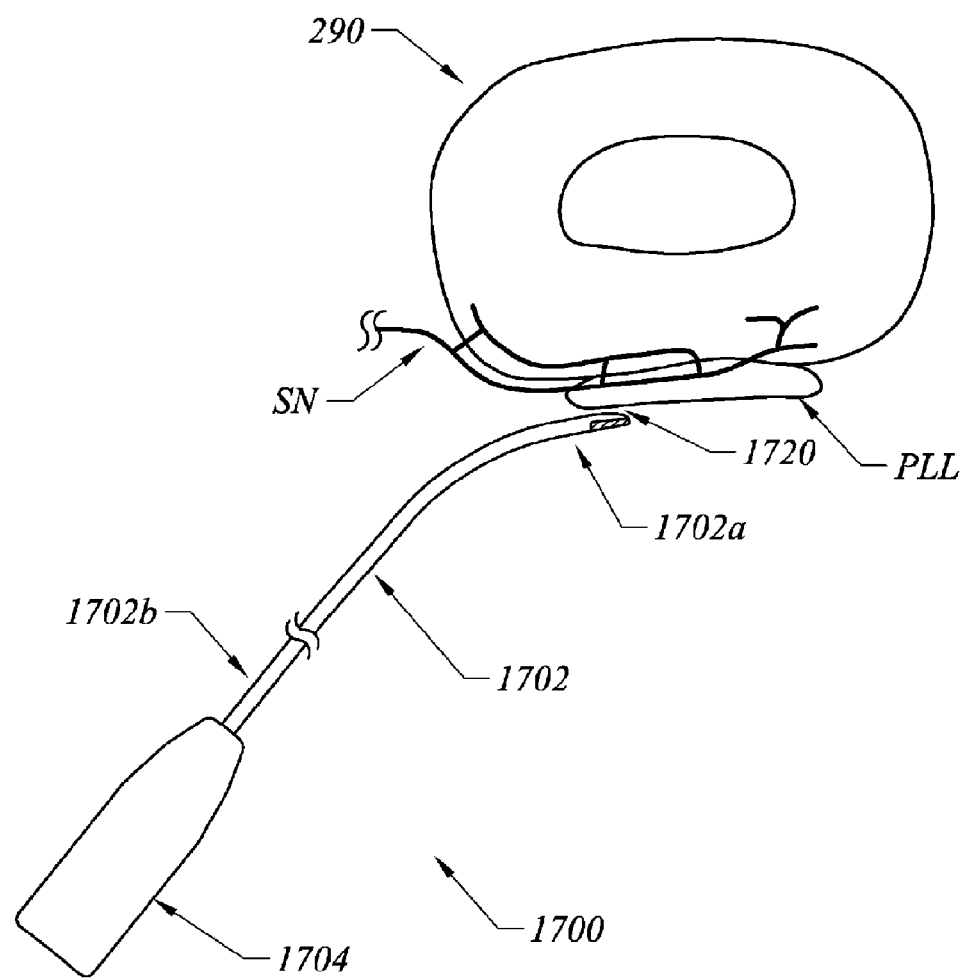
FIG. 59B schematically represents denervation of the posterior longitudinal ligament, according to another embodiment of the invention.

FIG. 59B schematically represents denervation of the posterior longitudinal ligament, PLL using an electrosurgical instrument 1700, according to another embodiment of the invention. Instrument 1700 includes a relatively long, narrow shaft 1702 having an electrode assembly 1720 disposed at shaft distal end 1702a. Shaft distal end 1702a typically has a low profile to facilitate access to a target site within the spine. Instrument 1700 may have certain other characteristics, features, and elements of instrument 1600 of FIG. 59A, or of other embodiments of the invention described hereinabove (e.g., with reference to FIGS. 1-46B, and 52-56). The exact configuration of the instrument and electrode assembly is to some extent a matter of design choice. Shaft distal end 1702a may be introduced into the patient and advanced towards the posterior longitudinal ligament in an open procedure, endoscopically, or percutaneously, as described hereinabove. Electrode assembly 1720 typically includes at least one active electrode terminal spaced from a return electrode by an electrically insulating spacer or electrode support.

Again with reference to FIG. 59B, electrode assembly 1720 is positioned in at least close proximity to the posterior longitudinal ligament. The posterior longitudinal ligament is richly innervated by branches of the sinuvertebral nerve. In one embodiment, the active electrode of the instrument is positioned in contact with, a target region of the posterior longitudinal ligament. Nervous tissue within the posterior longitudinal ligament may be inactivated, in a manner somewhat analogous to that described for denervation of an intervertebal disc (FIG. 59A), by the controlled application of heat. Typically, such controlled heating is effected by the application of a high frequency voltage, e.g., in the range of from about 20 volts RMS to 90 volts RMS, between the active electrode and the return electrode. Typically, the temperature used for denervation of the posterior longitudinal ligament according to the instant invention, e.g., in the range of from about 43° C. to 53° C., and usually from about 45° C. to 50° C., is substantially below the minimum temperature required for shrinkage of collagen fibers (Deak, G., et al., ibid.). Accordingly, denervation of the posterior longitudinal ligament according to the invention does not compromise the integrity of this ligament.

Figure 60:
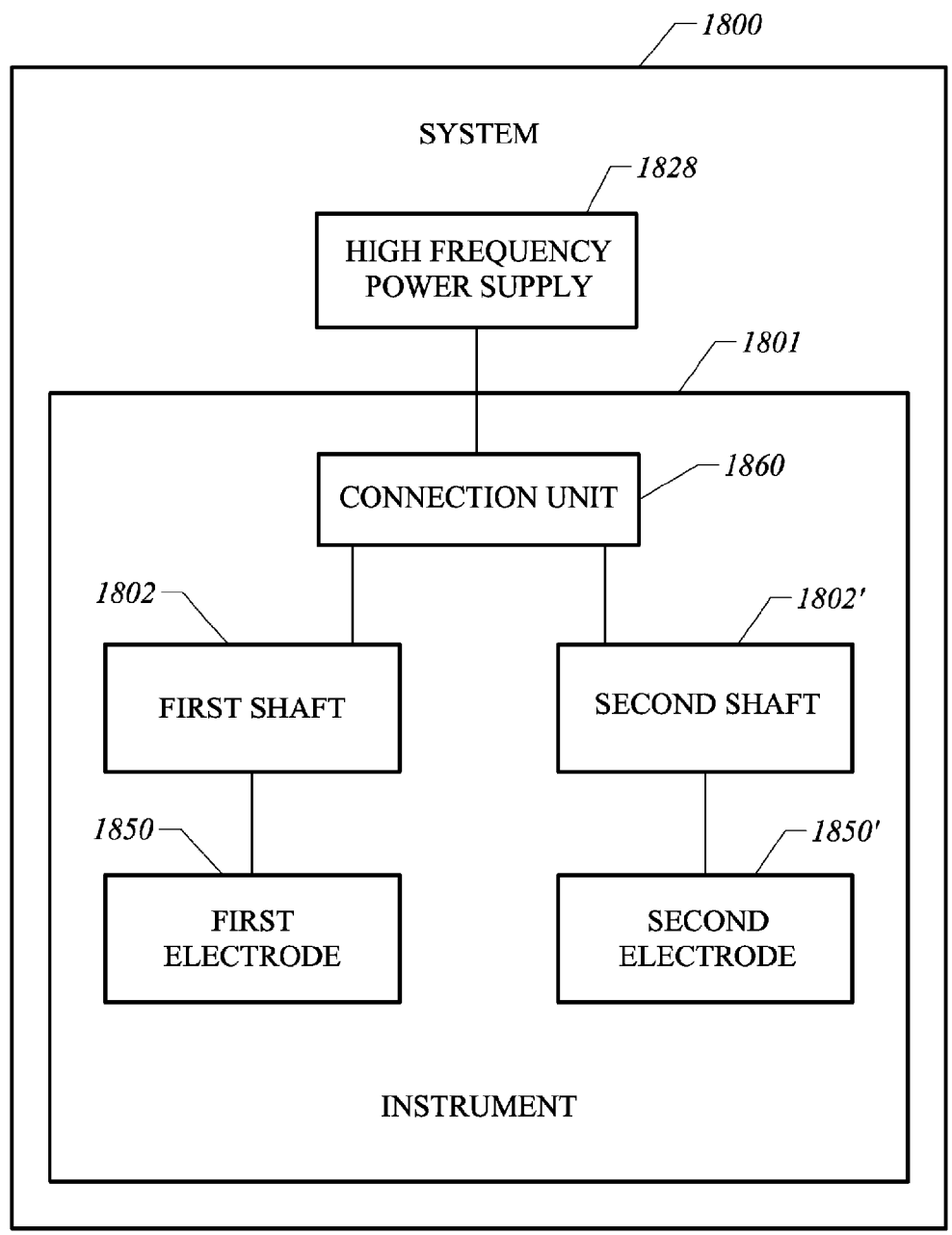
FIG. 60 is a block diagram schematically representing an electrosurgical system including a dual-shaft instrument, according to another embodiment of the invention.

FIG. 60 is a block diagram schematically representing an electrosurgical system 1800, according to another embodiment of the invention. System 1800 includes an electrosurgical probe or instrument 1801 coupled to a high frequency power supply 1828. Power supply 1828 may have features similar or analogous to those described hereinabove, e.g., with reference to FIG. 1. Instrument 1801 includes a first shaft 1802 and a second shaft 1802'. First and second shafts 1802, 1802' are typically arranged in the same general direction, such that instrument 1802 has a bifurcated configuration (e.g., FIG. 61). A first electrode 1850 is disposed on first shaft 1802, typically being located at a distal end of first shaft 1802. A second electrode 1850' is disposed on second shaft 1802', again typically being located at a distal end of second shaft 1802'. Instrument 1801 further includes a connection unit 1860. Each of first shaft 1802 and second shaft 1802' may be mechanically connected to connection unit 1860. In addition, first electrode 1850 and second electrode 1850' may be coupled to power supply 1828 via connection unit 1860. For example, connection unit 1860 may house a connection block, analogous to the connection blocks described hereinabove, e.g., with reference to FIG. 56A. In one embodiment, each of first shaft 1802 and second shaft 1802' is completely detachable from connection unit 1860. First shaft 1802 and second shaft 1802' may be substantially the same or identical, or first shaft 1802 and second shaft 1802' may differ from each other, in length, diameter/thickness, composition, as well as in other characteristics. Although connection unit 1860 is shown in FIG. 60 as a component of instrument 1801, in one embodiment the connection unit may be provided as a separate device.

In one embodiment, each of first shaft 1802 and second shaft 1802' may be independently manipulated and introduced into a patient. For example, first shaft 1802 may be advanced into a patient, e.g., in an open procedure, such that first electrode 1850 is positioned at a first location with respect to a target tissue to be treated. Thereafter, second shaft 1802' may be independently advanced into the patient, such that second electrode 1850' is positioned at a second location with respect to the target tissue. The configuration of each of first electrode 1850 and second electrode 1850' is to some extent a matter of design choice. As an example, first electrode 1850 may comprise one or more active electrode terminals or an active electrode array, while second electrode 1850' may comprise a return electrode.

Typically, first and second electrodes 1850, 1850' are positioned with respect to each other such that an electric current flows from first electrode 1850 towards second electrode 1850 upon application of a high frequency voltage between first and second electrodes 1850, 1850'. The distance or spacing between first and second electrodes 1850, 1850' can be selected by the physician by appropriate placement in the patient. In general, the spacing between first and second electrodes 1850, 1850' prior to treatment of a target tissue will depend on a number of factors or parameters, such as the type of procedure and the desired effect on the tissue (e.g., ablation, coagulation, etc.), the nature (e.g., electrical conductivity) of the tissue, the geometry of the electrodes, the intended voltage level, etc. In one embodiment, a lead extending from the electrode of each shaft is coupled to a coupling pin (not shown) at the proximal end of each shaft, and each coupling pin is coupled to a docking station (also not shown) of connection unit 1860, such that each electrode is electrically coupled to a connection block housed within connection unit 1860. System 1800 may include additional elements or features, such as those described hereinabove, e.g., with reference to FIGS. 1, 56A-B). Apparatus described with reference to FIG. 60 may be used in a broad range of electrosurgical procedures, and for treating or modifying many different types of tissue.

Figure 61:
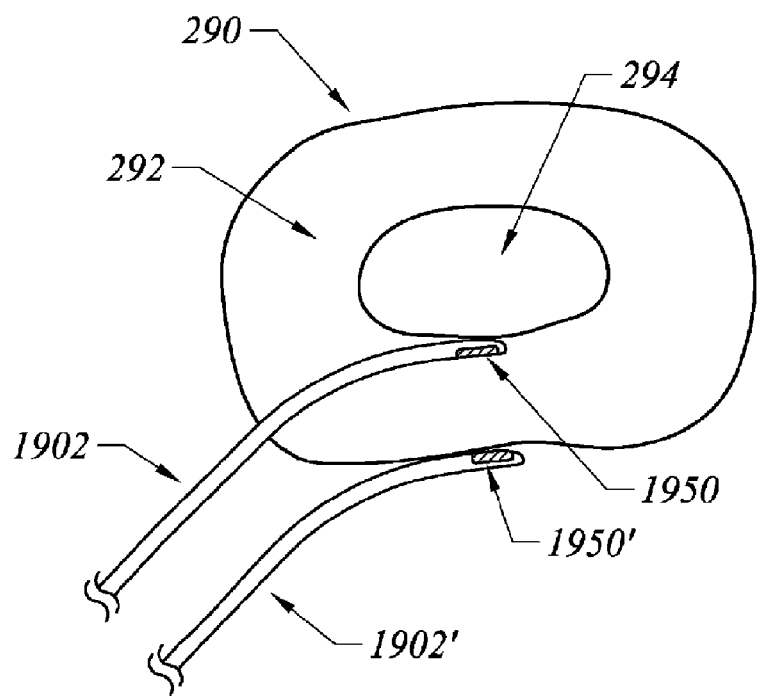
FIG. 61 schematically represents denervation of the posterior of an intervertebral disc, according to another embodiment of the invention.

FIG. 61 schematically represents denervation of the posterior of an intervertebral disc 290 using a bifurcated, dual-shaft electrosurgical instrument, according to another embodiment of the invention. A first shaft 1902 is introduced into the patient, e.g., during an open procedure, such that a first electrode 1950 is positioned within the annulus fibrosus 292 at a first location. The first location may be described as being adjacent to the posterior of the nucleus pulposus 294 (or, stated differently, the first location is adjacent to the inner wall of the annulus fibrosus). A second shaft 1902' is introduced into the patient, such that a second electrode 1950' is positioned at a second location adjacent, and external to, the posterior of the annulus fibrosus, i.e., outside the disc. Alternative locations for the first and second electrodes, i.e., locations other than those shown in FIG. 61, are also possible under the invention. For example, second electrode 1950' may be positioned within the disc adjacent to the outer wall of the annulus fibrosus.

After both first and second shafts 1902, 1902' have been suitably positioned with respect to the target tissue of the disc, a high frequency voltage may be applied between first and second electrodes 1850, 1850' via a high frequency power supply operating in the sub-ablation mode. The applied voltage is sufficient to heat at least a portion of the posterior of the annulus to a temperature sufficient to inactivate unmyelinated nervous tissue, e.g., nociceptors. In this way, nociceptors within the annulus fibrosus may be destroyed, thereby alleviating back pain associated with innervation of the intervertebral disc. First and second electrodes 1850, 1850' may be coupled to opposite poles of the power supply via a connection block housed within a connection unit, e.g., FIG. 60. Although, FIG. 61 shows treatment of an intervertebral disc, a bifurcated electrosurgical instrument of the invention may similarly be used for denervation of other tissue, such as the posterior longitudinal ligament, as well as for other types of procedures and for the treatment of a broad range of tissues.

Figure 62:
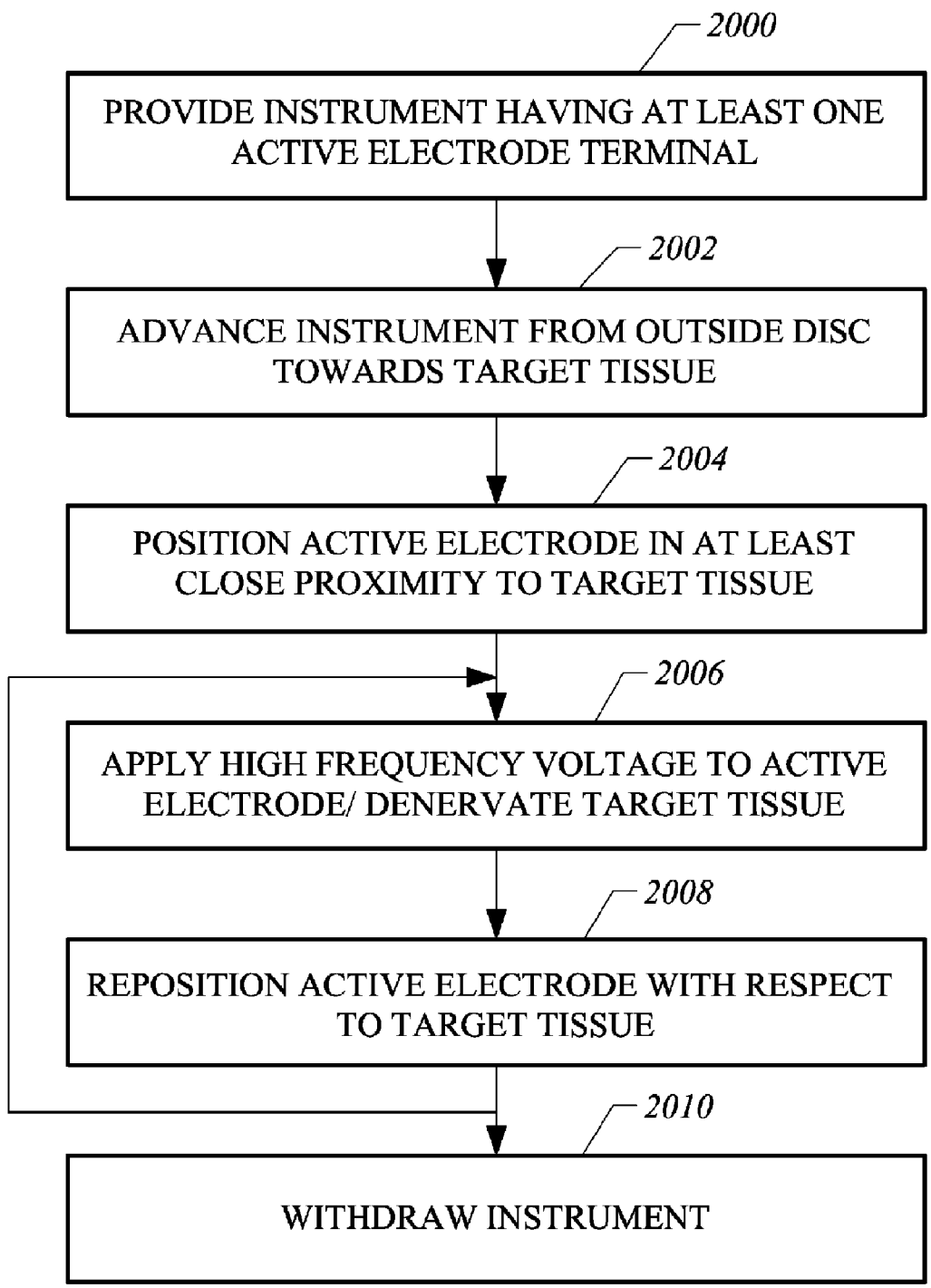
FIG. 62 represents a number of steps involved in a method for electrosurgically denervating a target tissue, according to another embodiment of the invention.

FIG. 62 represents a number of steps involved in a method for electrosurgically denervating a target tissue, according to the invention, wherein step 2000 involves providing an electrosurgical instrument. The electrosurgical instrument may comprise an electrosurgical probe or catheter, which may have various elements, characteristics, and features of the different embodiments of the invention described hereinabove. Typically, the instrument includes an elongate shaft having an electrode assembly at the shaft distal end, wherein the electrode assembly includes at least one active electrode or electrode terminal, and a return electrode spaced from the active electrode(s) by an electrically insulating spacer. In the description which follows and in the claims, reference may be made to the active electrode in the singular, it being understood that the instrument may have one active electrode, or more than one active electrodes, e.g., in the form of an electrode array.

In some embodiments the instrument shaft is biased, deflectable, or steerable, and is adapted for guiding the electrode assembly to a specific location with respect to a target tissue. In use, the electrosurgical instrument is coupled to a high frequency power supply to provide an electrosurgical system (e.g., FIGS. 1, 17, 56). The electrosurgical system is capable of operating in at least the sub-ablation mode for the controlled heating, denervation, coagulation, shrinkage, or other modification of a target tissue. In some embodiments, the electrosurgical system is adapted for being switched between the sub-ablation mode and the ablation mode. In the ablation mode, the apparatus is adapted for cutting, dissecting, ablating, or vaporizing a target tissue. In some embodiments, the system includes an introducer device (e.g., an introducer needle or a cannula) for introducing a working end of the instrument into the patient for advancement towards the target tissue.

Step 2002 involves advancing the instrument towards the target tissue. In one embodiment the target tissue is nervous tissue, in the form of nociceptors or unmyelinated nerve fibers, located within the posterior longitudinal ligament or the posterior of the annulus fibrosus Typically, in disc denervation procedures of the invention not involving disc decompression, step 2002 comprises advancing the electrode assembly towards the annulus fibrosus from a location outside the disc. That is to say, according to one embodiment of the instant invention, the instrument is advanced towards the annulus fibrosus without contacting the nucleus pulposus or inner portion of the disc. The instrument may be advanced toward the target tissue using a posterolateral approach, or from a midline incision involving a laminotomy. The instrument may be advanced into the patient with the aid of an introducer device (e.g., a hypodermic needle in the case of a probe having a needle-like shaft, or a cannula in the case of a flexible catheter). In one embodiment, the instrument may include one or more depth markings on the shaft to monitor the depth of penetration of the instrument into the patient's body.

Step 2004 involves positioning the active electrode in at least close proximity to the target tissue. In one embodiment, the active electrode is positioned within, or adjacent to, the annulus fibrosus without contacting or passing through the inner part of the disc or the nucleus pulposus. In another embodiment, the active electrode is positioned in contact with, or adjacent to, the posterior longitudinal ligament. Positioning the active electrode in relation to the target tissue in step 2004 may involve guiding or steering the shaft distal end of the instrument, e.g., using pull wires, shape memory actuators, and the like, as described hereinabove. Positioning the active electrode in relation to the target tissue may be performed under fluoroscopy. The instrument may include a radiopaque tracking device, e.g., disposed at the shaft distal end, to facilitate fluoroscopic visualization of the working end of the instrument.

While the active electrode is suitably positioned with respect to the target tissue, step 2006 involves applying a high frequency voltage between the active electrode and the return electrode, wherein the applied voltage is effective in denervating the target tissue. In this manner, nociceptors within the annulus, or branches of the sinuvertebral nerve supplying the posterior region of the target disc or a targeted region of the posterior longitudinal ligament, are inactivated or killed. Denervation of the target tissue alleviates back pain associated with afferent (sensory) nerve fibers leading to the sinuvertebral nerve.

The parameters of the voltage applied in step 2004, and the time of treatment, may be adjusted in order to heat the target tissue to a suitable temperature for inactivation of the target nervous tissue. In one embodiment, the temperature to which the target tissue is exposed may be sensed, and the sensed temperature compared with a pre-set temperature value as a basis for adjusting the voltage parameters and the rate at which heat is supplied to the target tissue. Generally, nociceptors and other unmyelinated nerve fibers are inactivated at a temperature of about 45° C., i.e., at a temperature substantially below the minimum temperature required for the irreversible contraction of mammalian collagen fibers. Accordingly, the invention allows the target tissue to be denervated without causing shrinkage and deformation of the annulus fibrosus or the posterior longitudinal ligament. Typically, the high frequency voltage applied in step 2004 is in the range of from about 20 volts RMS to 90 volts RMS, i.e., in the sub-ablation mode. In an alternative embodiment, targeted nervous tissue may be ablated by the application of a higher voltage level with the apparatus operating in the ablation mode. Before or during step 2006, an electrically conductive fluid (e.g., an electrically conductive gel, normal saline) may be delivered to the electrode assembly to provide a current flow path between the active electrode and the return electrode. After treating a first region of the target tissue, optional step 2008 involves repositioning the active electrode with respect to the target tissue in order to treat a subsequent region of the target tissue. After a suitable volume of the target tissue has been treated, the instrument is withdrawn from the patient in step 2010.

It has been noted hereinabove that damaged or defective discs may have increased innervation from the sinuvertebral nerve, as compared with normal discs, thereby enhancing the pain message from a region of the spine having one or more defective discs. Thus, there may be a need to perform disc denervation in combination with other spine procedures, including open procedures for vertebral fusion, or other posterior stabilization procedures. Such spine stabilization procedures performed in combination with electrosurgical denervation of the disc or posterior longitudinal ligament are also within the scope of the invention. Spine stabilization procedures, e.g., using bone grafts and pedicle screws, are well known in the art (see, for example, V. Moodey, MD, et al., Evaluation and Treatment of Low Back Pain, Clinical Symposia, Vol. 48, No. 4, 1996).

Figure 63:
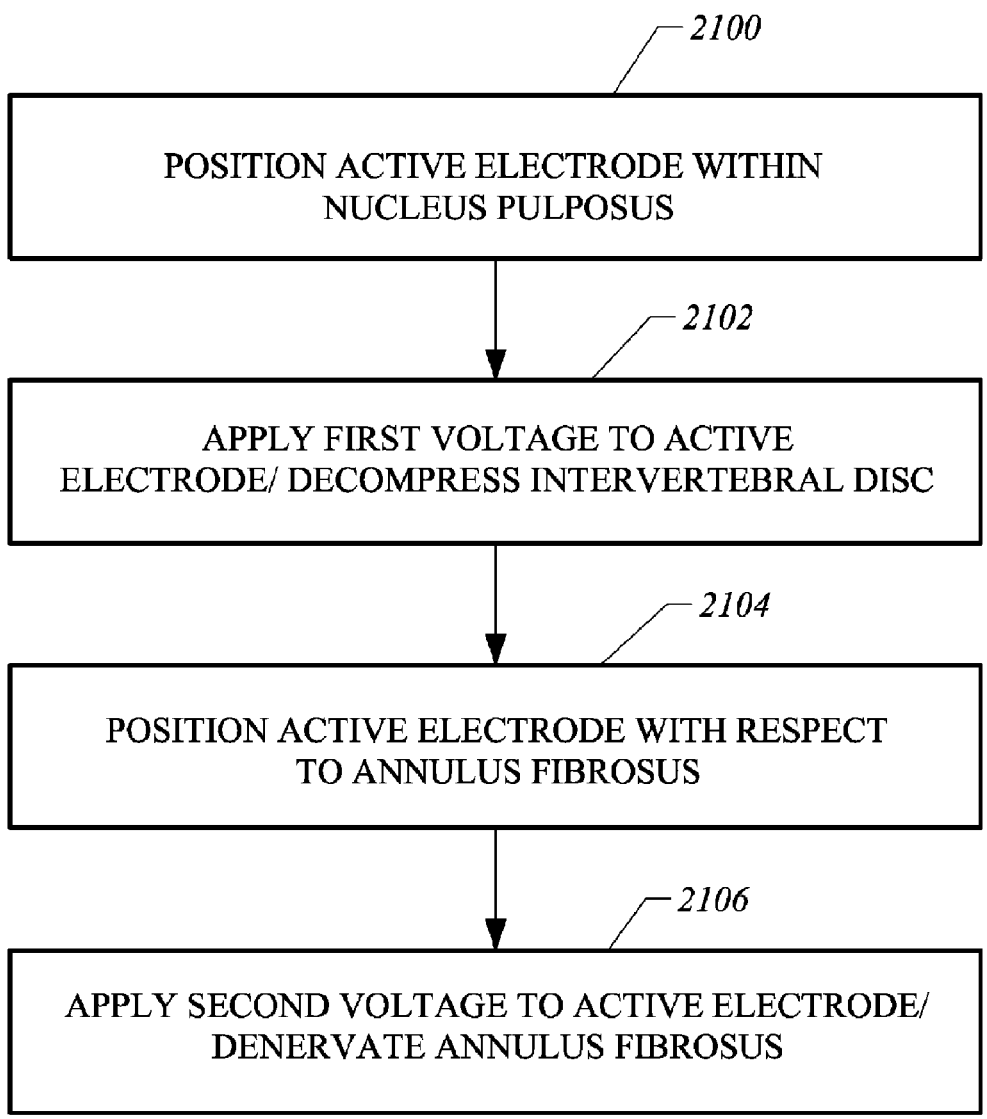
FIG. 63 represents a number of steps involved in a method for electrosurgically decompressing and denervating an intervertebral disc, according to another embodiment of the invention.

FIG. 63 represents a number of steps involved in a method for decompressing and denervating an intervertebral disc using one or more electrosurgical instruments, according to another embodiment of the invention. Each instrument typically includes an electrode assembly disposed at the working end of the instrument, wherein the electrode assembly comprises at least one active electrode. In addition, the instrument may possess those elements, characteristics, and features described hereinabove for various embodiments of the invention. Step 2100 involves positioning the active electrode within the nucleus pulposus of a disc to be treated. The disc to be treated typically has a defect associated with excessive pressure within the disc, such as a contained herniation or a partially extruded nucleus pulposus. While the active electrode is positioned according to step 2100, step 2102 involves applying a first high frequency voltage between the active electrode and a return electrode, such that the disc is decompressed. The disc may be decompressed by ablating a portion of the nucleus pulposus, by shrinking and/or stiffening the nucleus pulposus tissue, or by a combination of these effects. Parameters of the applied voltage, temperatures, and other factors involved in ablating and shrinking the nucleus pulposus for disc decompression are presented hereinabove.

After the disc has been suitably decompressed, the instrument may be withdrawn from the patient, and according to one embodiment, a second instrument may be advanced towards the annulus fibrosus of the disc such that an active electrode of the second instrument is positioned in at least close proximity to the annulus fibrosus (step 2104). In one embodiment, step 2104 comprises advancing the working end of the second instrument towards the disc from a location outside the disc, such that the active electrode of the second instrument is positioned in the annulus fibrosus without contacting or passing through the nucleus pulposus.

While the active electrode is suitably positioned with respect to the target tissue, step 2106 involves applying a second high frequency voltage between the active electrode and a return electrode. Typically, the second high frequency voltage is sufficient to heat the target tissue to a temperature effective for inactivating nervous tissue within the annulus in the absence of tissue contraction. Such a temperature may be in the range of from about 43° C. to 53° C., and often from about 45° C. to 50° C. In one embodiment, the temperature of the annulus fibrosus in the vicinity of the shaft distal end may be monitored during step 2106, e.g. via a temperature sensor unit (FIG. 56B), and the second high frequency voltage adjusted in response to the monitored temperature.

By using separate instruments for i) decompressing the nucleus, and ii) denervating the annulus, each instrument can be specifically configured for the respective tasks of decompression and denervation. As an example, for decompression of the nucleus the first instrument may have a terminal active electrode adapted for ablating nucleus pulposus tissue and for forming one or more channels within the nucleus. As another example, the second instrument may have one or more electrodes arranged laterally on the shaft distal end, wherein the instrument is adapted for heating tissue in a controlled manner to a relatively low temperature suitable for inactivating unmyelinated nerve fibers while having substantially no tissue-modifying (e.g., shrinkage) effect on the annulus fibrosus. The second instrument may include, or be in communication with, temperature monitoring and control devices or circuitry for regulating the amount of heat applied to the tissue (e.g., FIG. 56B).

In an alternative embodiment of the method of FIG. 63, i.e., in a procedure combining decompression and denervation of a target disc, the same instrument may be used both to decompress the disc and to denervate the posterior region of the annulus fibrosus. In which case, during step 2104 the shaft distal end and the electrode assembly may be advanced directly from the nucleus pulpous through the inner wall of the annulus to a location at the posterior of the annulus, and typically within the posterior one-half of the annulus.

Figure 64:
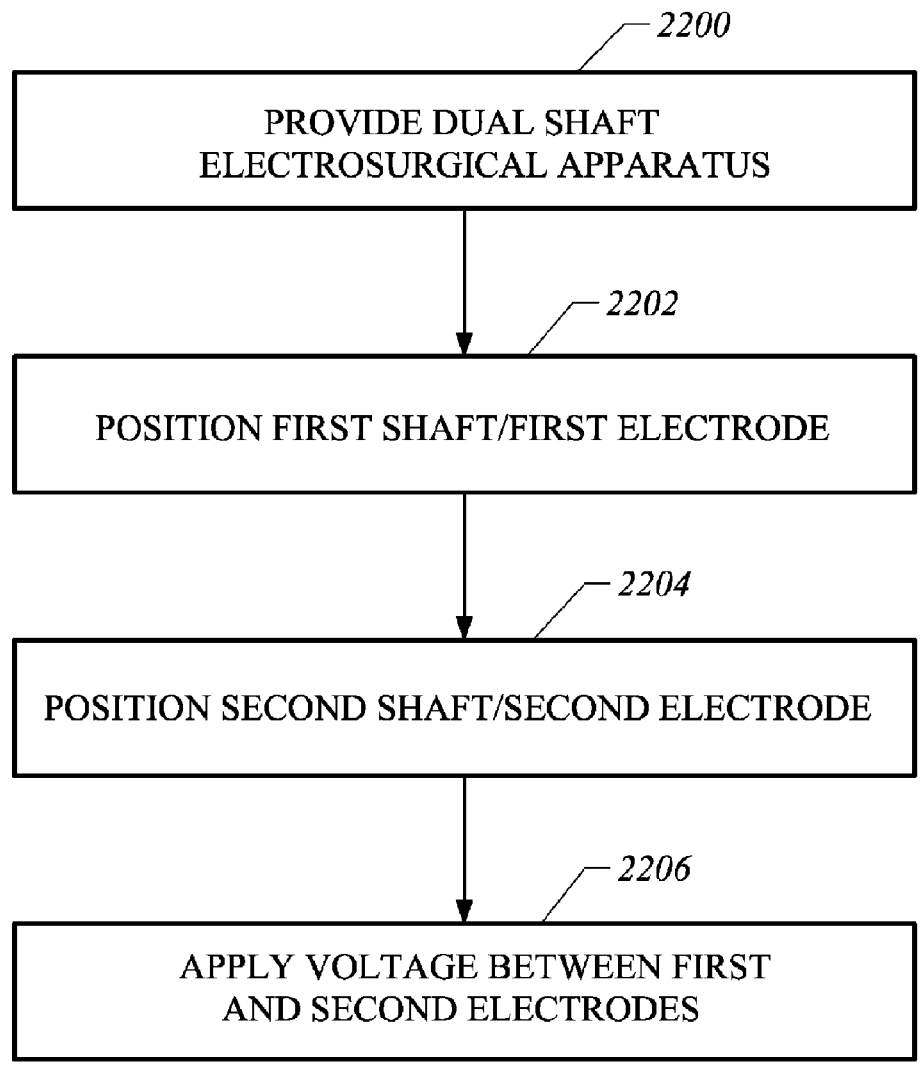
FIG. 64 represents a number of steps involved in a method for electrosurgically denervating a target tissue using a bifurcated, dual-shaft instrument, according to another embodiment of the invention.

FIG. 64 represents a number of steps involved in a method for denervating a target tissue, wherein step 2200 involves providing an electrosurgical apparatus or system comprising a dual-shaft instrument and a high frequency power supply. The instrument includes a first shaft and a second shaft, having a first electrode and a second electrode, respectively. Each shaft may be independently manipulated, and each shaft may be separately introduced into the patient. Each shaft may be deflectable, biased, or steerable to facilitate positioning of the first and second electrodes in relation to a target tissue. The first and second shafts may be the same or dissimilar in dimensions, composition, etc.

Step 2202 involves introducing the first shaft into the patient such that the first electrode is suitably positioned with respect to the target tissue. Step 2204 involves introducing the second shaft into the patient such that the second electrode is suitably positioned with respect to both the target tissue and the first electrode. As an example, the first electrode may comprise at least one active electrode terminal or an array of electrode terminals; while the second electrode may comprise a return electrode having a surface area substantially larger than that of the first electrode. Such an active electrode terminal or electrode array may have the characteristics or features of the various active electrodes described hereinabove. Similarly, the return electrode may have various characteristics or features of the return electrodes described hereinabove.

Typically, the first and second shafts are positioned during steps 2202 and 2204 such that the second electrode is spaced from the first electrode by a distance of up to several cm., usually from about 0.5 mm to 5 cm, and often from about 1 mm to 1 cm. After the first and second electrodes have been suitably positioned according to steps 2202 and 2204, step 2206 involves applying a high frequency voltage between the first and second electrodes from a high frequency power supply. According to one embodiment, the first and second electrodes are positioned in the spine to target nervous tissue within the posterior longitudinal ligament or within the posterior of the annulus fibrosus of an intervertebral disc. As an example, the first electrode may be positioned within the annulus adjacent to the posterior of the nucleus pulposus, while the second electrode may be positioned adjacent to the posterior of the annulus and external to the disc (e.g., FIG. 61). The applied voltage is sufficient to heat the target tissue to a temperature in the range of from about 43° C. to 53° C., and usually from about 45° C. to 50° C. Such temperatures are sufficient to inactivate unmyelinated nervous tissue, e.g., nociceptors, within the target issue, but insufficient to contract or shrink the target tissue. The actual voltage applied is typically within the ranges cited hereinabove for the subablation mode. The temperature of the target tissue may be monitored during step 2206, and the power output from the power supply to the electrodes may be shut off or adjusted in response to the monitored temperature.

By denervating the posterior longitudinal ligament and/or the posterior of the annulus fibrosus, back pain associated with innervation by the sinuvertebral nerve may be alleviated. Although the method represented by FIG. 64 is described primarily with respect to treatment of spinal tissue, an analogous method of the invention may similarly be used for the treatment, modification, or removal of other tissue, e.g., by appropriate placement of the first and second shafts/electrodes in relation to the target tissue, and by using various electrode configurations and voltage parameters. A variety of applications of a dual-shaft electrosurgical instrument and associated methods of use will be apparent to the skilled artisan.

Although the invention has been described primarily with respect to electrosurgical treatment of the spine, it is to be understood that the methods and apparatus of the invention are also applicable to the treatment of other tissue, organs, and bodily structures. Furthermore, while the exemplary embodiments of the present invention have been described in detail, by way of example and for clarity of understanding, a variety of changes, adaptations, and modifications will be apparent to those of skill in the art. For example, a target disc may be denervated by heating the posterior region of the annulus to a suitable temperature, wherein the heat is applied using ultrasound, various lasers, by delivering a pre-heated fluid to that portion of the disc, or in other ways. Therefore, the scope of the present invention is limited solely by the appended claims.

What is claimed is:

1. A method for treating discogenic pain, comprising:
   a) advancing an electrosurgical probe comprising an energy-applying element from a location outside an intervertebral disc towards a nucleus pulposus of the disc;
   b) positioning said energy-applying element within the nucleus pulposus of the disc;
   c) electrosurgically treating the nucleus pulposus of the disc by applying a first high frequency voltage at the energy-applying element;
   d) positioning said energy-applying element within the posterior of the annulus fibrosus; and
   e) electrosurgically coagulating nerve tissue within the posterior of the annulus fibrosus by applying heat using said energy-applying element, whereby the pain is alleviated.

2. The method of claim 1, wherein the probe includes a shaft having a steerable shaft distal end, and said step d) comprises steering the shaft distal end towards the posterior of the annulus fibrosus.

3. The method of claim 1, wherein said step d) comprises positioning the energy-applying element without contacting or passing through the nucleus pulposus of the disc.

4. The method of claim 1, wherein said step e) comprises applying a high frequency voltage between the energy-applying element and a return electrode.

5. The method of claim 4, wherein the probe includes a temperature sensor for monitoring a temperature of the annulus fibrosus, and the method further comprises adjusting the high frequency voltage applied between the energy-applying element and the return electrode in response to a sensed temperature.

6. The method of claim 1, wherein the probe includes a shaft and an electrode assembly disposed at the shaft distal end, the electrode assembly including the energy-applying element and a return electrode, and wherein said step c) comprises applying a high frequency voltage between the energy-applying element and the return electrode.

7. The method of claim 1, wherein said step e) comprises electrosurgically heating a portion of the posterior of the annulus fibrosus to a temperature sufficient to inactive unmyelinated nerve fibers within the posterior of the annulus fibrosus.

8. The method of claim 7, wherein the temperature is insufficient to cause contraction of collagen fibers within the annulus fibrosus.

9. The method of claim 1, wherein said step e) comprises inactivating one or more branches of the sinuvertebral nerve within the annulus fibrosus.

10. The method of claim 1, wherein said step e) comprises electrosurgically heating a portion of the annulus fibrosus to a temperature in the range of from about 43° C. to about 53° C.

11. The method of claim 1, wherein said step e) comprises electrosurgically heating a portion of the annulus fibrosus to a temperature in the range of from about 45° C. to about 50° C.

12. The method of claim 1, wherein said step e) comprises inactivating nociceptors within the annulus fibrosus.

13. The method of claim 1 further comprising:
   positioning said energy applying element within the annulus fibrosus and ablating nervous tissue within the annulus fibrosus.

14. The method of claim 1, wherein the energy-applying element comprises an active electrode.

15. A method for treating discogenic pain, comprising:
   a) advancing an electrosurgical probe comprising an energy-applying element from a location outside an intervertebral disc towards an annulus fibrosus of the disc;
   b) positioning said energy-applying element within the posterior of the annulus fibrosus and positioning a return electrode adjacent to an external surface of the posterior region of the annulus fibrosus; and
   c) electrosurgically coagulating nerve tissue within the posterior of the annulus fibrosus by applying heat using said energy-applying element, whereby the pain is alleviated.

16. The method of claim 15, wherein said step b) comprises positioning the return electrode at a location external to the disc.

17. The method of claim 15, wherein said step b) comprises positioning the energy-applying element within the annulus fibrosus adjacent to the nucleus pulposus.

18. The method of claim 16, wherein the energy-applying element is disposed on a first shaft and the return electrode is disposed on a second shaft.

19. A method for denervating an intervertebral disc, comprising:
   a) advancing an electrosurgical probe comprising an energy-applying element from a location outside an intervertebral disc towards a nucleus pulposus of the disc;
   b) positioning said energy-applying element within the nucleus pulposus of the disc;

c) electrosurgically treating the nucleus pulposus of the disc by applying a first high frequency voltage at the energy-applying element;

d) advancing the energy-applying element of an electrosurgical instrument from a location outside the disc towards a posterior region of an annulus fibrosus of the disc;

e) positioning the energy-applying element within the annulus fibrosus; and f) applying a high frequency voltage between the energy-applying element and a return electrode to coagulate tissue within the annulus fibrosus, wherein the posterior region of the annulus fibrosus is denervated.

20. The method of claim 19, wherein said step a) comprises accessing the disc in an open procedure.

21. The method of claim 20, wherein accessing the disc comprises:

forming an incision in the patient's back;

dissecting the underlying tissue to the lamina; and removing a portion of the lamina.

22. The method of claim 20, wherein the open procedure comprises stabilizing the spine.

23. The method of claim 22, wherein stabilizing the spine comprises fusing together two or more adjacent vertebrae.

24. The method of claim 19, wherein said step a) comprises accessing the disc percutaneously.

25. The method of claim 19, wherein said step a) comprises advancing the energy-applying element towards the disc via a posterolateral approach.

26. The method of claim 19, wherein said step f) comprises applying the high frequency voltage in the range of from about 20 volts RMS to about 90 volts RMS.

27. The method of claim 19, wherein said step f) effects heating of the annulus fibrosus in a region adjacent to the energy-applying element to a temperature in the range of from about 45° C. to 50° C.

28. The method of claim 19, wherein the energy-applying element is disposed on a distal end of a first shaft, and wherein said step e) comprises positioning the distal end of the first shaft within the annulus fibrosus at a location adjacent to the posterior of the nucleus pulposus of the disc.

29. The method of claim 19, wherein said energy-applying element comprises an active electrode.

30. A method for denervating an intervertebral disc, comprising:

a) advancing the energy-applying element of an electrosurgical instrument from a location outside the disc towards a posterior region of an annulus fibrosus of the disc, wherein the energy-applying element is disposed on a distal end of a first shaft;

b) positioning the energy-applying element within the annulus fibrosus at a location adjacent to the posterior of the nucleus pulposus of the disc;

c) applying a high frequency voltage between the energy-applying element and a return electrode to coagulate tissue within the annulus fibrosus, wherein the posterior region of the annulus fibrosus is denervated, and wherein the return electrode is disposed on a distal end of a second shaft; and d) advancing the distal end of the second shaft to a location adjacent to an outer wall of the annulus fibrosus.

31. The method of claim 30, wherein the return electrode is positioned external to the disc.

32. A method for treating an intervertebral disc, comprising:

a) advancing a first electrosurgical probe comprising a first energy-applying element from a location outside an intervertebral disc towards a nucleus pulposus of the disc;

b) positioning said first energy-applying element within the nucleus pulposus of the disc;

c) electrosurgically treating the nucleus pulposus of the disc by applying a first high frequency voltage at the first energy-applying element;

d) advancing an energy-applying element of a second electrosurgical instrument from a location outside the intervertebral disc into the annulus fibrosus; and e) electrosurgically coagulating collagen within the posterior of the annulus fibrosus by applying heat with a second energy-applying element of said second electrosurgical instrument.

33. The method of claim 32, wherein said step e) comprises inactivating nociceptors within the posterior of the annulus fibrosus.

34. The method of claim 32, wherein said step e) comprises applying a high frequency voltage between the second energy-applying element and the second return electrode, wherein the second instrument is operating in a sub-ablation mode.

35. The method of claim 32, wherein said step e) comprises coagulating nerve fibers within the posterior of the annulus fibrosus.

36. The method of claim 35, wherein said step e) comprises electrosurgically heating a posterior region of the annulus fibrosus to a temperature in the range of from about 45° C. to about 50° C.

37. The method of claim 32, wherein said energy-applying element is adapted for delivering a controlled depth of thermal heating of the tissue surrounding said disc.

38. A method for treating back pain, comprising:

a) electrosurgically applying heat at a target tissue within a posterior region of an annulus fibrosus of an intervertebral disc via an electrosurgical probe;

b) controlling the temperature to which the target tissue is exposed, such that the target tissue is exposed to a temperature in the range of from about 43° C. to 53° C.; and c) as a result of said steps a) and b), denervating at least a portion of the target tissue by coagulating nerve tissue therein, whereby the pain is alleviated; and wherein the probe includes an active electrode disposed on a working end of a first shaft of the probe and a return electrode disposed on a working end of a second shaft of the probe, and, prior to step a), the method further comprises:

d) advancing the working end of the first shaft through a portion of the annulus fibrosus such that the active electrode is positioned within the annulus fibrosus at a first location adjacent to the posterior of the nucleus pulposus; and e) advancing the working end of the second shaft towards the posterior of the annulus fibrosus such that the return electrode is positioned external to the annulus fibrosus at a second location adjacent to the posterior of the disc.

39. A method for treating an intervertebral disc, comprising:
- a) providing an electrosurgical instrument, the instrument having a first shaft and a second shaft, the first shaft having a first electrode disposed at the first shaft distal end, and the second shaft having a second electrode disposed at the second shaft distal end;
- b) positioning the first electrode at a first location, the first location within the annulus fibrosus adjacent to a posterior region of a nucleus pulposus of the disc;
- c) positioning the second electrode at a second location, the second location spaced from the first location in a direction towards the posterior of the disc; and
- d) applying a high frequency voltage between the first electrode and the second electrode, wherein a portion of the annulus fibrosus is at least partially denervated.

40. The method of claim 39, wherein the second location is spaced from the first location by a distance in the range of from about 1 mm to 1 cm.

41. The method of claim 39, wherein the second electrode is positioned external to the posterior of the disc.

* * * * *